(12) United States Patent
Hibiya et al.

(10) Patent No.: US 11,667,707 B2
(45) Date of Patent: Jun. 6, 2023

(54) SPNS2 NEUTRALIZING ANTIBODY

(71) Applicant: Teijin Pharma Limited, Tokyo (JP)

(72) Inventors: Kenta Hibiya, Tokyo (JP); Yusuke Kanamaru, Yokohama (JP); Hirotsugu Kato, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 0 days.

(21) Appl. No.: 17/045,398

(22) PCT Filed: Apr. 5, 2019

(86) PCT No.: PCT/JP2019/015208
§ 371 (c)(1),
(2) Date: Oct. 5, 2020

(87) PCT Pub. No.: WO2019/194314
PCT Pub. Date: Oct. 10, 2019

(65) Prior Publication Data
US 2021/0147523 A1 May 20, 2021

(30) Foreign Application Priority Data
Apr. 6, 2018 (JP) .............................. JP2018-073940

(51) Int. Cl.
| | |
|---|---|
| C07K 16/28 | (2006.01) |
| A61K 39/395 | (2006.01) |
| A61P 35/00 | (2006.01) |
| A61P 37/06 | (2006.01) |
| C07K 16/18 | (2006.01) |
| C12N 15/63 | (2006.01) |
| A61K 45/06 | (2006.01) |
| A61K 39/00 | (2006.01) |

(52) U.S. Cl.
CPC .......... *C07K 16/18* (2013.01); *A61K 39/3955* (2013.01); *A61P 35/00* (2018.01); *A61P 37/06* (2018.01); *C12N 15/63* (2013.01); *A61K 45/06* (2013.01); *A61K 2039/505* (2013.01); *C07K 2317/30* (2013.01); *C07K 2317/34* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/70* (2013.01); *C07K 2317/76* (2013.01); *C07K 2317/92* (2013.01)

(58) Field of Classification Search
CPC .. C07K 16/18; A61K 39/395; A61K 39/3955; A61P 35/00; A61P 37/06
See application file for complete search history.

(56) References Cited

U.S. PATENT DOCUMENTS

2006/0292074 A1* 12/2006 Heitner .............. A61K 51/1072
424/1.49

FOREIGN PATENT DOCUMENTS

| JP | 2010-77045 A | 4/2010 |
|---|---|---|
| JP | 2013-059273 A | 4/2013 |
| JP | 5885154 B2 | 3/2016 |
| WO | 2014/132647 A1 | 9/2014 |

OTHER PUBLICATIONS

Spiegel et al, 2019. Journal of Lipid Research. 60: 484-489.*
Nakajima et al., "Cutting Edge: Human Myeloid Cells Cutting Edge: Human Myeloid Cells (ILT1) That Associates with Fc Receptor γ-Chain", J. Immunol., 1999, vol. 162, No. 1, pp. 5-8 (5 pages total).
Nagahashi et al., "Sphingosine-1-Phosphate Transporters as Targets for Cancer Therapy", Biomed. Res. Int., vol. 2014, ID 651727, 2014 (7 pages total).
Spiegel et al., "Sphingosine-1-Phosphate: an Enigmatic Signaling Lipid", Nature Reviews Molecular Cell Biology, vol. 4, No. 5, May 2003, pp. 397-407 (11 pages total).
Liu et al., "Edg-1, the G protein-coupled receptor for sphingosine-1-phosphate, is essential for vascular maturation", J. Clin. Invest., vol. 106, vol. 8, pp. 951-961, 2000 (11 pages total).
Allende et al., "Expression of the Sphingosine 1-Phosphate Receptor, $S1P_1$, on T-cells Controls Thymic Emigration", The Journal of Biological Chemistry, vol. 279, No. 15, Apr. 9, 2004, pp. 15396-15401 (7 pages total).
Means et al., "$S1P_1$ Receptor Localization Confers Selectivity for $G_i$-mediated cAMP and Contractile Responses", The Journal of Biological Chemistry, vol. 283, No. 18, pp. 11954-11963, May 2, 2008 (11 pages total).
O'Sullivan et al., "The structure and function of the S1P1 receptor", Trends in Pharmacological Sciences, Jul. 2013, vol. 34, No. 7, pp. 401-412 (12 pages total).
MacLennan et al., "An essential role for the H218/AGR16/Edg-5/$LP_{B2}$ sphingosine 1-phosphate receptor in neuronal excitability", European Journal of Neuroscience, vol. 14, No. 2, pp. 203-209, 2001 (7 pages total).
MacLennan et al., "The $S1P_2$ sphingosine 1-phosphate receptor is essential for auditory and vestibular function", Hearing Research, vol. 220, Nos. 1-2 (2006) pp. 38-48 (11 pages total).
Kono et al., "The Sphingosine-1-phosphate Receptors $S1P_1$, $S1P_2$, and $S1P_3$ Function Coordinately during Embryonic Angiogenesis", The Journal of Biological Chemistry, vol. 279, No. 28, Jul. 9, 2004, pp. 29367-29373 (8 pages total).

(Continued)

*Primary Examiner* — Zachary C Howard
(74) *Attorney, Agent, or Firm* — Sughrue Mion, PLLC

(57) ABSTRACT

The purpose of the present invention is to provide an antibody that can be expected to have a therapeutic effect in autoimmune diseases and anticancer treatment by inhibiting S1P transport by SPNS2 to thereby inhibit lymphocyte migration. The present invention is an SPNS2 neutralizing antibody or a fragment thereof, or a derivative thereof, that specifically binds to vertebrate SPNS2 and has lymphocyte migration inhibitory activity through SW transport inhibition.

17 Claims, 20 Drawing Sheets
Specification includes a Sequence Listing.

(56) References Cited

OTHER PUBLICATIONS

Nofer et al., "HDL induces NO-dependent vasorelaxation via the lysophospholipid receptor S1P$_3$", J. Clin. Invest., vol. 113, vol. 4, pp. 569-581, 2004 (13 pages total).
Sanna et al., "Bitopic Sphingosine 1-Phosphate Receptor 3 (S1P3) Antagonist Rescue from Complete Heart Block: Pharmacological and Genetic Evidence for Direct S1P3 Regulation of Mouse Cardiac Conduction", Molecular Pharmacology, vol. 89, No. 1, pp. 176-186, Jan. 2016 (23 pages total).
Means et al., "Sphingosine 1-phosphate S1P$_2$ and S1P$_3$ receptor-mediated Akt activation protects against in vivo myocardial ischemia-reperfusion injury", Am J Physiol Heart Circ Physiol, vol. 292, No. 6, pp. H2944-H2951, 2007 (8 pages total).
Golfier et al., "Shaping of terminal megakaryocyte differentiation and proplatelet development by sphingosine-1-phosphate receptor S1P$_4$", The FASEB Journal, vol. 24, No. 12, pp. 4701-4710, Jan. 2018 (12 pages total).
Wang et al., "Type 4 sphingosine 1-phosphate G protein-coupled receptor (S1P$_4$) transduces S1P effects on T cell proliferation and cytokine secretion without signaling migration", The FASEB Journal, vol. 19, No. 12, 2005 (17 pages total).
Schulze et al., "Sphingosine-1-phospate receptor 4 (S1P$_4$) deficiency profoundly affects dendritic cell function and T$_H$17-cell differentiation in a murine model", The FASEB Journal, vol. 25, No. 11, pp. 4024-4036, Jan. 2018 (14 pages total).
Jaillard et al., "Edg8/S1P5: An Oligodendroglial Receptor with Dual Function on Process Retraction and Cell Survival", The Journal of Neuroscience, Feb. 9, 2005, vol. 25, No. 6, pp. 1459-1469 (11 pages total).
Jenne et al., "T-bet-dependent S1P$_5$ expression in NK cells promotes egress from lymph nodes and bone marrow", J. Exp. Med., vol. 206, No. 11, pp. 2469-2481, 2009 (13 pages total).
Lo et al., "Cyclical modulation of sphingosine-1-phosphate receptor 1 surface expression phosphate receptor 1 surface expression during lymphocyte recirculation and relationship to lymphoid organ transit", JEM, vol. 201, No. 2, Jan. 17, 2005, pp. 291-301 (11 pages total).
Chiba, "A New Therapeutic Approach for Autoimmune Diseases by the Sphingosine 1-Phosphate Receptor Modulator, Fingolimod (FTY720)", Yakugaku Zasshi, The Pharmaceutical Society of Japan, vol. 129, No. 6, pp. 655-665, 2009 (11 pages total).
Matloubian et al., "Lymphocyte egress from thymus and peripheral lymphoid organs is dependent on S1P receptor 1", Nature, vol. 427, No. 6972, pp. 355-360, Jan. 2004 (6 pages total).
Schwab et al., "Finding a way out: lymphocyte egress from lymphoid organs", Nature Immunology, vol. 8, No. 12, pp. 1295-1301, Dec. 2007 (7 pages total).
Nagahashi et al., "Sphingosine-1-Phosphate Transporters as Targets for Cancer Therapy", BioMed Research International, vol. 2014, Article ID 651727, 2014 (8 pages total).
Osborne et al., "The Spinster Homolog, Two of Hearts, Is Required for Sphingosine 1-Phosphate Signaling in Zebrafish", Current Biology, vol. 18, No. 23, pp. 1882-1888, Dec. 9, 2008 (7 pages total).
Kawahara et al., "The Sphingolipid Transporter Spns2 Functions in Migration of Zebrafish Myocardial Precursors", Science, vol. 323, No. 5913, Jan. 2009, pp. 524-527 (5 pages total).
Fukuhara et al., "The sphingosine-1-phosphate transporter Spns2 expressed on endothelial cells regulates lymphocyte trafficking in mice", The Journal of Clinical Investigation, vol. 122, No. 4, Apr. 2012, pp. 1416-1426 (11 pages total).
Nijnik et al., "The Role of Sphingosine-1-Phosphate Transporter Spns2 in Immune System Function", The Journal of Immunology, vol. 189, No. 1, pp. 102-111, 2012 (15 pages total).
Hisano et al., "Mouse SPNS2 Functions as a Sphingosine-1-Phosphate Transporter in Vascular Endothelial Cells", PLoS One, vol. 7, No. 6, e38941, 2012 (11 pages total).
Nagahashi et al., "Spns2, a transporter of phosphorylated sphingoid bases, regulates their blood and lymph levels and the lymphatic network", The FASEB Journal, vol. 27, No. 3, Mar. 2013 (11 pages total).
Perland et al., "Characteristics of 29 novel atypical solute carriers of major facilitator superfamily type evolutionary conservation, predicted structure and neuronal co-expression", Open Biol. vol. 7, No. 9, pii: 170142, Sep. 2017 (15 pages total).
Donoviel et al., "Spinster 2, a sphingosine-1-phosphate transporter, plays a critical role in inflammatory and autoimmune diseases", The FASEB Journal, vol. 29, No. 12, Dec. 2015 (11 pages total).
Van der Weyden et al., "Genome-wide in vivo screen identifies novel host regulators of metastatic colonization", Nature, vol. 541, No. 7636, pp. 233-249, Jan. 2017 (17 pages total).
Matsuura et al., "Effect of FTY720, a novel immunosuppressant, on adjuvant-induced arthritis in rats", Inflamm. res., vol. 49, No. 8, pp. 404-410, 2000 (7 pages total).
Wang et al., "Reduction of CD4 positive T cells and improvement of pathological changes of collagen-induced arthritis by FTY720", European Journal of Pharmacology, vol. 573, Nos. 1-3, pp. 230-240, 2007 (11 pages total).
Deguchi et al., "The S1P receptor modulator FTY720 prevents the development of experimental colitis in mice", Oncology Reports, vol. 16, No. 4, pp. 699-703, 2006 (5 pages total).
Idzko et al., "Local application of FTY720 to the lung abrogates experimental asthma by altering dendritic cell function", The Journal of Clinical Investigation, vol. 116, No. 11, pp. 2935-2944, Nov. 2006 (10 pages total).
Ando et al., "FTY720 exerts a survival advantage through the prevention of end-stage glomerular inflammation in lupus-prone BXSB mice", Biochemical and Biophysical Research Communications, vol. 394, No. 3, pp. 804-810, 2010 (7 pages total).
Okazaki et al., "Effects of FTY720 in MRL-lpr/lpr Mice: Therapeutic Potential in Systemic Lupus Erythematosus", The Journal of Rheumatology, vol. 29, No. 4, pp. 707-717, 2002 (11 pages total).
Sui et al., "The sphingosine-1-phosphate receptor agonist FTY720 prevents the development of anti-glomerular basement membrane glomerulonephritis", Mol Biol Rep, vol. 39, No. 1, pp. 389-397, 2012 (9 pages total).
Habicht et al., "Novel Insights into the Mechanism of Action of FTY720 in a Transgenic Model of Allograft Rejection: Implications for Therapy of Chronic Rejection", The Journal of Immunology, vol. 176, No. 1, pp. 36-42, 2006 (8 pages total).
D'Ambrosio et al., "Ponesimod, a selective S1P1 receptor modulator: a potential treatment for multiple sclerosis and other immune-mediated diseases", Therapeutic Advances in Chronic Disease, vol. 7, No. 1 pp. 18-33, 2016 (16 pages total).
Brinkmann et al., "The Immune Modulator FTY720 Targets Sphingosine 1-Phosphate Receptors", The Journal of Biological Chemistry, vol. 277, No. 24, pp. 21453-21457, Jun. 2002 (6 pages total).
Kappos et al., "A Placebo-Controlled Trial of Oral Fingolimod in Relapsing Multiple Sclerosis", The New England Journal of Medicine, vol. 362, No. 5, pp. 387-401, 2010 (15 pages total).
Cohen et al., "Oral Fingolimod or Intramuscular Interferon for Relapsing Multiple Sclerosis", The New England Journal of Medicine, vol. 362, No. 5, pp. 402-415, 2010 (14 pages total).
Koyrakh et al., "The Heart Rate Decrease Caused by Acute FTY720 Administration Is Mediated by the GProtein-Gated Potassium Channel I$_{KACh}$", American Journal of Transplantation, vol. 5, No. 3, pp. 529-536, 2005 (8 pages total).
Hoch et al., "Effect of Ponesimod, a Selective S1P$_1$ Receptor Modulator, on the QT Interval in Healthy Individuals", Basic & Clinical Pharmacology & Toxicology, vol. 116, No. 5, pp. 429-437, 2016 (9 pages total).
Legangneux et al., "Cardiac Effects of Siponimod (BAF312) Re-initiation After Variable Periods of Drug Discontinuation in Healthy Subjects", Clinical Therapeutics, vol. 38, No. 3, pp. 631-646, 2016 (16 pages total).
General Incorporated Association Foundation Japanese Skin Cancer Society, "Guidance for Pharmacotherapy of Malignant Melanomas", Skin Cancer, vol. 32, No. 1, Version 1, 2017 (7 pages total).

(56) References Cited

OTHER PUBLICATIONS

Smyth et al., "NKG2D function protects the host from tumor initiation", The Journal Experimental Medicine, vol. 205, No. 5, pp. 583-588, 2005 (6 pages total).

Xia et al., "Chimeric-antigen receptor T (CAR-T) cell therapy for solid tumors: challenges and opportunities", Oncotarget, vol. 8, No. 52, pp. 90521-90531, 2017 (11 pages total).

Kim et al., "In vivo natural killer cell activities revealed by natural killer cell-deficient mice", PNAS, vol. 97, No. 6, pp. 2731-2736, Mar. 14, 2000 (6 pages total).

Robert et al., "Nivolumab in Previously Untreated Melanoma without BRAF Mutation", The New England Journal of Medicine, vol. 372, No. 4, pp. 320-330, 2015 (11 pages total).

Schachter et al., "Pembrolizumab versus ipilimumab for advanced melanoma: final overall survival results of a multicentre, randomised, open-label phase 3 study (Keynote-006)", Lancet, vol. 390, No. 10105, pp. 1853-1862, 2017 (10 pages total).

Mócsai et al., "What is the future of targeted therapy in rheumatology: biologies or small molecules?", BMC Medicine, vol. 12, No. 43, 2014 (9 pages total).

International Search Report dated Jun. 18, 2019 from the International Searching Authority in International Application No. PCT/JP2019/015208.

Notice of Reasons for Refusal, dated Oct. 5, 2021, issued by the Japanese Patent Office in Japanese Application No. 2020-512340.

Communication, dated Dec. 3, 2021, issued by the European Patent Office in European Application No. 19781500.4.

Toni Celia-Terrassa et al., "Mouse genomic screen reveals novel host regulator of metastasis", Genome Biology, 2017, vol. 18, No. 31, pp. 1-3 (3 pages total).

\* cited by examiner

Fig. 2-1

```
Homo_sapiens      MMCLECASAAAGGAEEEEADAERRRRRRGAQRGAGGSGCCGARGAGGAGVSAAGDEVQTL   60
Macaca_mulatta    MMCLECASAAAGGAEEEEADAERRRRRRGAQRGAGGSGCCGARGAGGAGVSAADDEVQTL   60
Mus_musculus      MMCLECASAAAGGAEEEEADAERRRRRRGAQPGAGGSACCGARGVGGAGVVSADEEVQTL   60
Rattus_norvegicus MMCLECASAAAGGAEEEEADAERRRRRRGAQPGAGGSACCGARGVGGAGVVSADEEVQTL   60
Cavia_porcellus   MMCLECASAAAGGAEEEEADAERRRRRRGAQRGASGSGCCGTRDTGGAGVAAVNDEVQTL   60
                  *****************************  **.**  ***.* , ***** : :*****
```

N-terminal intracellular domain        Transmembrane
                                                        domain 1 (TM1)

```
Homo_sapiens      SGSVRRAPTGPPGTPGTPGCAATAKGPGAQQPKPASLGRGRAAAAILSLGNVLNYLDRY  120
Macaca_mulatta    SGSVRRAPTGPPGTPGTPGCAATAKGPGAQQPKPASLGRGRAAAAILSLGNVLNYLDRY  120
Mus_musculus      SGSVRRVPSGLPSIPSTPGCAAAAKGPSAPQPKPASLGRGRAAAAILSLGNVLNYLDRY  120
Rattus_norvegicus SGSVRRVPSGLPSIPSTPGCAAAAKGPGAPQPKPASLGRGRAAAAILSLGNVLNYLDRY  120
Cavia_porcellus   SGSVRRAPGPSSIPGTPGCAAAAKSPCAQQPKPASLGRGRAAAAILSLGNVLNYLDRY   120
                  ******.*:*  . *.******:*.* * *****************************
```

TM1    Loop1          TM2          Loop2     TM3
```
Homo_sapiens      TVAGVLLDIQQHFGVKDRGAGLLQSVFICSFMVAAPIFGYLGDRFNRKVILSCGIFFWSA  180
Macaca_mulatta    TVAGVLLDIQQHFGVKDRGAGLLQSVFICSFMVAAPIFGYLGDRFNRKVILSCGIFFWSA  180
Mus_musculus      TVAGVLLDIQQHFGVKDRGAGLLQSVFICSFMVAAPIFGYLGDRFNRKVILSCGIFFWSA  180
Rattus_norvegicus TVAGVLLDIQQHFGVKDRGAGLLQSVFICSFMVAAPIFGYLGDRFNRKVILSCGIFFWSA  180
Cavia_porcellus   TVAGVLLDIQQHFGVKDRGAGLLQSVFICSFMVAAPIFGYLGDRFNRKVILSCGIFFWSA  180
                  ************************************************************
```

TM3     Loop3       TM4      Loop 4     TM5
```
Homo_sapiens      VTFSSSFIPQQYFWLLVLSRGLVGIGEASYSTIAPTIIGDLFTKNTRTLMLSVFYFAIPL  240
Macaca_mulatta    VTFSSSFIPQQYFWLLVLSRGLVGIGEASYSTIAPTIIGDLFTKNTRTLMLSVFYFAIPL  240
Mus_musculus      VTFSSSFIPQQYFWLLVLSRGLVGIGEASYSTIAPTIIGDLFTKNTRTLMLSVFYFAIPL  240
Rattus_norvegicus VTFSSSFIPQQYFWLLVLSRGLVGIGEASYSTIAPTIIGDLFTKNTRTLMLSVFYFAIPL  240
Cavia_porcellus   VTFSSSFIPQQYFWLLVLSRGLVGIGEASYSTIAPTIIGDLFTKNTRTLMLSVFYFAIPL  240
                  ************************************************************
```

TM5    Loop 5     TM6         Loop6
```
Homo_sapiens      GSGLGYITGSSVKQAAGDMHWALRVSPVLGMITGTLILILYPATKRGHADQLGDQLKART  300
Macaca_mulatta    GSGLGYITGSSVKQAAGDMHWALRVSPVLGMITGTLILILYPATKRGHADQLGDQLKRT   300
Mus_musculus      GSGLGYITGSSVKQAAGDMHWALRVSPVLGMITGTLILILYPATKRGHADQLGGQLKART  300
Rattus_norvegicus GSGLGYITGSSVKQAAGDMHWALRVSPVLGMITGTLILILYPATKRGHADQLGGQLKART  300
Cavia_porcellus   GSGLGYITGSSVKQAAGDMHWALRVSPVLGMITGTLILILYPATKRGHADQLGGQLKART  300
                  ***********************************************. ***:**
```

Loop6            TM7           Loop7
```
Homo_sapiens      SWLRDMKALIRNRSYVFSSLATSAVSFATGALGMWIPLYLHRAQVVQKTAETCNSPPCGA  360
Macaca_mulatta    SWLRDMKALIRNRSYVFSSLATSAVSFATGALGMWIPLYLHRAQVVQKTAETCNSPPCGA  360
Mus_musculus      SWLRDMKALIRNRSYVFSSLATSAVSFATGALGMWIPLYLHRAQVVQKTAETCNSPPCGA  360
Rattus_norvegicus SWLRDMKALIRNRSYVFSSLATSAVSFATGALGMWIPLYLHRAQVVQKTAETCNSPPCGA  360
Cavia_porcellus   SWLRDMKALIRNRSYVFSSLATSAVSFATGALGMWIPLYLHRAQVVQKTAETCNSPPCGA  360
                  ************************************************:*******
```

Fig. 2-2

```
                    Loop7            TM8         Loop8          TM9          Loop9
Homo_sapiens        KDSLIFGAITCFTGFLGVVTGAGATRWCRLKTQRADPLVCAVGMLGSAIFICLIFVAAKS    420
Macaca_mulatta      KDSLIFGAITCFTGFLGVVTGAGATRWCRLKTQRADPLVCAVGMLGSAIFICLIFVAAKS    420
Mus_musculus        KDSLIFGAITCFTGFLGVVTGAGATRWCRLKTQRADPLVCAVGMLGSAIFICLIFVAAKT    420
Rattus_norvegicus   KDSLIFGAITCFTGFLGVVTGAGATRWCRLKTQRADPLVCAVGMLGSAIFICLIFVAAKT    420
Cavia_porcellus     KDSLIFGAITCFTGFLGVVTGAGATRWCRLKTQRADPLVCAVGMLGSAIFICLIFVAAKS    420

TM10            Loop10           TM11
Homo_sapiens        SIVGAYICIFVGETLLFSNWAITADILMYVVIPTRRATAVALQSFTSHLLGDAGSPYLIG    480
Macaca_mulatta      SIVGAYICIFVGETLLFSNWAITADILMYVVIPTRRATAVALQSFTSHLLGDAGSPYLIG    480
Mus_musculus        SIVGAYICIFVGETLLFSNWAITADILMYVVIPTRRATAVALQSFTSHLLGDAGSPYLIG    480
Rattus_norvegicus   SIVGAYICIFVGETLLFSNWAITADILMYVVIPTRRATAVALQSFTSHLLGDAGSPYLIG    480
Cavia_porcellus     SIVGAYICIFVGETLLFSNWAITADILMCVVIPTRRATAVALQSFTSHLLGDAGSPYLIG    480

TM11      Loop11           TM12           C-terminal
                                                                intracellular domain
Homo_sapiens        IFISDLIRQSTKDSPLWEFLSLGYALMLCPFVVVLGGMFFLATALFFLSDRARAEQQVNQL    540
Macaca_mulatta      IFISDLIRQSTKDSPLWEFLSLGYALMLCPFVVVLGGMFFLATALFFLSDRAKAEQQVNQL    540
Mus_musculus        IFISDLIRQSTKDSPLWEFLSLGYALMLCPFVVVLGGMFFLATALFFLSDRAKAEQQVNQL    540
Rattus_norvegicus   IFISDLIRQSTKDSPLWEFLSLGYALMLCPFVVVLGGMFFLATALFFLSDRAKAEQQVNQL    540
Cavia_porcellus     IFISDLIRQSTKDSPLWEFLSLGYALMLCPFVVVLGGMFFLATALFFLSDRAKAEQQVNQL    540

Homo_sapiens        AMPPASVKV    549
Macaca_mulatta      VMPPASVKV    549
Mus_musculus        VMPPASVKV    549
Rattus_norvegicus   VMPPASVKI    549
Cavia_porcellus     VLPRPPMKV    549
```

Group 1: H chain variable regions

| | Kabat No. | | 18-0211B | 49-0703G | 50-0704C | 89-1207D | | Kabat No. | | 18-0211B | 49-0703G | 50-0704C | 89-1207D |
|---|---|---|---|---|---|---|---|---|---|---|---|---|---|
| | H1 | 1 | A | K | E | E | | H61 | 62 | D | D | D | D |
| | H2 | 2 | V | V | V | V | CDR-H2 | H62 | 63 | S | S | S | S |
| | H3 | 3 | Q | Q | Q | Q | | H63 | 64 | V | V | V | V |
| | H4 | 4 | L | L | L | L | | H64 | 65 | K | K | K | K |
| | H5 | 5 | V | V | V | V | | H65 | 66 | G | G | G | G |
| | H6 | 6 | G | E | G | G | | H66 | 67 | R | R | R | R |
| | H7 | 7 | S | S | S | S | | H67 | 68 | F | F | F | F |
| | H8 | 8 | G | G | G | G | | H68 | 69 | T | T | T | T |
| | H9 | 9 | G | G | G | G | | H69 | 70 | I | I | I | I |
| | H10 | 10 | G | G | G | G | | H70 | 71 | S | S | S | S |
| | H11 | 11 | L | L | L | L | | H71 | 72 | R | R | R | R |
| | H12 | 12 | V | V | V | V | | H72 | 73 | D | D | D | D |
| | H13 | 13 | Q | Q | Q | Q | | H73 | 74 | N | N | N | N |
| | H14 | 14 | P | P | P | P | | H74 | 75 | T | A | A | A |
| | H15 | 15 | G | G | G | G | | H75 | 76 | R | K | R | R |
| | H16 | 16 | R | R | R | R | | H76 | 77 | S | S | S | S |
| | H17 | 17 | S | S | S | S | | H77 | 78 | T | T | T | I |
| | H18 | 18 | M | M | M | M | | H78 | 79 | L | L | L | L |
| | H19 | 19 | K | K | K | K | | H79 | 80 | S | Y | S | S |
| | H20 | 20 | L | L | L | L | | H80 | 81 | L | L | L | L |
| | H21 | 21 | S | S | S | S | | H81 | 82 | Q | Q | Q | Q |
| | H22 | 22 | C | C | C | C | | H82 | 83 | M | M | M | M |
| | H23 | 23 | E | A | E | E | | H82A | 84 | D | D | D | D |
| | H24 | 24 | A | A | A | A | | H82B | 85 | S | S | S | S |
| | H25 | 25 | S | S | S | S | | H82C | 86 | L | L | L | L |
| | H26 | 26 | G | G | G | G | | H83 | 87 | R | R | R | R |
| | H27 | 27 | F | F | F | F | | H84 | 88 | S | S | S | S |
| | H28 | 28 | T | T | T | T | | H85 | 89 | E | E | E | E |
| | H29 | 29 | F | F | F | F | | H86 | 90 | D | D | D | D |
| | H30 | 30 | S | S | S | S | | H87 | 91 | T | T | T | T |
| CDR-H1 | H31 | 31 | N | N | N | N | | H88 | 92 | A | A | A | A |
| | H32 | 32 | H | H | H | H | | H89 | 93 | T | T | T | T |
| | H33 | 33 | Y | Y | Y | Y | | H90 | 94 | Y | Y | Y | Y |
| | H34 | 34 | M | M | M | M | | H91 | 95 | Y | Y | Y | Y |
| | H35 | 35 | A | A | A | A | | H92 | 96 | C | C | C | C |
| | H36 | 36 | W | W | W | W | | H93 | 97 | T | A | A | A |
| | H37 | 37 | V | V | V | V | | H94 | 98 | R | R | R | R |
| | H38 | 38 | R | R | R | R | CDR-H3 | H95 | 99 | Q | Q | Q | Q |
| | H39 | 39 | Q | Q | Q | Q | | H96 | 100 | D | D | D | D |
| | H40 | 40 | A | A | A | A | | H97 | 101 | Y | Y | Y | Y |
| | H41 | 41 | P | P | P | P | | H98 | 102 | T | S | S | S |
| | H42 | 42 | T | T | T | T | | H99 | 103 | N | N | N | N |
| | H43 | 43 | K | K | K | K | | H100 | 104 | Y | Y | Y | Y |
| | H44 | 44 | G | G | G | G | | H100A | 105 | M | M | M | M |
| | H45 | 45 | L | L | L | L | | H100B | 106 | G | G | G | G |
| | H46 | 46 | E | E | E | E | | H100C | 107 | G | G | G | G |
| | H47 | 47 | W | W | W | W | | H100D | 108 | F | F | F | F |
| | H48 | 48 | V | V | V | V | | H101 | 109 | A | A | A | A |
| | H49 | 49 | A | A | A | A | | H102 | 110 | Y | Y | Y | Y |
| | H50 | 50 | T | S | T | T | | H103 | 111 | W | W | W | W |
| | H51 | 51 | I | I | I | I | | H104 | 112 | G | G | G | G |
| | H52 | 52 | S | S | S | S | | H105 | 113 | Q | Q | Q | Q |
| | H52A | 53 | T | T | T | T | | H106 | 114 | G | G | G | G |
| | H53 | 54 | G | G | G | G | | H107 | 115 | T | T | T | T |
| CDR-H2 | H54 | 55 | G | G | G | G | | H108 | 116 | L | L | L | L |
| | H55 | 56 | G | G | G | G | | H109 | 117 | V | V | V | V |
| | H56 | 57 | N | N | N | N | | H110 | 118 | T | T | T | T |
| | H57 | 58 | T | T | T | T | | H111 | 119 | V | V | V | V |
| | H58 | 59 | Y | Y | Y | Y | | H112 | 120 | S | S | S | S |
| | H59 | 60 | Y | Y | Y | Y | | H113 | 121 | S | S | S | S |
| | H60 | 61 | R | R | R | R | | | | | | | |

Fig. 11-1-2

Group 1: L chain variable regions

| | Kabat No. | 18-0211B | 49-0703G | 50-0704C | 89-1207D | | Kabat No. | 18-0211B | 49-0703G | 50-0704C | 89-1207D |
|---|---|---|---|---|---|---|---|---|---|---|---|
| | L1 | 1 | Q | Q | Q | Q | L57 | 58 | G | G | G | G |
| | L2 | 2 | F | F | F | F | L58 | 59 | V | V | V | V |
| | L3 | 3 | V | V | V | V | L59 | 60 | P | P | P | P |
| | L4 | 4 | L | L | L | L | L60 | 61 | D | D | D | D |
| | L5 | 5 | T | T | T | T | L61 | 62 | R | R | R | R |
| | L6 | 6 | Q | Q | Q | Q | L62 | 63 | F | F | F | F |
| | L7 | 7 | P | P | P | P | L63 | 64 | S | S | S | S |
| | L8 | 8 | N | N | N | N | L64 | 65 | G | G | G | G |
| | L9 | 9 | S | S | S | S | L65 | 66 | S | S | S | S |
| | L10 | | - | - | - | - | L66 | 67 | I | I | I | I |
| | L11 | 10 | V | V | V | V | L66A | 68 | D | D | D | D |
| | L12 | 11 | S | S | S | S | L66B | 69 | R | R | R | R |
| | L13 | 12 | T | T | T | T | L67 | 70 | S | S | S | S |
| | L14 | 13 | N | N | N | N | L68 | 71 | S | S | S | S |
| | L15 | 14 | L | L | L | L | L69 | 72 | N | N | N | N |
| | L16 | 15 | G | G | G | G | L70 | 73 | S | S | S | S |
| | L17 | 16 | S | S | S | S | L71 | 74 | A | A | A | A |
| | L18 | 17 | T | T | T | T | L72 | 75 | L | L | L | L |
| | L19 | 18 | V | V | V | V | L73 | 76 | L | L | L | L |
| | L20 | 19 | K | K | K | K | L74 | 77 | T | T | T | T |
| | L21 | 20 | L | L | L | L | L75 | 78 | I | I | I | I |
| | L22 | 21 | S | S | S | S | L76 | 79 | N | N | N | N |
| | L23 | 22 | C | C | C | C | L77 | 80 | S | S | S | N |
| CDR-L1 | L24 | 23 | T | K | T | T | L78 | 81 | V | V | V | V |
| | L25 | 24 | R | R | R | R | L79 | 82 | Q | Q | Q | Q |
| | L26 | 25 | S | S | S | S | L80 | 83 | T | T | T | T |
| | L27 | 26 | I | T | I | I | L81 | 84 | E | E | E | E |
| | L27A | 27 | G | G | G | G | L82 | 85 | D | D | D | D |
| | L27B | 28 | N | N | N | N | L83 | 86 | E | E | E | E |
| | L28 | 29 | I | I | I | I | L84 | 87 | A | A | A | A |
| | L29 | 30 | G | G | G | G | L85 | 88 | D | D | D | D |
| | L30 | 31 | N | N | N | N | L86 | 89 | Y | Y | Y | Y |
| | L31 | 32 | N | N | N | N | L87 | 90 | F | F | F | F |
| | L32 | 33 | Y | Y | Y | Y | L88 | 91 | C | C | C | C |
| | L33 | 34 | V | V | V | V | L89 | 92 | Q | Q | Q | Q |
| | L34 | 35 | N | N | N | N | L90 | 93 | S | S | S | S |
| | L35 | 36 | W | W | W | W | L91 | 94 | F | F | F | F |
| | L36 | 37 | Y | Y | Y | Y | CDR-L3 | L92 | 95 | S | S | S | S |
| | L37 | 38 | K | Q | K | K | L93 | 96 | S | N | S | S |
| | L38 | 39 | Q | Q | Q | Q | L94 | 97 | G | G | G | G |
| | L39 | 40 | Y | Y | Y | Y | L95 | 98 | I | M | I | M |
| | L40 | 41 | E | E | E | E | L96 | 99 | F | F | F | F |
| | L41 | 42 | G | G | G | G | L97 | 100 | I | I | I | I |
| | L42 | 43 | R | R | R | R | L98 | 101 | F | F | F | F |
| | L43 | 44 | S | S | S | S | L99 | 102 | G | A | G | G |
| | L44 | 45 | P | P | P | P | L100 | 103 | G | G | G | G |
| | L45 | 46 | T | T | T | T | L101 | 104 | G | G | G | G |
| | L46 | 47 | T | T | T | T | L102 | 105 | T | T | T | T |
| | L47 | 48 | L | M | M | M | L103 | 106 | T | Q | K | K |
| | L48 | 49 | I | I | I | I | L104 | 107 | L | L | L | L |
| | L49 | 50 | Y | Y | Y | Y | L105 | 108 | T | T | T | T |
| CDR-L2 | L50 | 51 | R | R | R | R | L106 | 109 | V | V | V | V |
| | L51 | 52 | D | D | D | D | L106A | 110 | L | L | L | L |
| | L52 | 53 | D | D | D | D | | | | | | |
| | L53 | 54 | E | E | E | E | | | | | | |
| | L54 | 55 | R | R | R | R | | | | | | |
| | L55 | 56 | P | P | P | P | | | | | | |
| | L56 | 57 | D | D | D | D | | | | | | |

Fig. 11-2-1

Group 2: H chain variable regions

| | Kabat No. | | 64-0807A | 64-1111F | | Kabat No. | | 64-0807A | 64-1111F |
|---|---|---|---|---|---|---|---|---|---|
| | H1 | 1 | E | E | | H59 | 60 | Y | Y |
| | H2 | 2 | V | V | | H60 | 61 | K | R |
| | H3 | 3 | Q | Q | | H61 | 62 | D | D |
| | H4 | 4 | V | V | CDR-H2 | H62 | 63 | S | S |
| | H5 | 5 | V | V | | H63 | 64 | V | V |
| | H6 | 6 | E | E | | H64 | 65 | K | K |
| | H7 | 7 | S | S | | H65 | 66 | G | G |
| | H8 | 8 | G | G | | H66 | 67 | R | R |
| | H9 | 9 | G | G | | H67 | 68 | F | F |
| | H10 | 10 | G | G | | H68 | 69 | T | T |
| | H11 | 11 | L | L | | H69 | 70 | I | I |
| | H12 | 12 | V | V | | H70 | 71 | S | S |
| | H13 | 13 | Q | Q | | H71 | 72 | R | R |
| | H14 | 14 | P | P | | H72 | 73 | D | D |
| | H15 | 15 | G | G | | H73 | 74 | N | N |
| | H16 | 16 | R | R | | H74 | 75 | A | A |
| | H17 | 17 | S | S | | H75 | 76 | K | K |
| | H18 | 18 | M | M | | H76 | 77 | S | S |
| | H19 | 19 | K | K | | H77 | 78 | T | T |
| | H20 | 20 | L | L | | H78 | 79 | L | L |
| | H21 | 21 | S | S | | H79 | 80 | Y | Y |
| | H22 | 22 | C | C | | H80 | 81 | L | L |
| | H23 | 23 | A | A | | H81 | 82 | Q | K |
| | H24 | 24 | A | A | | H82 | 83 | M | M |
| | H25 | 25 | L | L | | H82A | 84 | D | D |
| | H26 | 26 | G | G | | H82B | 85 | S | S |
| | H27 | 27 | F | F | | H82C | 86 | L | L |
| | H28 | 28 | T | T | | H83 | 87 | R | R |
| | H29 | 29 | F | F | | H84 | 88 | S | S |
| | H30 | 30 | R | R | | H85 | 89 | D | D |
| | H31 | 31 | D | D | | H86 | 90 | D | D |
| CDR-H1 | H32 | 32 | Y | Y | | H87 | 91 | T | T |
| | H33 | 33 | Y | Y | | H88 | 92 | A | A |
| | H34 | 34 | M | M | | H89 | 93 | T | T |
| | H35 | 35 | A | A | | H90 | 94 | Y | Y |
| | H36 | 36 | W | W | | H91 | 95 | Y | Y |
| | H37 | 37 | V | V | | H92 | 96 | C | C |
| | H38 | 38 | R | R | | H93 | 97 | A | A |
| | H39 | 39 | Q | Q | | H94 | 98 | R | R |
| | H40 | 40 | T | T | | H95 | 99 | N | N |
| | H41 | 41 | P | P | | H96 | 100 | P | P |
| | H42 | 42 | T | T | | H97 | 101 | Y | Y |
| | H43 | 43 | K | K | CDR-H3 | H98 | 102 | G | G |
| | H44 | 44 | G | G | | H99 | 103 | N | N |
| | H45 | 45 | L | L | | H100 | 104 | Y | Y |
| | H46 | 46 | E | E | | H100A | 105 | F | F |
| | H47 | 47 | W | W | | H101 | 106 | D | D |
| | H48 | 48 | V | V | | H102 | 107 | Y | Y |
| | H49 | 49 | A | A | | H103 | 108 | W | W |
| | H50 | 50 | A | A | | H104 | 109 | G | G |
| | H51 | 51 | I | I | | H105 | 110 | Q | Q |
| | H52 | 52 | S | S | | H106 | 111 | G | G |
| | H52A | 53 | T | T | | H107 | 112 | V | V |
| CDR-H2 | H53 | 54 | G | G | | H108 | 113 | M | M |
| | H54 | 55 | G | G | | H109 | 114 | V | V |
| | H55 | 56 | G | G | | H110 | 115 | T | T |
| | H56 | 57 | N | N | | H111 | 116 | V | V |
| | H57 | 58 | T | T | | H112 | 117 | S | S |
| | H58 | 59 | Y | Y | | H113 | 118 | S | S |

Fig. 11-2-2

Group 2: L chain variable regions

| | Kabat No. | | B4-8887A | B4-1111F | | Kabat No. | | B4-8887A | B4-1111F |
|---|---|---|---|---|---|---|---|---|---|
| | L1 | 1 | Q | Q | | L57 | 58 | G | G |
| | L2 | 2 | P | P | | L58 | 59 | V | V |
| | L3 | 3 | V | V | | L59 | 60 | P | P |
| | L4 | 4 | L | L | | L60 | 61 | D | D |
| | L5 | 5 | S | S | | L61 | 62 | R | R |
| | L6 | 6 | Q | Q | | L62 | 63 | F | F |
| | L7 | 7 | P | P | | L63 | 64 | S | S |
| | L8 | 8 | N | N | | L64 | 65 | G | G |
| | L9 | 9 | S | S | | L65 | 66 | S | S |
| | L10 | | - | - | | L66 | 67 | I | I |
| | L11 | 10 | V | V | | L66A | 68 | D | D |
| | L12 | 11 | S | S | | L66B | 69 | R | R |
| | L13 | 12 | T | T | | L67 | 70 | S | S |
| | L14 | 13 | N | N | | L68 | 71 | S | S |
| | L15 | 14 | L | L | | L69 | 72 | N | N |
| | L16 | 15 | G | G | | L70 | 73 | S | S |
| | L17 | 16 | S | S | | L71 | 74 | A | A |
| | L18 | 17 | T | T | | L72 | 75 | L | L |
| | L19 | 18 | V | V | | L73 | 76 | L | L |
| | L20 | 19 | K | K | | L74 | 77 | T | T |
| | L21 | 20 | L | L | | L75 | 78 | I | I |
| | L22 | 21 | S | S | | L76 | 79 | N | N |
| | L23 | 22 | C | C | | L77 | 80 | N | N |
| CDR-L1 | L24 | 23 | K | K | | L78 | 81 | V | V |
| | L25 | 24 | R | R | | L79 | 82 | Q | Q |
| | L26 | 25 | S | S | | L80 | 83 | T | T |
| | L27 | 26 | T | T | | L81 | 84 | E | E |
| | L27A | 27 | G | G | | L82 | 85 | D | D |
| | L27B | 28 | N | N | | L83 | 86 | E | E |
| | L28 | 29 | I | I | | L84 | 87 | A | A |
| | L29 | 30 | G | G | | L85 | 88 | D | D |
| | L30 | 31 | S | S | | L86 | 89 | Y | Y |
| | L31 | 32 | N | N | | L87 | 90 | F | F |
| | L32 | 33 | Y | Y | | L88 | 91 | C | C |
| | L33 | 34 | V | V | CDR-L3 | L89 | 92 | Q | Q |
| | L34 | 35 | H | H | | L90 | 93 | S | S |
| | L35 | 36 | W | W | | L91 | 94 | Y | Y |
| | L36 | 37 | Y | Y | | L92 | 95 | S | S |
| | L37 | 38 | Q | Q | | L93 | 96 | G | G |
| | L38 | 39 | R | R | | L94 | 97 | G | G |
| | L39 | 40 | H | H | | L95 | 98 | M | M |
| | L40 | 41 | E | E | | L96 | 99 | Y | Y |
| | L41 | 42 | G | G | | L97 | 100 | L | L |
| | L42 | 43 | R | R | | L98 | 101 | F | F |
| | L43 | 44 | S | S | | L99 | 102 | G | G |
| | L44 | 45 | P | P | | L100 | 103 | G | G |
| | L45 | 46 | T | T | | L101 | 104 | G | G |
| | L46 | 47 | T | T | | L102 | 105 | T | T |
| | L47 | 48 | L | M | | L103 | 106 | K | T |
| | L48 | 49 | I | I | | L104 | 107 | L | L |
| | L49 | 50 | Y | Y | | L105 | 108 | T | T |
| CDR-L2 | L50 | 51 | R | R | | L106 | 109 | V | V |
| | L51 | 52 | D | D | | L106A | 110 | L | L |
| | L52 | 53 | D | D | | | | | |
| | L53 | 54 | K | K | | | | | |
| | L54 | 55 | R | R | | | | | |
| | L55 | 56 | P | P | | | | | |
| | L56 | 57 | N | N | | | | | |

Fig. 11-3-1

Group 3: H chain variable regions

| | Kabat No. | | 90-1104A | 93-1310F | 95-1403F | | Kabat No. | | 90-1104A | 93-1310F | 95-1403F |
|---|---|---|---|---|---|---|---|---|---|---|---|
| | H1 | 1 | E | K | E | | H61 | 84 | E | E | K |
| | H2 | 2 | V | V | V | | H62 | 85 | S | S | S |
| | H3 | 3 | Q | Q | Q | CDR-H2 | H63 | 86 | V | V | I |
| | H4 | 4 | L | L | L | | H64 | 87 | K | K | K |
| | H5 | 5 | V | V | V | | H65 | 88 | G | G | G |
| | H6 | 6 | E | E | E | | H66 | 89 | R | R | R |
| | H7 | 7 | T | T | T | | H67 | 70 | F | F | F |
| | H8 | 8 | G | G | G | | H68 | 71 | T | T | T |
| | H9 | 9 | G | G | G | | H69 | 72 | I | I | I |
| | H10 | 10 | G | G | G | | H70 | 73 | S | S | S |
| | H11 | 11 | L | L | L | | H71 | 74 | R | R | R |
| | H12 | 12 | V | V | V | | H72 | 75 | D | D | D |
| | H13 | 13 | Q | Q | S | | H73 | 76 | D | D | D |
| | H14 | 14 | P | P | P | | H74 | 77 | S | S | S |
| | H15 | 15 | G | G | G | | H75 | 78 | K | K | K |
| | H16 | 16 | S | S | S | | H76 | 79 | R | R | R |
| | H17 | 17 | S | S | S | | H77 | 80 | R | R | R |
| | H18 | 18 | L | L | L | | H78 | 81 | V | V | V |
| | H19 | 19 | K | K | K | | H79 | 82 | Y | Y | Y |
| | H20 | 20 | L | L | L | | H80 | 83 | L | L | L |
| | H21 | 21 | S | S | S | | H81 | 84 | Q | Q | Q |
| | H22 | 22 | C | C | C | | H82 | 85 | M | M | M |
| | H23 | 23 | R | A | A | | H82A | 86 | Y | F | N |
| | H24 | 24 | T | T | T | | H82B | 87 | T | T | T |
| | H25 | 25 | S | S | S | | H82C | 88 | L | L | L |
| | H26 | 26 | G | G | G | | H83 | 89 | R | R | R |
| | H27 | 27 | F | F | F | | H84 | 90 | D | D | D |
| | H28 | 28 | T | T | T | | H85 | 91 | Q | Q | Q |
| | H29 | 29 | F | F | F | | H86 | 92 | D | D | D |
| | H30 | 30 | S | S | S | | H87 | 93 | T | T | T |
| | H31 | 31 | K | D | D | | H88 | 94 | A | A | A |
| CDR-H1 | H32 | 32 | T | T | T | | H89 | 95 | T | T | T |
| | H33 | 33 | W | W | W | | H90 | 96 | Y | Y | Y |
| | H34 | 34 | M | M | M | | H91 | 97 | Y | Y | Y |
| | H35 | 35 | S | S | S | | H92 | 98 | C | C | C |
| | H36 | 36 | W | W | W | | H93 | 99 | T | T | T |
| | H37 | 37 | V | V | V | | H94 | 100 | S | S | S |
| | H38 | 38 | R | R | R | | H95 | 101 | H | H | H |
| | H39 | 39 | Q | Q | Q | | H96 | 102 | E | E | E |
| | H40 | 40 | A | A | A | | H97 | 103 | D | D | D |
| | H41 | 41 | P | P | P | | H98 | 104 | F | F | F |
| | H42 | 42 | G | G | G | | H99 | 105 | Y | Y | Y |
| | H43 | 43 | K | K | K | | H100 | 106 | Y | Y | Y |
| | H44 | 44 | G | G | G | CDR-H3 | H100A | 107 | Y | Y | Y |
| | H45 | 45 | L | L | L | | H100B | 108 | S | S | S |
| | H46 | 46 | E | E | E | | H100C | 109 | S | S | S |
| | H47 | 47 | W | W | W | | H100D | 110 | Y | Y | Y |
| | H48 | 48 | V | V | V | | H100E | 111 | Y | Y | Y |
| | H49 | 49 | G | A | A | | H100F | 112 | F | F | F |
| | H50 | 50 | L | L | L | | H101 | 113 | D | D | D |
| | H51 | 51 | I | I | I | | H102 | 114 | Y | Y | Y |
| | H52 | 52 | K | K | K | | H103 | 115 | W | W | W |
| | H52A | 53 | D | D | D | | H104 | 116 | G | G | G |
| | H52B | 54 | K | K | K | | H105 | 117 | Q | R | Q |
| | H52C | 55 | N | N | N | | H106 | 118 | G | G | G |
| CDR-H2 | H53 | 56 | S | S | S | | H107 | 119 | V | V | V |
| | H54 | 57 | N | N | N | | H108 | 120 | M | M | M |
| | H55 | 58 | Y | Y | S | | H109 | 121 | V | V | V |
| | H56 | 59 | E | E | E | | H110 | 122 | T | T | T |
| | H57 | 60 | A | A | A | | H111 | 123 | V | V | V |
| | H58 | 61 | N | N | N | | H112 | 124 | S | S | S |
| | H59 | 62 | Y | Y | Y | | H113 | 125 | S | S | S |
| | H60 | 63 | A | A | A | | | | | | |

Fig. 11-3-2

Group 3: L chain variable regions

| | Kabat No. | | 80-1104A | 93-1310F | 96-1403F |
|---|---|---|---|---|---|
| | L1 | 1 | D | D | D |
| | L2 | 2 | I | I | I |
| | L3 | 3 | V | V | V |
| | L4 | 4 | L | L | L |
| | L5 | 5 | T | T | T |
| | L6 | 6 | Q | Q | Q |
| | L7 | 7 | S | S | S |
| | L8 | 8 | P | P | P |
| | L9 | 9 | A | A | R |
| | L10 | 10 | T | T | T |
| | L11 | 11 | L | L | L |
| | L12 | 12 | S | S | S |
| | L13 | 13 | V | V | V |
| | L14 | 14 | T | T | T |
| | L15 | 15 | P | P | P |
| | L16 | 16 | G | G | G |
| | L17 | 17 | E | E | E |
| | L18 | 18 | S | S | S |
| | L19 | 19 | V | V | V |
| | L20 | 20 | S | S | S |
| | L21 | 21 | L | L | L |
| | L22 | 22 | S | S | S |
| | L23 | 23 | C | C | C |
| CDR-L1 | L24 | 24 | R | R | R |
| | L25 | 25 | A | A | A |
| | L26 | 26 | S | S | S |
| | L27 | 27 | Q | Q | Q |
| | L28 | 28 | G | G | G |
| | L29 | 29 | I | I | I |
| | L30 | 30 | S | S | S |
| | L31 | 31 | T | T | T |
| | L32 | 32 | S | S | S |
| | L33 | 33 | I | I | I |
| | L34 | 34 | H | H | H |
| | L35 | 35 | W | W | W |
| | L36 | 36 | Y | Y | Y |
| | L37 | 37 | Q | Q | Q |
| | L38 | 38 | Q | Q | Q |
| | L39 | 39 | K | K | R |
| | L40 | 40 | S | S | S |
| | L41 | 41 | N | N | N |
| | L42 | 42 | E | Q | E |
| | L43 | 43 | S | S | S |
| | L44 | 44 | P | P | P |
| | L45 | 45 | R | R | R |
| | L46 | 46 | L | L | L |
| | L47 | 47 | L | L | L |
| | L48 | 48 | I | I | I |
| | L49 | 49 | K | K | K |
| CDR-L2 | L50 | 50 | Y | Y | Y |
| | L51 | 51 | A | A | A |
| | L52 | 52 | S | S | S |
| | L53 | 53 | Q | Q | Q |
| | L54 | 54 | S | S | S |
| | L55 | 55 | N | I | I |
| | L56 | 56 | S | S | A |

| | Kabat No. | | 80-1104A | 93-1310F | 96-1403F |
|---|---|---|---|---|---|
| | L57 | 57 | G | G | G |
| | L58 | 58 | I | I | I |
| | L59 | 59 | P | P | P |
| | L60 | 60 | S | S | S |
| | L61 | 61 | R | R | R |
| | L62 | 62 | F | F | F |
| | L63 | 63 | S | S | S |
| | L64 | 64 | G | G | G |
| | L65 | 65 | S | S | S |
| | L66 | 66 | G | G | G |
| | L67 | 67 | S | S | S |
| | L68 | 68 | G | G | G |
| | L69 | 69 | T | T | T |
| | L70 | 70 | D | D | D |
| | L71 | 71 | F | F | F |
| | L72 | 72 | T | T | I |
| | L73 | 73 | L | L | L |
| | L74 | 74 | R | R | S |
| | L75 | 75 | I | I | I |
| | L76 | 76 | N | N | N |
| | L77 | 77 | R | R | R |
| | L78 | 78 | V | V | V |
| | L79 | 79 | E | E | E |
| | L80 | 80 | S | S | S |
| | L81 | 81 | E | E | E |
| | L82 | 82 | D | D | D |
| | L83 | 83 | F | F | F |
| | L84 | 84 | S | S | S |
| | L85 | 85 | V | V | V |
| | L86 | 86 | Y | Y | Y |
| | L87 | 87 | Y | Y | Y |
| | L88 | 88 | C | C | C |
| CDR-L3 | L89 | 89 | Q | Q | Q |
| | L90 | 90 | Q | Q | Q |
| | L91 | 91 | S | T | T |
| | L92 | 92 | Y | Y | Y |
| | L93 | 93 | N | S | S |
| | L94 | 94 | L | L | L |
| | L95 | 95 | P | P | P |
| | L96 | 96 | L | L | L |
| | L97 | 97 | T | T | T |
| | L98 | 98 | F | F | F |
| | L99 | 99 | G | G | G |
| | L100 | 100 | S | S | P |
| | L101 | 101 | G | G | G |
| | L102 | 102 | T | T | T |
| | L103 | 103 | K | R | K |
| | L104 | 104 | L | L | L |
| | L105 | 105 | E | E | E |
| | L106 | 106 | I | I | V |
| | L107 | 107 | K | K | K |
| | L108 | 108 | R | R | R |

Fig. 11-4-1

Group 4: H chain variable regions

| | Kabat No. | | 37-0511F | 93-0707E | 94-1311E |
|---|---|---|---|---|---|
| | H1 | 1 | E | E | E |
| | H2 | 2 | V | V | V |
| | H3 | 3 | H | Q | Q |
| | H4 | 4 | L | L | L |
| | H5 | 5 | Q | Q | Q |
| | H6 | 6 | Q | Q | Q |
| | H7 | 7 | S | S | S |
| | H8 | 8 | G | G | G |
| | H9 | 9 | A | A | A |
| | H10 | 10 | A | E | E |
| | H11 | 11 | L | L | L |
| | H12 | 12 | V | V | V |
| | H13 | 13 | R | R | R |
| | H14 | 14 | P | P | P |
| | H15 | 15 | R | R | R |
| | H16 | 16 | A | T | T |
| | H17 | 17 | S | S | S |
| | H18 | 18 | V | V | V |
| | H19 | 19 | K | K | R |
| | H20 | 20 | L | L | L |
| | H21 | 21 | S | S | S |
| | H22 | 22 | C | C | C |
| | H23 | 23 | K | K | K |
| | H24 | 24 | V | V | T |
| | H25 | 25 | S | S | S |
| | H26 | 26 | G | G | G |
| | H27 | 27 | D | D | D |
| | H28 | 28 | S | S | S |
| | H29 | 29 | I | I | I |
| | H30 | 30 | S | T | T |
| | H31 | 31 | R | R | A |
| CDR-H1 | H32 | 32 | Y | Y | Y |
| | H33 | 33 | Y | Y | Y |
| | H34 | 34 | V | V | V |
| | H35 | 35 | H | H | H |
| | H36 | 36 | F | F | F |
| | H37 | 37 | V | V | V |
| | H38 | 38 | K | K | K |
| | H39 | 39 | Q | Q | Q |
| | H40 | 40 | R | R | R |
| | H41 | 41 | P | P | P |
| | H42 | 42 | G | G | G |
| | H43 | 43 | Q | Q | Q |
| | H44 | 44 | G | G | G |
| | H45 | 45 | L | L | L |
| | H46 | 46 | E | E | E |
| | H47 | 47 | W | W | W |
| | H48 | 48 | I | I | I |
| | H49 | 49 | G | G | G |
| | H50 | 50 | R | R | R |
| | H51 | 51 | I | I | I |
| | H52 | 52 | D | D | D |
| | H52A | 53 | P | P | P |
| CDR-H2 | H53 | 54 | E | E | E |
| | H54 | 55 | D | D | D |
| | H55 | 56 | D | D | D |
| | H56 | 57 | T | T | S |
| | H57 | 58 | T | T | T |
| | H58 | 59 | K | K | K |

| | Kabat No. | | 37-0511F | 93-0707E | 94-1311E |
|---|---|---|---|---|---|
| | H59 | 60 | Y | Y | Y |
| | H60 | 61 | S | S | S |
| CDR-H2 | H61 | 62 | E | E | E |
| | H62 | 63 | K | K | K |
| | H63 | 64 | F | F | F |
| | H64 | 65 | K | K | K |
| | H65 | 66 | N | K | N |
| | H66 | 67 | R | K | K |
| | H67 | 68 | A | A | A |
| | H68 | 69 | T | T | T |
| | H69 | 70 | L | L | L |
| | H70 | 71 | T | T | T |
| | H71 | 72 | A | A | A |
| | H72 | 73 | D | D | D |
| | H73 | 74 | A | A | V |
| | H74 | 75 | S | S | S |
| | H75 | 76 | S | S | S |
| | H76 | 77 | D | N | S |
| | H77 | 78 | T | T | T |
| | H78 | 79 | A | A | A |
| | H79 | 80 | S | Y | Y |
| | H80 | 81 | L | L | L |
| | H81 | 82 | I | I | I |
| | H82 | 83 | L | E | L |
| | H82A | 84 | S | S | S |
| | H82B | 85 | G | G | N |
| | H82C | 86 | L | L | L |
| | H83 | 87 | T | T | T |
| | H84 | 88 | S | S | S |
| | H85 | 89 | D | E | D |
| | H86 | 90 | D | D | D |
| | H87 | 91 | T | T | S |
| | H88 | 92 | A | A | A |
| | H89 | 93 | T | T | T |
| | H90 | 94 | Y | Y | Y |
| | H91 | 95 | F | F | F |
| | H92 | 96 | C | C | C |
| | H93 | 97 | S | S | S |
| | H94 | 98 | T | T | T |
| | H95 | 99 | L | L | L |
| | H96 | 100 | T | T | T |
| | H97 | 101 | G | G | G |
| CDR-H3 | H98 | 102 | L | L | L |
| | H99 | | - | - | - |
| | H100 | | - | - | - |
| | H101 | 103 | D | D | D |
| | H102 | 104 | Y | Y | Y |
| | H103 | 105 | W | W | W |
| | H104 | 106 | G | G | G |
| | H105 | 107 | Q | Q | Q |
| | H106 | 108 | G | G | G |
| | H107 | 109 | V | V | V |
| | H108 | 110 | M | M | M |
| | H109 | 111 | V | V | V |
| | H110 | 112 | T | T | T |
| | H111 | 113 | V | V | V |
| | H112 | 114 | S | S | S |
| | H113 | 115 | S | S | S |

Fig. 11-4-2

Group 4: L chain variable regions

| | Kabat No. | | 37-0311F | 93-0707E | 94-1311E |
|---|---|---|---|---|---|
| | L1 | 1 | D | D | D |
| | L2 | 2 | I | I | I |
| | L3 | 3 | Q | Q | Q |
| | L4 | 4 | M | M | M |
| | L5 | 5 | T | T | T |
| | L6 | 6 | Q | Q | Q |
| | L7 | 7 | S | S | S |
| | L8 | 8 | P | P | P |
| | L9 | 9 | P | P | P |
| | L10 | 10 | V | V | V |
| | L11 | 11 | L | L | L |
| | L12 | 12 | S | S | S |
| | L13 | 13 | T | T | A |
| | L14 | 14 | S | S | S |
| | L15 | 15 | V | V | V |
| | L16 | 16 | G | G | G |
| | L17 | 17 | D | D | D |
| | L18 | 18 | R | R | R |
| | L19 | 19 | V | V | V |
| | L20 | 20 | T | T | T |
| | L21 | 21 | L | L | L |
| | L22 | 22 | R | R | S |
| | L23 | 23 | C | C | C |
| CDR-L1 | L24 | 24 | K | K | K |
| | L25 | 25 | P | A | A |
| | L26 | 26 | S | S | S |
| | L27 | 27 | Q | Q | Q |
| | L28 | 28 | N | N | S |
| | L29 | 29 | V | V | V |
| | L30 | 30 | H | H | H |
| | L31 | 31 | S | S | N |
| | L32 | 32 | K | K | K |
| | L33 | 33 | L | L | L |
| | L34 | 34 | D | D | D |
| | L35 | 35 | W | W | W |
| | L36 | 36 | Y | Y | Y |
| | L37 | 37 | Q | Q | Q |
| | L38 | 38 | Q | Q | Q |
| | L39 | 39 | K | K | K |
| | L40 | 40 | H | H | H |
| | L41 | 41 | G | G | G |
| | L42 | 42 | E | E | E |
| | L43 | 43 | A | A | A |
| | L44 | 44 | P | P | P |
| | L45 | 45 | K | K | K |
| | L46 | 46 | L | L | L |
| | L47 | 47 | L | L | L |
| | L48 | 48 | I | I | I |
| | L49 | 49 | Y | Y | Y |
| CDR-L2 | L50 | 50 | Y | Y | Y |
| | L51 | 51 | T | T | T |
| | L52 | 52 | H | H | H |
| | L53 | 53 | N | N | N |
| | L54 | 54 | L | L | L |
| | L55 | 55 | Q | Q | Q |
| | L56 | 56 | T | T | T |

| | Kabat No. | | 37-0311F | 93-0707E | 94-1311E |
|---|---|---|---|---|---|
| | L57 | 57 | G | G | G |
| | L58 | 58 | I | I | I |
| | L59 | 59 | P | P | P |
| | L60 | 60 | S | S | S |
| | L61 | 61 | R | R | R |
| | L62 | 62 | F | F | F |
| | L63 | 63 | S | S | S |
| | L64 | 64 | G | G | G |
| | L65 | 65 | S | S | S |
| | L66 | 66 | G | G | G |
| | L67 | 67 | S | S | S |
| | L68 | 68 | G | G | G |
| | L69 | 69 | T | T | S |
| | L70 | 70 | D | D | D |
| | L71 | 71 | Y | Y | Y |
| | L72 | 72 | T | T | T |
| | L73 | 73 | L | L | L |
| | L74 | 74 | T | T | T |
| | L75 | 75 | I | I | I |
| | L76 | 76 | S | S | S |
| | L77 | 77 | S | S | S |
| | L78 | 78 | L | L | L |
| | L79 | 79 | Q | Q | R |
| | L80 | 80 | P | P | A |
| | L81 | 81 | E | E | E |
| | L82 | 82 | D | D | D |
| | L83 | 83 | V | V | V |
| | L84 | 84 | A | A | A |
| | L85 | 85 | T | T | T |
| | L86 | 86 | Y | Y | Y |
| | L87 | 87 | Y | Y | Y |
| | L88 | 88 | C | C | C |
| CDR-L3 | L89 | 89 | F | F | F |
| | L90 | 90 | Q | Q | Q |
| | L91 | 91 | Y | Y | Y |
| | L92 | 92 | Y | Y | Y |
| | L93 | 93 | S | S | S |
| | L94 | 94 | G | G | G |
| | L95 | 95 | W | W | W |
| | L96 | 96 | T | T | T |
| | L97 | 97 | F | F | F |
| | L98 | 98 | G | G | G |
| | L99 | 99 | G | G | G |
| | L100 | 100 | G | G | G |
| | L101 | 101 | T | T | T |
| | L102 | 102 | K | K | K |
| | L103 | 103 | L | L | L |
| | L104 | 104 | E | E | E |
| | L105 | 105 | M | M | M |
| | L106 | 106 | K | K | K |
| | L107 | 107 | R | R | R |

Fig. 11-5-1

Others than Groups 1 to 4: H chain variable regions

|  | Kabat No. | 33-0803E | | 65-0810G | | 83-1110B | |
|---|---|---|---|---|---|---|---|
|  | H1 | 1 | E | 1 | E | 1 | E |
|  | H2 | 2 | V | 2 | V | 2 | V |
|  | H3 | 3 | Q | 3 | H | 3 | Q |
|  | H4 | 4 | L | 4 | L | 4 | L |
|  | H5 | 5 | V | 5 | V | 5 | Q |
|  | H6 | 6 | E | 6 | E | 6 | Q |
|  | H7 | 7 | S | 7 | S | 7 | S |
|  | H8 | 8 | G | 8 | G | 8 | G |
|  | H9 | 9 | G | 9 | G | 9 | P |
|  | H10 | 10 | G | 10 | G | 10 | E |
|  | H11 | 11 | L | 11 | L | 11 | F |
|  | H12 | 12 | V | 12 | V | 12 | V |
|  | H13 | 13 | R | 13 | Q | 13 | R |
|  | H14 | 14 | P | 14 | P | 14 | P |
|  | H15 | 15 | G | 15 | G | 15 | G |
|  | H16 | 16 | G | 16 | R | 16 | T |
|  | H17 | 17 | S | 17 | S | 17 | S |
|  | H18 | 18 | M | 18 | M | 18 | V |
|  | H19 | 19 | K | 19 | K | 19 | K |
|  | H20 | 20 | L | 20 | L | 20 | F |
|  | H21 | 21 | S | 21 | S | 21 | S |
|  | H22 | 22 | C | 22 | C | 22 | C |
|  | H23 | 23 | G | 23 | T | 23 | K |
|  | H24 | 24 | A | 24 | A | 24 | V |
|  | H25 | 25 | S | 25 | S | 25 | S |
|  | H26 | 26 | G | 26 | G | 26 | G |
|  | H27 | 27 | F | 27 | F | 27 | G |
|  | H28 | 28 | I | 28 | T | 28 | S |
|  | H29 | 29 | F | 29 | F | 29 | I |
|  | H30 | 30 | D | 30 | N | 30 | T |
| CDR-H1 | H31 | 31 | N | 31 | N | 31 | S |
|  | H32 | 32 | Y | 32 | Y | 32 | Y |
|  | H33 | 33 | Y | 33 | Y | 33 | F |
|  | H34 | 34 | M | 34 | M | 34 | I |
|  | H35 | 35 | T | 35 | A | 35 | H |
|  | H36 | 36 | W | 36 | W | 36 | F |
|  | H37 | 37 | V | 37 | V | 37 | V |
|  | H38 | 38 | R | 38 | R | 38 | K |
|  | H39 | 39 | Q | 39 | Q | 39 | Q |
|  | H40 | 40 | A | 40 | A | 40 | R |
|  | H41 | 41 | P | 41 | P | 41 | P |
|  | H42 | 42 | T | 42 | T | 42 | P |
|  | H43 | 43 | K | 43 | K | 43 | Q |
|  | H44 | 44 | G | 44 | G | 44 | G |
|  | H45 | 45 | L | 45 | L | 45 | L |
|  | H46 | 46 | E | 46 | E | 46 | E |
|  | H47 | 47 | W | 47 | W | 47 | W |
|  | H48 | 48 | V | 48 | V | 48 | I |
|  | H49 | 49 | A | 49 | A | 49 | G |
| CDR-H2 | H50 | 50 | S | 50 | S | 50 | K |
|  | H51 | 51 | I | 51 | I | 51 | I |
|  | H52 | 52 | S | 52 | S | 52 | D |
|  | H52A | 53 | S | 53 | T | 53 | P |
|  | H53 | 54 | S | 54 | G | 54 | E |
|  | H54 | 55 | G | 55 | G | 55 | D |
|  | H55 | 56 | G | 56 | G | 56 | D |
|  | H56 | 57 | N | 57 | Y | 57 | S |
|  | H57 | 58 | T | 58 | T | 58 | T |
|  | H58 | 59 | Y | 59 | Y | 59 | K |
|  | H59 | 60 | Y | 60 | Y | 60 | Y |

|  | Kabat No. | 33-0803E | | 65-0810G | | 83-1110B | |
|---|---|---|---|---|---|---|---|
|  | H60 | 61 | R | 61 | R | 61 | G |
|  | H61 | 62 | D | 62 | D | 62 | E |
| CDR-H2 | H62 | 63 | S | 63 | S | 63 | K |
|  | H63 | 64 | V | 64 | V | 64 | F |
|  | H64 | 65 | R | 65 | K | 65 | K |
|  | H65 | 66 | G | 66 | G | 66 | N |
|  | H66 | 67 | R | 67 | R | 67 | K |
|  | H67 | 68 | F | 68 | F | 68 | A |
|  | H68 | 69 | T | 69 | T | 69 | T |
|  | H69 | 70 | I | 70 | I | 70 | L |
|  | H70 | 71 | S | 71 | S | 71 | T |
|  | H71 | 72 | R | 72 | R | 72 | A |
|  | H72 | 73 | D | 73 | D | 73 | D |
|  | H73 | 74 | N | 74 | N | 74 | T |
|  | H74 | 75 | A | 75 | T | 75 | S |
|  | H75 | 76 | G | 76 | G | 76 | S |
|  | H76 | 77 | N | 77 | N | 77 | N |
|  | H77 | 78 | T | 78 | T | 78 | T |
|  | H78 | 79 | L | 79 | L | 79 | A |
|  | H79 | 80 | S | 80 | Y | 80 | F |
|  | H80 | 81 | L | 81 | L | 81 | L |
|  | H81 | 82 | Q | 82 | Q | 82 | K |
|  | H82 | 83 | M | 83 | M | 83 | L |
|  | H82A | 84 | G | 84 | D | 84 | S |
|  | H82B | 85 | S | 85 | S | 85 | S |
|  | H82C | 86 | L | 86 | L | 86 | L |
|  | H83 | 87 | R | 87 | R | 87 | T |
|  | H84 | 88 | A | 88 | S | 88 | S |
|  | H85 | 89 | E | 89 | E | 89 | E |
|  | H86 | 90 | D | 90 | D | 90 | D |
|  | H87 | 91 | T | 91 | T | 91 | T |
|  | H88 | 92 | A | 92 | A | 92 | A |
|  | H89 | 93 | T | 93 | T | 93 | I |
|  | H90 | 94 | Y | 94 | Y | 94 | Y |
|  | H91 | 95 | Y | 95 | Y | 95 | F |
|  | H92 | 96 | C | 96 | C | 96 | C |
|  | H93 | 97 | A | 97 | A | 97 | T |
|  | H94 | 98 | R | 98 | R | 98 | T |
|  | H95 | 99 | E | 99 | C | 99 | L |
|  | H96 | 100 | G | 100 | W | 100 | T |
|  | H97 | 101 | Y | 101 | E | 101 | G |
|  | H98 | 102 | R | 102 | L | 102 | L |
| CDR-H3 | H99 | 103 | G | | - | | - |
|  | H100 | 104 | R | | - | | - |
|  | H100A | 105 | Y | | | | |
|  | H100B | 106 | F | | | | |
|  | H101 | 107 | D | 103 | P | 103 | D |
|  | H102 | 108 | Y | 104 | Y | 104 | Y |
|  | H103 | 109 | W | 105 | W | 105 | W |
|  | H104 | 110 | G | 106 | G | 106 | G |
|  | H105 | 111 | Q | 107 | Q | 107 | Q |
|  | H106 | 112 | G | 108 | G | 108 | G |
|  | H107 | 113 | V | 109 | V | 109 | V |
|  | H108 | 114 | M | 110 | M | 110 | M |
|  | H109 | 115 | V | 111 | V | 111 | V |
|  | H110 | 116 | T | 112 | T | 112 | T |
|  | H111 | 117 | V | 113 | V | 113 | V |
|  | H112 | 118 | S | 114 | S | 114 | S |
|  | H113 | 119 | S | 115 | S | 115 | S |

Fig. 11-5-2

Others than Groups 1 to 4: L chain variable regions

|  | Kabat No. |  | 33-0903E |  | 65-0810G |  | 83-1119B |
|---|---|---|---|---|---|---|---|
|  | L1 | 1 | Q | 1 | Q | 1 | D |
|  | L2 | 2 | V | 2 | P | 2 | I |
|  | L3 | 3 | V | 3 | V | 3 | Q |
|  | L4 | 4 | L | 4 | L | 4 | M |
|  | L5 | 5 | T | 5 | T | 5 | T |
|  | L6 | 6 | Q | 6 | Q | 6 | Q |
|  | L7 | 7 | P | 7 | P | 7 | S |
|  | L8 | 8 | N | 8 | N | 8 | P |
|  | L9 | 9 | S | 9 | S | 9 | S |
|  | L10 |  |  |  |  | 10 | V |
|  | L11 | 10 | V | 10 | V | 11 | L |
|  | L12 | 11 | S | 11 | S | 12 | S |
|  | L13 | 12 | T | 12 | T | 13 | A |
|  | L14 | 13 | N | 13 | N | 14 | A |
|  | L15 | 14 | L | 14 | L | 15 | V |
|  | L16 | 15 | G | 15 | G | 16 | G |
|  | L17 | 16 | S | 16 | S | 17 | D |
|  | L18 | 17 | T | 17 | T | 18 | R |
|  | L19 | 18 | V | 18 | V | 19 | V |
|  | L20 | 19 | K | 19 | K | 20 | T |
|  | L21 | 20 | L | 20 | L | 21 | L |
|  | L22 | 21 | S | 21 | S | 22 | S |
|  | L23 | 22 | C | 22 | C | 23 | C |
| CDR-L1 | L24 | 23 | K | 23 | R | 24 | K |
|  | L25 | 24 | R | 24 | R | 25 | A |
|  | L26 | 25 | T | 25 | S | 26 | S |
|  | L27 | 26 | T | 26 | S | 27 | R |
|  | L27A | 27 | G | 27 | G |  |  |
|  | L27B | 28 | N | 28 | N |  |  |
|  | L28 | 29 | I | 29 | I | 28 | S |
|  | L29 | 30 | G | 30 | G | 29 | L |
|  | L30 | 31 | S | 31 | N | 30 | N |
|  | L31 | 32 | N | 32 | N | 31 | K |
|  | L32 | 33 | Y | 33 | Y | 32 | N |
|  | L33 | 34 | V | 34 | V | 33 | L |
|  | L34 | 35 | N | 35 | N | 34 | D |
|  | L35 | 36 | W | 36 | W | 35 | W |
|  | L36 | 37 | Y | 37 | Y | 36 | Y |
|  | L37 | 38 | Q | 38 | R | 37 | Q |
|  | L38 | 39 | Q | 39 | Q | 38 | Q |
|  | L39 | 40 | H | 40 | H | 39 | R |
|  | L40 | 41 | E | 41 | E | 40 | H |
|  | L41 | 42 | G | 42 | G | 41 | G |
|  | L42 | 43 | R | 43 | R | 42 | E |
|  | L43 | 44 | S | 44 | S | 43 | T |
|  | L44 | 45 | P | 45 | P | 44 | P |
|  | L45 | 46 | T | 46 | T | 45 | K |
|  | L46 | 47 | T | 47 | T | 46 | L |
|  | L47 | 48 | M | 48 | M | 47 | L |
|  | L48 | 49 | I | 49 | I | 48 | I |
|  | L49 | 50 | Y | 50 | Y | 49 | Y |
| CDR-L2 | L50 | 51 | R | 51 | R | 50 | R |
|  | L51 | 52 | D | 52 | D | 51 | T |
|  | L52 | 53 | D | 53 | D | 52 | H |
|  | L53 | 54 | E | 54 | T | 53 | N |
|  | L54 | 55 | R | 55 | R | 54 | L |
|  | L55 | 56 | P | 56 | P | 55 | Q |
|  | L56 | 57 | D | 57 | D | 56 | T |

|  | Kabat No. |  | 33-0903E |  | 65-0810G |  | 83-1119B |
|---|---|---|---|---|---|---|---|
|  | L57 | 58 | G | 58 | G | 57 | G |
|  | L58 | 59 | V | 59 | V | 58 | I |
|  | L59 | 60 | P | 60 | P | 59 | P |
|  | L60 | 61 | D | 61 | N | 60 | S |
|  | L61 | 62 | R | 62 | R | 61 | R |
|  | L62 | 63 | F | 63 | F | 62 | F |
|  | L63 | 64 | S | 64 | S | 63 | S |
|  | L64 | 65 | G | 65 | G | 64 | G |
|  | L65 | 66 | S | 66 | S | 65 | S |
|  | L66 | 67 | I | 67 | I | 66 | G |
|  | L66A | 68 | D | 68 | D |  |  |
|  | L66B | 69 | B | 69 | R |  |  |
|  | L67 | 70 | S | 70 | S | 67 | S |
|  | L68 | 71 | S | 71 | S | 68 | D |
|  | L69 | 72 | N | 72 | N | 69 | T |
|  | L70 | 73 | S | 73 | S | 70 | D |
|  | L71 | 74 | A | 74 | A | 71 | Y |
|  | L72 | 75 | L | 75 | L | 72 | T |
|  | L73 | 76 | L | 76 | L | 73 | L |
|  | L74 | 77 | T | 77 | T | 74 | T |
|  | L75 | 78 | I | 78 | I | 75 | I |
|  | L76 | 79 | N | 79 | N | 76 | S |
|  | L77 | 80 | N | 80 | N | 77 | S |
|  | L78 | 81 | V | 81 | V | 78 | L |
|  | L79 | 82 | Q | 82 | R | 79 | Q |
|  | L80 | 83 | T | 83 | P | 80 | T |
|  | L81 | 84 | E | 84 | E | 81 | E |
|  | L82 | 85 | D | 85 | D | 82 | D |
|  | L83 | 86 | E | 86 | E | 83 | V |
|  | L84 | 87 | A | 87 | A | 84 | A |
|  | L85 | 88 | E | 88 | Y | 85 | T |
|  | L86 | 89 | Y | 89 | Y | 86 | Y |
|  | L87 | 90 | F | 90 | F | 87 | Y |
|  | L88 | 91 | C | 91 | C | 88 | C |
| CDR-L3 | L89 | 92 | Q | 92 | Q | 89 | Y |
|  | L90 | 93 | S | 93 | S | 90 | Q |
|  | L91 | 94 | Y | 94 | Y | 91 | Y |
|  | L92 | 95 | S | 95 | S | 92 | H |
|  | L93 | 96 | S | 96 | G | 93 | S |
|  | L94 | 97 | S | 97 | S | 94 | G |
|  | L95 | 98 | I | 98 | I | 95 | W |
|  | L96 | 99 | - | 99 | Y | 96 | T |
|  | L97 | 100 | L | 100 | L | 97 | F |
|  | L98 | 101 | F | 101 | F | 98 | G |
|  | L99 | 102 | G | 102 | G | 99 | G |
|  | L100 | 103 | G | 103 | G | 100 | G |
|  | L101 | 104 | G | 104 | G | 101 | T |
|  | L102 | 105 | T | 105 | T | 102 | R |
|  | L103 | 106 | K | 106 | K | 103 | L |
|  | L104 | 107 | L | 107 | L | 104 | E |
|  | L105 | 108 | T | 108 | T | 105 | L |
|  | L106 | 109 | V | 109 | V | 106 | R |
|  | L106A | 110 | L | 110 | L |  | - |
|  | L107 |  |  |  |  | 107 | K |

SEQUENCE LISTING

<160> NUMBER OF SEQ ID NOS: 348

<210> SEQ ID NO 1
<211> LENGTH: 549
<212> TYPE: PRT
<213> ORGANISM: Homo sapiens

<400> SEQUENCE: 1

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Ala
            35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
    115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

```
Ala Asp Gln Leu Gly Asp Gln Leu Lys Ala Arg Thr Ser Trp Leu Arg
    290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
        355                 360                 365
Ile Thr Cys Phe Thr Gly Phe Leu Gly Val Val Thr Gly Ala Gly Ala
    370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
            420                 425                 430
Glu Thr Leu Leu Phe Ser Asn Trp Ala Ile Thr Ala Asp Ile Leu Met
        435                 440                 445
Tyr Val Val Ile Pro Thr Arg Arg Ala Thr Val Ala Leu Gln Ser
    450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
            500                 505                 510
Val Leu Gly Gly Met Phe Phe Leu Ala Thr Ala Leu Phe Phe Val Ser
        515                 520                 525
Asp Arg Ala Arg Ala Glu Gln Gln Val Asn Gln Leu Ala Met Pro Pro
    530                 535                 540
Ala Ser Val Lys Val
545

<210> SEQ ID NO 2
<211> LENGTH: 1650
<212> TYPE: DNA
<213> ORGANISM: Homo sapiens

<400> SEQUENCE: 2
atgatgtgcc tggaatgcgc ctcggcggcg gcgggcggcg cggaggagga ggaggcggac    60
gcggagcggc ggcgccggcg ccggggggcg cagcgagggg ctgcggtag cggttgctgc   120 ggggcgcggg gcgcgggcgg cgctggagtc tcggccgcgg gcgatgaggt gcagacgctg   180
tcgggcagcg taaggcgggc cccgaccgga cccccggca cccccggcac cccggctgc    240 gcagctactg caaagggccc cggcgctcag cagcccaaac cggccagctt gggccgcggg   300
cggggggcag ccgccgccat cctcagcttg gcaacgtgc tcaactacct ggacaggtac   360
accgtggcag gcgtccttct ggacatccag cagcactttg ggtcaagga ccgaggcgcc   420 ggcctgctgc agtcagtgtt catctgtagc ttcatggtgg ctgcccccat cttcggctac   480
ctgggcgacc gcttcaacag gaaggtgatt ctcagctgcg cattttctt ctggtcggcc   540 gtcaccttct ccagctcctt cattccccag cagtacttct ggctgctggt cctgtcccgg   600
```

| | |
|---|---|
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca cagcccgccc tgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 3
<211> LENGTH: 13
<212> TYPE: PRT
<213> ORGANISM: Homo sapiens

<400> SEQUENCE: 3

Leu Asp Ile Gln Gln His Phe Gly Val Lys Asp Arg Gly
1               5                   10

<210> SEQ ID NO 4
<211> LENGTH: 14
<212> TYPE: PRT
<213> ORGANISM: Homo sapiens

<400> SEQUENCE: 4

Pro Gln Gln Tyr Phe Trp Leu Leu Val Leu Ser Arg Gly Leu
1               5                   10

<210> SEQ ID NO 5
<211> LENGTH: 9
<212> TYPE: PRT
<213> ORGANISM: Homo sapiens

<400> SEQUENCE: 5

Val Lys Gln Ala Ala Gly Asp Trp His
1               5

<210> SEQ ID NO 6
<211> LENGTH: 26
<212> TYPE: PRT
<213> ORGANISM: Homo sapiens

<400> SEQUENCE: 6

Pro Leu Tyr Leu His Arg Ala Gln Val Val Gln Lys Thr Ala Glu Thr
1               5                   10                  15

Cys Asn Ser Pro Pro Cys Gly Ala Lys Asp
            20                  25

<210> SEQ ID NO 7
<211> LENGTH: 4
<212> TYPE: PRT
<213> ORGANISM: Homo sapiens

<400> SEQUENCE: 7

Ala Lys Ser Ser
1

<210> SEQ ID NO 8
<211> LENGTH: 19
<212> TYPE: PRT
<213> ORGANISM: Homo sapiens

<400> SEQUENCE: 8

Arg Gln Ser Thr Lys Asp Ser Pro Leu Trp Glu Phe Leu Ser Leu Gly
1               5                   10                  15

Tyr Ala Leu

<210> SEQ ID NO 9
<211> LENGTH: 26
<212> TYPE: DNA
<213> ORGANISM: Artificial Sequence
<220> FEATURE:
<223> OTHER INFORMATION: Homo sapiens

<400> SEQUENCE: 9
aagcttatga tgtgcctgga atgcgc                                        26

<210> SEQ ID NO 10
<211> LENGTH: 28
<212> TYPE: DNA
<213> ORGANISM: Artificial Sequence
<220> FEATURE:
<223> OTHER INFORMATION: Homo sapiens

<400> SEQUENCE: 10
gcggccgctc agactttcac agatgcgg                                      28

<210> SEQ ID NO 11
<211> LENGTH: 26
<212> TYPE: DNA
<213> ORGANISM: Artificial Sequence
<220> FEATURE:
<223> OTHER INFORMATION: Homo sapiens

<400> SEQUENCE: 11
gaattcatgt ccgctcaagt tctggg                                        26

<210> SEQ ID NO 12
<211> LENGTH: 29
<212> TYPE: DNA
<213> ORGANISM: Artificial Sequence
<220> FEATURE:
<223> OTHER INFORMATION: Homo Sapiens

<400> SEQUENCE: 12
gcggccgctc ataagggctc ttctggcgg                                     29

<210> SEQ ID NO 13
<211> LENGTH: 470

```
<212> TYPE: PRT
<213> ORGANISM: Homo sapiens

<400> SEQUENCE: 13

Met Ser Ala Gln Val Leu Gly Phe Leu Arg Ser Trp Thr Pro Leu Pro
1               5                   10                  15

Leu Ala Ala Pro Arg Gly Pro Ala Ala Gly Asn Asp Ala Gly Ala
            20                  25                  30

Pro Thr Ala Thr Ala Pro Gly Gly Glu Gly Glu Pro His Ser Arg Pro
            35                  40                  45

Cys Asp Ala Arg Leu Gly Ser Thr Asp Lys Glu Leu Lys Ala Gly Ala
        50                  55                  60

Ala Ala Thr Gly Ser Ala Pro Thr Ala Pro Gly Thr Pro Trp Gln Arg
65                  70                  75                  80

Glu Pro Arg Val Glu Val Met Asp Pro Ala Gly Gly Pro Arg Gly Val
                85                  90                  95

Leu Pro Arg Pro Cys Arg Val Leu Val Leu Leu Asn Pro Arg Gly Gly
            100                 105                 110

Lys Gly Lys Ala Leu Gln Leu Phe Arg Ser His Val Gln Pro Leu Leu
        115                 120                 125

Ala Glu Ala Glu Ile Ser Phe Thr Leu Met Leu Thr Glu Arg Arg Asn
130                 135                 140

His Ala Arg Glu Leu Val Arg Ser Glu Glu Leu Gly Arg Trp Asp Ala
145                 150                 155                 160

Leu Val Val Met Ser Gly Asp Gly Leu Met His Glu Val Val Asn Gly
                165                 170                 175

Leu Met Glu Arg Pro Asp Trp Glu Thr Ala Ile Gln Lys Pro Leu Cys
            180                 185                 190

Ser Leu Pro Ala Gly Ser Gly Asn Ala Leu Ala Ala Ser Leu Asn His
        195                 200                 205

Tyr Ala Gly Tyr Glu Gln Val Thr Asn Glu Asp Leu Leu Thr Asn Cys
210                 215                 220

Thr Leu Leu Leu Cys Arg Arg Leu Leu Ser Pro Met Asn Leu Leu Ser
225                 230                 235                 240

Leu His Thr Ala Ser Gly Leu Arg Leu Phe Ser Val Leu Ser Leu Ala
                245                 250                 255

Trp Gly Phe Ile Ala Asp Val Asp Leu Glu Ser Glu Lys Tyr Arg Arg
            260                 265                 270

Leu Gly Glu Met Arg Phe Thr Leu Gly Thr Phe Leu Arg Leu Ala Ala
        275                 280                 285

Leu Arg Thr Tyr Arg Gly Arg Leu Ala Tyr Leu Pro Val Gly Arg Val
290                 295                 300

Gly Ser Lys Thr Pro Ala Ser Pro Val Val Gln Gln Gly Pro Val
305                 310                 315                 320

Asp Ala His Leu Val Pro Leu Glu Glu Pro Val Pro Ser His Trp Thr
                325                 330                 335

Val Val Pro Asp Glu Asp Phe Val Leu Val Leu Ala Leu Leu His Ser
            340                 345                 350

His Leu Gly Ser Glu Met Phe Ala Ala Pro Met Gly Arg Cys Ala Ala
        355                 360                 365

Gly Val Met His Leu Phe Tyr Val Arg Ala Gly Val Ser Arg Ala Met
370                 375                 380

Leu Leu Arg Leu Phe Leu Ala Met Glu Lys Gly Arg His Met Glu Tyr
385                 390                 395                 400
```

Glu Cys Pro Tyr Leu Val Tyr Val Pro Val Val Ala Phe Arg Leu Glu
            405                 410                 415

Pro Lys Asp Gly Lys Gly Val Phe Ala Val Asp Gly Glu Leu Met Val
        420                 425                 430

Ser Glu Ala Val Gln Gly Val His Pro Asn Tyr Phe Trp Met Val
        435                 440                 445

Ser Gly Cys Val Glu Pro Pro Ser Trp Lys Pro Gln Gln Met Pro
    450                 455                 460

Pro Pro Glu Glu Pro Leu
465             470

<210> SEQ ID NO 14
<211> LENGTH: 1413
<212> TYPE: DNA
<213> ORGANISM: Homo sapiens

<400> SEQUENCE: 14

| | | | | | |
|---|---|---|---|---|---|
| atgtccgctc | aagttctggg | atttttacgc | agctggactc | ccctcccct | ggcagccccg | 60 |
| aggggtccag | ccgccgcagg | gaatgacgcc | ggtgctccta | cagccacggc | tccgggcggg | 120 |
| gaaggcgagc | cccacagccg | gccctgcgac | gcccgcctgg | gcagcaccga | taaggagctg | 180 |
| aaggcaggag | ccgccgccac | gggcagcgcc | cccacagcgc | cagggacccc | ctggcagcgg | 240 |
| gagccgcggg | tcgaggttat | ggatccagcg | gcgccccc | ggggcgtgct | cccgcggcc | 300 |
| tgccgcgtgc | tggtgctgct | gaacccgcgc | ggcggcaagg | gcaaggcctt | gcagctcttc | 360 |
| cggagtcacg | tgcagcccct | tttggctgag | gctgaaatct | ccttcacgct | gatgctcact | 420 |
| gagcggcgga | accacgcgcg | ggagctggtg | cggtcggagg | agctgggccg | ctgggacgct | 480 |
| ctggtggtca | tgtctggaga | cgggctgatg | cacgaggtgg | tgaacgggct | catggagcgg | 540 |
| cctgactggg | agaccgccat | ccagaagccc | ctgtgtagcc | tcccagcagg | ctctggcaac | 600 |
| gcgctggcag | cttccttgaa | ccattatgct | ggctatgagc | aggtcaccaa | tgaagacctc | 660 |
| ctgaccaact | gcacgctatt | gctgtgccgc | cggctgctgt | cacccatgaa | cctgctgtct | 720 |
| ctgcacacgg | cttcggggct | gcgcctcttc | tctgtgctca | gctggcctg | gggcttcatt | 780 |
| gctgatgtgg | acctagagag | tgagaagtat | cggcgtctgg | gggagatgcg | cttcactctg | 840 |
| ggcaccttcc | tgcgtctggc | agccctgcgc | acctaccgcg | gccgactggc | ctacctccct | 900 |
| gtaggaagag | tgggttccaa | gacacctgcc | tccccgttg | tggtccagca | gggcccggta | 960 |
| gatgcacacc | ttgtgccact | ggaggagcca | gtgccctctc | actggacagt | ggtgcccgac | 1020 |
| gaggactttg | tgctagtcct | ggcactgctg | cactcgcacc | tgggcagtga | gatgtttgct | 1080 |
| gcacccatgg | gccgctgtgc | agctggcgtc | atgcatctgt | tctacgtgcg | ggcgggagtg | 1140 |
| tctcgtgcca | tgctgctgcg | cctcttcctg | gccatggaga | agggcaggca | tatggagtat | 1200 |
| gaatgcccct | acttggtata | tgtgcccgtg | gtcgccttcc | gcttggagcc | caaggatggg | 1260 |
| aaaggtgtgt | ttgcagtgga | tggggaattg | atggttagcg | aggccgtgca | gggccaggtg | 1320 |
| cacccaaaact | acttctggat | ggtcagcggt | tgcgtggagc | cccgcccag | ctggaagccc | 1380 |
| cagcagatgc | caccgccaga | agagcccta | tga | | | 1413 |

<210> SEQ ID NO 15
<211> LENGTH: 37
<212> TYPE: DNA
<213> ORGANISM: Artificial Sequence
<220> FEATURE:
<223> OTHER INFORMATION: Homo sapiens -continued

<400> SEQUENCE: 15
ggggaattcc caccatggca actgccctcc cgccgcg                                37

<210> SEQ ID NO 16
<211> LENGTH: 35
<212> TYPE: DNA
<213> ORGANISM: Artificial Sequence
<220> FEATURE:
<223> OTHER INFORMATION: Homo Sapiens

<400> SEQUENCE: 16
aaagcggccg ctcagttgca gaagatccca ttctg                                  35

<210> SEQ ID NO 17
<211> LENGTH: 378
<212> TYPE: PRT
<213> ORGANISM: Homo sapiens

<400> SEQUENCE: 17

```
Met Ala Thr Ala Leu Pro Pro Arg Leu Gln Pro Val Arg Gly Asn Glu
1               5                   10                  15

Thr Leu Arg Glu His Tyr Gln Tyr Val Gly Lys Leu Ala Gly Arg Leu
            20                  25                  30

Lys Glu Ala Ser Glu Gly Ser Thr Leu Thr Thr Val Leu Phe Leu Val
        35                  40                  45

Ile Cys Ser Phe Ile Val Leu Glu Asn Leu Met Val Leu Ile Ala Ile
    50                  55                  60

Trp Lys Asn Asn Lys Phe His Asn Arg Met Tyr Phe Phe Ile Gly Asn
65                  70                  75                  80

Leu Ala Leu Cys Asp Leu Leu Ala Gly Ile Ala Tyr Lys Val Asn Ile
                85                  90                  95

Leu Met Ser Gly Lys Lys Thr Phe Ser Leu Ser Pro Thr Val Trp Phe
            100                 105                 110

Leu Arg Glu Gly Ser Met Phe Val Ala Leu Gly Ala Ser Thr Cys Ser
        115                 120                 125

Leu Leu Ala Ile Ala Ile Glu Arg His Leu Thr Met Ile Lys Met Arg
    130                 135                 140

Pro Tyr Asp Ala Asn Lys Arg His Arg Val Phe Leu Leu Ile Gly Met
145                 150                 155                 160

Cys Trp Leu Ile Ala Phe Thr Leu Gly Ala Leu Pro Ile Leu Gly Trp
                165                 170                 175

Asn Cys Leu His Asn Leu Pro Asp Cys Ser Thr Ile Leu Pro Leu Tyr
            180                 185                 190

Ser Lys Lys Tyr Ile Ala Phe Cys Ile Ser Ile Phe Thr Ala Ile Leu
        195                 200                 205

Val Thr Ile Val Ile Leu Tyr Ala Arg Ile Tyr Phe Leu Val Lys Ser
    210                 215                 220

Ser Ser Arg Lys Val Ala Asn His Asn Asn Ser Glu Arg Ser Met Ala
225                 230                 235                 240

Leu Leu Arg Thr Val Val Ile Val Val Ser Val Phe Ile Ala Cys Trp
                245                 250                 255

Ser Pro Leu Phe Ile Leu Phe Leu Ile Asp Val Ala Cys Arg Val Gln
            260                 265                 270

Ala Cys Pro Ile Leu Phe Lys Ala Gln Trp Phe Ile Val Leu Ala Val
        275                 280                 285
```

-continued

Leu Asn Ser Ala Met Asn Pro Val Ile Tyr Thr Leu Ala Ser Lys Glu
        290                 295                 300

Met Arg Arg Ala Phe Phe Arg Leu Val Cys Asn Cys Leu Val Arg Gly
305                 310                 315                 320

Arg Gly Ala Arg Ala Ser Pro Ile Gln Pro Ala Leu Asp Pro Ser Arg
                325                 330                 335

Ser Lys Ser Ser Ser Asn Asn Ser Ser His Ser Pro Lys Val Lys
            340                 345                 350

Glu Asp Leu Pro His Thr Ala Pro Ser Ser Cys Ile Met Asp Lys Asn
                355                 360                 365

Ala Ala Leu Gln Asn Gly Ile Phe Cys Asn
        370                 375

<210> SEQ ID NO 18
<211> LENGTH: 1137
<212> TYPE: DNA
<213> ORGANISM: Homo sapiens

<400> SEQUENCE: 18
atggcaactg ccctcccgcc gcgtctccag ccggtgcggg ggaacgagac cctgcgggag      60
cattaccagt acgtggggaa gttggcgggc aggctgaagg aggcctccga ggcagcacg     120 ctcaccaccg tgctcttctt ggtcatctgc agcttcatcg tcttggagaa cctgatggtt     180
ttgattgcca tctggaaaaa caataaattt cacaaccgca tgtacttttt cattggcaac     240
ctggctctct gcgacctgct ggccggcatc gcttacaagg tcaacattct gatgtctggc     300
aagaagacgt tcagcctgtc tcccacggtc tggttcctca gggagggcag tatgttcgtg     360
gcccttgggg cgtccacctg cagcttactg ccatcgcca tcgagcggca cttgacaatg     420
atcaaaatga ggccttacga cgccaacaag aggcaccgcg tcttcctcct gatcgggatg     480
tgctggctca ttgccttcac gctgggcgcc ctgcccattc tgggctggaa ctgcctgcac     540
aatctccctg actgctctac catcctgccc ctctactcca agaagtacat tgccttctgc     600
atcagcatct tcacggccat cctggtgacc atcgtgatcc tctacgcacg catctacttc     660
ctggtgaagt ccagcagccg taaggtggcc aaccacaaca ctcggagcg tccatggca     720 ctgctgcgga ccgtggtgat tgtggtgagc gtgttcatcg cctgctggtc cccactcttc     780
atcctcttcc tcattgatgt ggcctgcagg gtgcaggcgt gccccatcct cttcaaggct     840
cagtggttca tcgtgttggc tgtgctcaac tccgccatga acccggtcat ctacacgctg     900
gccagcaagg agatgcggcg ggccttcttc cgtctggtct gcaactgcct ggtcagggga     960 cgggggccc gcgcctcacc catccagcct gcgctcgacc caagcagaag taaatcaagc    1020
agcagcaaca atagcagcca ctctccgaag gtcaaggaag acctgcccca cacagcccc    1080 tcatcctgca tcatggacaa gaacgcagca cttcagaatg ggatcttctg caactga        1137

<210> SEQ ID NO 19
<211> LENGTH: 549
<212> TYPE: PRT
<213> ORGANISM: Mus musculus

<400> SEQUENCE: 19

Met Met Cys Leu Glu Cys Ala Ser Ala Ala Ala Gly Gly Ala Glu Glu
1               5                   10                  15

Glu Glu Ala Asp Ala Glu Arg Arg Arg Arg Arg Gly Ala Gln Pro
            20                  25                  30

Gly Ala Gly Gly Ser Ala Cys Cys Gly Ala Arg Gly Val Gly Gly Ala

```
                35                  40                  45
Gly Val Val Ser Ala Asp Glu Val Gln Thr Leu Ser Gly Ser Val
 50                  55                  60

Arg Arg Val Pro Ser Gly Leu Pro Ser Ile Pro Ser Thr Pro Gly Cys
 65                  70                  75                  80

Ala Ala Ala Ala Lys Gly Pro Ser Ala Pro Gln Pro Lys Pro Ala Ser
                 85                  90                  95

Leu Gly Arg Gly Arg Gly Ala Ala Ala Ile Leu Ser Leu Gly Asn
             100                 105                 110

Val Leu Asn Tyr Leu Asp Arg Tyr Thr Val Ala Gly Val Leu Leu Asp
         115                 120                 125

Ile Gln Gln His Phe Gly Val Lys Asp Arg Gly Ala Gly Leu Leu Gln
 130                 135                 140

Ser Val Phe Ile Cys Ser Phe Met Val Ala Pro Ile Phe Gly Tyr
 145                 150                 155                 160

Leu Gly Asp Arg Phe Asn Arg Lys Val Ile Leu Ser Cys Gly Ile Phe
             165                 170                 175

Phe Trp Ser Ala Val Thr Phe Ser Ser Ser Phe Ile Pro Gln Gln Tyr
             180                 185                 190

Phe Trp Leu Leu Val Leu Ser Arg Gly Leu Val Gly Ile Gly Glu Ala
             195                 200                 205

Ser Tyr Ser Thr Ile Ala Pro Thr Ile Ile Gly Asp Leu Phe Thr Lys
 210                 215                 220

Asn Thr Arg Thr Leu Met Leu Ser Val Phe Tyr Phe Ala Ile Pro Leu
 225                 230                 235                 240

Gly Ser Gly Leu Gly Tyr Ile Thr Gly Ser Ser Val Lys Gln Ala Ala
             245                 250                 255

Gly Asp Trp His Trp Ala Leu Arg Val Ser Pro Val Leu Gly Met Ile
             260                 265                 270

Thr Gly Thr Leu Ile Leu Ile Leu Val Pro Ala Thr Lys Arg Gly His
             275                 280                 285

Ala Asp Gln Leu Gly Gly Gln Leu Lys Ala Arg Thr Ser Trp Leu Arg
 290                 295                 300

Asp Met Lys Ala Leu Ile Arg Asn Arg Ser Tyr Val Phe Ser Ser Leu
 305                 310                 315                 320

Ala Thr Ser Ala Val Ser Phe Ala Thr Gly Ala Leu Gly Met Trp Ile
             325                 330                 335

Pro Leu Tyr Leu His Arg Ala Gln Val Gln Lys Thr Ala Glu Thr
             340                 345                 350

Cys Asn Ser Pro Pro Cys Gly Ala Lys Asp Ser Leu Ile Phe Gly Ala
             355                 360                 365

Ile Thr Cys Phe Thr Gly Phe Leu Gly Val Val Thr Gly Ala Gly Ala
 370                 375                 380

Thr Arg Trp Cys Arg Leu Arg Thr Gln Arg Ala Asp Pro Leu Val Cys
 385                 390                 395                 400

Ala Val Gly Met Leu Gly Ser Ala Ile Phe Ile Cys Leu Ile Phe Val
             405                 410                 415

Ala Ala Lys Thr Ser Ile Val Gly Ala Tyr Ile Cys Ile Phe Val Gly
             420                 425                 430

Glu Thr Leu Leu Phe Ser Asn Trp Ala Ile Thr Ala Asp Ile Leu Met
             435                 440                 445

Tyr Val Val Ile Pro Thr Arg Arg Ala Thr Ala Val Ala Leu Gln Ser
 450                 455                 460
```

```
Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
        500                 505                 510

Val Leu Gly Gly Met Phe Phe Leu Ala Thr Ala Leu Phe Phe Leu Ser
        515                 520                 525

Asp Arg Ala Lys Ala Glu Gln Gln Val Asn Gln Leu Val Met Pro Pro
        530                 535                 540

Ala Ser Val Lys Val
545
```

<210> SEQ ID NO 20
<211> LENGTH: 1650
<212> TYPE: DNA
<213> ORGANISM: Mus musculus

<400> SEQUENCE: 20

| | | | | | |
|---|---|---|---|---|---|
| atgatgtgcc | tggaatgcgc | ctcggcggcg | gcgggcggcg | cggaggagga | ggaggcggac | 60 |
| gccgagcggc | ggcgccggcg | ccggggggcg | cagccagggg | ctggaggtag | cgcttgctgc | 120 |
| ggggcgcggg | gtgttggggg | cgctggagtc | gtgtccgccg | acgaagaggt | gcagacgttg | 180 |
| tccggcagcg | tgaggcgggt | cccgtccgga | ctccccagca | tccccagcac | ccctggctgc | 240 |
| gcagcagctg | ccaagggccc | cagcgcgccg | cagcccaaac | cggccagctt | aggccgaggg | 300 |
| cggggggcag | ctgctgccat | cctgagttta | ggcaacgtgc | tcaactacct | ggacaggtac | 360 |
| actgtggcag | tgttcttct  | ggacatccag | cagcactttg | gggtcaagga | ccggggcgcc | 420 |
| ggcttgctgc | agtcagtgtt | catctgcagc | ttcatggtgg | ctgccccat  | ctttggctac | 480 |
| ctgggcgacc | gcttcaatag | aaaggtgatc | ctcagctgtg | gcatcttctt | ctggtctgct | 540 |
| gtcaccttct | cgagttcttt | catccctcag | cagtacttct | ggctactagt | cctgtcccga | 600 |
| gggctagtag | gtattggtga | agccagctac | tccaccatag | cacccaccat | cattggcgac | 660 |
| ttgtttacca | agaacacacg | cacattgatg | ctatctgtct | tctattttgc | catccccctg | 720 |
| ggcagtggcc | tgggctatat | cacaggttcc | agcgtgaagc | aggcagctgg | agactggcat | 780 |
| tgggccctgc | gggtttcccc | cgtcctgggc | atgatcacag | gaacactcat | cctcatcttg | 840 |
| gtcccagcca | ctaagagagg | ccatgctgat | caacttgggg | ggcagctcaa | agcacggacc | 900 |
| tcctggcttc | gagacatgaa | ggccctgatc | cgaaaccgca | gttacgtctt | ctcctccctg | 960 |
| gccacatccg | ctgtgtcctt | cgccacaggg | gccctgggca | tgtggattcc | cctctatctt | 1020 |
| caccgtgctc | aagttgtaca | aaagacagca | gagacttgca | acagcccgcc | ctgtggagcc | 1080 |
| aaagacagcc | tcatctttgg | agccattacc | tgctttactg | gcttcctggg | cgtagtcacg | 1140 |
| ggcgcgggag | ccactcgttg | gtgccgcctg | cggactcaac | gtgctgaccc | attggtgtgt | 1200 |
| gctgtgggca | tgctgggatc | cgccatcttc | atctgcctca | tctttgtggc | tgccaagacc | 1260 |
| agcattgtag | cgcttatat  | ctgcatttt  | gttggagaga | cactgctgtt | ttctaactgg | 1320 |
| gccatcactg | cagacatcct | catgtatgtg | gtcatcccca | ctcggcgagc | cactgctgtg | 1380 |
| gccctgcaga | gcttcaccct | ccatctgctg | ggggacgctg | aagccccta  | cctcattggc | 1440 |
| tttatctcgg | acctaatccg | ccagagcacc | aaggactccc | cgctctggga | gttcctgagc | 1500 |
| ctgggctatg | ccctcatgct | gtgccctttt | gtcgtggtcc | tgggtggcat | gttcttcctt | 1560 |

```
gccactgctc tcttcttcct cagcgaccgt gccaaggctg agcagcaggt gaaccagctg    1620
gtgatgcctc ctgcatccgt gaaagtctga                                    1650
```

<210> SEQ ID NO 21
<211> LENGTH: 17
<212> TYPE: DNA
<213> ORGANISM: Artificial Sequence
<220> FEATURE:
<223> OTHER INFORMATION: M13

<400> SEQUENCE: 21

```
gtaaaacgac ggccagt                                                    17
```

<210> SEQ ID NO 22
<211> LENGTH: 8
<212> TYPE: PRT
<213> ORGANISM: Artificial Sequence
<220> FEATURE:
<223> OTHER INFORMATION: Flag tag

<400> SEQUENCE: 22

Asp Tyr Lys Asp Asp Asp Asp Lys
1               5

<210> SEQ ID NO 23
<211> LENGTH: 59
<212> TYPE: DNA
<213> ORGANISM: Artificial Sequence
<220> FEATURE:
<223> OTHER INFORMATION: Homo sapiens

<400> SEQUENCE: 23

```
aagcttgaat tcatggatta caaggatgac gacgataaga tgatgtgcct ggaatgcgc     59
```

<210> SEQ ID NO 24
<211> LENGTH: 29
<212> TYPE: DNA
<213> ORGANISM: Artificial Sequence
<220> FEATURE:
<223> OTHER INFORMATION: Homo sapiens

<400> SEQUENCE: 24

```
agcggccgct cagactttca cagatgcgg                                      29
```

<210> SEQ ID NO 25
<211> LENGTH: 32
<212> TYPE: DNA
<213> ORGANISM: Artificial Sequence
<220> FEATURE:
<223> OTHER INFORMATION: Homo Sapiens

<400> SEQUENCE: 25

```
aagcttgaat tcatgatgtg cctggaatgc gc                                  32
```

<210> SEQ ID NO 26
<211> LENGTH: 52
<212> TYPE: DNA
<213> ORGANISM: Artificial Sequence
<220> FEATURE:
<223> OTHER INFORMATION: Homo Sapiens

<400> SEQUENCE: 26

```
gcggccgctc acttatcgtc gtcatccttg taatcgactt tcacagatgc gg            52
```

<210> SEQ ID NO 27

<211> LENGTH: 558
<212> TYPE: PRT
<213> ORGANISM: Artificial Sequence
<220> FEATURE:
<223> OTHER INFORMATION: N' Flag

<400> SEQUENCE: 27

```
Met Asp Tyr Lys Asp Asp Asp Lys Met Met Cys Leu Glu Cys Ala
1               5                   10                  15

Ser Ala Ala Ala Gly Gly Ala Glu Glu Glu Ala Asp Ala Glu Arg
            20                  25                  30

Arg Arg Arg Arg Arg Gly Ala Gln Arg Gly Ala Gly Gly Ser Gly Cys
        35                  40                  45

Cys Gly Ala Arg Gly Ala Gly Gly Ala Gly Val Ser Ala Ala Gly Asp
    50                  55                  60

Glu Val Gln Thr Leu Ser Gly Ser Val Arg Arg Ala Pro Thr Gly Pro
65                  70                  75                  80

Pro Gly Thr Pro Gly Thr Pro Gly Cys Ala Ala Thr Ala Lys Gly Pro
                85                  90                  95

Gly Ala Gln Gln Pro Lys Pro Ala Ser Leu Gly Arg Gly Arg Gly Ala
                100                 105                 110

Ala Ala Ala Ile Leu Ser Leu Gly Asn Val Leu Asn Tyr Leu Asp Arg
            115                 120                 125

Tyr Thr Val Ala Gly Val Leu Leu Asp Ile Gln Gln His Phe Gly Val
            130                 135                 140

Lys Asp Arg Gly Ala Gly Leu Leu Gln Ser Val Phe Ile Cys Ser Phe
145                 150                 155                 160

Met Val Ala Ala Pro Ile Phe Gly Tyr Leu Gly Asp Arg Phe Asn Arg
                165                 170                 175

Lys Val Ile Leu Ser Cys Gly Ile Phe Phe Trp Ser Ala Val Thr Phe
                180                 185                 190

Ser Ser Ser Phe Ile Pro Gln Gln Tyr Phe Trp Leu Leu Val Leu Ser
            195                 200                 205

Arg Gly Leu Val Gly Ile Gly Glu Ala Ser Tyr Ser Thr Ile Ala Pro
        210                 215                 220

Thr Ile Ile Gly Asp Leu Phe Thr Lys Asn Thr Arg Thr Leu Met Leu
225                 230                 235                 240

Ser Val Phe Tyr Phe Ala Ile Pro Leu Gly Ser Gly Leu Gly Tyr Ile
                245                 250                 255

Thr Gly Ser Ser Val Lys Gln Ala Ala Gly Asp Trp His Trp Ala Leu
            260                 265                 270

Arg Val Ser Pro Val Leu Gly Met Ile Thr Gly Thr Leu Ile Leu Ile
            275                 280                 285

Leu Val Pro Ala Thr Lys Arg Gly His Ala Asp Gln Leu Gly Asp Gln
        290                 295                 300

Leu Lys Ala Arg Thr Ser Trp Leu Arg Asp Met Lys Ala Leu Ile Arg
305                 310                 315                 320

Asn Arg Ser Tyr Val Phe Ser Ser Leu Ala Thr Ser Ala Val Ser Phe
                325                 330                 335

Ala Thr Gly Ala Leu Gly Met Trp Ile Pro Leu Tyr Leu His Arg Ala
            340                 345                 350

Gln Val Val Gln Lys Thr Ala Glu Thr Cys Asn Ser Pro Pro Cys Gly
            355                 360                 365

Ala Lys Asp Ser Leu Ile Phe Gly Ala Ile Thr Cys Phe Thr Gly Phe
        370                 375                 380
```

Leu Gly Val Val Thr Gly Ala Gly Ala Thr Arg Trp Cys Arg Leu Lys
385                 390                 395                 400

Thr Gln Arg Ala Asp Pro Leu Val Cys Ala Val Gly Met Leu Gly Ser
            405                 410                 415

Ala Ile Phe Ile Cys Leu Ile Phe Val Ala Ala Lys Ser Ser Ile Val
            420                 425                 430

Gly Ala Tyr Ile Cys Ile Phe Val Gly Glu Thr Leu Leu Phe Ser Asn
            435                 440                 445

Trp Ala Ile Thr Ala Asp Ile Leu Met Tyr Val Ile Pro Thr Arg
    450                 455                 460

Arg Ala Thr Ala Val Ala Leu Gln Ser Phe Thr Ser His Leu Leu Gly
465                 470                 475                 480

Asp Ala Gly Ser Pro Tyr Leu Ile Gly Phe Ile Ser Asp Leu Ile Arg
            485                 490                 495

Gln Ser Thr Lys Asp Ser Pro Leu Trp Glu Phe Leu Ser Leu Gly Tyr
            500                 505                 510

Ala Leu Met Leu Cys Pro Phe Val Val Leu Gly Gly Met Phe Phe
            515                 520                 525

Leu Ala Thr Ala Leu Phe Phe Val Ser Asp Arg Ala Arg Ala Glu Gln
            530                 535                 540

Gln Val Asn Gln Leu Ala Met Pro Pro Ala Ser Val Lys Val
545                 550                 555

<210> SEQ ID NO 28
<211> LENGTH: 1677
<212> TYPE: DNA
<213> ORGANISM: Artificial Sequence
<220> FEATURE:
<223> OTHER INFORMATION: N' Flag

<400> SEQUENCE: 28
atggattaca aggatgacga cgataagatg atgtgcctgg aatgcgcctc ggcggcggcg      60
ggcggcgcgg aggaggagga ggcggacgcg gagcggcggc gccggcgccg ggggcgcag     120 cgagggctg gcggtagcgg ttgctgcggg gcgcggggcg cgggcggcgc tggagtctcg     180
gccgcgggcg atgaggtgca gacgctgtcg ggcagcgtaa ggcgggcccc gaccggaccc     240
cccggcaccc ccggcaccc cggctgcgca gctactgcaa agggccccgg cgctcagcag     300
cccaaaccgg ccagcttggg ccgcgggcgg ggggcagccg ccgccatcct cagcttgggc     360
aacgtgctca actacctgga caggtacacc gtggcaggcg tccttctgga catccagcag     420
cactttgggg tcaaggaccg aggcgccggc ctgctgcagt cagtgttcat ctgtagcttc     480
atggtggctg cccccatctt cggctacctg ggcgaccgct tcaacaggaa ggtgattctc     540
agctgcggca ttttcttctg gtcggccgtc accttctcca gctccttcat tccccagcag     600
tacttctggc tgctggtcct gtcccggggg ctggtgggca tcggggaggc cagctactcc     660
accatcgccc ccactatcat ggcgacctc ttcaccaaga cacgcgtac gctcatgctg     720 tccgtcttct acttcgccat cccactgggc agtggcctgg gctacattac tggctccagc     780
gtgaagcagg cagccggaga ctggcactgg gcattgcggg tgtccctgt cctgggcatg     840 atcacaggaa cactcatcct cattctggtc ccagccacta aaggggtca tgccgaccag     900 ctcggggacc agctcaaggc ccggacctca tggctccgag atatgaaggc cctgattcga     960
aaccgcagct acgtcttctc ctcccctggcc acgtcggctg tctccttcgc cacggggcc    1020 ctgggcatgt ggatcccgct ctacctgcac cgcgcccaag ttgtgcagaa gacagcagag    1080

```
acgtgcaaca gcccgccctg tggggccaag gacagcctca tctttggggc catcacctgc   1140
tttacgggat ttctgggcgt ggtcacgggg gcaggagcca cgcgctggtg ccgcctgaag   1200
acccagcggg ccgacccact ggtgtgtgcc gtgggcatgc tgggctctgc catcttcatc   1260
tgcctgatct tcgtggctgc caagagcagc atcgtaggag cctatatctg tatcttcgtc   1320
ggggagacgc tgctgttttc taactgggcc atcactgcag acatcctcat gtacgtggtc   1380
atccccacgc ggcgcgccac tgccgtggcc ttgcagagct tcacctccca cctgctgggg   1440
gacgccggga gcccctacct cattggcttt atctcagacc tgatccgcca gagcactaag   1500
gactccccgc tctgggagtt cctgagcctg ggctacgcgc tcatgctctg ccctttcgtc   1560
gtggtcctgg cggcatgtt cttcctcgcc actgcgctct tcttcgtcag cgaccgcgcc   1620
agggctgagc agcaggtgaa ccagctggcg atgccgcccg catctgtgaa agtctga     1677
```

<210> SEQ ID NO 29
<211> LENGTH: 557
<212> TYPE: PRT
<213> ORGANISM: Artificial Sequence
<220> FEATURE:
<223> OTHER INFORMATION: C' Flag

<400> SEQUENCE: 29

```
Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255
```

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val Asp Tyr Lys Asp Asp Asp Lys
545                 550                 555

```
<210> SEQ ID NO 30
<211> LENGTH: 1674
<212> TYPE: DNA
<213> ORGANISM: Artificial Sequence
<220> FEATURE:
<223> OTHER INFORMATION: C' Flag

<400> SEQUENCE: 30
atgatgtgcc tggaatgcgc ctcggcggcg gcgggcggcg cggaggagga ggaggcggac    60
gcggagcggc ggcgccggcg ccgggggggcg cagcgagggg ctggcggtag cggttgctgc   120
ggggcgcggg gcgcgggcgg cgctggagtc tcggccgcgg gcgatgaggt gcagacgctg   180
tcgggcagcg taaggcgggc cccgaccgga ccccccggca ccccccggca ccccggctgc   240
gcagctactg caaagggccc cggcgctcag cagcccaaac cggccagctt gggccgcggg   300 cgggggggcag ccgccgccat cctcagcttg ggcaacgtgc tcaactacct ggacaggtac   360
```

```
accgtggcag gcgtccttct ggacatccag cagcactttg gggtcaagga ccgaggcgcc      420
ggcctgctgc agtcagtgtt catctgtagc ttcatggtgg ctgcccccat cttcggctac      480
ctgggcgacc gcttcaacag gaaggtgatt ctcagctgcg cattttcctt ctggtcggcc      540
gtcaccttct ccagctcctt cattccccag cagtacttct ggctgctggt cctgtcccgg      600
gggctggtgg catcggggga ggccagctac tccaccatcg cccccactat cattggcgac      660
ctcttcacca agaacacgcg tacgctcatg ctgtccgtct tctacttcgc catcccactg      720
ggcagtggcc tgggctacat tactggctcc agcgtgaagc aggcagccgg agactggcac      780
tgggcattgc gggtgtcccc tgtcctgggc atgatcacag aacactcat cctcattctg       840 gtcccagcca ctaaaagggg tcatgccgac cagctcgggg accagctcaa ggcccggacc      900
tcatggctcc gagatatgaa ggccctgatt cgaaaccgca gctacgtctt ctcctccctg      960
gccacgtcgg ctgtctcctt cgccacgggg gccctgggca tgtggatccc gctctacctg     1020
caccgcgccc aagttgtgca gaagacagca gagacgtgca cagcccgcc ctgtggggcc      1080 aaggacagcc tcatctttgg ggccatcacc tgctttacgg gatttctggg cgtggtcacg     1140
ggggcaggag ccacgcgctg gtgccgcctg aagacccagc gggccgaccc actggtgtgt     1200
gccgtgggca tgctgggctc tgccatcttc atctgcctga tcttcgtggc tgccaagagc     1260
agcatcgtag agcctatat ctgtatcttc gtcggggaga cgctgctgtt ttctaactgg      1320
gccatcactg cagacatcct catgtacgtg gtcatcccca cgcggcgcgc cactgccgtg     1380
gccttgcaga gcttcacctc ccacctgctg ggggacgccg ggagcccta cctcattggc      1440 tttatctcag acctgatccg ccagagcact aaggactccc cgctctggga gttcctgagc     1500
ctgggctacg cgctcatgct ctgccctttc gtcgtggtcc tgggcggcat gttcttcctc     1560
gccactgcgc tcttcttcgt cagcgaccgc gccagggctg agcagcaggt gaaccagctg     1620
gcgatgccgc ccgcatctgt gaaagtcgat tacaaggatg acgacgataa gtga           1674
```

<210> SEQ ID NO 31
<211> LENGTH: 549
<212> TYPE: PRT
<213> ORGANISM: Macaca mulatta

<400> SEQUENCE: 31

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Ala
            35                  40                  45

Gly Val Ser Ala Ala Asp Asp Glu Val Gln Thr Leu Ser Gly Ser Val
50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140
```

```
Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Thr Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Leu Ser
        515                 520                 525

Asp Arg Ala Lys Ala Glu Gln Gln Val Asn Gln Leu Val Met Pro Pro
    530                 535                 540

Ala Ser Val Lys Val
545
```

-continued

```
<210> SEQ ID NO 32
<211> LENGTH: 549
<212> TYPE: PRT
<213> ORGANISM: Cavia porcellus

<400> SEQUENCE: 32
```

| | | | | | | | | | | | | | | |
|---|---|---|---|---|---|---|---|---|---|---|---|---|---|---|
| Met | Met | Cys | Leu | Glu | Cys | Ala | Ser | Ala | Ala | Gly | Gly | Ala | Glu | Glu |
| 1 | | | | 5 | | | | | 10 | | | | | 15 |
| Glu | Glu | Ala | Asp | Ala | Glu | Arg | Arg | Arg | Arg | Arg | Gly | Ala | Gln | Arg |
| | | | 20 | | | | | 25 | | | | | 30 | |
| Gly | Ala | Ser | Gly | Ser | Gly | Cys | Cys | Gly | Thr | Arg | Asp | Thr | Gly | Ala |
| | | 35 | | | | | 40 | | | | | 45 | | |
| Gly | Val | Ala | Ala | Val | Asn | Asp | Glu | Val | Gln | Thr | Leu | Ser | Gly | Ser | Val |
| | 50 | | | | | 55 | | | | | 60 | | | | |
| Arg | Arg | Ala | Pro | Ala | Gly | Pro | Ser | Ser | Ile | Pro | Gly | Thr | Pro | Gly | Cys |
| 65 | | | | | 70 | | | | | 75 | | | | | 80 |
| Ala | Ala | Ala | Ala | Lys | Ser | Pro | Cys | Ala | Gln | Gln | Pro | Lys | Pro | Ala | Ser |
| | | | | 85 | | | | | 90 | | | | | 95 | |
| Leu | Gly | Arg | Gly | Arg | Gly | Ala | Ala | Ala | Ile | Leu | Ser | Leu | Gly | Asn |
| | | | 100 | | | | | 105 | | | | | 110 | |
| Val | Leu | Asn | Tyr | Leu | Asp | Arg | Tyr | Thr | Val | Ala | Gly | Val | Leu | Leu | Asp |
| | | | 115 | | | | | 120 | | | | | 125 | | |
| Ile | Gln | Gln | His | Phe | Gly | Val | Lys | Asp | Arg | Gly | Ala | Gly | Leu | Leu | Gln |
| | 130 | | | | | 135 | | | | | 140 | | | | |
| Ser | Val | Phe | Ile | Cys | Ser | Phe | Met | Val | Ala | Ala | Pro | Ile | Phe | Gly | Tyr |
| 145 | | | | | 150 | | | | | 155 | | | | | 160 |
| Leu | Gly | Asp | Arg | Phe | Asn | Arg | Lys | Val | Ile | Leu | Ser | Cys | Gly | Ile | Phe |
| | | | | 165 | | | | | 170 | | | | | 175 | |
| Phe | Trp | Ser | Ala | Val | Thr | Phe | Ser | Ser | Ser | Phe | Ile | Pro | Gln | Gln | Tyr |
| | | | 180 | | | | | 185 | | | | | 190 | | |
| Phe | Trp | Leu | Leu | Val | Leu | Ser | Arg | Gly | Leu | Val | Gly | Ile | Gly | Glu | Ala |
| | | 195 | | | | | 200 | | | | | 205 | | | |
| Ser | Tyr | Ser | Thr | Ile | Ala | Pro | Thr | Ile | Ile | Gly | Asp | Leu | Phe | Thr | Lys |
| | 210 | | | | | 215 | | | | | 220 | | | | |
| Asn | Thr | Arg | Thr | Leu | Met | Leu | Ser | Val | Phe | Tyr | Phe | Ala | Ile | Pro | Leu |
| 225 | | | | | 230 | | | | | 235 | | | | | 240 |
| Gly | Ser | Gly | Leu | Gly | Tyr | Ile | Thr | Gly | Ser | Ser | Val | Lys | Gln | Ala | Ala |
| | | | | 245 | | | | | 250 | | | | | 255 | |
| Gly | Asp | Trp | His | Trp | Ala | Leu | Arg | Val | Ser | Pro | Val | Leu | Gly | Met | Ile |
| | | | 260 | | | | | 265 | | | | | 270 | | |
| Thr | Gly | Thr | Leu | Ile | Leu | Ile | Leu | Val | Pro | Ala | Thr | Lys | Arg | Gly | His |
| | | 275 | | | | | 280 | | | | | 285 | | | |
| Ala | Asp | Gln | Leu | Gly | Gly | Gln | Leu | Lys | Ala | Arg | Thr | Ser | Trp | Leu | Arg |
| | 290 | | | | | 295 | | | | | 300 | | | | |
| Asp | Met | Lys | Ala | Leu | Ile | Arg | Asn | Arg | Ser | Tyr | Val | Phe | Ser | Ser | Leu |
| 305 | | | | | 310 | | | | | 315 | | | | | 320 |
| Ala | Thr | Ser | Ala | Val | Ser | Phe | Ala | Thr | Gly | Ala | Leu | Gly | Met | Trp | Ile |
| | | | | 325 | | | | | 330 | | | | | 335 | |
| Pro | Leu | Tyr | Leu | His | Arg | Ala | Gln | Val | Val | Gln | Lys | Thr | Ala | Glu | Thr |
| | | | 340 | | | | | 345 | | | | | 350 | | |
| Cys | His | Ser | Pro | Pro | Cys | Gly | Ala | Lys | Asp | Ser | Leu | Ile | Phe | Gly | Ala |
| | | 355 | | | | | 360 | | | | | 365 | | | |
| Ile | Thr | Cys | Phe | Thr | Gly | Phe | Leu | Gly | Val | Val | Thr | Gly | Ala | Gly | Ala |
| | 370 | | | | | 375 | | | | | 380 | | | | |

```
Thr Arg Trp Cys Arg Leu Arg Thr Gln Arg Ala Asp Pro Leu Val Cys
385                 390                 395                 400

Ala Val Gly Met Leu Gly Ser Ala Ile Phe Ile Cys Leu Ile Phe Val
            405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Cys Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Leu Ser
            515                 520                 525

Asp Arg Ala Lys Ala Glu Gln Gln Val Asn Gln Leu Val Leu Pro Arg
530                 535                 540

Pro Pro Met Lys Val
545

<210> SEQ ID NO 33
<211> LENGTH: 549
<212> TYPE: PRT
<213> ORGANISM: Rattus norvegicus

<400> SEQUENCE: 33

Met Met Cys Leu Glu Cys Ala Ser Ala Ala Ala Gly Gly Ala Glu Glu
1               5                   10                  15

Glu Glu Ala Asp Ala Glu Arg Arg Arg Arg Arg Gly Ala Gln Pro
            20                  25                  30

Gly Ala Gly Gly Ser Ala Cys Cys Gly Ala Arg Gly Val Gly Gly Ala
            35                  40                  45

Gly Val Val Ser Ala Asp Glu Glu Val Gln Thr Leu Ser Gly Ser Val
50                  55                  60

Arg Arg Val Pro Ser Gly Leu Pro Ser Ile Pro Ser Thr Pro Gly Cys
65                  70                  75                  80

Ala Ala Ala Ala Lys Gly Pro Gly Ala Pro Gln Pro Lys Pro Ala Ser
            85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
            130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205
```

```
Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Gly Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Arg Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Thr Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Leu Ser
        515                 520                 525

Asp Arg Ala Lys Ala Glu Gln Gln Val Asn Gln Leu Val Met Pro Pro
530                 535                 540

Ala Ser Val Lys Ile
545

<210> SEQ ID NO 34
<211> LENGTH: 121
<212> TYPE: PRT
<213> ORGANISM: Rattus norvegicus

<400> SEQUENCE: 34

Ala Val Gln Leu Val Gly Ser Gly Gly Gly Leu Val Gln Pro Gly Arg
1               5                   10                  15

Ser Met Lys Leu Ser Cys Glu Ala Ser Gly Phe Thr Phe Ser Asn His
```

```
                 20                  25                  30
Tyr Met Ala Trp Val Arg Gln Ala Pro Thr Arg Gly Leu Glu Trp Val
             35                  40                  45

Ala Thr Ile Ser Thr Gly Gly Asn Thr Tyr Tyr Arg Asp Ser Val
         50                  55                  60

Lys Gly Arg Phe Thr Ile Ser Arg Asp Asn Thr Arg Ser Thr Leu Ser
 65                  70                  75                  80

Leu Gln Met Asp Ser Leu Arg Ser Glu Asp Thr Ala Thr Tyr Tyr Cys
                 85                  90                  95

Thr Arg Gln Asp Tyr Thr Asn Tyr Met Gly Gly Phe Ala Tyr Trp Gly
             100                 105                 110

Gln Gly Thr Leu Val Thr Val Ser Ser
         115                 120

<210> SEQ ID NO 35
<211> LENGTH: 363
<212> TYPE: DNA
<213> ORGANISM: Rattus norvegicus

<400> SEQUENCE: 35
gcggtgcagc tggtggggtc tgggggaggc ttagtgcagc ctggaaggtc catgaaactc      60
tcctgtgaag cctcaggatt cactttcagt aaccattaca tggcctgggt ccgccaggca     120
ccaacaaggg gtctggagtg ggtcgcgacc attagtactg gtggtggtaa tacttactat     180
cgcgactccg tgaagggccg attcactatc tccagagata tacaagaag cacctatcc      240 ctgcagatgg acagtctgag gtctgaggac acggccactt attactgtac aagacaagat     300
tatactaact atatggggg gtttgcttac tggggccagg gcactctggt cactgtctct     360
tca                                                                   363

<210> SEQ ID NO 36
<211> LENGTH: 119
<212> TYPE: PRT
<213> ORGANISM: Rattus norvegicus

<400> SEQUENCE: 36

Glu Val Gln Leu Val Glu Ser Gly Gly Gly Leu Val Arg Pro Gly Gly
 1               5                  10                  15

Ser Met Lys Leu Ser Cys Gly Ala Ser Gly Phe Ile Phe Asp Asn Tyr
             20                  25                  30

Tyr Met Thr Trp Val Arg Gln Ala Pro Thr Lys Gly Leu Glu Trp Val
             35                  40                  45

Ala Ser Ile Ser Ser Ser Gly Gly Asn Thr Tyr Tyr Arg Asp Ser Val
         50                  55                  60

Arg Gly Arg Phe Thr Ile Ser Arg Asp Asn Ala Gly Asn Thr Leu Ser
 65                  70                  75                  80

Leu Gln Met Gly Ser Leu Arg Ala Glu Asp Thr Ala Thr Tyr His Cys
                 85                  90                  95

Ala Lys Glu Gly Tyr Arg Gly Arg Tyr Phe Asp Tyr Trp Gly Gln Gly
             100                 105                 110

Val Met Val Thr Val Ser Ser
         115

<210> SEQ ID NO 37
<211> LENGTH: 357
<212> TYPE: DNA
<213> ORGANISM: Rattus norvegicus
```

<400> SEQUENCE: 37

```
gaggtgcaac tggtggagtc tgggggaggc ttagtgcggc ctgggggtc catgaaactc      60
tcctgtggag cctcaggatt cattttcgat aactattaca tgacctgggt ccgccaggct     120
ccaacgaagg gtctggagtg gtcgcatcc attagttcta gtggtggtaa cacttactat     180
cgagattccg tgaggggccg gttcactatc tccagagata atgcaggaaa cacctatcc     240
ctgcaaatgg gcagtctgag ggctgaggac acggccactt atcactgtgc gaaagagggc     300
tacaggggtc ggtactttga ttactggggc caaggagtca tggtcacagt ctcctca        357
```

<210> SEQ ID NO 38
<211> LENGTH: 115
<212> TYPE: PRT
<213> ORGANISM: Rattus norvegicus

<400> SEQUENCE: 38

```
Glu Val His Leu Gln Gln Ser Gly Ala Ala Leu Val Arg Pro Arg Ala
1               5                   10                  15
Ser Val Lys Leu Ser Cys Lys Val Ser Gly Asp Ser Ile Ser Arg Tyr
                20                  25                  30
Tyr Val His Phe Val Lys Gln Arg Pro Gly Gln Gly Leu Glu Trp Ile
            35                  40                  45
Gly Arg Ile Asp Pro Glu Asp Asp Thr Thr Lys Tyr Ser Glu Lys Phe
        50                  55                  60
Lys Asn Arg Ala Thr Leu Thr Ala Asp Ala Ser Ser Asp Thr Ala Ser
65                  70                  75                  80
Leu Ile Leu Ser Gly Leu Thr Ser Asp Asp Thr Ala Thr Tyr Phe Cys
                85                  90                  95
Ser Thr Leu Thr Gly Leu Asp Tyr Trp Gly Gln Gly Val Met Val Thr
            100                 105                 110
Val Ser Ser
        115
```

<210> SEQ ID NO 39
<211> LENGTH: 345
<212> TYPE: DNA
<213> ORGANISM: Rattus norvegicus

<400> SEQUENCE: 39

```
gaagtccacc tgcagcagtc tggggctgcg cttgtgagac ctagggcctc tgtgaagtta     60
tcttgcaaag tttctggcga ttccatttca agatactacg tgcactttgt gaagcaaagg    120
cctggacagg gtctggaatg gataggaagg attgatcctg aggatgatac tactaagtat    180
tctgagaagt tcaaaaacag gcgacactc actgcagatg catcctccga cacagcctcc     240
ctgattctca gcggcctgac ctctgacgac actgcaacct attttttgtag cactctaact    300
ggccttgatt actggggcca aggagtcatg gtcacggtct cctca                    345
```

<210> SEQ ID NO 40
<211> LENGTH: 121
<212> TYPE: PRT
<213> ORGANISM: Rattus norvegicus

<400> SEQUENCE: 40

```
Glu Val Gln Leu Val Glu Ser Gly Gly Gly Leu Val Gln Pro Gly Arg
1               5                   10                  15
Ser Met Lys Leu Ser Cys Ala Ala Ser Gly Phe Thr Phe Ser Asn His
```

```
                    20                  25                  30

Tyr Met Ala Trp Val Arg Gln Ala Pro Thr Lys Gly Leu Glu Trp Val
            35                  40                  45

Ala Ser Ile Ser Thr Gly Gly Asn Thr Tyr Tyr Arg Asp Ser Val
        50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Gln Asp Tyr Ser Asn Tyr Met Gly Gly Phe Ala Tyr Trp Gly
            100                 105                 110

Gln Gly Thr Leu Val Thr Val Ser Ser
            115                 120

<210> SEQ ID NO 41
<211> LENGTH: 363
<212> TYPE: DNA
<213> ORGANISM: Rattus norvegicus

<400> SEQUENCE: 41
gaggtgcagc tggtggagtc tgggggaggc ttagtgcagc ctggaaggtc catgaagctc      60
tcctgtgcag cctcaggatt cactttcagt aaccattaca tggcctgggt ccgccaggca     120
ccaacaaagg gtctggagtg ggtcgcgtcc attagtactg gtggtggtaa tacttattat     180
cgagactccg tgaagggccg attcactatc tccagagata tgcaaaaag caccctttat      240 ctgcaaatgg acagtctgag gtctgaggac acggccactt attattgtgc cagacaagac     300
tatagtaact atatgggggg gtttgcttac tggggccaag gcactctggt cactgtctct     360
tca                                                                    363

<210> SEQ ID NO 42
<211> LENGTH: 121
<212> TYPE: PRT
<213> ORGANISM: Rattus norvegicus

<400> SEQUENCE: 42

Glu Val Gln Leu Val Gly Ser Gly Gly Gly Leu Val Gln Pro Gly Arg
1               5                   10                  15

Ser Met Lys Leu Ser Cys Glu Ala Ser Gly Phe Thr Phe Ser Asn His
            20                  25                  30

Tyr Met Ala Trp Val Arg Gln Ala Pro Thr Lys Gly Leu Glu Trp Val
            35                  40                  45

Ala Thr Ile Ser Thr Gly Gly Asn Thr Tyr Tyr Arg Asp Ser Val
        50                  55                  60

Lys Gly Arg Phe Thr Ile Ser Arg Asp Asn Ala Arg Ser Thr Leu Ser
65                  70                  75                  80

Leu Gln Met Asp Ser Leu Arg Ser Glu Asp Thr Ala Thr Tyr Tyr Cys
                85                  90                  95

Ala Arg Gln Asp Tyr Ser Asn Tyr Met Gly Gly Phe Ala Tyr Trp Gly
            100                 105                 110

Gln Gly Thr Leu Val Thr Val Ser Ser
            115                 120

<210> SEQ ID NO 43
<211> LENGTH: 363
<212> TYPE: DNA
<213> ORGANISM: Rattus norvegicus
```

<400> SEQUENCE: 43

```
gaggtgcagc tggtggggtc tgggggaggc ttagtgcagc ctggaaggtc catgaaactc      60
tcctgtgaag cctcaggatt cactttcagt aaccattaca tggcctgggt ccgccaggca     120
ccaacaaagg gtctggagtg ggtcgcgacc attagtactg gtggtggtaa tacttactat     180
cgcgactccg tgaagggccg attcactatc tccagagata tgcaagaag  caccctatcc     240
ctgcagatgg acagtctgag gtctgaggac acggccactt attactgtgc aagacaagat     300
tatagtaact atatggggg  gtttgcttac tggggccagg gcactctggt cactgtctct     360
tca                                                                   363
```

<210> SEQ ID NO 44
<211> LENGTH: 115
<212> TYPE: PRT
<213> ORGANISM: Rattus norvegicus

<400> SEQUENCE: 44

```
Glu Val Gln Leu Gln Gln Ser Gly Ala Glu Leu Val Arg Pro Arg Thr
1               5                   10                  15
Ser Val Lys Leu Ser Cys Lys Val Ser Gly Asp Ser Ile Thr Arg Tyr
            20                  25                  30
Tyr Val His Phe Val Lys Gln Arg Pro Gly Gln Gly Leu Glu Trp Ile
        35                  40                  45
Gly Arg Ile Asp Pro Glu Asp Asp Thr Thr Lys Tyr Ser Glu Lys Phe
    50                  55                  60
Lys Lys Lys Ala Thr Leu Thr Ala Asp Ala Ser Ser Asn Thr Ala Tyr
65                  70                  75                  80
Leu Ile Phe Ser Gly Leu Thr Ser Glu Asp Thr Ala Thr Tyr Phe Cys
                85                  90                  95
Ser Thr Leu Thr Gly Leu Asp Tyr Trp Gly Gln Gly Val Met Val Thr
            100                 105                 110
Val Ser Ser
        115
```

<210> SEQ ID NO 45
<211> LENGTH: 345
<212> TYPE: DNA
<213> ORGANISM: Rattus norvegicus

<400> SEQUENCE: 45

```
gaagtccagc tgcagcagtc tggggctgag cttgtgagac ctaggacctc tgtgaagtta      60
tcttgcaaag tttctggcga ttccattaca agatactacg tgcactttgt gaagcaaagg     120
cctggacagg gtctggaatg gataggaagg attgatcctg aggatgatac tactaagtat     180
tctgagaagt tcaaaaagaa ggcgacactc actgcagatg catcctccaa cacagcctac     240
ctgattttca gcggcctgac ctctgaggac actgcaacct attttgtag  cactctaact     300
ggccttgatt actggggcca aggagtcatg gtcacggtct cctca                     345
```

<210> SEQ ID NO 46
<211> LENGTH: 118
<212> TYPE: PRT
<213> ORGANISM: Rattus norvegicus

<400> SEQUENCE: 46

```
Glu Val Gln Val Val Glu Ser Gly Gly Gly Leu Val Gln Pro Gly Arg
1               5                   10                  15
```

```
Ser Met Lys Leu Ser Cys Ala Ala Leu Gly Phe Thr Phe Arg Asp Tyr
            20                  25                  30

Tyr Met Ala Trp Val Arg Gln Thr Pro Thr Lys Gly Leu Glu Trp Val
            35                  40                  45

Ala Ala Ile Ser Thr Gly Gly Asn Thr Tyr Tyr Arg Asp Ser Val
 50                      55                  60

Lys Gly Arg Phe Thr Ile Ser Arg Asp Asn Ala Lys Ser Thr Leu Tyr
 65                      70                  75                  80

Leu Gln Met Asp Ser Leu Arg Ser Asp Asp Thr Ala Thr Tyr Tyr Cys
                    85                  90                  95

Ala Arg Asn Pro Tyr Gly Asn Tyr Phe Asp Tyr Trp Gly Gln Gly Val
                100                 105                 110

Met Val Thr Val Ser Ser
            115
```

<210> SEQ ID NO 47
<211> LENGTH: 354
<212> TYPE: DNA
<213> ORGANISM: Rattus norvegicus

<400> SEQUENCE: 47

```
gaggtgcagg tggtggagtc tgggggaggc ttagtgcagc ctggaaggtc catgaaactc    60
tcctgtgcag ccttaggatt cactttccgt gactattaca tggcctgggt ccgccagaca   120
ccaacaaagg gtctggagtg ggtcgcagcc attagtactg gtggtggaaa cacttactat   180
cgagactccg tgaagggccg attcactatc tccagagata atgcaaaaag cacccttat    240
ctgcaaatgg acagtctgag gtctgacgac acggccactt attactgtgc aagaaacccc   300
tacggcaact actttgatta ttggggccaa ggagtcatgg tcacagtctc ctct         354
```

<210> SEQ ID NO 48
<211> LENGTH: 115
<212> TYPE: PRT
<213> ORGANISM: Rattus norvegicus

<400> SEQUENCE: 48

```
Glu Val His Leu Val Glu Ser Gly Gly Gly Leu Val Gln Pro Gly Arg
 1               5                  10                  15

Ser Met Lys Leu Ser Cys Thr Ala Ser Gly Phe Thr Phe Asn Asn Tyr
            20                  25                  30

Tyr Met Ala Trp Val Arg Gln Ala Pro Thr Lys Gly Leu Glu Trp Val
            35                  40                  45

Ala Ser Ile Ser Thr Gly Gly Tyr Thr Tyr Tyr Arg Asp Ser Val
 50                      55                  60

Lys Gly Arg Phe Thr Ile Ser Arg Asp Asn Gly Asn Thr Leu Tyr
 65                      70                  75                  80

Leu Gln Met Asp Ser Leu Arg Ser Glu Asp Thr Ala Thr Tyr Tyr Cys
                    85                  90                  95

Ala Arg Cys Trp Glu Leu Pro Tyr Trp Gly Gln Gly Val Met Val Thr
                100                 105                 110

Val Ser Ser
        115
```

<210> SEQ ID NO 49
<211> LENGTH: 345
<212> TYPE: DNA
<213> ORGANISM: Rattus norvegicus

<400> SEQUENCE: 49

```
gaggtgcacc tggtggagtc tgggggaggc ttagtgcagc ctggaaggtc catgaaactc      60
tcctgtacag cctcaggatt cactttcaat aactattaca tggcctgggt ccgtcaggct     120
ccaacgaagg gtctggagtg ggtcgcgtcc attagtactg gtggtggtta cacttactat     180
cgagactccg tgaagggccg atttactatc tccagagata tacaggaaa cacccctgtat    240
ctgcaaatgg acagtctgag gtctgaggac acggccactt attactgtgc aagatgttgg    300
gagctgcctt attggggcca aggagtcatg gtcacagtct cctca                    345
```

<210> SEQ ID NO 50
<211> LENGTH: 125
<212> TYPE: PRT
<213> ORGANISM: Rattus norvegicus

<400> SEQUENCE: 50

```
Glu Val Gln Leu Val Glu Thr Gly Gly Gly Leu Val Gln Pro Gly Ser
1               5                   10                  15
Ser Leu Lys Leu Ser Cys Ser Thr Ser Gly Phe Thr Phe Ser Glu Thr
            20                  25                  30
Trp Met Ser Trp Val Arg Gln Ala Pro Gly Lys Gly Leu Glu Trp Val
        35                  40                  45
Gly Leu Ile Lys Asp Lys Asn Ser Asn Tyr Glu Ala Asn Tyr Ala Glu
    50                  55                  60
Ser Val Lys Gly Arg Phe Thr Ile Ser Arg Asp Asp Ser Lys Arg Arg
65                  70                  75                  80
Val Tyr Leu Gln Met Tyr Thr Leu Arg Asp Gln Asp Thr Ala Thr Tyr
                85                  90                  95
Tyr Cys Thr Ser His Glu Asp Phe Tyr Tyr Ser Ser Tyr Tyr Phe
            100                 105                 110
Asp Tyr Trp Gly Gln Gly Val Met Val Thr Val Ser Ser
        115                 120                 125
```

<210> SEQ ID NO 51
<211> LENGTH: 375
<212> TYPE: DNA
<213> ORGANISM: Rattus norvegicus

<400> SEQUENCE: 51

```
gaggtgcagc tcgtggagac aggaggaggc ttggtgcagc ctgggagttc tctaaaactc      60
tcctgttcaa cctctggatt tacattcagt gaaacctgga tgagctgggt tcgccaggct    120
ccagggaagg ggctcgagtg ggttggtcta attaaagata aaaatagtaa ttatgaagca    180
aactatgcag agtctgtcaa aggcagattc accatctcaa gagacgattc gaaacgcaga    240
gtctacttac agatgtacac cttaagggat caggacactg ccacttatta ctgtacaagt    300
cacgaggatt tttattacta cagcagctat tactttgatt actggggcca aggagtcatg    360
gtcacagtct cctca                                                     375
```

<210> SEQ ID NO 52
<211> LENGTH: 115
<212> TYPE: PRT
<213> ORGANISM: Rattus norvegicus

<400> SEQUENCE: 52

```
Glu Val Gln Leu Gln Gln Ser Gly Pro Glu Phe Val Arg Pro Gly Thr
1               5                   10                  15
```

Ser Val Lys Phe Ser Cys Lys Val Ser Gly Ser Ile Thr Ser Tyr
            20                  25                  30

Phe Ile His Phe Val Lys Gln Arg Pro Gly Gln Gly Leu Glu Trp Ile
        35                  40                  45

Gly Lys Ile Asp Pro Glu Asp Asp Ser Thr Lys Tyr Gly Glu Lys Phe
 50                  55                  60

Lys Asn Lys Ala Thr Leu Thr Ala Asp Thr Ser Ser Asn Thr Ala Phe
65                  70                  75                  80

Leu Lys Leu Ser Ser Leu Thr Ser Glu Asp Thr Ala Ile Tyr Phe Cys
                85                  90                  95

Thr Thr Leu Thr Gly Leu Asp Tyr Trp Gly Gln Gly Val Met Val Thr
            100                 105                 110

Val Ser Ser
        115

<210> SEQ ID NO 53
<211> LENGTH: 345
<212> TYPE: DNA
<213> ORGANISM: Rattus norvegicus

<400> SEQUENCE: 53
gaagtccagc tgcagcagtc tgggcctgag tttgtgaggc ctgggacctc tgtgaagttt     60
tcttgcaaag tctctggcgg ttccattaca tcatacttca tacactttgt gaaacaaagg    120
cctggacagg gtctggaatg gataggaaag attgatcctg aggatgatag tactaaatat    180
ggtgagaagt tcaaaaacaa ggcgacactc actgccgata catcctccaa cacagccttc    240
ctgaagctca gcagcctgac ctctgaggac actgcaatct atttttgcac cactctaact    300
ggccttgatt actggggcca aggagtcatg gtcacagtct cctca                    345

<210> SEQ ID NO 54
<211> LENGTH: 118
<212> TYPE: PRT
<213> ORGANISM: Rattus norvegicus

<400> SEQUENCE: 54

Glu Val Gln Val Val Glu Ser Gly Gly Gly Leu Val Gln Pro Gly Arg
1               5                   10                  15

Ser Met Lys Leu Ser Cys Ala Ala Leu Gly Phe Thr Phe Arg Asp Tyr
            20                  25                  30

Tyr Met Ala Trp Val Arg Gln Thr Pro Thr Lys Gly Leu Glu Trp Val
        35                  40                  45

Ala Ala Ile Ser Thr Gly Gly Gly Asn Thr Tyr Tyr Arg Asp Ser Val
 50                  55                  60

Lys Gly Arg Phe Thr Ile Ser Arg Asp Asn Ala Lys Ser Thr Leu Tyr
65                  70                  75                  80

Leu Lys Met Asp Ser Leu Arg Ser Asp Asp Thr Ala Thr Tyr Tyr Cys
                85                  90                  95

Ala Arg Asn Pro Tyr Gly Asn Tyr Phe Asp Tyr Trp Gly Gln Gly Val
            100                 105                 110

Met Val Thr Val Ser Ser
        115

<210> SEQ ID NO 55
<211> LENGTH: 354
<212> TYPE: DNA
<213> ORGANISM: Rattus norvegicus

<400> SEQUENCE: 55

```
gaggtgcagg tggtggagtc tgggggaggc ttagtgcagc ctggaaggtc catgaaactc    60
tcctgtgcag ccttaggatt cactttccgt gactattaca tggcctgggt ccgccagaca   120
ccaacaaagg gtctggagtg ggtcgcagcc attagtactg gtggtggaaa cacttactat   180
cgagactccg tgaagggccg attcactatc tccagagata tgcaaaaag cacccttat   240
ctgaaaatgg acagtctgag gtctgacgac acggccactt attactgtgc aagaaaccc   300
tacggcaact actttgatta ttggggccaa ggagtcatgg tcacagtctc ctct         354
```

<210> SEQ ID NO 56
<211> LENGTH: 121
<212> TYPE: PRT
<213> ORGANISM: Rattus norvegicus

<400> SEQUENCE: 56

```
Glu Val Gln Leu Val Gly Ser Gly Gly Leu Val Gln Pro Gly Arg
1               5                   10                  15

Ser Met Lys Leu Ser Cys Glu Ala Ser Gly Phe Thr Phe Ser Asn His
            20                  25                  30

Tyr Met Ala Trp Val Arg Gln Ala Pro Thr Lys Gly Leu Glu Trp Val
        35                  40                  45

Ala Thr Ile Ser Thr Gly Gly Gly Asn Thr Tyr Tyr Arg Asp Ser Val
    50                  55                  60

Lys Gly Arg Phe Thr Ile Ser Arg Asp Asn Ala Arg Ser Ile Leu Ser
65                  70                  75                  80

Leu Gln Met Asp Ser Leu Arg Ser Glu Asp Thr Ala Thr Tyr Tyr Cys
                85                  90                  95

Ala Arg Gln Asp Tyr Ser Asn Tyr Met Gly Gly Phe Ala Tyr Trp Gly
            100                 105                 110

Gln Gly Thr Leu Val Thr Val Ser Ser
        115                 120
```

<210> SEQ ID NO 57
<211> LENGTH: 363
<212> TYPE: DNA
<213> ORGANISM: Rattus norvegicus

<400> SEQUENCE: 57

```
gaggtgcagc tggtggggtc tgggggaggc ttagtgcagc ctggaaggtc catgaaactc    60
tcctgtgaag cctcaggatt cactttcagt aaccattaca tggcctgggt ccgccaggca   120
ccaacaaagg gtctggagtg ggtcgcgacc attagtactg gtggtggtaa tacttactat   180
cgagactccg tgaagggccg attcactatc tccagagata tgcaagaag cattctatcc   240
ctacagatgg acagtctgag gtctgaggac acggccactt attactgtgc aagacaagat   300
tatagtaact atatgggggg gtttgcttac tggggccagg gcactctggt cactgtctct   360
tca                                                                  363
```

<210> SEQ ID NO 58
<211> LENGTH: 125
<212> TYPE: PRT
<213> ORGANISM: Rattus norvegicus

<400> SEQUENCE: 58

```
Glu Val Gln Leu Val Glu Thr Gly Gly Gly Leu Val Gln Pro Gly Ser
1               5                   10                  15
```

```
Ser Leu Lys Leu Ser Cys Ala Thr Ser Gly Phe Thr Phe Ser Asp Thr
        20                  25                  30

Trp Met Ser Trp Val Arg Gln Ala Pro Gly Lys Gly Leu Glu Trp Val
            35                  40                  45

Ala Leu Ile Lys Asp Lys Asn Ser Asn Tyr Glu Ala Asn Tyr Ala Glu
        50                  55                  60

Ser Val Lys Gly Arg Phe Thr Ile Ser Arg Asp Asp Ser Lys Arg Arg
65                  70                  75                  80

Val Tyr Leu Gln Met Phe Thr Leu Arg Asp Gln Asp Thr Ala Thr Tyr
                85                  90                  95

Tyr Cys Thr Ser His Glu Asp Phe Tyr Tyr Ser Ser Tyr Tyr Phe
            100                 105                 110

Asp Tyr Trp Gly His Gly Val Met Val Thr Val Ser Ser
            115                 120                 125

<210> SEQ ID NO 59
<211> LENGTH: 375
<212> TYPE: DNA
<213> ORGANISM: Rattus norvegicus

<400> SEQUENCE: 59
gaggtgcagc tcgtggagac aggaggaggc ttggtgcagc ctggagttc tctaaaactc      60 tcctgtgcaa cctctggatt tacattcagt gacacctgga tgagctgggt cgccaggct     120 ccagggaagg ggctcgagtg ggttgctcta attaagata aaatagtaa ttatgaagca      180 aactatgcag agtctgtaaa aggcagattc accatctcaa gagacgattc gaaacgaga    240 gtctacttac agatgttcac cttacgggat caggacactg ccacttatta ctgtacaagt   300
cacgaggatt tttattacta tagcagctat tactttgatt actggggcca cggagtcatg   360
gtcacagtct cctca                                                    375

<210> SEQ ID NO 60
<211> LENGTH: 115
<212> TYPE: PRT
<213> ORGANISM: Rattus norvegicus

<400> SEQUENCE: 60

Glu Val Gln Leu Gln Gln Ser Gly Ala Gly Leu Val Arg Pro Arg Thr
1               5                   10                  15

Ser Val Arg Leu Ser Cys Lys Ile Ser Gly Asp Ser Ile Thr Ala Tyr
            20                  25                  30

Tyr Val His Phe Val Lys Gln Arg Pro Gly Gln Gly Leu Glu Trp Ile
        35                  40                  45

Gly Arg Ile Asp Pro Glu Asp Asp Ser Thr Lys Tyr Ser Glu Lys Phe
    50                  55                  60

Lys Asn Lys Ala Thr Leu Thr Ala Asp Val Ser Ser Ser Thr Ala Tyr
65                  70                  75                  80

Leu Ile Leu Ser Ser Leu Thr Ser Asp Asp Ser Ala Thr Tyr Phe Cys
                85                  90                  95

Ser Thr Leu Thr Gly Leu Asp Tyr Trp Gly Gln Gly Val Met Val Thr
            100                 105                 110

Val Ser Ser
        115

<210> SEQ ID NO 61
<211> LENGTH: 345
```

```
<212> TYPE: DNA
<213> ORGANISM: Rattus norvegicus

<400> SEQUENCE: 61
gaagtccagc tgcagcagtc tggggctgga cttgtgagac ctaggacctc tgtgaggtta      60
tcttgcaaaa tttctggcga ttccattaca gcatattacg tgcactttgt gaaacaaagg     120
cctggacagg gtctggaatg gataggaaga attgatcctg aggatgatag tactaaatat     180
tctgagaagt tcaaaaacaa ggcgacactc actgcagatg tatcctccag cacagcctac     240
ctgattctca gcagcctgac ctctgacgac tctgcaacct atttttgttc cactctgact     300
ggccttgatt actggggcca gggagtcatg gtcacggtct cctca                     345

<210> SEQ ID NO 62
<211> LENGTH: 125
<212> TYPE: PRT
<213> ORGANISM: Rattus norvegicus

<400> SEQUENCE: 62

Glu Val Gln Leu Val Glu Thr Gly Gly Gly Leu Val Arg Pro Gly Ser
1               5                   10                  15

Ser Leu Lys Leu Ser Cys Ala Thr Ser Gly Phe Thr Phe Ser Asp Thr
            20                  25                  30

Trp Met Ser Trp Val Arg Gln Ala Pro Gly Lys Gly Leu Glu Trp Val
        35                  40                  45

Ala Leu Ile Lys Asp Lys Asn Ser Asn Ser Glu Ala Asn Tyr Ala Glu
    50                  55                  60

Ser Ile Lys Gly Arg Phe Thr Ile Ser Arg Asp Ser Lys Ser Arg
65                  70                  75                  80

Val Tyr Leu Gln Met Asn Thr Leu Arg Asp Gln Asp Thr Ala Thr Tyr
                85                  90                  95

Tyr Cys Thr Arg His Glu Asp Phe Tyr Tyr Tyr Ser Gly Tyr Tyr Phe
            100                 105                 110

Asp Tyr Trp Gly Gln Gly Val Met Val Thr Val Ser Ser
        115                 120                 125

<210> SEQ ID NO 63
<211> LENGTH: 375
<212> TYPE: DNA
<213> ORGANISM: Rattus norvegicus

<400> SEQUENCE: 63
gaggtgcagc tcgtggagac aggaggaggc ttggtgcggc ctgggagttc tctaaaactc      60
tcctgtgcaa cctctggatt tacattcagt gacacctgga tgagctgggt tcgccaggct     120
ccagggaagg ggctcgagtg ggttgctcta attaaagata aaaatagtaa ttctgaagca     180
aactatgcag agtctataaa aggcagattc accatctcaa gagacgattc gaaaagcaga     240
gtctacttac agatgaacac cttaagggat caggacactg ccacttatta ctgtacaagg     300
cacgaggatt tttattacta tagtggctat tactttgatt actggggcca aggagtcatg     360
gtcacagtct cctca                                                      375

<210> SEQ ID NO 64
<211> LENGTH: 118
<212> TYPE: PRT
<213> ORGANISM: Rattus norvegicus

<400> SEQUENCE: 64
```

```
Gln Val Gln Leu Gln Gln Ser Gly Val Glu Leu Ala Lys Pro Gly Ser
1               5                   10                  15

Ser Val Lys Ile Ser Cys Lys Ala Ser Gly Asn Thr Phe Thr Ser Asn
            20                  25                  30

Tyr Ile Thr Trp Ile Lys Gln Thr Pro Gly Gln Gly Leu Glu Tyr Ile
        35                  40                  45

Gly Tyr Ile Asn Thr Gly Ser Gly Lys Thr Tyr Tyr Asn Glu Lys Phe
50                  55                  60

Lys Gly Lys Ala Thr Leu Thr Ala Asp Lys Ser Ser Thr Ala Phe
65                  70                  75                  80

Met Gln Leu Ser Ser Leu Thr Pro Asp Asp Ser Ala Val Tyr Phe Cys
                85                  90                  95

Ala Ser Leu Thr Gly Val Asp Tyr Phe Asp Asp Trp Gly Gln Gly Val
            100                 105                 110

Met Val Thr Val Ser Ser
            115
```

<210> SEQ ID NO 65
<211> LENGTH: 354
<212> TYPE: DNA
<213> ORGANISM: Rattus norvegicus

<400> SEQUENCE: 65

```
caggtccagc tgcagcagtc tggagttgag ctggcaaagc ctggctcttc agtgaagatc      60
tcctgtaagg cctctggcaa caccttcacc agcaattata taacctggat aaagcagacg     120
cctggacagg gccttgagta tattggatat attaatacgg gaagtggaaa aacttactac     180
aatgagaagt tcaagggcaa ggccacattg actgcagaca atcctccag cacagccttc      240
atgcaactca gcagcctgac acctgacgac tctgcggtct atttctgtgc aagtctaact     300
ggggtcgact actttgatga ctggggccaa ggagtcatgg tcacagtctc ctca           354
```

<210> SEQ ID NO 66
<211> LENGTH: 110
<212> TYPE: PRT
<213> ORGANISM: Rattus norvegicus

<400> SEQUENCE: 66

```
Gln Phe Val Leu Thr Gln Pro Asn Ser Val Ser Thr Asn Leu Gly Ser
1               5                   10                  15

Thr Val Lys Leu Ser Cys Thr Arg Ser Ile Gly Asn Ile Gly Asn Asn
            20                  25                  30

Tyr Val Asn Trp Tyr Lys Gln Tyr Glu Gly Arg Ser Pro Thr Thr Leu
        35                  40                  45

Ile Tyr Arg Asp Asp Glu Arg Pro Asp Gly Val Pro Asp Arg Phe Ser
50                  55                  60

Gly Ser Ile Asp Arg Ser Ser Asn Ser Ala Leu Leu Thr Ile Asn Ser
65                  70                  75                  80

Val Gln Thr Glu Asp Gly Ala Asp Tyr Phe Cys Gln Ser Phe Ser Ser
                85                  90                  95

Gly Ile Phe Ile Phe Gly Gly Gly Thr Thr Leu Thr Val Leu
            100                 105                 110
```

<210> SEQ ID NO 67
<211> LENGTH: 330
<212> TYPE: DNA
<213> ORGANISM: Rattus norvegicus

<400> SEQUENCE: 67

```
cagtttgtac ttacgcagcc aaactctgtg tctacgaatc tcggaagcac agtcaaactg      60
tcttgcacgc gcagcattgg taacattgga acaattatg tgaactggta caagcagtat      120
gagggaagat ctcccaccac tctgatttat agggatgatg agagaccaga tggagttcct      180
gacaggttct ctggctccat tgacagatct tccaactcag ccctcctgac aatcaatagt      240
gtgcagactg aagatggagc tgactacttc tgtcagtctt tcagtagtgg tatctttatt      300
tttggcggtg gaaccacgct cactgtcctg                                       330
```

<210> SEQ ID NO 68
<211> LENGTH: 109
<212> TYPE: PRT
<213> ORGANISM: Rattus norvegicus

<400> SEQUENCE: 68

```
Gln Val Val Leu Thr Gln Pro Asn Ser Val Ser Thr Asn Leu Gly Ser
1               5                   10                  15

Thr Val Lys Leu Ser Cys Lys Arg Thr Thr Gly Asn Ile Gly Ser Asn
            20                  25                  30

Tyr Val Asn Trp Tyr Gln Gln His Glu Gly Arg Ser Pro Thr Thr Met
        35                  40                  45

Ile Tyr Arg Asp Asp Glu Arg Pro Asp Gly Val Pro Asp Arg Phe Ser
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Glu Tyr Phe Cys Gln Ser Tyr Ser Ser
                85                  90                  95

Gly Ile Ile Phe Gly Gly Gly Thr Lys Leu Thr Val Leu
            100                 105
```

<210> SEQ ID NO 69
<211> LENGTH: 327
<212> TYPE: DNA
<213> ORGANISM: Rattus norvegicus

<400> SEQUENCE: 69

```
caggtggtgc ttactcagcc aaactctgtg tctacgaatc tcggaagcac agtcaaactg      60
tcttgcaagc gcaccactgg taacattggt agcaattatg tgaactggta tcagcagcat      120
gagggaagat ctcccaccac tatgatttat agggatgatg agagaccaga tggagttcct      180
gacaggttct ctggctccat tgacagatcg tccaactcag ccctcctgac aatcaataat      240
gtgcagactg aagatgaagc tgaatacttc tgtcagtctt acagtagtgg tattattttc      300
ggcggtggaa ccaagctcac tgtccta                                          327
```

<210> SEQ ID NO 70
<211> LENGTH: 107
<212> TYPE: PRT
<213> ORGANISM: Rattus norvegicus

<400> SEQUENCE: 70

```
Asp Ile Gln Met Thr Gln Ser Pro Pro Val Leu Ser Ser Val Gly
1               5                   10                  15

Asp Arg Val Thr Leu Arg Cys Lys Pro Ser Gln Asn Val His Ser Lys
            20                  25                  30

Leu Asp Trp Tyr Gln Gln Lys His Gly Glu Ala Pro Lys Leu Leu Ile
        35                  40                  45
```

```
Tyr Tyr Thr His Asn Leu Gln Thr Gly Ile Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Glu Asp Val Ala Thr Tyr Tyr Cys Phe Gln Tyr Tyr Ser Gly Trp Thr
                 85                  90                  95

Phe Gly Gly Gly Thr Lys Leu Glu Met Lys Arg
            100                 105

<210> SEQ ID NO 71
<211> LENGTH: 321
<212> TYPE: DNA
<213> ORGANISM: Rattus norvegicus

<400> SEQUENCE: 71
gacatccaga tgacccagtc tcctccagtc ctgtctacat ctgtgggaga cagagtcact      60
ctcaggtgca aaccaagtca gaatgttcat agcaagttag actggtatca gcagaaacat    120
ggagaggctc cgaaactcct gatatattat acacacaatt tgcaaacggg catcccatca    180
aggttcagtg gcagtggatc cggtacagat tacaccctca ccatcagcag cctgcagcct    240
gaagatgttg ccacatatta ctgttttcaa tattacagtg gtggacgtt cggtggaggc     300 accaagctgg aaatgaaacg g                                              321

<210> SEQ ID NO 72
<211> LENGTH: 110
<212> TYPE: PRT
<213> ORGANISM: Rattus norvegicus

<400> SEQUENCE: 72

Gln Phe Val Leu Thr Gln Pro Asn Ser Val Ser Thr Asn Leu Gly Ser
 1               5                  10                  15

Thr Val Lys Leu Ser Cys Lys Arg Ser Thr Gly Asn Ile Gly Asn Asn
             20                  25                  30

Tyr Val Asn Trp Tyr Gln Gln Tyr Glu Gly Arg Ser Pro Thr Thr Met
         35                  40                  45

Ile Tyr Arg Asp Asp Glu Arg Pro Asp Gly Val Pro Asp Arg Phe Ser
 50                  55                  60

Gly Ser Ile Asp Arg Ser Ser Asn Ser Ala Leu Leu Thr Ile Asn Asn
 65                  70                  75                  80

Val Gln Thr Glu Asp Glu Ala Asp Tyr Phe Cys Gln Ser Phe Ser Asn
                 85                  90                  95

Gly Met Phe Ile Phe Ala Gly Gly Thr Gln Leu Thr Val Leu
            100                 105                 110

<210> SEQ ID NO 73
<211> LENGTH: 330
<212> TYPE: DNA
<213> ORGANISM: Rattus norvegicus

<400> SEQUENCE: 73
cagtttgtac ttactcagcc aaactctgtg tctacgaatc tcggaagcac agtcaaactg      60
tcttgcaagc gcagcactgg taacattgga aacaattatg tgaactggta ccagcagtat    120
gagggaagat ctcccactac tatgatttat aggatgatg agagaccaga tggagttcct     180
gacaggttct ctggctccat tgacagatct tccaactcag cctcctgac aatcaataat     240 gtgcagactg aggatgaagc tgactacttc tgtcagtctt tcagtaacgg tatgtttatt    300
```
tttgccggtg aacccagct cactgtccta                                    330

<210> SEQ ID NO 74
<211> LENGTH: 110
<212> TYPE: PRT
<213> ORGANISM: Rattus norvegicus

<400> SEQUENCE: 74

Gln Phe Val Leu Thr Gln Pro Asn Ser Val Ser Thr Asn Leu Gly Ser
1               5                   10                  15

Thr Val Lys Leu Ser Cys Thr Arg Ser Ile Gly Asn Ile Gly Asn Asn
            20                  25                  30

Tyr Val Asn Trp Tyr Lys Gln Tyr Glu Gly Arg Ser Pro Thr Thr Met
        35                  40                  45

Ile Tyr Arg Asp Asp Glu Arg Pro Asp Gly Val Pro Asp Arg Phe Ser
    50                  55                  60

Gly Ser Ile Asp Arg Ser Ser Asn Ser Ala Leu Leu Thr Ile Asn Ser
65                  70                  75                  80

Val Gln Thr Glu Asp Glu Ala Asp Tyr Phe Cys Gln Ser Phe Ser Ser
                85                  90                  95

Gly Ile Phe Ile Phe Gly Gly Gly Thr Lys Leu Thr Val Leu
            100                 105                 110

<210> SEQ ID NO 75
<211> LENGTH: 330
<212> TYPE: DNA
<213> ORGANISM: Rattus norvegicus

<400> SEQUENCE: 75
cagtttgtac ttacgcagcc aaactctgtg tctacgaatc tcggaagcac agtcaaactg    60
tcttgcacgc gcagcattgg taacattgga acaattatg tgaattggta caagcagtat   120
gagggaagat ctcccaccac tatgatttat agggatgatg agagaccaga tggagttcct   180
gacaggttct ctggctccat tgacagatct tccaactcag ccctcctgac aatcaatagt   240
gtgcagactg aagatgaagc tgactacttc tgtcagtctt tcagtagtgg tatctttatt   300
tttggcggtg aaccaagct cactgtccta                                    330

<210> SEQ ID NO 76
<211> LENGTH: 107
<212> TYPE: PRT
<213> ORGANISM: Rattus norvegicus

<400> SEQUENCE: 76

Asp Ile Gln Met Thr Gln Ser Pro Pro Val Leu Ser Thr Ser Val Gly
1               5                   10                  15

Asp Arg Val Thr Leu Arg Cys Lys Ala Ser Gln Asn Val His Ser Lys
            20                  25                  30

Leu Asp Trp Tyr Gln Gln Lys His Gly Glu Ala Pro Lys Leu Leu Ile
        35                  40                  45

Tyr Tyr Thr His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Phe Gln Tyr Tyr Ser Gly Trp Thr
                85                  90                  95

Phe Gly Gly Gly Thr Lys Leu Glu Met Lys Arg
            100                 105

<210> SEQ ID NO 77
<211> LENGTH: 321
<212> TYPE: DNA
<213> ORGANISM: Rattus norvegicus

<400> SEQUENCE: 77

```
gacatccaga tgacccagtc tcctccagtc ctgtctacat ctgtgggaga cagagtcact    60
ctcaggtgca aagcaagtca gaatgttcat agtaagttag actggtatca gcagaaacat   120
ggagaggctc cgaaactcct gatatattat acacacaatt tgcaaacggg catcccatca   180
aggttcagtg gcagtggatc cggtacagat tacacccctca ccatcagcag cctgcagcct   240
gaagatgttg ccacatatta ctgttttcaa tattacagtg ggtggacgtt cggtggaggc   300
accaagctgg aaatgaaacg g                                             321
```

<210> SEQ ID NO 78
<211> LENGTH: 110
<212> TYPE: PRT
<213> ORGANISM: Rattus norvegicus

<400> SEQUENCE: 78

```
Gln Phe Val Leu Ser Gln Pro Asn Ser Val Ser Thr Asn Leu Gly Ser
1               5                   10                  15

Thr Val Lys Leu Ser Cys Lys Arg Ser Thr Gly Asn Ile Gly Ser Asn
            20                  25                  30

Tyr Val His Trp Tyr Gln Arg His Glu Gly Arg Ser Pro Thr Thr Leu
        35                  40                  45

Ile Tyr Arg Asp Asp Lys Arg Pro Asn Gly Val Pro Asp Arg Phe Ser
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Gly
                85                  90                  95

Gly Met Tyr Leu Phe Gly Gly Gly Thr Lys Leu Thr Val Leu
            100                 105                 110
```

<210> SEQ ID NO 79
<211> LENGTH: 330
<212> TYPE: DNA
<213> ORGANISM: Rattus norvegicus

<400> SEQUENCE: 79

```
cagtttgtgc ttagtcagcc aaactctgtg tcgacgaatc tcggaagcac agtcaaactg    60
tcttgcaagc gcagcactgg taacattgga agcaattatg tgcactggta ccagcgacat   120
gagggaagat ctcccaccac tctgatttat agggatgata agagaccaaa tggagttcct   180
gacaggtttt ctggctccat tgacagatct tccaactcag ccctcctgac aatcaataat   240
gtgcagactg aagatgaagc tgactacttc tgtcagtctt acagtggtgg tatgtatctt   300
ttcggcggtg gaaccaagct cactgtccta                                    330
```

<210> SEQ ID NO 80
<211> LENGTH: 110
<212> TYPE: PRT
<213> ORGANISM: Rattus norvegicus

<400> SEQUENCE: 80

Gln Phe Val Leu Thr Gln Pro Asn Ser Val Ser Thr Asn Leu Gly Ser
1               5                   10                  15

Thr Val Lys Leu Ser Cys Arg Arg Ser Ser Gly Asn Ile Gly Asn Asn
            20                  25                  30

Tyr Val Asn Trp Tyr Arg Gln His Glu Gly Arg Ser Pro Thr Thr Met
        35                  40                  45

Ile Tyr Arg Asp Asp Thr Arg Pro Asp Gly Val Pro Asn Arg Phe Ser
    50                  55                  60

Gly Ser Ile Asp Arg Ser Ser Asn Ser Ala Leu Leu Thr Ile Asn Asn
65                  70                  75                  80

Val Arg Pro Glu Asp Glu Ala Tyr Tyr Phe Cys Gln Ser Tyr Ser Gly
                85                  90                  95

Ser Ile Tyr Ile Phe Gly Gly Gly Thr Lys Leu Thr Val Leu
            100                 105                 110

<210> SEQ ID NO 81
<211> LENGTH: 330
<212> TYPE: DNA
<213> ORGANISM: Rattus norvegicus

<400> SEQUENCE: 81
cagtttgtgc ttactcagcc aaactctgtg tctacgaatc tcggaagcac agtcaaactg      60
tcttgcaggc gcagcagtgg taacattgga acaattatg taaactggta ccgacagcat     120
gagggaagat ctcccaccac tatgatttat agggatgata cgagaccaga tggagttcct     180
aacaggttct ctggctccat tgacagatct tccaactcag ccctcctgac aatcaataat     240
gtgcggcctg aggatgaagc ttactacttc tgtcagtctt acagtggtag tatctatatt     300
ttcggcggtg ggaccaagct cactgtcctg                                      330

<210> SEQ ID NO 82
<211> LENGTH: 108
<212> TYPE: PRT
<213> ORGANISM: Rattus norvegicus

<400> SEQUENCE: 82

Asp Ile Val Leu Thr Gln Ser Pro Ala Thr Leu Ser Val Thr Pro Gly
1               5                   10                  15

Glu Ser Val Ser Leu Ser Cys Arg Ala Ser Gln Gly Ile Ser Thr Ser
            20                  25                  30

Ile His Trp Tyr Gln Gln Lys Ser Asn Glu Ser Pro Arg Leu Leu Ile
        35                  40                  45

Lys Tyr Ala Ser Gln Ser Met Ser Gly Ile Pro Ser Arg Phe Ser Gly
    50                  55                  60

Ser Gly Ser Gly Thr Asp Phe Thr Leu Arg Ile Asn Arg Val Glu Ser
65                  70                  75                  80

Glu Asp Phe Ser Val Tyr Tyr Cys Gln Gln Ser Tyr Asn Leu Pro Leu
                85                  90                  95

Thr Phe Gly Ser Gly Thr Lys Leu Glu Ile Lys Arg
            100                 105

<210> SEQ ID NO 83
<211> LENGTH: 324
<212> TYPE: DNA
<213> ORGANISM: Rattus norvegicus

<400> SEQUENCE: 83
gacatcgtgc tgactcagtc tccagccacc ctgtctgtga ctccaggaga gagtgtgagt      60

```
ctctcgtgca gggccagtca gggtattagt actagcatac actggtatca gcaaaaatca    120
aatgagtctc caaggcttct catcaagtat gcttcccagt ccatgtctgg aatcccctcc    180
aggttcagtg gcagtggatc agggacagat ttcactctca gaatcaacag agtagaatct    240
gaggattttt cagtttatta ctgtcaacag agttacaact tgcccctcac gttcggctca    300
gggacgaagt tggaaataaa acgg                                           324
```

<210> SEQ ID NO 84
<211> LENGTH: 107
<212> TYPE: PRT
<213> ORGANISM: Rattus norvegicus

<400> SEQUENCE: 84

```
Asp Ile Gln Met Thr Gln Ser Pro Val Leu Ser Ala Ala Val Gly
1               5                   10                  15

Asp Arg Val Thr Leu Ser Cys Lys Ala Ser Arg Ser Leu Asn Lys Asn
            20                  25                  30

Leu Asp Trp Tyr Gln Gln Lys His Gly Glu Thr Pro Lys Leu Leu Ile
        35                  40                  45

Tyr His Thr His Asn Leu Gln Thr Gly Ile Pro Ser Arg Phe Ser Gly
    50                  55                  60

Ser Gly Ser Asp Thr Asp Tyr Thr Leu Thr Ile Ser Ser Leu Gln Thr
65                  70                  75                  80

Glu Asp Val Ala Thr Tyr Tyr Cys Tyr Gln Tyr His Ser Gly Trp Thr
                85                  90                  95

Phe Gly Gly Gly Thr Arg Leu Glu Leu Arg Arg
            100                 105
```

<210> SEQ ID NO 85
<211> LENGTH: 321
<212> TYPE: DNA
<213> ORGANISM: Rattus norvegicus

<400> SEQUENCE: 85

```
gacatccaga tgacccagtc tcctccagtc ctgtctgcag ctgtgggaga cagagtcact    60
ctcagctgca agcaagtcg gagtcttaat aagaacttag actggtatca gcaaaagcat    120
ggagaaactc caaaactcct gatatatcat acacacaatt tgcaacgggg catcccttcg    180
aggttcagtg gcagtggatc tgatactgat tacacactca ccatcagtag cctgcagact    240
gaagatgttg ccacatatta ctgctatcag tatcacagtg gtggacgtt cggtgggggc    300 accaggctgg aattgagacg g                                              321
```

<210> SEQ ID NO 86
<211> LENGTH: 110
<212> TYPE: PRT
<213> ORGANISM: Rattus norvegicus

<400> SEQUENCE: 86

```
Gln Phe Val Leu Ser Gln Pro Asn Ser Val Ser Thr Asn Leu Gly Ser
1               5                   10                  15

Thr Val Lys Leu Ser Cys Lys Arg Ser Thr Gly Asn Ile Gly Ser Asn
            20                  25                  30

Tyr Val His Trp Tyr Gln Arg His Glu Gly Arg Ser Pro Thr Thr Met
        35                  40                  45

Ile Tyr Arg Asp Asp Lys Arg Pro Asn Gly Val Pro Asp Arg Phe Ser
    50                  55                  60
```

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Gly
                85                  90                  95

Gly Met Tyr Leu Phe Gly Gly Gly Thr Thr Leu Thr Val Leu
            100                 105                 110

<210> SEQ ID NO 87
<211> LENGTH: 330
<212> TYPE: DNA
<213> ORGANISM: Rattus norvegicus

<400> SEQUENCE: 87
cagtttgtgc ttagtcagcc aaactctgtg tcgacgaatc tcggaagcac agtcaaactg    60
tcttgcaagc gcagcactgg taacattgga agcaattatg tgcactggta ccagcgacat   120
gagggaagat ctcccaccac tatgatttat agggatgata agagaccaaa cggagttcct   180
gacaggtttt ctggctccat tgacagatct tccaactcag ccctcctgac aatcaataat   240
gtgcagactg aagatgaagc tgactacttc tgtcagtctt acagtggtgg tatgtatctt   300
ttcggcggtg gaaccacgct cactgtccta                                    330

<210> SEQ ID NO 88
<211> LENGTH: 110
<212> TYPE: PRT
<213> ORGANISM: Rattus norvegicus

<400> SEQUENCE: 88

Gln Phe Val Leu Thr Gln Pro Asn Ser Val Ser Thr Asn Leu Gly Ser
1               5                   10                  15

Thr Val Lys Leu Ser Cys Thr Arg Ser Ile Gly Asn Ile Gly Asn Asn
            20                  25                  30

Tyr Val Asn Trp Tyr Lys Gln Tyr Glu Gly Arg Ser Pro Thr Thr Met
        35                  40                  45

Ile Tyr Arg Asp Asp Glu Arg Pro Asp Gly Val Pro Asp Arg Phe Ser
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Phe Ser Ser
                85                  90                  95

Gly Met Phe Ile Phe Gly Gly Gly Thr Lys Leu Thr Val Leu
            100                 105                 110

<210> SEQ ID NO 89
<211> LENGTH: 330
<212> TYPE: DNA
<213> ORGANISM: Rattus norvegicus

<400> SEQUENCE: 89
cagtttgtac ttacgcagcc aaactctgtg tctacgaatc tcggaagcac agtcaaactg    60
tcttgcacgc gcagcattgg taacattgga acaattatg tgaactggta taagcagtat    120
gagggaagat ctcccaccac tatgatttat agggatgatg agagaccaga tggagttcct   180
gacaggttct ctggctccat tgacagatct tccaactcag ccctcctgac aatcaataat   240
gtgcagactg aagatgaagc tgactacttc tgtcagtctt tcagtagtgg tatgtttatt   300
tttggcggtg gaaccaaact cactgtccta                                    330

<210> SEQ ID NO 90
<211> LENGTH: 108
<212> TYPE: PRT
<213> ORGANISM: Rattus norvegicus

<400> SEQUENCE: 90

Asp Ile Val Leu Thr Gln Ser Pro Ala Thr Leu Ser Val Thr Pro Gly
1               5                   10                  15

Glu Ser Val Ser Leu Ser Cys Arg Ala Ser Gln Gly Ile Ser Thr Ser
            20                  25                  30

Ile His Trp Tyr Gln Gln Lys Ser Asn Gly Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Arg Ile Asn Arg Val Glu Ser
65                  70                  75                  80

Glu Asp Phe Ser Val Tyr Tyr Cys Gln Gln Thr Tyr Ser Leu Pro Leu
                85                  90                  95

Thr Phe Gly Ser Gly Thr Arg Leu Glu Ile Lys Arg
            100                 105

<210> SEQ ID NO 91
<211> LENGTH: 324
<212> TYPE: DNA
<213> ORGANISM: Rattus norvegicus

<400> SEQUENCE: 91
gacatcgtgc tgactcagtc tccagccacc ctgtctgtga ctccaggaga gagtgtgagt      60
ctctcctgca gggccagtca gggtattagt actagcattc actggtatca gcaaaaatca    120
aatgggtctc caaggcttct catcaagtat gcttcccagt ccatctctgg aatcccctcc    180
aggttcagtg gcagtggatc aggacagat ttcactctca gaatcaacag agtagaatct     240
gaagattttt cagtttatta ctgtcaacag acttacagct tgcccctcac gttcggctca    300
gggacgaggt tggaaataaa acgg                                           324

<210> SEQ ID NO 92
<211> LENGTH: 107
<212> TYPE: PRT
<213> ORGANISM: Rattus norvegicus

<400> SEQUENCE: 92

Asp Ile Gln Met Thr Gln Ser Pro Pro Val Leu Ser Ala Ser Val Gly
1               5                   10                  15

Asp Arg Val Thr Leu Ser Cys Lys Ala Ser Gln Ser Val His Asn Lys
            20                  25                  30

Leu Asp Trp Tyr Gln Gln Lys His Gly Glu Ala Pro Lys Leu Leu Ile
        35                  40                  45

Tyr Tyr Thr His Asn Leu Gln Thr Gly Ile Pro Ser Arg Phe Ser Gly
    50                  55                  60

Ser Gly Ser Gly Ser Asp Tyr Thr Leu Thr Ile Ser Ser Leu Arg Ala
65                  70                  75                  80

Glu Asp Val Ala Thr Tyr Tyr Cys Phe Gln Tyr Tyr Ser Gly Trp Thr
                85                  90                  95

Phe Gly Gly Gly Thr Lys Leu Glu Met Lys Arg
            100                 105

<210> SEQ ID NO 93
<211> LENGTH: 321
<212> TYPE: DNA
<213> ORGANISM: Rattus norvegicus

<400> SEQUENCE: 93

```
gacatccaga tgacccagtc tcccccagtc ctgtctgcat ctgtgggaga cagagtcact    60
ctcagctgca aagcaagtca gagtgttcat aacaagttag actggtatca gcaaaagcat   120
ggagaggctc cgaaactcct gatttattat acacacaatt tacaaacggg catcccatca   180
aggttcagtg gcagtggatc cggttcagat tacacactca ccatcagcag cctgcgggct   240
gaagatgttg ccacatatta ctgttttcaa tattacagtg ggtggacgtt cggtggaggc   300
accaagctgg aaatgaaacg g                                             321
```

<210> SEQ ID NO 94
<211> LENGTH: 108
<212> TYPE: PRT
<213> ORGANISM: Rattus norvegicus

<400> SEQUENCE: 94

```
Asp Ile Val Leu Thr Gln Ser Pro Pro Thr Leu Ser Val Thr Pro Gly
1               5                   10                  15
Glu Ser Val Ser Leu Ser Cys Arg Ala Ser Gln Gly Ile Ser Thr Ser
            20                  25                  30
Ile His Trp Tyr Gln Gln Arg Ser Asn Glu Ser Pro Arg Leu Leu Ile
        35                  40                  45
Lys Tyr Ala Ser Gln Ser Ile Ala Gly Ile Pro Ser Arg Phe Ser Gly
    50                  55                  60
Ser Gly Ser Gly Thr Asp Phe Ile Leu Ser Ile Asn Arg Val Glu Ser
65                  70                  75                  80
Glu Asp Phe Ser Val Tyr Tyr Cys Gln Gln Thr Tyr Ser Leu Pro Leu
                85                  90                  95
Thr Phe Gly Pro Gly Thr Lys Leu Glu Val Lys Arg
            100                 105
```

<210> SEQ ID NO 95
<211> LENGTH: 324
<212> TYPE: DNA
<213> ORGANISM: Rattus norvegicus

<400> SEQUENCE: 95

```
gacatcgtgc tgactcagtc tccacccacc ctgtctgtga ctccaggaga gagtgtgagt    60
ctctcctgca gggccagtca gggtattagt actagcatac tggtatcaa caaagatca    120
aatgagtctc caaggcttct catcaagtat gcttcccagt ccattgctgg aatcccctcc   180
aggttcagtg gcagtggatc aggacagat ttcatcctca gtatcaacag agtagaatct   240
gaagatttt cagtttatta ctgtcaacag acttacagct gccctcac gttcggccca    300
gggacgaagt tggaagtaaa acgg                                           324
```

<210> SEQ ID NO 96
<211> LENGTH: 112
<212> TYPE: PRT
<213> ORGANISM: Rattus norvegicus

<400> SEQUENCE: 96

```
Asp Asp Ile Val Leu Thr Gln Ser Pro Ala Leu Ala Pro Ser Leu Gly
1               5                   10                  15
```

```
Gln Arg Ala Thr Ile Ser Cys Arg Ala Ser Gln Ser Val Arg Met Ser
                20                  25                  30

Gly Tyr Asn Leu Met His Trp Tyr Gln Gln Lys Pro Gly Gln Gln Pro
            35                  40                  45

Lys Leu Leu Ile Tyr Asp Ala Ser Lys Leu Ala Ser Gly Ile Pro Ala
 50                  55                  60

Arg Phe Ser Gly Ser Gly Ser Gly Thr Asp Phe Thr Leu Thr Ile Asp
 65                  70                  75                  80

Pro Val Gln Ser Asp Asp Ile Ala Thr Tyr Tyr Cys Gln Gln Ser Lys
                85                  90                  95

Asp Asp Pro Tyr Thr Phe Gly Ala Gly Thr Lys Leu Glu Leu Arg Arg
            100                 105                 110

<210> SEQ ID NO 97
<211> LENGTH: 336
<212> TYPE: DNA
<213> ORGANISM: Rattus norvegicus

<400> SEQUENCE: 97
gatgacattg tgctgaccca gtctccagct ttggctccgt ctctagggca gagggccaca    60
atctcctgta gagccagcca aagtgtcagg atgtctggct ataatctcat gcactggtac   120
caacagaaac caggacaaca gcccaaactc ctcatctatg atgcatccaa gctagcatct   180
gggatccctg ccaggttcag tggcagtggg tctgggacag acttcaccct caccattgat   240
cctgtgcagt ctgatgatat tgcaacctat tactgtcagc agagtaagga tgatccgtac   300
acgtttggag ctgggaccaa gctggaactg cgacgg                              336

<210> SEQ ID NO 98
<211> LENGTH: 5
<212> TYPE: PRT
<213> ORGANISM: Rattus norvegicus

<400> SEQUENCE: 98

Asn His Tyr Met Ala
 1               5

<210> SEQ ID NO 99
<211> LENGTH: 5
<212> TYPE: PRT
<213> ORGANISM: Rattus norvegicus

<400> SEQUENCE: 99

Asn Tyr Tyr Met Thr
 1               5

<210> SEQ ID NO 100
<211> LENGTH: 5
<212> TYPE: PRT
<213> ORGANISM: Rattus norvegicus

<400> SEQUENCE: 100

Arg Tyr Tyr Val His
 1               5

<210> SEQ ID NO 101
<211> LENGTH: 5
<212> TYPE: PRT
<213> ORGANISM: Rattus norvegicus

<400> SEQUENCE: 101
```

Asp Tyr Tyr Met Ala
1               5

<210> SEQ ID NO 102
<211> LENGTH: 5
<212> TYPE: PRT
<213> ORGANISM: Rattus norvegicus

<400> SEQUENCE: 102

Asn Tyr Tyr Met Ala
1               5

<210> SEQ ID NO 103
<211> LENGTH: 5
<212> TYPE: PRT
<213> ORGANISM: Rattus norvegicus

<400> SEQUENCE: 103

Glu Thr Trp Met Ser
1               5

<210> SEQ ID NO 104
<211> LENGTH: 5
<212> TYPE: PRT
<213> ORGANISM: Rattus norvegicus

<400> SEQUENCE: 104

Ser Tyr Phe Ile His
1               5

<210> SEQ ID NO 105
<211> LENGTH: 5
<212> TYPE: PRT
<213> ORGANISM: Rattus norvegicus

<400> SEQUENCE: 105

Asp Thr Trp Met Ser
1               5

<210> SEQ ID NO 106
<211> LENGTH: 5
<212> TYPE: PRT
<213> ORGANISM: Rattus norvegicus

<400> SEQUENCE: 106

Ala Tyr Tyr Val His
1               5

<210> SEQ ID NO 107
<211> LENGTH: 5
<212> TYPE: PRT
<213> ORGANISM: Rattus norvegicus

<400> SEQUENCE: 107

Ser Asn Tyr Ile Thr
1               5

<210> SEQ ID NO 108
<211> LENGTH: 17
<212> TYPE: PRT
<213> ORGANISM: Rattus norvegicus

<400> SEQUENCE: 108

Thr Ile Ser Thr Gly Gly Gly Asn Thr Tyr Tyr Arg Asp Ser Val Lys
1               5                   10                  15

Gly

<210> SEQ ID NO 109
<211> LENGTH: 17
<212> TYPE: PRT
<213> ORGANISM: Rattus norvegicus

<400> SEQUENCE: 109

Ser Ile Ser Ser Ser Gly Gly Asn Thr Tyr Tyr Arg Asp Ser Val Arg
1               5                   10                  15

Gly

<210> SEQ ID NO 110
<211> LENGTH: 17
<212> TYPE: PRT
<213> ORGANISM: Rattus norvegicus

<400> SEQUENCE: 110

Arg Ile Asp Pro Glu Asp Asp Thr Thr Lys Tyr Ser Glu Lys Phe Lys
1               5                   10                  15

Asn

<210> SEQ ID NO 111
<211> LENGTH: 17
<212> TYPE: PRT
<213> ORGANISM: Rattus norvegicus

<400> SEQUENCE: 111

Ser Ile Ser Thr Gly Gly Gly Asn Thr Tyr Tyr Arg Asp Ser Val Lys
1               5                   10                  15

Gly

<210> SEQ ID NO 112
<211> LENGTH: 17
<212> TYPE: PRT
<213> ORGANISM: Rattus norvegicus

<400> SEQUENCE: 112

Arg Ile Asp Pro Glu Asp Asp Thr Thr Lys Tyr Ser Glu Lys Phe Lys
1               5                   10                  15

Lys

<210> SEQ ID NO 113
<211> LENGTH: 17
<212> TYPE: PRT
<213> ORGANISM: Rattus norvegicus

<400> SEQUENCE: 113

Ala Ile Ser Thr Gly Gly Gly Asn Thr Tyr Tyr Arg Asp Ser Val Lys
1               5                   10                  15

Gly

<210> SEQ ID NO 114
<211> LENGTH: 17
<212> TYPE: PRT
<213> ORGANISM: Rattus norvegicus

<400> SEQUENCE: 114

Ser Ile Ser Thr Gly Gly Gly Tyr Thr Tyr Tyr Arg Asp Ser Val Lys
1               5                   10                  15

Gly

<210> SEQ ID NO 115
<211> LENGTH: 19
<212> TYPE: PRT
<213> ORGANISM: Rattus norvegicus

<400> SEQUENCE: 115

Leu Ile Lys Asp Lys Asn Ser Asn Tyr Glu Ala Asn Tyr Ala Glu Ser
1               5                   10                  15

Val Lys Gly

<210> SEQ ID NO 116
<211> LENGTH: 17
<212> TYPE: PRT
<213> ORGANISM: Rattus norvegicus

<400> SEQUENCE: 116

Lys Ile Asp Pro Glu Asp Asp Ser Thr Lys Tyr Gly Glu Lys Phe Lys
1               5                   10                  15

Asn

<210> SEQ ID NO 117
<211> LENGTH: 17
<212> TYPE: PRT
<213> ORGANISM: Rattus norvegicus

<400> SEQUENCE: 117

Arg Ile Asp Pro Glu Asp Asp Ser Thr Lys Tyr Ser Glu Lys Phe Lys
1               5                   10                  15

Asn

<210> SEQ ID NO 118
<211> LENGTH: 19
<212> TYPE: PRT
<213> ORGANISM: Rattus norvegicus

<400> SEQUENCE: 118

Leu Ile Lys Asp Lys Asn Ser Asn Ser Glu Ala Asn Tyr Ala Glu Ser
1               5                   10                  15

Ile Lys Gly

<210> SEQ ID NO 119
<211> LENGTH: 17
<212> TYPE: PRT
<213> ORGANISM: Rattus norvegicus

<400> SEQUENCE: 119

Tyr Ile Asn Thr Gly Ser Gly Lys Thr Tyr Tyr Asn Glu Lys Phe Lys
1               5                   10                  15

Gly

<210> SEQ ID NO 120
<211> LENGTH: 12
<212> TYPE: PRT
<213> ORGANISM: Rattus norvegicus

<400> SEQUENCE: 120

Gln Asp Tyr Thr Asn Tyr Met Gly Gly Phe Ala Tyr
1               5                   10

```
<210> SEQ ID NO 121
<211> LENGTH: 10
<212> TYPE: PRT
<213> ORGANISM: Rattus norvegicus

<400> SEQUENCE: 121

Glu Gly Tyr Arg Gly Arg Tyr Phe Asp Tyr
1               5                   10

<210> SEQ ID NO 122
<211> LENGTH: 6
<212> TYPE: PRT
<213> ORGANISM: Rattus norvegicus

<400> SEQUENCE: 122

Leu Thr Gly Leu Asp Tyr
1               5

<210> SEQ ID NO 123
<211> LENGTH: 12
<212> TYPE: PRT
<213> ORGANISM: Rattus norvegicus

<400> SEQUENCE: 123

Gln Asp Tyr Ser Asn Tyr Met Gly Gly Phe Ala Tyr
1               5                   10

<210> SEQ ID NO 124
<211> LENGTH: 9
<212> TYPE: PRT
<213> ORGANISM: Rattus norvegicus

<400> SEQUENCE: 124

Asn Pro Tyr Gly Asn Tyr Phe Asp Tyr
1               5

<210> SEQ ID NO 125
<211> LENGTH: 6
<212> TYPE: PRT
<213> ORGANISM: Rattus norvegicus

<400> SEQUENCE: 125

Cys Trp Glu Leu Pro Tyr
1               5

<210> SEQ ID NO 126
<211> LENGTH: 14
<212> TYPE: PRT
<213> ORGANISM: Rattus norvegicus

<400> SEQUENCE: 126

His Glu Asp Phe Tyr Tyr Tyr Ser Ser Tyr Tyr Phe Asp Tyr
1               5                   10

<210> SEQ ID NO 127
<211> LENGTH: 14
<212> TYPE: PRT
<213> ORGANISM: Rattus norvegicus

<400> SEQUENCE: 127

His Glu Asp Phe Tyr Tyr Tyr Ser Gly Tyr Tyr Phe Asp Tyr
1               5                   10

<210> SEQ ID NO 128
<211> LENGTH: 9
```

```
<212> TYPE: PRT
<213> ORGANISM: Rattus norvegicus

<400> SEQUENCE: 128

Leu Thr Gly Val Asp Tyr Phe Asp Asp
1               5

<210> SEQ ID NO 129
<211> LENGTH: 13
<212> TYPE: PRT
<213> ORGANISM: Rattus norvegicus

<400> SEQUENCE: 129

Thr Arg Ser Ile Gly Asn Ile Gly Asn Asn Tyr Val Asn
1               5                   10

<210> SEQ ID NO 130
<211> LENGTH: 13
<212> TYPE: PRT
<213> ORGANISM: Rattus norvegicus

<400> SEQUENCE: 130

Lys Arg Thr Thr Gly Asn Ile Gly Ser Asn Tyr Val Asn
1               5                   10

<210> SEQ ID NO 131
<211> LENGTH: 11
<212> TYPE: PRT
<213> ORGANISM: Rattus norvegicus

<400> SEQUENCE: 131

Lys Pro Ser Gln Asn Val His Ser Lys Leu Asp
1               5                   10

<210> SEQ ID NO 132
<211> LENGTH: 13
<212> TYPE: PRT
<213> ORGANISM: Rattus norvegicus

<400> SEQUENCE: 132

Lys Arg Ser Thr Gly Asn Ile Gly Asn Asn Tyr Val Asn
1               5                   10

<210> SEQ ID NO 133
<211> LENGTH: 11
<212> TYPE: PRT
<213> ORGANISM: Rattus norvegicus

<400> SEQUENCE: 133

Lys Ala Ser Gln Asn Val His Ser Lys Leu Asp
1               5                   10

<210> SEQ ID NO 134
<211> LENGTH: 13
<212> TYPE: PRT
<213> ORGANISM: Rattus norvegicus

<400> SEQUENCE: 134

Lys Arg Ser Thr Gly Asn Ile Gly Ser Asn Tyr Val His
1               5                   10

<210> SEQ ID NO 135
<211> LENGTH: 13
<212> TYPE: PRT
<213> ORGANISM: Rattus norvegicus
```

<400> SEQUENCE: 135

Arg Arg Ser Ser Gly Asn Ile Gly Asn Asn Tyr Val Asn
1               5                   10

<210> SEQ ID NO 136
<211> LENGTH: 11
<212> TYPE: PRT
<213> ORGANISM: Rattus norvegicus

<400> SEQUENCE: 136

Arg Ala Ser Gln Gly Ile Ser Thr Ser Ile His
1               5                   10

<210> SEQ ID NO 137
<211> LENGTH: 11
<212> TYPE: PRT
<213> ORGANISM: Rattus norvegicus

<400> SEQUENCE: 137

Lys Ala Ser Arg Ser Leu Asn Lys Asn Leu Asp
1               5                   10

<210> SEQ ID NO 138
<211> LENGTH: 11
<212> TYPE: PRT
<213> ORGANISM: Rattus norvegicus

<400> SEQUENCE: 138

Lys Ala Ser Gln Ser Val His Asn Lys Leu Asp
1               5                   10

<210> SEQ ID NO 139
<211> LENGTH: 15
<212> TYPE: PRT
<213> ORGANISM: Rattus norvegicus

<400> SEQUENCE: 139

Arg Ala Ser Gln Ser Val Arg Met Ser Gly Tyr Asn Leu Met His
1               5                   10                  15

<210> SEQ ID NO 140
<211> LENGTH: 7
<212> TYPE: PRT
<213> ORGANISM: Rattus norvegicus

<400> SEQUENCE: 140

Arg Asp Asp Glu Arg Pro Asp
1               5

<210> SEQ ID NO 141
<211> LENGTH: 7
<212> TYPE: PRT
<213> ORGANISM: Rattus norvegicus

<400> SEQUENCE: 141

Tyr Thr His Asn Leu Gln Thr
1               5

<210> SEQ ID NO 142
<211> LENGTH: 7
<212> TYPE: PRT
<213> ORGANISM: Rattus norvegicus

<400> SEQUENCE: 142

```
Arg Asp Asp Lys Arg Pro Asn
1               5

<210> SEQ ID NO 143
<211> LENGTH: 7
<212> TYPE: PRT
<213> ORGANISM: Rattus norvegicus

<400> SEQUENCE: 143

Arg Asp Asp Thr Arg Pro Asp
1               5

<210> SEQ ID NO 144
<211> LENGTH: 7
<212> TYPE: PRT
<213> ORGANISM: Rattus norvegicus

<400> SEQUENCE: 144

Tyr Ala Ser Gln Ser Met Ser
1               5

<210> SEQ ID NO 145
<211> LENGTH: 7
<212> TYPE: PRT
<213> ORGANISM: Rattus norvegicus

<400> SEQUENCE: 145

His Thr His Asn Leu Gln Thr
1               5

<210> SEQ ID NO 146
<211> LENGTH: 7
<212> TYPE: PRT
<213> ORGANISM: Rattus norvegicus

<400> SEQUENCE: 146

Tyr Ala Ser Gln Ser Ile Ser
1               5

<210> SEQ ID NO 147
<211> LENGTH: 7
<212> TYPE: PRT
<213> ORGANISM: Rattus norvegicus

<400> SEQUENCE: 147

Tyr Ala Ser Gln Ser Ile Ala
1               5

<210> SEQ ID NO 148
<211> LENGTH: 7
<212> TYPE: PRT
<213> ORGANISM: Rattus norvegicus

<400> SEQUENCE: 148

Asp Ala Ser Lys Leu Ala Ser
1               5

<210> SEQ ID NO 149
<211> LENGTH: 9
<212> TYPE: PRT
<213> ORGANISM: Rattus norvegicus

<400> SEQUENCE: 149

Gln Ser Phe Ser Ser Gly Ile Phe Ile
```

```
1               5
```

<210> SEQ ID NO 150
<211> LENGTH: 8
<212> TYPE: PRT
<213> ORGANISM: Rattus norvegicus

<400> SEQUENCE: 150

```
Gln Ser Tyr Ser Ser Gly Ile Ile
1               5
```

<210> SEQ ID NO 151
<211> LENGTH: 9
<212> TYPE: PRT
<213> ORGANISM: Rattus norvegicus

<400> SEQUENCE: 151

```
Phe Gln Tyr Tyr Ser Gly Trp Thr Phe
1               5
```

<210> SEQ ID NO 152
<211> LENGTH: 9
<212> TYPE: PRT
<213> ORGANISM: Rattus norvegicus

<400> SEQUENCE: 152

```
Gln Ser Phe Ser Asn Gly Met Phe Ile
1               5
```

<210> SEQ ID NO 153
<211> LENGTH: 9
<212> TYPE: PRT
<213> ORGANISM: Rattus norvegicus

<400> SEQUENCE: 153

```
Gln Ser Tyr Ser Gly Gly Met Tyr Leu
1               5
```

<210> SEQ ID NO 154
<211> LENGTH: 9
<212> TYPE: PRT
<213> ORGANISM: Rattus norvegicus

<400> SEQUENCE: 154

```
Gln Ser Tyr Ser Gly Ser Ile Tyr Ile
1               5
```

<210> SEQ ID NO 155
<211> LENGTH: 9
<212> TYPE: PRT
<213> ORGANISM: Rattus norvegicus

<400> SEQUENCE: 155

```
Gln Gln Ser Tyr Asn Leu Pro Leu Thr
1               5
```

<210> SEQ ID NO 156
<211> LENGTH: 9
<212> TYPE: PRT
<213> ORGANISM: Rattus norvegicus

<400> SEQUENCE: 156

```
Tyr Gln Tyr His Ser Gly Trp Thr Phe
1               5
```

```
<210> SEQ ID NO 157
<211> LENGTH: 9
<212> TYPE: PRT
<213> ORGANISM: Rattus norvegicus

<400> SEQUENCE: 157

Gln Ser Phe Ser Ser Gly Met Phe Ile
1               5

<210> SEQ ID NO 158
<211> LENGTH: 9
<212> TYPE: PRT
<213> ORGANISM: Rattus norvegicus

<400> SEQUENCE: 158

Gln Gln Thr Tyr Ser Leu Pro Leu Thr
1               5

<210> SEQ ID NO 159
<211> LENGTH: 9
<212> TYPE: PRT
<213> ORGANISM: Rattus norvegicus

<400> SEQUENCE: 159

Gln Gln Ser Lys Asp Asp Pro Tyr Thr
1               5

<210> SEQ ID NO 160
<211> LENGTH: 557
<212> TYPE: PRT
<213> ORGANISM: Artificial Sequence
<220> FEATURE:
<223> OTHER INFORMATION: Homo sapiens

<400> SEQUENCE: 160

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Asp Tyr Lys Asp Asp Asp Lys Gly Val Lys
    130                 135                 140

Asp Arg Gly Ala Gly Leu Leu Gln Ser Val Phe Ile Cys Ser Phe Met
145                 150                 155                 160

Val Ala Ala Pro Ile Phe Gly Tyr Leu Gly Asp Arg Phe Asn Arg Lys
                165                 170                 175

Val Ile Leu Ser Cys Gly Ile Phe Phe Trp Ser Ala Val Thr Phe Ser
            180                 185                 190
```

```
Ser Ser Phe Ile Pro Gln Gln Tyr Phe Trp Leu Leu Val Leu Ser Arg
        195                 200                 205

Gly Leu Val Gly Ile Gly Glu Ala Ser Tyr Ser Thr Ile Ala Pro Thr
210                 215                 220

Ile Ile Gly Asp Leu Phe Thr Lys Asn Thr Arg Thr Leu Met Leu Ser
225                 230                 235                 240

Val Phe Tyr Phe Ala Ile Pro Leu Gly Ser Gly Leu Gly Tyr Ile Thr
                245                 250                 255

Gly Ser Ser Val Lys Gln Ala Ala Gly Asp Trp His Trp Ala Leu Arg
                260                 265                 270

Val Ser Pro Val Leu Gly Met Ile Thr Gly Thr Leu Ile Leu Ile Leu
            275                 280                 285

Val Pro Ala Thr Lys Arg Gly His Ala Asp Gln Leu Gly Asp Gln Leu
290                 295                 300

Lys Ala Arg Thr Ser Trp Leu Arg Asp Met Lys Ala Leu Ile Arg Asn
305                 310                 315                 320

Arg Ser Tyr Val Phe Ser Ser Leu Ala Thr Ser Ala Val Ser Phe Ala
                325                 330                 335

Thr Gly Ala Leu Gly Met Trp Ile Pro Leu Tyr Leu His Arg Ala Gln
                340                 345                 350

Val Val Gln Lys Thr Ala Glu Thr Cys Asn Ser Pro Pro Cys Gly Ala
            355                 360                 365

Lys Asp Ser Leu Ile Phe Gly Ala Ile Thr Cys Phe Thr Gly Phe Leu
370                 375                 380

Gly Val Val Thr Gly Ala Gly Ala Thr Arg Trp Cys Arg Leu Lys Thr
385                 390                 395                 400

Gln Arg Ala Asp Pro Leu Val Cys Ala Val Gly Met Leu Gly Ser Ala
                405                 410                 415

Ile Phe Ile Cys Leu Ile Phe Val Ala Ala Lys Ser Ser Ile Val Gly
                420                 425                 430

Ala Tyr Ile Cys Ile Phe Val Gly Glu Thr Leu Leu Phe Ser Asn Trp
            435                 440                 445

Ala Ile Thr Ala Asp Ile Leu Met Tyr Val Val Ile Pro Thr Arg Arg
450                 455                 460

Ala Thr Ala Val Ala Leu Gln Ser Phe Thr Ser His Leu Leu Gly Asp
465                 470                 475                 480

Ala Gly Ser Pro Tyr Leu Ile Gly Phe Ile Ser Asp Leu Ile Arg Gln
                485                 490                 495

Ser Thr Lys Asp Ser Pro Leu Trp Glu Phe Leu Ser Leu Gly Tyr Ala
                500                 505                 510

Leu Met Leu Cys Pro Phe Val Val Val Leu Gly Gly Met Phe Phe Leu
            515                 520                 525

Ala Thr Ala Leu Phe Phe Val Ser Asp Arg Ala Arg Ala Glu Gln Gln
530                 535                 540

Val Asn Gln Leu Ala Met Pro Pro Ala Ser Val Lys Val
545                 550                 555

<210> SEQ ID NO 161
<211> LENGTH: 1674
<212> TYPE: DNA
<213> ORGANISM: Artificial Sequence
<220> FEATURE:
<223> OTHER INFORMATION: Homo sapiens

<400> SEQUENCE: 161
```

```
atgatgtgcc tggaatgcgc ctcggcggcg gcgggcggcg cggaggagga ggaggcggac    60
gcggagcggc ggcgccggcg ccggggggcg cagcgagggg ctggcggtag cggttgctgc   120
ggggcgcggg gcgcgggcgg cgctggagtc tcggccgcgg gcgatgaggt gcagacgctg   180
tcgggcagcg taaggcgggc cccgaccgga ccccccggca ccccggcac ccccggctgc    240
gcagctactg caaagggccc cggcgctcag cagcccaaac cggccagctt gggccgcggg   300
cgggggcag ccgccgccat cctcagcttg ggcaacgtgc tcaactacct ggacaggtac    360
accgtggcag gcgtccttct ggacatccag cagcactttg attacaagga tgacgacgat   420
aagggggtca aggaccgagg cgccggcctg ctgcagtcag tgttcatctg tagcttcatg   480
gtggctgccc ccatcttcgg ctacctgggc gaccgcttca caggaaggt gattctcagc    540
tgcggcattt tcttctggtc ggccgtcacc ttctccagct ccttcattcc ccagcagtac   600
ttctggctgc tggtcctgtc ccgggggctg gtgggcatcg gggaggccag ctactccacc   660
atcgccccca ctatcattgg cgacctcttc accaagaaca cgcgtacgct catgctgtcc   720
gtcttctact tcgccatccc actgggcagt ggcctgggct acattactgg ctccagcgtg   780
aagcaggcag ccggagactg gcactgggca ttgcgggtgt ccctgtcct gggcatgatc    840
acaggaacac tcatcctcat tctggtccca gccactaaaa ggggtcatgc cgaccagctc   900
ggggaccagc tcaaggcccg gacctcatgg ctccgagata tgaaggccct gattcgaaac   960
cgcagctacg tcttctcctc cctggccacg tcggctgtct ccttcgccac gggggccctg  1020
ggcatgtgga tcccgctcta cctgcaccgc gcccaagttg tgcagaagac agcagagacg  1080
tgcaacagcc cgccctgtgg ggccaaggac agcctcatct tggggccat cacctgcttt   1140
acgggatttc tgggcgtggt cacgggggca ggagccacgc gctggtgccg cctgaagacc  1200
cagcggggcc g acccactggt gtgtgccgtg ggcatgctgg gctctgccat cttcatctgc  1260
ctgatcttcg tggctgccaa gagcagcatc gtaggagcct atatctgtat cttcgtcggg  1320
gagacgctgc tgttttctaa ctgggccatc actgcagaca tcctcatgta cgtggtcatc  1380
cccacgcggc gcgccactgc cgtggccttg cagagcttca cctcccacct gctggggac   1440
gccgggagcc cctacctcat tggctttatc tcagacctga tccgccagag cactaaggac  1500
tccccgctct gggagttcct gagcctgggc tacgcgctca tgctctgccc tttcgtcgtg  1560
gtcctgggcg gcatgttctt cctcgccact gcgctcttct tcgtcagcga ccgcgccagg  1620
gctgagcagc aggtgaacca gctggcgatg ccgcccgcat ctgtgaaagt ctga         1674
```

<210> SEQ ID NO 162
<211> LENGTH: 557
<212> TYPE: PRT
<213> ORGANISM: Artificial Sequence
<220> FEATURE:
<223> OTHER INFORMATION: Homo sapiens

<400> SEQUENCE: 162

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Gly Ala
                35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys

```
            65                  70                  75                  80
Ala Ala Thr Ala Lys Gly Pro Gly Ala Gln Gln Pro Lys Pro Ala Ser
                85                  90                  95
Leu Gly Arg Gly Arg Gly Ala Ala Ala Ile Leu Ser Leu Gly Asn
            100                 105                 110
Val Leu Asn Tyr Leu Asp Arg Tyr Thr Val Ala Gly Val Leu Leu Asp
            115                 120                 125
Ile Gln Gln His Phe Gly Val Lys Asp Arg Gly Ala Gly Leu Leu Gln
            130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Ser Phe Ile Pro Gln Gln Tyr
            180                 185                 190
Phe Trp Leu Asp Tyr Lys Asp Asp Asp Lys Leu Val Leu Ser Arg
            195                 200                 205
Gly Leu Val Gly Ile Gly Glu Ala Ser Tyr Ser Thr Ile Ala Pro Thr
210                 215                 220
Ile Ile Gly Asp Leu Phe Thr Lys Asn Thr Arg Thr Leu Met Leu Ser
225                 230                 235                 240
Val Phe Tyr Phe Ala Ile Pro Leu Gly Ser Gly Leu Gly Tyr Ile Thr
                245                 250                 255
Gly Ser Ser Val Lys Gln Ala Ala Gly Asp Trp His Trp Ala Leu Arg
                260                 265                 270
Val Ser Pro Val Leu Gly Met Ile Thr Gly Thr Leu Ile Leu Ile Leu
            275                 280                 285
Val Pro Ala Thr Lys Arg Gly His Ala Asp Gln Leu Gly Asp Gln Leu
            290                 295                 300
Lys Ala Arg Thr Ser Trp Leu Arg Asp Met Lys Ala Leu Ile Arg Asn
305                 310                 315                 320
Arg Ser Tyr Val Phe Ser Ser Leu Ala Thr Ser Ala Val Ser Phe Ala
                325                 330                 335
Thr Gly Ala Leu Gly Met Trp Ile Pro Leu Tyr Leu His Arg Ala Gln
                340                 345                 350
Val Val Gln Lys Thr Ala Glu Thr Cys Asn Ser Pro Pro Cys Gly Ala
            355                 360                 365
Lys Asp Ser Leu Ile Phe Gly Ala Ile Thr Cys Phe Thr Gly Phe Leu
            370                 375                 380
Gly Val Val Thr Gly Ala Gly Ala Thr Arg Trp Cys Arg Leu Lys Thr
385                 390                 395                 400
Gln Arg Ala Asp Pro Leu Val Cys Ala Val Gly Met Leu Gly Ser Ala
                405                 410                 415
Ile Phe Ile Cys Leu Ile Phe Val Ala Ala Lys Ser Ser Ile Val Gly
                420                 425                 430
Ala Tyr Ile Cys Ile Phe Val Gly Glu Thr Leu Leu Phe Ser Asn Trp
            435                 440                 445
Ala Ile Thr Ala Asp Ile Leu Met Tyr Val Val Ile Pro Thr Arg Arg
            450                 455                 460
Ala Thr Ala Val Ala Leu Gln Ser Phe Thr Ser His Leu Leu Gly Asp
465                 470                 475                 480
Ala Gly Ser Pro Tyr Leu Ile Gly Phe Ile Ser Asp Leu Ile Arg Gln
                485                 490                 495
```

Ser Thr Lys Asp Ser Pro Leu Trp Glu Phe Leu Ser Leu Gly Tyr Ala
                500                 505                 510

Leu Met Leu Cys Pro Phe Val Val Leu Gly Gly Met Phe Phe Leu
        515                 520                 525

Ala Thr Ala Leu Phe Phe Val Ser Asp Arg Ala Arg Ala Glu Gln Gln
        530                 535                 540

Val Asn Gln Leu Ala Met Pro Pro Ala Ser Val Lys Val
545                 550                 555

<210> SEQ ID NO 163
<211> LENGTH: 1674
<212> TYPE: DNA
<213> ORGANISM: Artificial Sequence
<220> FEATURE:
<223> OTHER INFORMATION: Homo sapiens

<400> SEQUENCE: 163

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | cccccggcac | ccccggctgc | 240 |
| gcagctactg | caaagggccc | cggcgctcag | cagcccaaac | cggccagctt | gggccgcggg | 300 |
| cgggggggcag | ccgccgccat | cctcagcttg | ggcaacgtgc | tcaactacct | ggacaggtac | 360 |
| accgtggcag | gcgtccttct | ggacatccag | cagcactttg | gggtcaagga | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | gcattttctt | ctggtcggcc | 540 |
| gtcaccttct | ccagctcctt | cattccccag | cagtacttct | ggctggatta | caaggatgac | 600 |
| gacgataagc | tggtcctgtc | ccgggggctg | gtgggcatcg | gggaggccag | ctactccacc | 660 |
| atcgccccca | ctatcattgg | cgacctcttc | accaagaaca | cgcgtacgct | catgctgtcc | 720 |
| gtcttctact | tcgccatccc | actgggcagt | ggcctgggct | acattactgg | ctccagcgtg | 780 |
| aagcaggcag | ccggagactg | gcactgggca | ttgcgggtgt | cccctgtcct | gggcatgatc | 840 |
| acaggaacac | tcatcctcat | tctggtccca | gccactaaaa | ggggtcatgc | cgaccagctc | 900 |
| ggggaccagc | tcaaggcccg | gacctcatgg | ctccgagata | tgaaggccct | gattcgaaac | 960 |
| cgcagctacg | tcttctcctc | cctggccacg | tcggctgtct | ccttcgccac | gggggccctg | 1020 |
| ggcatgtgga | tccgctcta | cctgcaccgc | gcccaagttg | tgcagaagac | agcagagacg | 1080 |
| tgcaacagcc | cgccctgtgg | ggccaaggac | agcctcatct | ttggggccat | cacctgcttt | 1140 |
| acgggatttc | tgggcgtggt | cacggggggca | ggagccacgc | gctggtgccg | cctgaagacc | 1200 |
| cagcgggccg | acccactggt | gtgtgccgtg | ggcatgctgg | gctctgccat | cttcatctgc | 1260 |
| ctgatcttcg | tggctgccaa | gagcagcatc | gtaggagcc | atatctgtat | cttcgtcggg | 1320 |
| gagacgctgc | tgtttctaa | ctgggccatc | actgcagaca | tcctcatgta | cgtggtcatc | 1380 |
| cccacgcggc | gcgccactgc | cgtggccttg | cagagcttca | cctcccacct | gctggggac | 1440 |
| gccgggagcc | cctacctcat | tggctttatc | tcagacctga | tccgcagag | cactaaggac | 1500 |
| tccccgctct | gggagttcct | gagcctgggc | tacgcgctca | tgctctgccc | tttcgtcgtg | 1560 |
| gtcctgggcg | catgttcatt | cctgccacct | gcgctcttct | tcgtcagcga | ccgcgccagg | 1620 |
| gctgagcagc | aggtgaacca | gctggcgatg | ccgcccgcat | ctgtgaaagt | ctga | 1674 |

<210> SEQ ID NO 164
<211> LENGTH: 557
<212> TYPE: PRT
<213> ORGANISM: Artificial Sequence
<220> FEATURE:
<223> OTHER INFORMATION: Homo Sapiens

<400> SEQUENCE: 164

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Asp
                245                 250                 255

Tyr Lys Asp Asp Asp Lys Ala Gly Asp Trp His Trp Ala Leu Arg
            260                 265                 270

Val Ser Pro Val Leu Gly Met Ile Thr Gly Thr Leu Ile Leu Ile Leu
        275                 280                 285

Val Pro Ala Thr Lys Arg Gly His Ala Asp Gln Leu Gly Asp Gln Leu
    290                 295                 300

Lys Ala Arg Thr Ser Trp Leu Arg Asp Met Lys Ala Leu Ile Arg Asn
305                 310                 315                 320

Arg Ser Tyr Val Phe Ser Ser Leu Ala Thr Ser Ala Val Ser Phe Ala
                325                 330                 335

Thr Gly Ala Leu Gly Met Trp Ile Pro Leu Tyr Leu His Arg Ala Gln
            340                 345                 350

Val Val Gln Lys Thr Ala Glu Thr Cys Asn Ser Pro Pro Cys Gly Ala
        355                 360                 365
```

```
Lys Asp Ser Leu Ile Phe Gly Ala Ile Thr Cys Phe Thr Gly Phe Leu
    370                 375                 380

Gly Val Val Thr Gly Ala Gly Ala Thr Arg Trp Cys Arg Leu Lys Thr
385                 390                 395                 400

Gln Arg Ala Asp Pro Leu Val Cys Ala Val Gly Met Leu Gly Ser Ala
                405                 410                 415

Ile Phe Ile Cys Leu Ile Phe Val Ala Ala Lys Ser Ser Ile Val Gly
            420                 425                 430

Ala Tyr Ile Cys Ile Phe Val Gly Glu Thr Leu Leu Phe Ser Asn Trp
            435                 440                 445

Ala Ile Thr Ala Asp Ile Leu Met Tyr Val Val Ile Pro Thr Arg Arg
450                 455                 460

Ala Thr Ala Val Ala Leu Gln Ser Phe Thr Ser His Leu Leu Gly Asp
465                 470                 475                 480

Ala Gly Ser Pro Tyr Leu Ile Gly Phe Ile Ser Asp Leu Ile Arg Gln
                485                 490                 495

Ser Thr Lys Asp Ser Pro Leu Trp Glu Phe Leu Ser Leu Gly Tyr Ala
                500                 505                 510

Leu Met Leu Cys Pro Phe Val Val Val Leu Gly Gly Met Phe Phe Leu
            515                 520                 525

Ala Thr Ala Leu Phe Phe Val Ser Asp Arg Arg Ala Glu Gln Gln
530                 535                 540

Val Asn Gln Leu Ala Met Pro Pro Ala Ser Val Lys Val
545                 550                 555
```

<210> SEQ ID NO 165
<211> LENGTH: 1674
<212> TYPE: DNA
<213> ORGANISM: Artificial Sequence
<220> FEATURE:
<223> OTHER INFORMATION: Homo sapiens

<400> SEQUENCE: 165

```
atgatgtgcc tggaatgcgc ctcggcggcg gcgggcggcg cggaggagga ggaggcggac    60
gcggagcggc ggcgccggcg ccggggggcg cagcgagggg ctggcggtag cggttgctgc   120
ggggcgcggg gcgcgggcgg cgctggagtc tcggccgcgg gcgatgaggt gcagacgctg   180
tcgggcagcg taaggcgggc cccgaccgga cccccggca cccccggcac cccccggctgc   240
gcagctactg caaagggccc cggcgctcag cagcccaaac cggccagctt gggccgcggg   300
cggggggcag ccgccgccat cctcagcttg gcaacgtgc tcaactacct ggacaggtac   360
accgtggcag gcgtccttct ggacatccag cagcactttg ggtcaagga ccgaggcgcc   420
ggcctgctgc agtcagtgtt catctgtagc ttcatggtgg ctgcccccat cttcggctac   480
ctgggcgacc gcttcaacag gaaggtgatt ctcagctgcg gcattttctt ctggtcggcc   540
gtcaccttct ccagctcctt cattcccag cagtacttct ggctgctggt cctgtcccgg   600
gggctggtgg gcatcgggga ggccagctac tccaccatcg cccccactat cattggcgac   660
ctcttcacca agaacacgcg tacgctcatg ctgtccgtct tctacttcgc catcccactg   720
ggcagtggcc tgggctacat tactggctcc agcgtgaagc aggcagatta caaggatgac   780
gacgataagg ccggagactg gcactgggca ttgcgggtgt ccctgtcct gggcatgatc   840
acaggaacac tcatcctcat tctggtccca gccactaaaa ggggtcatgc cgaccagctc   900
ggggaccagc tcaaggcccg gacctcatgg ctccgagata tgaaggccct gattcgaaac   960
cgcagctacg tcttctcctc cctggccacg tcggctgtct ccttcgccac ggggggccctg  1020
```

-continued

```
ggcatgtgga tcccgctcta cctgcaccgc gcccaagttg tgcagaagac agcagagacg    1080
tgcaacagcc cgccctgtgg ggccaaggac agcctcatct ttggggccat cacctgcttt    1140
acgggatttc tgggcgtggt cacgggggca ggagccacgc gctggtgccg cctgaagacc    1200
cagcgggccg acccactggt gtgtgccgtg ggcatgctgg gctctgccat cttcatctgc    1260
ctgatcttcg tggctgccaa gagcagcatc gtaggagcct atatctgtat cttcgtcggg    1320
gagacgctgc tgtttctaa ctgggccatc actgcagaca tcctcatgta cgtggtcatc    1380
cccacgcggc gcgccactgc cgtggccttg cagagcttca cctcccacct gctggggac    1440 gccgggagcc cctacctcat tggctttatc tcagacctga tccgccagag cactaaggac    1500
tccccgctct gggagttcct gagcctgggc tacgcgctca tgctctgccc tttcgtcgtg    1560
gtcctgggcg gcatgttctt cctgccact gcgctcttct tcgtcagcga ccgcgccagg    1620
gctgagcagc aggtgaacca gctggcgatg ccgcccgcat ctgtgaaagt ctga         1674
```

<210> SEQ ID NO 166
<211> LENGTH: 557
<212> TYPE: PRT
<213> ORGANISM: Artificial Sequence
<220> FEATURE:
<223> OTHER INFORMATION: Homo sapiens

<400> SEQUENCE: 166

```
Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
```

```
                    245                 250                 255
Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Asp Tyr
            340                 345                 350

Lys Asp Asp Asp Asp Lys Glu Thr Cys Asn Ser Pro Cys Gly Ala
        355                 360                 365

Lys Asp Ser Leu Ile Phe Gly Ala Ile Thr Cys Phe Thr Gly Phe Leu
    370                 375                 380

Gly Val Val Thr Gly Ala Gly Ala Thr Arg Trp Cys Arg Leu Lys Thr
385                 390                 395                 400

Gln Arg Ala Asp Pro Leu Val Cys Ala Val Gly Met Leu Gly Ser Ala
                405                 410                 415

Ile Phe Ile Cys Leu Ile Phe Val Ala Ala Lys Ser Ser Ile Val Gly
            420                 425                 430

Ala Tyr Ile Cys Ile Phe Val Gly Glu Thr Leu Leu Phe Ser Asn Trp
        435                 440                 445

Ala Ile Thr Ala Asp Ile Leu Met Tyr Val Val Ile Pro Thr Arg Arg
    450                 455                 460

Ala Thr Ala Val Ala Leu Gln Ser Phe Thr Ser His Leu Leu Gly Asp
465                 470                 475                 480

Ala Gly Ser Pro Tyr Leu Ile Gly Phe Ile Ser Asp Leu Ile Arg Gln
                485                 490                 495

Ser Thr Lys Asp Ser Pro Leu Trp Glu Phe Leu Ser Leu Gly Tyr Ala
            500                 505                 510

Leu Met Leu Cys Pro Phe Val Val Val Leu Gly Gly Met Phe Phe Leu
        515                 520                 525

Ala Thr Ala Leu Phe Phe Val Ser Asp Arg Ala Arg Ala Glu Gln Gln
    530                 535                 540

Val Asn Gln Leu Ala Met Pro Pro Ala Ser Val Lys Val
545                 550                 555

<210> SEQ ID NO 167
<211> LENGTH: 1674
<212> TYPE: DNA
<213> ORGANISM: Artificial Sequence
<220> FEATURE:
<223> OTHER INFORMATION: Homo sapiens

<400> SEQUENCE: 167
atgatgtgcc tggaatgcgc ctcggcggcg gcgggcggcg cggaggagga ggaggcggac      60
gcggagcggc ggcgccggcg ccgggggggcg cagcgagggc ctggcggtag cggttgctgc    120
ggggcgcggg gcgcgggcgg cgctggagtc tcggccgcgg gcgatgaggt gcagacgctg    180
tcgggcagcg taaggcgggc cccgaccgga cccccggca cccccggcac cccggctgc      240 gcagctactg caaagggccc cggcgctcag cagcccaaac cggccagctt gggccgcggg    300
```

```
cgggggggcag ccgccgccat cctcagcttg gcaacgtgc  tcaactacct ggacaggtac    360
accgtggcag cgtccttct ggacatccag cagcactttg  gggtcaagga ccgaggcgcc    420
ggcctgctgc agtcagtgtt catctgtagc ttcatggtgg  ctgccccat cttcggctac    480 ctgggcgacc gcttcaacag gaaggtgatt ctcagctgcg  gcattttctt ctggtcggcc    540
gtcaccttct ccagctcctt cattccccag cagtacttct  ggctgctggt cctgtcccgg    600
gggctggtgg gcatcgggga ggccagctac tccaccatcg  cccccactat cattggcgac    660
ctcttcacca gaacacgcg tacgctcatg ctgtccgtct  tctacttcgc catcccactg    720
ggcagtggcc tgggctacat tactggctcc agcgtgaagc  aggcagccgg agactggcac    780
tgggcattgc gggtgtcccc tgtcctgggc atgatcacag  aacactcat cctcattctg    840 gtcccagcca ctaaaagggg tcatgccgac cagctcgggg  accagctcaa ggcccggacc    900
tcatggctcc gagatatgaa ggccctgatt cgaaaccgca  gctacgtctt ctcctccctg    960
gccacgtcgg ctgtctcctt cgccacgggg gccctgggca  tgtggatccc gctctacctg   1020
caccgcgccc aagttgtgca gaagacagca gattacaagg  atgacgacga taaggagacg   1080
tgcaacagcc cgccctgtgg ggccaaggac agcctcatct  ttgggccat cacctgcttt   1140 acgggatttc tgggcgtggt cacggggca ggagccacgc  gctggtgccg cctgaagacc   1200
cagcgggccg acccactggt gtgtgccgtg gcatgctgg   gctctgccat cttcatctgc   1260
ctgatcttcg tggctgccaa gagcagcatc gtaggagcc  atatctgtat cttcgtcggg   1320
gagacgctgc tgttttctaa ctgggccatc actgcagaca  tcctcatgta cgtggtcatc   1380
cccacgcggc gcgccactgc cgtggccttg cagagcttca  cctcccacct gctgggggac   1440
gccgggagcc cctacctcat tggctttatc tcagacctga  tccgccagag cactaaggac   1500
tccccgctct gggagttcct gagcctgggc tacgcgctca  tgctctgccc tttcgtcgtg   1560
gtcctgggcg gcatgttctt cctcgccact gcgctcttct  tcgtcagcga ccgcgccagg   1620
gctgagcagc aggtgaacca gctggcgatg ccgcccgcat  ctgtgaaagt ctga        1674
```

<210> SEQ ID NO 168
<211> LENGTH: 557
<212> TYPE: PRT
<213> ORGANISM: Artificial Sequence
<220> FEATURE:
<223> OTHER INFORMATION: Homo sapiens

<400> SEQUENCE: 168

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
            115                 120                 125
```

```
Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Asp Tyr Lys Asp Asp Asp Lys Ser Ser Ile Val Gly
            420                 425                 430

Ala Tyr Ile Cys Ile Phe Val Gly Glu Thr Leu Leu Phe Ser Asn Trp
    435                 440                 445

Ala Ile Thr Ala Asp Ile Leu Met Tyr Val Val Ile Pro Thr Arg Arg
450                 455                 460

Ala Thr Ala Val Ala Leu Gln Ser Phe Thr Ser His Leu Leu Gly Asp
465                 470                 475                 480

Ala Gly Ser Pro Tyr Leu Ile Gly Phe Ile Ser Asp Leu Ile Arg Gln
                485                 490                 495

Ser Thr Lys Asp Ser Pro Leu Trp Glu Phe Leu Ser Leu Gly Tyr Ala
            500                 505                 510

Leu Met Leu Cys Pro Phe Val Val Leu Gly Gly Met Phe Phe Leu
        515                 520                 525

Ala Thr Ala Leu Phe Phe Val Ser Asp Arg Ala Arg Ala Glu Gln Gln
    530                 535                 540
```

Val Asn Gln Leu Ala Met Pro Pro Ala Ser Val Lys Val
545                 550                 555

<210> SEQ ID NO 169
<211> LENGTH: 1674
<212> TYPE: DNA
<213> ORGANISM: Artificial Sequence
<220> FEATURE:
<223> OTHER INFORMATION: Homo sapiens

<400> SEQUENCE: 169

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | cccccggcac | ccccggctgc | 240 |
| gcagctactg | caaagggccc | cggcgctcag | cagcccaaac | cggccagctt | gggccgcggg | 300 |
| cggggggcag | ccgccgccat | cctcagcttg | ggcaacgtgc | tcaactacct | ggacaggtac | 360 |
| accgtggcag | gcgtccttct | ggacatccag | cagcactttg | gggtcaagga | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | gcattttctt | ctggtcggcc | 540 |
| gtcaccttct | ccagctcctt | cattccccag | cagtacttct | ggctgctggt | cctgtcccgg | 600 |
| gggctggtgg | gcatcgggga | ggccagctac | tccaccatcg | cccccactat | cattggcgac | 660 |
| ctcttcacca | gaacacgcg | tacgctcatg | ctgtccgtct | tctacttcgc | catcccactg | 720 |
| ggcagtggcc | tgggctacat | tactggctcc | agcgtgaagc | aggcagccgg | agactggcac | 780 |
| tgggcattgc | gggtgtcccc | tgtcctgggc | atgatcacag | gaacactcat | cctcattctg | 840 |
| gtcccagcca | ctaaaagggg | tcatgccgac | cagctcgggg | accagctcaa | ggcccggacc | 900 |
| tcatggctcc | gagatatgaa | ggccctgatt | cgaaaccgca | gctacgtctt | ctcctccctg | 960 |
| gccacgtcgg | ctgtctcctt | cgccacgggg | gccctgggca | tgtggatccc | gctctacctg | 1020 |
| caccgcgccc | aagttgtgca | gaagacagca | gagacgtgca | acagcccgcc | ctgtggggcc | 1080 |
| aaggacagcc | tcatctttgg | ggccatcacc | tgctttacgg | gatttctggg | cgtggtcacg | 1140 |
| ggggcaggag | ccacgcgctg | gtgccgcctg | aagacccagc | gggccgaccc | actggtgtgt | 1200 |
| gccgtgggca | tgctgggctc | tgccatcttc | atctgcctga | tcttcgtggc | tgccaaggat | 1260 |
| tacaaggatg | acgacgataa | gagcagcatc | gtaggagcct | atatctgtat | cttcgtcggg | 1320 |
| gagacgctgc | tgttttctaa | ctgggccatc | actgcagaca | tcctcatgta | cgtggtcatc | 1380 |
| cccacgcggc | gcgccactgc | cgtggccttg | cagagcttca | cctcccacct | gctggggac | 1440 |
| gccgggagcc | cctacctcat | tggctttatc | tcagacctga | tccgccagag | cactaaggac | 1500 |
| tccccgctct | gggagttcct | gagcctgggc | tacgcgctca | tgctctgccc | tttcgtcgtg | 1560 |
| gtcctgggcg | gcatgttctt | cctgccacct | gcgctcttct | tcgtcagcga | ccgcgccagg | 1620 |
| gctgagcagc | aggtgaacca | gctggcgatg | ccgcccgcat | ctgtgaaagt | ctga | 1674 |

<210> SEQ ID NO 170
<211> LENGTH: 557
<212> TYPE: PRT
<213> ORGANISM: Artificial Sequence
<220> FEATURE:
<223> OTHER INFORMATION: Homo sapiens

<400> SEQUENCE: 170

```
Met Met Cys Leu Glu Cys Ala Ser Ala Ala Ala Gly Gly Ala Glu Glu
1               5                   10                  15
Glu Glu Ala Asp Ala Glu Arg Arg Arg Arg Arg Gly Ala Gln Arg
        20                  25                  30
Gly Ala Gly Gly Ser Gly Cys Cys Gly Ala Arg Gly Ala Gly Gly Ala
        35                  40                  45
Gly Val Ser Ala Ala Gly Asp Glu Val Gln Thr Leu Ser Gly Ser Val
    50                  55                  60
Arg Arg Ala Pro Thr Gly Pro Pro Gly Thr Pro Gly Thr Pro Gly Cys
65              70                  75                  80
Ala Ala Thr Ala Lys Gly Pro Gly Ala Gln Gln Pro Lys Pro Ala Ser
                85                  90                  95
Leu Gly Arg Gly Arg Gly Ala Ala Ala Ile Leu Ser Leu Gly Asn
            100                 105                 110
Val Leu Asn Tyr Leu Asp Arg Tyr Thr Val Ala Gly Val Leu Leu Asp
            115                 120                 125
Ile Gln Gln His Phe Gly Val Lys Asp Arg Gly Ala Gly Leu Leu Gln
    130                 135                 140
Ser Val Phe Ile Cys Ser Phe Met Val Ala Ala Pro Ile Phe Gly Tyr
145             150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Phe Ile Pro Gln Gln Tyr
            180                 185                 190
Phe Trp Leu Leu Val Leu Ser Arg Gly Leu Val Gly Ile Gly Glu Ala
        195                 200                 205
Ser Tyr Ser Thr Ile Ala Pro Thr Ile Ile Gly Asp Leu Phe Thr Lys
    210                 215                 220
Asn Thr Arg Thr Leu Met Leu Ser Val Phe Tyr Phe Ala Ile Pro Leu
225             230                 235                 240
Gly Ser Gly Leu Gly Tyr Ile Thr Gly Ser Ser Val Lys Gln Ala Ala
                245                 250                 255
Gly Asp Trp His Trp Ala Leu Arg Val Ser Pro Val Leu Gly Met Ile
        260                 265                 270
Thr Gly Thr Leu Ile Leu Ile Leu Val Pro Ala Thr Lys Arg Gly His
        275                 280                 285
Ala Asp Gln Leu Gly Asp Gln Leu Lys Ala Arg Thr Ser Trp Leu Arg
        290                 295                 300
Asp Met Lys Ala Leu Ile Arg Asn Arg Ser Tyr Val Phe Ser Ser Leu
305             310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
            355                 360                 365
Ile Thr Cys Phe Thr Gly Phe Leu Gly Val Val Thr Gly Ala Gly Ala
    370                 375                 380
Thr Arg Trp Cys Arg Leu Lys Thr Gln Arg Ala Asp Pro Leu Val Cys
385             390                 395                 400
Ala Val Gly Met Leu Gly Ser Ala Ile Phe Ile Cys Leu Ile Phe Val
            405                 410                 415
Ala Ala Lys Ser Ser Ile Val Gly Ala Tyr Ile Cys Ile Phe Val Gly
```

```
                   420                 425                 430
Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
        450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Asp Tyr Lys Asp Asp Asp Lys Glu Phe Leu Ser Leu Gly Tyr Ala
            500                 505                 510

Leu Met Leu Cys Pro Phe Val Val Leu Gly Gly Met Phe Phe Leu
            515                 520                 525

Ala Thr Ala Leu Phe Phe Val Ser Asp Arg Ala Arg Ala Glu Gln Gln
            530                 535                 540

Val Asn Gln Leu Ala Met Pro Pro Ala Ser Val Lys Val
545                 550                 555

<210> SEQ ID NO 171
<211> LENGTH: 1674
<212> TYPE: DNA
<213> ORGANISM: Artificial Sequence
<220> FEATURE:
<223> OTHER INFORMATION: Homo sapiens

<400> SEQUENCE: 171
```

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccgggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | ccccggcac | ccccggctgc | 240 |
| gcagctactg | caaagggccc | cggcgctcag | cagcccaaac | cggccagctt | gggccgcggg | 300 |
| cgggggggcag | ccgccgccat | cctcagcttg | gcaacgtgc | tcaactacct | ggacaggtac | 360 |
| accgtggcag | gcgtccttct | ggacatccag | cagcactttg | gggtcaagga | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | cattttctt | ctggtcggcc | 540 |
| gtcaccttct | ccagctcctt | cattccccag | cagtacttct | ggctgctggt | cctgtcccgg | 600 |
| gggctggtgg | gcatcgggga | ggccagctac | tccaccatcg | ccccactat | cattggcgac | 660 |
| ctcttcacca | gaacacgcg | tacgctcatg | ctgtccgtct | tctacttcgc | catcccactg | 720 |
| ggcagtggcc | tgggctacat | tactggctcc | agcgtgaagc | aggcagccgg | agactggcac | 780 |
| tgggcattgc | gggtgtcccc | tgtcctgggc | atgatcacag | gaacactcat | cctcattctg | 840 |
| gtcccagcca | ctaaaagggg | tcatgccgac | cagctcgggg | accagctcaa | ggcccggacc | 900 |
| tcatggctcc | gagatatgaa | ggccctgatt | cgaaaccgca | gctacgtctt | ctcctccctg | 960 |
| gccacgtcgg | ctgtctcctt | cgccacgggg | gccctgggca | tgtggatccc | gctctacctg | 1020 |
| caccgcgccc | aagttgtgca | gaagacagca | gagacgtgca | acagcccgcc | ctgtggggcc | 1080 |
| aaggacagcc | tcatctttgg | ggccatcacc | tgctttacgg | gatttctggg | cgtggtcacg | 1140 |
| ggggcaggag | ccacgcgctg | gtgccgcctg | aagacccagc | gggccgaccc | actggtgtgt | 1200 |
| gccgtgggca | tgctgggctc | tgccatcttc | atctgcctga | tcttcgtggc | tgccaagagc | 1260 |
| agcatcgtag | gagcctatat | ctgtatcttc | gtcggggaga | cgctgctgtt | ttctaactgg | 1320 |

```
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga ttacaaggat    1500
gacgacgata aggagttcct gagcctgggc tacgcgctca tgctctgccc tttcgtcgtg    1560
gtcctgggcg gcatgttctt cctcgccact gcgctcttct tcgtcagcga ccgcgccagg    1620
gctgagcagc aggtgaacca gctggcgatg ccgcccgcat ctgtgaaagt ctga          1674
```

<210> SEQ ID NO 172
<211> LENGTH: 549
<212> TYPE: PRT
<213> ORGANISM: Artificial Sequence
<220> FEATURE:
<223> OTHER INFORMATION: Homo sapiens

<400> SEQUENCE: 172

```
Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Ala
        35                  40                  45

Gly Val Ser Ala Ala Gly Asp Glu Val Gln Thr Leu Ser Gly Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Ala Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300
```

```
Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 173
<211> LENGTH: 549
<212> TYPE: PRT
<213> ORGANISM: Artificial Sequence
<220> FEATURE:
<223> OTHER INFORMATION: Homo sapiens

<400> SEQUENCE: 173

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
                20                  25                  30

Gly Ala Gly Gly Ser Cys Cys Gly Ala Arg Gly Ala Gly Gly Ala
            35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110
```

-continued

```
Val Leu Asn Tyr Leu Asp Arg Tyr Thr Val Ala Gly Val Leu Leu Ala
            115                 120                 125
Ile Gln Gln His Phe Gly Val Lys Asp Arg Gly Ala Gly Leu Leu Gln
        130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Ser Phe Ile Pro Gln Gln Tyr
            180                 185                 190
Phe Trp Leu Leu Val Leu Ser Arg Gly Leu Val Gly Ile Gly Glu Ala
            195                 200                 205
Ser Tyr Ser Thr Ile Ala Pro Thr Ile Ile Gly Asp Leu Phe Thr Lys
        210                 215                 220
Asn Thr Arg Thr Leu Met Leu Ser Val Phe Tyr Phe Ala Ile Pro Leu
225                 230                 235                 240
Gly Ser Gly Leu Gly Tyr Ile Thr Gly Ser Ser Val Lys Gln Ala Ala
                245                 250                 255
Gly Asp Trp His Trp Ala Leu Arg Val Ser Pro Val Leu Gly Met Ile
            260                 265                 270
Thr Gly Thr Leu Ile Leu Ile Leu Val Pro Ala Thr Lys Arg Gly His
        275                 280                 285
Ala Asp Gln Leu Gly Asp Gln Leu Lys Ala Arg Thr Ser Trp Leu Arg
        290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
        355                 360                 365
Ile Thr Cys Phe Thr Gly Phe Leu Gly Val Val Thr Gly Ala Gly Ala
        370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
            420                 425                 430
Glu Thr Leu Leu Phe Ser Asn Trp Ala Ile Thr Ala Asp Ile Leu Met
        435                 440                 445
Tyr Val Val Ile Pro Thr Arg Arg Ala Thr Ala Val Ala Leu Gln Ser
        450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
            500                 505                 510
Val Leu Gly Gly Met Phe Phe Leu Ala Thr Ala Leu Phe Phe Val Ser
            515                 520                 525
```

Asp Arg Ala Arg Ala Glu Gln Gln Val Asn Gln Leu Ala Met Pro Pro
            530                 535                 540

Ala Ser Val Lys Val
545

<210> SEQ ID NO 174
<211> LENGTH: 549
<212> TYPE: PRT
<213> ORGANISM: Artificial Sequence
<220> FEATURE:
<223> OTHER INFORMATION: Homo sapiens

<400> SEQUENCE: 174

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ala Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

```
Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
        370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
530                 535                 540

Ala Ser Val Lys Val
545

<210> SEQ ID NO 175
<211> LENGTH: 549
<212> TYPE: PRT
<213> ORGANISM: Artificial Sequence
<220> FEATURE:
<223> OTHER INFORMATION: Homo sapiens

<400> SEQUENCE: 175

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Ala Gln His Phe Gly Val Lys Asp Arg Gly Ala Gly Leu Leu Gln
    130                 135                 140
```

```
Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
            165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
            245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
            325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
            370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
            405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
530                 535                 540

Ala Ser Val Lys Val
545
```

```
<210> SEQ ID NO 176
<211> LENGTH: 549
<212> TYPE: PRT
<213> ORGANISM: Artificial Sequence
<220> FEATURE:
<223> OTHER INFORMATION: Homo sapiens

<400> SEQUENCE: 176
```

| Met | Met | Cys | Leu | Glu | Cys | Ala | Ser | Ala | Ala | Gly | Gly | Ala | Glu | Glu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
            115                 120                 125

Ile Gln Ala His Phe Gly Val Lys Asp Arg Gly Ala Gly Leu Leu Gln
        130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala

```
                370                 375                 380
Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
        450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
        530                 535                 540

Ala Ser Val Lys Val
545

<210> SEQ ID NO 177
<211> LENGTH: 549
<212> TYPE: PRT
<213> ORGANISM: Artificial Sequence
<220> FEATURE:
<223> OTHER INFORMATION: Homo sapiens

<400> SEQUENCE: 177

Met Met Cys Leu Glu Cys Ala Ser Ala Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln Ala Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
```

```
                180             185             190
Phe Trp Leu Leu Val Leu Ser Arg Gly Leu Val Gly Ile Gly Glu Ala
            195             200             205
Ser Tyr Ser Thr Ile Ala Pro Thr Ile Ile Gly Asp Leu Phe Thr Lys
        210             215             220
Asn Thr Arg Thr Leu Met Leu Ser Val Phe Tyr Phe Ala Ile Pro Leu
225             230             235             240
Gly Ser Gly Leu Gly Tyr Ile Thr Gly Ser Ser Val Lys Gln Ala Ala
                245             250             255
Gly Asp Trp His Trp Ala Leu Arg Val Ser Pro Val Leu Gly Met Ile
            260             265             270
Thr Gly Thr Leu Ile Leu Ile Leu Val Pro Ala Thr Lys Arg Gly His
        275             280             285
Ala Asp Gln Leu Gly Asp Gln Leu Lys Ala Arg Thr Ser Trp Leu Arg
        290             295             300
Asp Met Lys Ala Leu Ile Arg Asn Arg Ser Tyr Val Phe Ser Ser Leu
305             310             315             320
Ala Thr Ser Ala Val Ser Phe Ala Thr Gly Ala Leu Gly Met Trp Ile
                325             330             335
Pro Leu Tyr Leu His Arg Ala Gln Val Val Gln Lys Thr Ala Glu Thr
            340             345             350
Cys Asn Ser Pro Pro Cys Gly Ala Lys Asp Ser Leu Ile Phe Gly Ala
        355             360             365
Ile Thr Cys Phe Thr Gly Phe Leu Gly Val Val Thr Gly Ala Gly Ala
        370             375             380
Thr Arg Trp Cys Arg Leu Lys Thr Gln Arg Ala Asp Pro Leu Val Cys
385             390             395             400
Ala Val Gly Met Leu Gly Ser Ala Ile Phe Ile Cys Leu Ile Phe Val
                405             410             415
Ala Ala Lys Ser Ser Ile Val Gly Ala Tyr Ile Cys Ile Phe Val Gly
            420             425             430
Glu Thr Leu Leu Phe Ser Asn Trp Ala Ile Thr Ala Asp Ile Leu Met
        435             440             445
Tyr Val Val Ile Pro Thr Arg Arg Ala Thr Ala Val Ala Leu Gln Ser
    450             455             460
Phe Thr Ser His Leu Leu Gly Asp Ala Gly Ser Pro Tyr Leu Ile Gly
465             470             475             480
Phe Ile Ser Asp Leu Ile Arg Gln Ser Thr Lys Asp Ser Pro Leu Trp
                485             490             495
Glu Phe Leu Ser Leu Gly Tyr Ala Leu Met Leu Cys Pro Phe Val Val
            500             505             510
Val Leu Gly Gly Met Phe Phe Leu Ala Thr Ala Leu Phe Phe Val Ser
        515             520             525
Asp Arg Ala Arg Ala Glu Gln Gln Val Asn Gln Leu Ala Met Pro Pro
        530             535             540
Ala Ser Val Lys Val
545

<210> SEQ ID NO 178
<211> LENGTH: 549
<212> TYPE: PRT
<213> ORGANISM: Artificial Sequence
<220> FEATURE:
<223> OTHER INFORMATION: Homo sapiens
```

<400> SEQUENCE: 178

| | | | | | | | | | | | | | | |
|---|---|---|---|---|---|---|---|---|---|---|---|---|---|---|
Met Met Cys Leu Glu Cys Ala Ser Ala Ala Gly Gly Ala Glu Glu
1               5                  10                 15
Glu Glu Ala Asp Ala Glu Arg Arg Arg Arg Arg Gly Ala Gln Arg
                20                 25                 30
Gly Ala Gly Gly Ser Gly Cys Cys Gly Ala Arg Gly Ala Gly Ala
            35                 40                 45
Gly Val Ser Ala Ala Gly Asp Glu Val Gln Thr Leu Ser Gly Ser Val
        50                 55                 60
Arg Arg Ala Pro Thr Gly Pro Pro Gly Thr Pro Gly Thr Pro Gly Cys
65                 70                 75                 80
Ala Ala Thr Ala Lys Gly Pro Gly Ala Gln Gln Pro Lys Pro Ala Ser
                85                 90                 95
Leu Gly Arg Gly Arg Gly Ala Ala Ala Ile Leu Ser Leu Gly Asn
                100                105                110
Val Leu Asn Tyr Leu Asp Arg Tyr Thr Val Ala Gly Val Leu Leu Asp
            115                120                125
Ile Gln Gln His Ala Gly Val Lys Asp Arg Gly Ala Gly Leu Leu Gln
130                135                140
Ser Val Phe Ile Cys Ser Phe Met Val Ala Ala Pro Ile Phe Gly Tyr
145                150                155                160
Leu Gly Asp Arg Phe Asn Arg Lys Val Ile Leu Ser Cys Gly Ile Phe
                165                170                175
Phe Trp Ser Ala Val Thr Phe Ser Ser Ser Phe Ile Pro Gln Gln Tyr
            180                185                190
Phe Trp Leu Leu Val Leu Ser Arg Gly Leu Val Gly Ile Gly Glu Ala
            195                200                205
Ser Tyr Ser Thr Ile Ala Pro Thr Ile Ile Gly Asp Leu Phe Thr Lys
210                215                220
Asn Thr Arg Thr Leu Met Leu Ser Val Phe Tyr Phe Ala Ile Pro Leu
225                230                235                240
Gly Ser Gly Leu Gly Tyr Ile Thr Gly Ser Ser Val Lys Gln Ala Ala
                245                250                255
Gly Asp Trp His Trp Ala Leu Arg Val Ser Pro Val Leu Gly Met Ile
                260                265                270
Thr Gly Thr Leu Ile Leu Ile Leu Val Pro Ala Thr Lys Arg Gly His
                275                280                285
Ala Asp Gln Leu Gly Asp Gln Leu Lys Ala Arg Thr Ser Trp Leu Arg
        290                295                300
Asp Met Lys Ala Leu Ile Arg Asn Arg Ser Tyr Val Phe Ser Ser Leu
305                310                315                320
Ala Thr Ser Ala Val Ser Phe Ala Thr Gly Ala Leu Gly Met Trp Ile
                325                330                335
Pro Leu Tyr Leu His Arg Ala Gln Val Val Gln Lys Thr Ala Glu Thr
                340                345                350
Cys Asn Ser Pro Pro Cys Gly Ala Lys Asp Ser Leu Ile Phe Gly Ala
            355                360                365
Ile Thr Cys Phe Thr Gly Phe Leu Gly Val Val Thr Gly Ala Gly Ala
        370                375                380
Thr Arg Trp Cys Arg Leu Lys Thr Gln Arg Ala Asp Pro Leu Val Cys
385                390                395                400
Ala Val Gly Met Leu Gly Ser Ala Ile Phe Ile Cys Leu Ile Phe Val
                405                410                415

```
Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
            450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
            530                 535                 540

Ala Ser Val Lys Val
545

<210> SEQ ID NO 179
<211> LENGTH: 549
<212> TYPE: PRT
<213> ORGANISM: Artificial Sequence
<220> FEATURE:
<223> OTHER INFORMATION: Homo sapiens

<400> SEQUENCE: 179

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys
65              70                  75                  80

Ala Ala Thr Ala Lys Gly Pro Gly Ala Gln Gln Pro Lys Pro Ala Ser
            85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Ala Val Lys Asp Arg Gly Ala Gly Leu Leu Gln
            130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
210                 215                 220
```

```
Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
            245                 250                 255

Gly Asp Trp His Trp Ala Leu Arg Val Ser Pro Val Leu Gly Met Ile
        260                 265                 270

Thr Gly Thr Leu Ile Leu Ile Leu Val Pro Ala Thr Lys Arg Gly His
    275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Val Ala Leu Gln Ser
                450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
                515                 520                 525

Asp Arg Ala Arg Ala Glu Gln Gln Val Asn Gln Leu Ala Met Pro Pro
530                 535                 540

Ala Ser Val Lys Val
545

<210> SEQ ID NO 180
<211> LENGTH: 549
<212> TYPE: PRT
<213> ORGANISM: Artificial Sequence
<220> FEATURE:
<223> OTHER INFORMATION: Homo sapiens

<400> SEQUENCE: 180

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30
```

```
Gly Ala Gly Gly Ser Gly Cys Cys Gly Ala Arg Gly Ala Gly Gly Ala
             35                  40                  45

Gly Val Ser Ala Ala Gly Asp Glu Val Gln Thr Leu Ser Gly Ser Val
         50                  55                  60

Arg Arg Ala Pro Thr Gly Pro Pro Gly Thr Pro Gly Thr Pro Gly Cys
 65                  70                  75                  80

Ala Ala Thr Ala Lys Gly Pro Gly Ala Gln Gln Pro Lys Pro Ala Ser
                 85                  90                  95

Leu Gly Arg Gly Arg Gly Ala Ala Ala Ile Leu Ser Leu Gly Asn
             100                 105                 110

Val Leu Asn Tyr Leu Asp Arg Tyr Thr Val Ala Gly Val Leu Leu Asp
             115                 120                 125

Ile Gln Gln His Phe Gly Ala Lys Asp Arg Gly Ala Gly Leu Leu Gln
             130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                 165                 170                 175

Phe Trp Ser Ala Val Thr Phe Ser Ser Phe Ile Pro Gln Gln Tyr
             180                 185                 190

Phe Trp Leu Leu Val Leu Ser Arg Gly Leu Val Gly Ile Gly Glu Ala
             195                 200                 205

Ser Tyr Ser Thr Ile Ala Pro Thr Ile Ile Gly Asp Leu Phe Thr Lys
             210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                 245                 250                 255

Gly Asp Trp His Trp Ala Leu Arg Val Ser Pro Val Leu Gly Met Ile
                 260                 265                 270

Thr Gly Thr Leu Ile Leu Ile Leu Val Pro Ala Thr Lys Arg Gly His
             275                 280                 285

Ala Asp Gln Leu Gly Asp Gln Leu Lys Ala Arg Thr Ser Trp Leu Arg
             290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                 325                 330                 335

Pro Leu Tyr Leu His Arg Ala Gln Val Val Gln Lys Thr Ala Glu Thr
             340                 345                 350

Cys Asn Ser Pro Pro Cys Gly Ala Lys Asp Ser Leu Ile Phe Gly Ala
             355                 360                 365

Ile Thr Cys Phe Thr Gly Phe Leu Gly Val Val Thr Gly Ala Gly Ala
370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                 405                 410                 415

Ala Ala Lys Ser Ser Ile Val Gly Ala Tyr Ile Cys Ile Phe Val Gly
             420                 425                 430

Glu Thr Leu Leu Phe Ser Asn Trp Ala Ile Thr Ala Asp Ile Leu Met
             435                 440                 445
```

```
Tyr Val Val Ile Pro Thr Arg Arg Ala Thr Ala Val Ala Leu Gln Ser
        450             455             460

Phe Thr Ser His Leu Leu Gly Asp Ala Gly Ser Pro Tyr Leu Ile Gly
465             470             475             480

Phe Ile Ser Asp Leu Ile Arg Gln Ser Thr Lys Asp Ser Pro Leu Trp
                485             490             495

Glu Phe Leu Ser Leu Gly Tyr Ala Leu Met Leu Cys Pro Phe Val Val
            500             505             510

Val Leu Gly Gly Met Phe Phe Leu Ala Thr Ala Leu Phe Phe Val Ser
            515             520             525

Asp Arg Ala Arg Ala Glu Gln Gln Val Asn Gln Leu Ala Met Pro Pro
530             535             540

Ala Ser Val Lys Val
545

<210> SEQ ID NO 181
<211> LENGTH: 549
<212> TYPE: PRT
<213> ORGANISM: Artificial Sequence
<220> FEATURE:
<223> OTHER INFORMATION: Homo sapiens

<400> SEQUENCE: 181

Met Met Cys Leu Glu Cys Ala Ser Ala Ala Gly Gly Ala Glu Glu
1               5               10              15

Glu Glu Ala Asp Ala Glu Arg Arg Arg Arg Gly Ala Gln Arg
        20              25              30

Gly Ala Gly Gly Ser Gly Cys Cys Gly Ala Arg Gly Ala Gly Gly Ala
            35              40              45

Gly Val Ser Ala Ala Gly Asp Glu Val Gln Thr Leu Ser Gly Ser Val
50              55              60

Arg Arg Ala Pro Thr Gly Pro Pro Gly Thr Pro Gly Thr Pro Gly Cys
65              70              75              80

Ala Ala Thr Ala Lys Gly Pro Gly Ala Gln Gln Pro Lys Pro Ala Ser
                85              90              95

Leu Gly Arg Gly Arg Gly Ala Ala Ala Ile Leu Ser Leu Gly Asn
            100             105             110

Val Leu Asn Tyr Leu Asp Arg Tyr Thr Val Ala Gly Val Leu Leu Asp
        115             120             125

Ile Gln Gln His Phe Gly Val Ala Asp Arg Gly Ala Gly Leu Leu Gln
130             135             140

Ser Val Phe Ile Cys Ser Phe Met Val Ala Ala Pro Ile Phe Gly Tyr
145             150             155             160

Leu Gly Asp Arg Phe Asn Arg Lys Val Ile Leu Ser Cys Gly Ile Phe
                165             170             175

Phe Trp Ser Ala Val Thr Phe Ser Ser Ser Phe Ile Pro Gln Gln Tyr
            180             185             190

Phe Trp Leu Leu Val Leu Ser Arg Gly Leu Val Gly Ile Gly Glu Ala
        195             200             205

Ser Tyr Ser Thr Ile Ala Pro Thr Ile Ile Gly Asp Leu Phe Thr Lys
    210             215             220

Asn Thr Arg Thr Leu Met Leu Ser Val Phe Tyr Phe Ala Ile Pro Leu
225             230             235             240

Gly Ser Gly Leu Gly Tyr Ile Thr Gly Ser Ser Val Lys Gln Ala Ala
                245             250             255
```

-continued

```
Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 182
<211> LENGTH: 549
<212> TYPE: PRT
<213> ORGANISM: Artificial Sequence
<220> FEATURE:
<223> OTHER INFORMATION: Homo sapiens

<400> SEQUENCE: 182

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60
```

```
Arg Arg Ala Pro Thr Gly Pro Pro Gly Thr Pro Gly Thr Pro Gly Cys
 65                  70                  75                  80

Ala Ala Thr Ala Lys Gly Pro Gly Ala Gln Gln Pro Lys Pro Ala Ser
                 85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
                115                 120                 125

Ile Gln Gln His Phe Gly Val Lys Ala Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
                180                 185                 190

Phe Trp Leu Leu Val Leu Ser Arg Gly Leu Val Gly Ile Gly Glu Ala
                195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
                275                 280                 285

Ala Asp Gln Leu Gly Asp Gln Leu Lys Ala Arg Thr Ser Trp Leu Arg
                290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Ala Val Ala Leu Gln Ser
                450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
```

-continued

```
                    485                 490                 495
Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
530                 535                 540

Ala Ser Val Lys Val
545

<210> SEQ ID NO 183
<211> LENGTH: 549
<212> TYPE: PRT
<213> ORGANISM: Artificial Sequence
<220> FEATURE:
<223> OTHER INFORMATION: Homo sapiens

<400> SEQUENCE: 183

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Ala Gly Ala Gly Leu Leu Gln
    130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
```

```
    290             295             300
Asp Met Lys Ala Leu Ile Arg Asn Arg Ser Tyr Val Phe Ser Ser Leu
305             310             315             320

Ala Thr Ser Ala Val Ser Phe Ala Thr Gly Ala Leu Gly Met Trp Ile
            325             330             335

Pro Leu Tyr Leu His Arg Ala Gln Val Val Gln Lys Thr Ala Glu Thr
            340             345             350

Cys Asn Ser Pro Pro Cys Gly Ala Lys Asp Ser Leu Ile Phe Gly Ala
            355             360             365

Ile Thr Cys Phe Thr Gly Phe Leu Gly Val Val Thr Gly Ala Gly Ala
            370             375             380

Thr Arg Trp Cys Arg Leu Lys Thr Gln Arg Ala Asp Pro Leu Val Cys
385             390             395             400

Ala Val Gly Met Leu Gly Ser Ala Ile Phe Ile Cys Leu Ile Phe Val
            405             410             415

Ala Ala Lys Ser Ser Ile Val Gly Ala Tyr Ile Cys Ile Phe Val Gly
            420             425             430

Glu Thr Leu Leu Phe Ser Asn Trp Ala Ile Thr Ala Asp Ile Leu Met
            435             440             445

Tyr Val Val Ile Pro Thr Arg Arg Ala Thr Val Ala Leu Gln Ser
            450             455             460

Phe Thr Ser His Leu Leu Gly Asp Ala Gly Ser Pro Tyr Leu Ile Gly
465             470             475             480

Phe Ile Ser Asp Leu Ile Arg Gln Ser Thr Lys Asp Ser Pro Leu Trp
            485             490             495

Glu Phe Leu Ser Leu Gly Tyr Ala Leu Met Leu Cys Pro Phe Val Val
            500             505             510

Val Leu Gly Gly Met Phe Phe Leu Ala Thr Ala Leu Phe Phe Val Ser
            515             520             525

Asp Arg Ala Arg Ala Glu Gln Gln Val Asn Gln Leu Ala Met Pro Pro
            530             535             540

Ala Ser Val Lys Val
545

<210> SEQ ID NO 184
<211> LENGTH: 549
<212> TYPE: PRT
<213> ORGANISM: Artificial Sequence
<220> FEATURE:
<223> OTHER INFORMATION: Homo sapiens

<400> SEQUENCE: 184

Met Met Cys Leu Glu Cys Ala Ser Ala Ala Gly Gly Ala Glu Glu
1               5               10              15

Glu Glu Ala Asp Ala Glu Arg Arg Arg Arg Gly Ala Gln Arg
            20              25              30

Gly Ala Gly Gly Ser Gly Cys Cys Gly Ala Arg Gly Ala Gly Gly Ala
            35              40              45

Gly Val Ser Ala Ala Gly Asp Glu Val Gln Thr Leu Ser Gly Ser Val
            50              55              60

Arg Arg Ala Pro Thr Gly Pro Pro Gly Thr Gly Thr Pro Gly Cys
65              70              75              80

Ala Ala Thr Ala Lys Gly Pro Gly Ala Gln Gln Pro Lys Pro Ala Ser
            85              90              95

Leu Gly Arg Gly Arg Gly Ala Ala Ala Ala Ile Leu Ser Leu Gly Asn
```

```
                100                 105                 110
Val Leu Asn Tyr Leu Asp Arg Tyr Thr Val Ala Gly Val Leu Leu Asp
            115                 120                 125
Ile Gln Gln His Phe Gly Val Lys Asp Arg Ala Ala Gly Leu Leu Gln
            130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Ser Phe Ile Pro Gln Gln Tyr
            180                 185                 190
Phe Trp Leu Leu Val Leu Ser Arg Gly Leu Val Gly Ile Gly Glu Ala
            195                 200                 205
Ser Tyr Ser Thr Ile Ala Pro Thr Ile Ile Gly Asp Leu Phe Thr Lys
            210                 215                 220
Asn Thr Arg Thr Leu Met Leu Ser Val Phe Tyr Phe Ala Ile Pro Leu
225                 230                 235                 240
Gly Ser Gly Leu Gly Tyr Ile Thr Gly Ser Ser Val Lys Gln Ala Ala
                245                 250                 255
Gly Asp Trp His Trp Ala Leu Arg Val Ser Pro Val Leu Gly Met Ile
                260                 265                 270
Thr Gly Thr Leu Ile Leu Ile Leu Val Pro Ala Thr Lys Arg Gly His
            275                 280                 285
Ala Asp Gln Leu Gly Asp Gln Leu Lys Ala Arg Thr Ser Trp Leu Arg
            290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
            355                 360                 365
Ile Thr Cys Phe Thr Gly Phe Leu Gly Val Val Thr Gly Ala Gly Ala
            370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
            420                 425                 430
Glu Thr Leu Leu Phe Ser Asn Trp Ala Ile Thr Ala Asp Ile Leu Met
            435                 440                 445
Tyr Val Val Ile Pro Thr Arg Arg Ala Thr Ala Val Ala Leu Gln Ser
            450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
            500                 505                 510
Val Leu Gly Gly Met Phe Phe Leu Ala Thr Ala Leu Phe Phe Val Ser
            515                 520                 525
```

Asp Arg Ala Arg Ala Glu Gln Gln Val Asn Gln Leu Ala Met Pro Pro
            530                 535                 540

Ala Ser Val Lys Val
545

<210> SEQ ID NO 185
<211> LENGTH: 549
<212> TYPE: PRT
<213> ORGANISM: Artificial Sequence
<220> FEATURE:
<223> OTHER INFORMATION: Homo sapiens

<400> SEQUENCE: 185

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Ala Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

-continued

```
Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
530                 535                 540

Ala Ser Val Lys Val
545

<210> SEQ ID NO 186
<211> LENGTH: 549
<212> TYPE: PRT
<213> ORGANISM: Artificial Sequence
<220> FEATURE:
<223> OTHER INFORMATION: Homo sapiens

<400> SEQUENCE: 186

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
        130                 135                 140
```

```
Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Ala Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Gln Lys Thr Ala Glu Thr
            340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
            450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
530                 535                 540

Ala Ser Val Lys Val
545
```

<210> SEQ ID NO 187
<211> LENGTH: 549
<212> TYPE: PRT
<213> ORGANISM: Artificial Sequence
<220> FEATURE:
<223> OTHER INFORMATION: Homo sapiens

<400> SEQUENCE: 187

```
Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
        130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Ala Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365
```

```
Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
                515                 520                 525

Asp Arg Ala Arg Ala Glu Gln Gln Val Asn Gln Leu Ala Met Pro Pro
530                 535                 540

Ala Ser Val Lys Val
545
```

<210> SEQ ID NO 188
<211> LENGTH: 549
<212> TYPE: PRT
<213> ORGANISM: Artificial Sequence
<220> FEATURE:
<223> OTHER INFORMATION: Homo sapiens

<400> SEQUENCE: 188

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175
```

Phe Trp Ser Ala Val Thr Phe Ser Ser Ser Phe Ile Pro Gln Gln Ala
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 189
<211> LENGTH: 549
<212> TYPE: PRT
<213> ORGANISM: Artificial Sequence
<220> FEATURE:
<223> OTHER INFORMATION: Homo sapiens

<400> SEQUENCE: 189

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65              70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
    115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Ala Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
```

```
                      405                 410                 415
Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
        450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 190
<211> LENGTH: 549
<212> TYPE: PRT
<213> ORGANISM: Artificial Sequence
<220> FEATURE:
<223> OTHER INFORMATION: Homo sapiens

<400> SEQUENCE: 190

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Ala Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
```

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
            245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
            325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
            370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
            405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
            450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
            530                 535                 540

Ala Ser Val Lys Val
545

<210> SEQ ID NO 191
<211> LENGTH: 549
<212> TYPE: PRT
<213> ORGANISM: Artificial Sequence
<220> FEATURE:
<223> OTHER INFORMATION: Homo sapiens

<400> SEQUENCE: 191

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg

-continued

```
               20                  25                  30
Gly Ala Gly Gly Ser Gly Cys Cys Gly Ala Arg Gly Ala Gly Gly Ala
            35                  40                  45
Gly Val Ser Ala Ala Gly Asp Glu Val Gln Thr Leu Ser Gly Ser Val
50                  55                  60
Arg Arg Ala Pro Thr Gly Pro Pro Gly Thr Pro Gly Thr Pro Gly Cys
65                  70                  75                  80
Ala Ala Thr Ala Lys Gly Pro Gly Ala Gln Gln Pro Lys Pro Ala Ser
                85                  90                  95
Leu Gly Arg Gly Arg Gly Ala Ala Ala Ile Leu Ser Leu Gly Asn
            100                 105                 110
Val Leu Asn Tyr Leu Asp Arg Tyr Thr Val Ala Gly Val Leu Leu Asp
            115                 120                 125
Ile Gln Gln His Phe Gly Val Lys Asp Arg Gly Ala Gly Leu Leu Gln
            130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Ser Phe Ile Pro Gln Gln Tyr
            180                 185                 190
Phe Trp Ala Leu Val Leu Ser Arg Gly Leu Val Gly Ile Gly Glu Ala
            195                 200                 205
Ser Tyr Ser Thr Ile Ala Pro Thr Ile Ile Gly Asp Leu Phe Thr Lys
            210                 215                 220
Asn Thr Arg Thr Leu Met Leu Ser Val Phe Tyr Phe Ala Ile Pro Leu
225                 230                 235                 240
Gly Ser Gly Leu Gly Tyr Ile Thr Gly Ser Ser Val Lys Gln Ala Ala
                245                 250                 255
Gly Asp Trp His Trp Ala Leu Arg Val Ser Pro Val Leu Gly Met Ile
            260                 265                 270
Thr Gly Thr Leu Ile Leu Ile Leu Val Pro Ala Thr Lys Arg Gly His
            275                 280                 285
Ala Asp Gln Leu Gly Asp Gln Leu Lys Ala Arg Thr Ser Trp Leu Arg
            290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
            355                 360                 365
Ile Thr Cys Phe Thr Gly Phe Leu Gly Val Val Thr Gly Ala Gly Ala
            370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
            420                 425                 430
Glu Thr Leu Leu Phe Ser Asn Trp Ala Ile Thr Ala Asp Ile Leu Met
            435                 440                 445
```

```
Tyr Val Val Ile Pro Thr Arg Arg Ala Thr Ala Val Ala Leu Gln Ser
        450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
                515                 520                 525

Asp Arg Ala Arg Ala Glu Gln Gln Val Asn Gln Leu Ala Met Pro Pro
                530                 535                 540

Ala Ser Val Lys Val
545

<210> SEQ ID NO 192
<211> LENGTH: 549
<212> TYPE: PRT
<213> ORGANISM: Artificial Sequence
<220> FEATURE:
<223> OTHER INFORMATION: Homo sapiens

<400> SEQUENCE: 192

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
                35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ala Ile Leu Ser Leu Gly Asn
                100                 105                 110

Val Leu Asn Tyr Leu Asp Arg Tyr Thr Val Ala Gly Val Leu Leu Asp
                115                 120                 125

Ile Gln Gln His Phe Gly Val Lys Asp Arg Gly Ala Gly Leu Leu Gln
            130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
                180                 185                 190

Phe Trp Leu Ala Val Leu Ser Arg Gly Leu Val Gly Ile Gly Glu Ala
                195                 200                 205

Ser Tyr Ser Thr Ile Ala Pro Thr Ile Ile Gly Asp Leu Phe Thr Lys
                210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255
```

Gly Asp Trp His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
        290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 193
<211> LENGTH: 549
<212> TYPE: PRT
<213> ORGANISM: Artificial Sequence
<220> FEATURE:
<223> OTHER INFORMATION: Homo sapiens

<400> SEQUENCE: 193

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

```
Arg Arg Ala Pro Thr Gly Pro Pro Gly Thr Pro Thr Pro Gly Cys
 65                  70                  75                  80

Ala Ala Thr Ala Lys Gly Pro Gly Ala Gln Gln Pro Lys Pro Ala Ser
                 85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
            130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
                180                 185                 190

Phe Trp Leu Leu Ala Leu Ser Arg Gly Leu Val Gly Ile Gly Glu Ala
                195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
                275                 280                 285

Ala Asp Gln Leu Gly Asp Gln Leu Lys Ala Arg Thr Ser Trp Leu Arg
                290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
                370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Ala Val Ala Leu Gln Ser
                450                 455                 460

Phe Thr Ser His Leu Leu Gly Asp Ala Gly Ser Pro Tyr Leu Ile Gly
465                 470                 475                 480
```

```
Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
            530                 535                 540

Ala Ser Val Lys Val
545
```

<210> SEQ ID NO 194
<211> LENGTH: 549
<212> TYPE: PRT
<213> ORGANISM: Artificial Sequence
<220> FEATURE:
<223> OTHER INFORMATION: Homo sapiens

<400> SEQUENCE: 194

```
Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Gly Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln His Phe Gly Val Lys Asp Arg Gly Ala Gly Leu Leu Gln
            130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Ala Ser Arg Gly Leu Val Gly Ile Gly Glu Ala
            195                 200                 205

Ser Tyr Ser Thr Ile Ala Pro Thr Ile Ile Gly Asp Leu Phe Thr Lys
            210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285
```

```
Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
                515                 520                 525

Asp Arg Ala Arg Ala Glu Gln Gln Val Asn Gln Leu Ala Met Pro Pro
                530                 535                 540

Ala Ser Val Lys Val
545

<210> SEQ ID NO 195
<211> LENGTH: 549
<212> TYPE: PRT
<213> ORGANISM: Artificial Sequence
<220> FEATURE:
<223> OTHER INFORMATION: Homo sapiens

<400> SEQUENCE: 195

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
                20                  25                  30

Gly Ala Gly Gly Ser Gly Cys Cys Gly Ala Arg Gly Ala Gly Gly Ala
                35                  40                  45

Gly Val Ser Ala Ala Gly Asp Glu Val Gln Thr Leu Ser Gly Ser Val
                50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95
```

```
Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ala Arg Gly Leu Val Gly Ile Gly Glu Ala
            195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
```

```
                515                 520                 525
Asp Arg Ala Arg Ala Glu Gln Gln Val Asn Gln Leu Ala Met Pro Pro
    530                 535                 540

Ala Ser Val Lys Val
545

<210> SEQ ID NO 196
<211> LENGTH: 549
<212> TYPE: PRT
<213> ORGANISM: Artificial Sequence
<220> FEATURE:
<223> OTHER INFORMATION: Homo sapiens

<400> SEQUENCE: 196

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
                20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Ala Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
```

```
                    325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
            355                 360                 365
Ile Thr Cys Phe Thr Gly Phe Leu Gly Val Val Thr Gly Ala Gly Ala
            370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
                420                 425                 430
Glu Thr Leu Leu Phe Ser Asn Trp Ala Ile Thr Ala Asp Ile Leu Met
                435                 440                 445
Tyr Val Val Ile Pro Thr Arg Arg Ala Thr Ala Val Ala Leu Gln Ser
            450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
                500                 505                 510
Val Leu Gly Gly Met Phe Phe Leu Ala Thr Ala Leu Phe Phe Val Ser
                515                 520                 525
Asp Arg Ala Arg Ala Glu Gln Gln Val Asn Gln Leu Ala Met Pro Pro
            530                 535                 540
Ala Ser Val Lys Val
545

<210> SEQ ID NO 197
<211> LENGTH: 549
<212> TYPE: PRT
<213> ORGANISM: Artificial Sequence
<220> FEATURE:
<223> OTHER INFORMATION: Homo sapiens

<400> SEQUENCE: 197

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
        50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
```

```
            130                 135                 140
Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Ala Leu Val Gly Ile Gly Glu Ala
            195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
            370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
            435                 440                 445

Tyr Val Val Ile Pro Thr Arg Arg Ala Thr Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
530                 535                 540

Ala Ser Val Lys Val
545
```

```
<210> SEQ ID NO 198
<211> LENGTH: 549
<212> TYPE: PRT
<213> ORGANISM: Artificial Sequence
<220> FEATURE:
<223> OTHER INFORMATION: Homo sapiens

<400> SEQUENCE: 198
```

| | | | | | | | | | | | | | | | |
|---|---|---|---|---|---|---|---|---|---|---|---|---|---|---|---|
| Met | Met | Cys | Leu | Glu | Cys | Ala | Ser | Ala | Ala | Gly | Gly | Ala | Glu | Glu | |
| 1 | | | | 5 | | | | | 10 | | | | | 15 | |
| Glu | Glu | Ala | Asp | Ala | Glu | Arg | Arg | Arg | Arg | Arg | Gly | Ala | Gln | Arg | |
| | | | 20 | | | | | 25 | | | | | 30 | | |
| Gly | Ala | Gly | Gly | Ser | Gly | Cys | Cys | Gly | Ala | Arg | Gly | Ala | Gly | Gly | Ala |
| | | 35 | | | | | 40 | | | | | 45 | | | |
| Gly | Val | Ser | Ala | Ala | Gly | Asp | Glu | Val | Gln | Thr | Leu | Ser | Gly | Ser | Val |
| | 50 | | | | | 55 | | | | | 60 | | | | |
| Arg | Arg | Ala | Pro | Thr | Gly | Pro | Pro | Gly | Thr | Pro | Gly | Thr | Pro | Gly | Cys |
| 65 | | | | | 70 | | | | | 75 | | | | | 80 |
| Ala | Ala | Thr | Ala | Lys | Gly | Pro | Gly | Ala | Gln | Gln | Pro | Lys | Pro | Ala | Ser |
| | | | | 85 | | | | | 90 | | | | | 95 | |
| Leu | Gly | Arg | Gly | Arg | Gly | Ala | Ala | Ala | Ile | Leu | Ser | Leu | Gly | Asn | |
| | | | 100 | | | | | 105 | | | | | 110 | | |
| Val | Leu | Asn | Tyr | Leu | Asp | Arg | Tyr | Thr | Val | Ala | Gly | Val | Leu | Leu | Asp |
| | | 115 | | | | | 120 | | | | | 125 | | | |
| Ile | Gln | Gln | His | Phe | Gly | Val | Lys | Asp | Arg | Gly | Ala | Gly | Leu | Leu | Gln |
| | 130 | | | | | 135 | | | | | 140 | | | | |
| Ser | Val | Phe | Ile | Cys | Ser | Phe | Met | Val | Ala | Ala | Pro | Ile | Phe | Gly | Tyr |
| 145 | | | | | 150 | | | | | 155 | | | | | 160 |
| Leu | Gly | Asp | Arg | Phe | Asn | Arg | Lys | Val | Ile | Leu | Ser | Cys | Gly | Ile | Phe |
| | | | | 165 | | | | | 170 | | | | | 175 | |
| Phe | Trp | Ser | Ala | Val | Thr | Phe | Ser | Ser | Ser | Phe | Ile | Pro | Gln | Gln | Tyr |
| | | | 180 | | | | | 185 | | | | | 190 | | |
| Phe | Trp | Leu | Leu | Val | Leu | Ser | Arg | Gly | Ala | Val | Gly | Ile | Gly | Glu | Ala |
| | | 195 | | | | | 200 | | | | | 205 | | | |
| Ser | Tyr | Ser | Thr | Ile | Ala | Pro | Thr | Ile | Ile | Gly | Asp | Leu | Phe | Thr | Lys |
| | 210 | | | | | 215 | | | | | 220 | | | | |
| Asn | Thr | Arg | Thr | Leu | Met | Leu | Ser | Val | Phe | Tyr | Phe | Ala | Ile | Pro | Leu |
| 225 | | | | | 230 | | | | | 235 | | | | | 240 |
| Gly | Ser | Gly | Leu | Gly | Tyr | Ile | Thr | Gly | Ser | Ser | Val | Lys | Gln | Ala | Ala |
| | | | | 245 | | | | | 250 | | | | | 255 | |
| Gly | Asp | Trp | His | Trp | Ala | Leu | Arg | Val | Ser | Pro | Val | Leu | Gly | Met | Ile |
| | | | 260 | | | | | 265 | | | | | 270 | | |
| Thr | Gly | Thr | Leu | Ile | Leu | Ile | Leu | Val | Pro | Ala | Thr | Lys | Arg | Gly | His |
| | | 275 | | | | | 280 | | | | | 285 | | | |
| Ala | Asp | Gln | Leu | Gly | Asp | Gln | Leu | Lys | Ala | Arg | Thr | Ser | Trp | Leu | Arg |
| | 290 | | | | | 295 | | | | | 300 | | | | |
| Asp | Met | Lys | Ala | Leu | Ile | Arg | Asn | Arg | Ser | Tyr | Val | Phe | Ser | Ser | Leu |
| 305 | | | | | 310 | | | | | 315 | | | | | 320 |
| Ala | Thr | Ser | Ala | Val | Ser | Phe | Ala | Thr | Gly | Ala | Leu | Gly | Met | Trp | Ile |
| | | | | 325 | | | | | 330 | | | | | 335 | |
| Pro | Leu | Tyr | Leu | His | Arg | Ala | Gln | Val | Val | Gln | Lys | Thr | Ala | Glu | Thr |
| | | | 340 | | | | | 345 | | | | | 350 | | |
| Cys | Asn | Ser | Pro | Pro | Cys | Gly | Ala | Lys | Asp | Ser | Leu | Ile | Phe | Gly | Ala |
| | | 355 | | | | | 360 | | | | | 365 | | | |

```
Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
                515                 520                 525

Asp Arg Ala Arg Ala Glu Gln Gln Val Asn Gln Leu Ala Met Pro Pro
530                 535                 540

Ala Ser Val Lys Val
545
```

<210> SEQ ID NO 199
<211> LENGTH: 549
<212> TYPE: PRT
<213> ORGANISM: Artificial Sequence
<220> FEATURE:
<223> OTHER INFORMATION: Homo sapiens

<400> SEQUENCE: 199

```
Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175
```

```
Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Ser Ser Ala Lys Gln Ala Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 200
<211> LENGTH: 549
<212> TYPE: PRT
<213> ORGANISM: Artificial Sequence
<220> FEATURE:
```

<223> OTHER INFORMATION: Homo sapiens

<400> SEQUENCE: 200

```
Met Met Cys Leu Glu Cys Ala Ser Ala Ala Gly Gly Ala Glu Glu
 1               5                  10                  15

Glu Glu Ala Asp Ala Glu Arg Arg Arg Arg Arg Gly Ala Gln Arg
                20                  25                  30

Gly Ala Gly Gly Ser Gly Cys Cys Gly Ala Arg Gly Ala Gly Ala
                35                  40                  45

Gly Val Ser Ala Ala Gly Asp Glu Val Gln Thr Leu Ser Gly Ser Val
                50                  55                  60

Arg Arg Ala Pro Thr Gly Pro Pro Gly Thr Pro Gly Thr Pro Gly Cys
 65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
                115                 120                 125

Ile Gln Gln His Phe Gly Val Lys Asp Arg Gly Ala Gly Leu Leu Gln
                130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
                180                 185                 190

Phe Trp Leu Leu Val Leu Ser Arg Gly Leu Val Gly Ile Gly Glu Ala
                195                 200                 205

Ser Tyr Ser Thr Ile Ala Pro Thr Ile Ile Gly Asp Leu Phe Thr Lys
                210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Val Ala Gln Ala Ala
                245                 250                 255

Gly Asp Trp His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
                275                 280                 285

Ala Asp Gln Leu Gly Asp Gln Leu Lys Ala Arg Thr Ser Trp Leu Arg
                290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
                370                 375                 380

Thr Arg Trp Cys Arg Leu Lys Thr Gln Arg Ala Asp Pro Leu Val Cys
385                 390                 395                 400
```

-continued

```
Ala Val Gly Met Leu Gly Ser Ala Ile Phe Ile Cys Leu Ile Phe Val
            405                 410                 415
Ala Ala Lys Ser Ser Ile Val Gly Ala Tyr Ile Cys Ile Phe Val Gly
        420                 425                 430
Glu Thr Leu Leu Phe Ser Asn Trp Ala Ile Thr Ala Asp Ile Leu Met
            435                 440                 445
Tyr Val Val Ile Pro Thr Arg Arg Ala Thr Val Ala Leu Gln Ser
    450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
            500                 505                 510
Val Leu Gly Gly Met Phe Phe Leu Ala Thr Ala Leu Phe Phe Val Ser
        515                 520                 525
Asp Arg Ala Arg Ala Glu Gln Gln Val Asn Gln Leu Ala Met Pro Pro
    530                 535                 540
Ala Ser Val Lys Val
545

<210> SEQ ID NO 201
<211> LENGTH: 549
<212> TYPE: PRT
<213> ORGANISM: Artificial Sequence
<220> FEATURE:
<223> OTHER INFORMATION: Homo sapiens

<400> SEQUENCE: 201

Met Met Cys Leu Glu Cys Ala Ser Ala Ala Gly Gly Ala Glu Glu
1               5                   10                  15
Glu Glu Ala Asp Ala Glu Arg Arg Arg Arg Arg Gly Ala Gln Arg
            20                  25                  30
Gly Ala Gly Gly Ser Gly Cys Cys Gly Ala Arg Gly Ala Gly Gly Ala
        35                  40                  45
Gly Val Ser Ala Ala Gly Asp Glu Val Gln Thr Leu Ser Gly Ser Val
    50                  55                  60
Arg Arg Ala Pro Thr Gly Pro Pro Gly Thr Pro Gly Thr Pro Gly Cys
65                  70                  75                  80
Ala Ala Thr Ala Lys Gly Pro Gly Ala Gln Gln Pro Lys Pro Ala Ser
                85                  90                  95
Leu Gly Arg Gly Arg Gly Ala Ala Ala Ile Leu Ser Leu Gly Asn
            100                 105                 110
Val Leu Asn Tyr Leu Asp Arg Tyr Thr Val Ala Gly Val Leu Leu Asp
        115                 120                 125
Ile Gln Gln His Phe Gly Val Lys Asp Arg Gly Ala Gly Leu Leu Gln
    130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                165                 170                 175
Phe Trp Ser Ala Val Thr Phe Ser Ser Ser Phe Ile Pro Gln Gln Tyr
            180                 185                 190
Phe Trp Leu Leu Val Leu Ser Arg Gly Leu Val Gly Ile Gly Glu Ala
        195                 200                 205
```

```
Ser Tyr Ser Thr Ile Ala Pro Thr Ile Ile Gly Asp Leu Phe Thr Lys
    210                 215                 220
Asn Thr Arg Thr Leu Met Leu Ser Val Phe Tyr Phe Ala Ile Pro Leu
225                 230                 235                 240
Gly Ser Gly Leu Gly Tyr Ile Thr Gly Ser Ser Val Lys Ala Ala Ala
                245                 250                 255
Gly Asp Trp His Trp Ala Leu Arg Val Ser Pro Val Leu Gly Met Ile
            260                 265                 270
Thr Gly Thr Leu Ile Leu Ile Leu Val Pro Ala Thr Lys Arg Gly His
        275                 280                 285
Ala Asp Gln Leu Gly Asp Gln Leu Lys Ala Arg Thr Ser Trp Leu Arg
    290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                325                 330                 335
Pro Leu Tyr Leu His Arg Ala Gln Val Val Gln Lys Thr Ala Glu Thr
            340                 345                 350
Cys Asn Ser Pro Pro Cys Gly Ala Lys Asp Ser Leu Ile Phe Gly Ala
        355                 360                 365
Ile Thr Cys Phe Thr Gly Phe Leu Gly Val Val Thr Gly Ala Gly Ala
    370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                405                 410                 415
Ala Ala Lys Ser Ser Ile Val Gly Ala Tyr Ile Cys Ile Phe Val Gly
            420                 425                 430
Glu Thr Leu Leu Phe Ser Asn Trp Ala Ile Thr Ala Asp Ile Leu Met
        435                 440                 445
Tyr Val Val Ile Pro Thr Arg Arg Ala Thr Ala Val Ala Leu Gln Ser
    450                 455                 460
Phe Thr Ser His Leu Leu Gly Asp Ala Gly Ser Pro Tyr Leu Ile Gly
465                 470                 475                 480
Phe Ile Ser Asp Leu Ile Arg Gln Ser Thr Lys Asp Ser Pro Leu Trp
                485                 490                 495
Glu Phe Leu Ser Leu Gly Tyr Ala Leu Met Leu Cys Pro Phe Val Val
            500                 505                 510
Val Leu Gly Gly Met Phe Phe Leu Ala Thr Ala Leu Phe Phe Val Ser
        515                 520                 525
Asp Arg Ala Arg Ala Glu Gln Gln Val Asn Gln Leu Ala Met Pro Pro
    530                 535                 540
Ala Ser Val Lys Val
545

<210> SEQ ID NO 202
<211> LENGTH: 549
<212> TYPE: PRT
<213> ORGANISM: Artificial Sequence
<220> FEATURE:
<223> OTHER INFORMATION: Homo sapiens

<400> SEQUENCE: 202

Met Met Cys Leu Glu Cys Ala Ser Ala Ala Gly Gly Ala Glu Glu
1               5                   10                  15
```

-continued

```
Glu Glu Ala Asp Ala Glu Arg Arg Arg Arg Arg Gly Ala Gln Arg
             20                  25                  30
Gly Ala Gly Gly Ser Gly Cys Cys Gly Ala Arg Gly Ala Gly Gly Ala
         35                  40                  45
Gly Val Ser Ala Ala Gly Asp Glu Val Gln Thr Leu Ser Gly Ser Val
     50                  55                  60
Arg Arg Ala Pro Thr Gly Pro Pro Gly Thr Pro Gly Thr Pro Gly Cys
 65                  70                  75                  80
Ala Ala Thr Ala Lys Gly Pro Gly Ala Gln Gln Pro Lys Pro Ala Ser
                 85                  90                  95
Leu Gly Arg Gly Arg Gly Ala Ala Ala Ile Leu Ser Leu Gly Asn
             100                 105                 110
Val Leu Asn Tyr Leu Asp Arg Tyr Thr Val Ala Gly Val Leu Leu Asp
         115                 120                 125
Ile Gln Gln His Phe Gly Val Lys Asp Arg Gly Ala Gly Leu Leu Gln
     130                 135                 140
Ser Val Phe Ile Cys Ser Phe Met Val Ala Ala Pro Ile Phe Gly Tyr
145                 150                 155                 160
Leu Gly Asp Arg Phe Asn Arg Lys Val Ile Leu Ser Cys Gly Ile Phe
                 165                 170                 175
Phe Trp Ser Ala Val Thr Phe Ser Ser Ser Phe Ile Pro Gln Gln Tyr
             180                 185                 190
Phe Trp Leu Leu Val Leu Ser Arg Gly Leu Val Gly Ile Gly Glu Ala
         195                 200                 205
Ser Tyr Ser Thr Ile Ala Pro Thr Ile Ile Gly Asp Leu Phe Thr Lys
     210                 215                 220
Asn Thr Arg Thr Leu Met Leu Ser Val Phe Tyr Phe Ala Ile Pro Leu
225                 230                 235                 240
Gly Ser Gly Leu Gly Tyr Ile Thr Gly Ser Ser Val Lys Gln Ala Ala
                 245                 250                 255
Ala Asp Trp His Trp Ala Leu Arg Val Ser Pro Val Leu Gly Met Ile
             260                 265                 270
Thr Gly Thr Leu Ile Leu Ile Leu Val Pro Ala Thr Lys Arg Gly His
         275                 280                 285
Ala Asp Gln Leu Gly Asp Gln Leu Lys Ala Arg Thr Ser Trp Leu Arg
     290                 295                 300
Asp Met Lys Ala Leu Ile Arg Asn Arg Ser Tyr Val Phe Ser Ser Leu
305                 310                 315                 320
Ala Thr Ser Ala Val Ser Phe Ala Thr Gly Ala Leu Gly Met Trp Ile
                 325                 330                 335
Pro Leu Tyr Leu His Arg Ala Gln Val Val Gln Lys Thr Ala Glu Thr
             340                 345                 350
Cys Asn Ser Pro Pro Cys Gly Ala Lys Asp Ser Leu Ile Phe Gly Ala
         355                 360                 365
Ile Thr Cys Phe Thr Gly Phe Leu Gly Val Val Thr Gly Ala Gly Ala
     370                 375                 380
Thr Arg Trp Cys Arg Leu Lys Thr Gln Arg Ala Asp Pro Leu Val Cys
385                 390                 395                 400
Ala Val Gly Met Leu Gly Ser Ala Ile Phe Ile Cys Leu Ile Phe Val
                 405                 410                 415
Ala Ala Lys Ser Ser Ile Val Gly Ala Tyr Ile Cys Ile Phe Val Gly
             420                 425                 430
Glu Thr Leu Leu Phe Ser Asn Trp Ala Ile Thr Ala Asp Ile Leu Met
```

```
                435                 440                 445
Tyr Val Val Ile Pro Thr Arg Arg Ala Thr Ala Val Ala Leu Gln Ser
            450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
            530                 535                 540

Ala Ser Val Lys Val
545

<210> SEQ ID NO 203
<211> LENGTH: 549
<212> TYPE: PRT
<213> ORGANISM: Artificial Sequence
<220> FEATURE:
<223> OTHER INFORMATION: Homo sapiens

<400> SEQUENCE: 203

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
            20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
            50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
            130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
                180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
            210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
```

```
                        245                 250                 255
Gly Ala Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
        290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
            355                 360                 365

Ile Thr Cys Phe Thr Gly Phe Leu Gly Val Val Thr Gly Ala Gly Ala
        370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
                500                 505                 510

Val Leu Gly Gly Met Phe Phe Leu Ala Thr Ala Leu Phe Phe Val Ser
            515                 520                 525

Asp Arg Ala Arg Ala Glu Gln Gln Val Asn Gln Leu Ala Met Pro Pro
        530                 535                 540

Ala Ser Val Lys Val
545

<210> SEQ ID NO 204
<211> LENGTH: 549
<212> TYPE: PRT
<213> ORGANISM: Artificial Sequence
<220> FEATURE:
<223> OTHER INFORMATION: Homo sapiens

<400> SEQUENCE: 204

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
```

-continued

```
            50                  55                  60
Arg Arg Ala Pro Thr Gly Pro Pro Gly Thr Pro Gly Thr Pro Gly Cys
 65                  70                  75                  80

Ala Ala Thr Ala Lys Gly Pro Gly Ala Gln Gln Pro Lys Pro Ala Ser
                 85                  90                  95

Leu Gly Arg Gly Arg Gly Ala Ala Ala Ile Leu Ser Leu Gly Asn
                100                 105                 110

Val Leu Asn Tyr Leu Asp Arg Tyr Thr Val Ala Gly Val Leu Leu Asp
                115                 120                 125

Ile Gln Gln His Phe Gly Val Lys Asp Arg Gly Ala Gly Leu Leu Gln
130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
                180                 185                 190

Phe Trp Leu Leu Val Leu Ser Arg Gly Leu Val Gly Ile Gly Glu Ala
                195                 200                 205

Ser Tyr Ser Thr Ile Ala Pro Thr Ile Ile Gly Asp Leu Phe Thr Lys
210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Ala His Trp Ala Leu Arg Val Ser Pro Val Leu Gly Met Ile
                260                 265                 270

Thr Gly Thr Leu Ile Leu Ile Leu Val Pro Ala Thr Lys Arg Gly His
                275                 280                 285

Ala Asp Gln Leu Gly Asp Gln Leu Lys Ala Arg Thr Ser Trp Leu Arg
                290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
                340                 345                 350

Cys Asn Ser Pro Pro Cys Gly Ala Lys Asp Ser Leu Ile Phe Gly Ala
                355                 360                 365

Ile Thr Cys Phe Thr Gly Phe Leu Gly Val Val Thr Gly Ala Gly Ala
                370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
                420                 425                 430

Glu Thr Leu Leu Phe Ser Asn Trp Ala Ile Thr Ala Asp Ile Leu Met
                435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480
```

```
Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 205
<211> LENGTH: 549
<212> TYPE: PRT
<213> ORGANISM: Artificial Sequence
<220> FEATURE:
<223> OTHER INFORMATION: Homo sapiens

<400> SEQUENCE: 205

Met Met Cys Leu Glu Cys Ala Ser Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
        195                 200                 205

Ser Tyr Ser Thr Ile Ala Pro Thr Ile Ile Gly Asp Leu Phe Thr Lys
    210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Ala
                245                 250                 255

Gly Asp Trp Ala Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285
```

```
Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510

Val Leu Gly Gly Met Phe Phe Leu Ala Thr Ala Leu Phe Phe Val Ser
        515                 520                 525

Asp Arg Ala Arg Ala Glu Gln Gln Val Asn Gln Leu Ala Met Pro Pro
    530                 535                 540

Ala Ser Val Lys Val
545

<210> SEQ ID NO 206
<211> LENGTH: 549
<212> TYPE: PRT
<213> ORGANISM: Artificial Sequence
<220> FEATURE:
<223> OTHER INFORMATION: Homo sapiens

<400> SEQUENCE: 206

Met Met Cys Leu Glu Cys Ala Ser Ala Ala Ala Gly Gly Ala Glu Glu
1               5                   10                  15

Glu Glu Ala Asp Ala Glu Arg Arg Arg Arg Arg Gly Ala Gln Arg
            20                  25                  30

Gly Ala Gly Gly Ser Gly Cys Cys Gly Ala Arg Gly Ala Gly Gly Ala
        35                  40                  45

Gly Val Ser Ala Ala Gly Asp Glu Val Gln Thr Leu Ser Gly Ser Val
    50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95
```

```
Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
        115                 120                 125

Ile Gln Gln His Phe Gly Val Lys Asp Arg Gly Ala Gly Leu Leu Gln
    130                 135                 140

Ser Val Phe Ile Cys Ser Phe Met Val Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
        210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Phe Ala
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
        275                 280                 285

Ala Asp Gln Leu Gly Asp Gln Leu Lys Ala Arg Thr Ser Trp Leu Arg
    290                 295                 300

Asp Met Lys Ala Leu Ile Arg Asn Arg Ser Tyr Val Phe Ser Ser Leu
305                 310                 315                 320

Ala Thr Ser Ala Val Ser Phe Ala Thr Gly Ala Leu Gly Met Trp Ile
                325                 330                 335

Pro Leu Tyr Leu His Arg Ala Gln Val Val Gln Lys Thr Ala Glu Thr
            340                 345                 350

Cys Asn Ser Pro Pro Cys Gly Ala Lys Asp Ser Leu Ile Phe Gly Ala
        355                 360                 365

Ile Thr Cys Phe Thr Gly Phe Leu Gly Val Val Thr Gly Ala Gly Ala
    370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
                405                 410                 415

Ala Ala Lys Ser Ser Ile Val Gly Ala Tyr Ile Cys Ile Phe Val Gly
            420                 425                 430

Glu Thr Leu Leu Phe Ser Asn Trp Ala Ile Thr Ala Asp Ile Leu Met
        435                 440                 445

Tyr Val Val Ile Pro Thr Arg Arg Ala Thr Ala Val Ala Leu Gln Ser
    450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
                485                 490                 495

Glu Phe Leu Ser Leu Gly Tyr Ala Leu Met Leu Cys Pro Phe Val Val
            500                 505                 510
```

```
Val Leu Gly Gly Met Phe Phe Leu Ala Thr Ala Leu Phe Val Ser
            515                 520                 525

Asp Arg Ala Arg Ala Glu Gln Gln Val Asn Gln Leu Ala Met Pro Pro
530                 535                 540

Ala Ser Val Lys Val
545

<210> SEQ ID NO 207
<211> LENGTH: 549
<212> TYPE: PRT
<213> ORGANISM: Artificial Sequence
<220> FEATURE:
<223> OTHER INFORMATION: Homo sapiens

<400> SEQUENCE: 207

Met Met Cys Leu Glu Cys Ala Ser Ala Ala Gly Gly Ala Glu Glu
1               5                   10                  15

Glu Glu Ala Asp Ala Glu Arg Arg Arg Arg Gly Ala Gln Arg
                20                  25                  30

Gly Ala Gly Gly Ser Gly Cys Cys Gly Ala Arg Gly Ala Gly Gly Ala
            35                  40                  45

Gly Val Ser Ala Ala Gly Asp Glu Val Gln Thr Leu Ser Gly Ser Val
50                  55                  60

Arg Arg Ala Pro Thr Gly Pro Pro Gly Thr Pro Gly Thr Pro Gly Cys
65                  70                  75                  80

Ala Ala Thr Ala Lys Gly Pro Gly Ala Gln Gln Pro Lys Pro Ala Ser
                85                  90                  95

Leu Gly Arg Gly Arg Gly Ala Ala Ala Ile Leu Ser Leu Gly Asn
            100                 105                 110

Val Leu Asn Tyr Leu Asp Arg Tyr Thr Val Ala Gly Val Leu Leu Asp
            115                 120                 125

Ile Gln Gln His Phe Gly Val Lys Asp Arg Gly Ala Gly Leu Leu Gln
            130                 135                 140

Ser Val Phe Ile Cys Ser Phe Met Val Ala Ala Pro Ile Phe Gly Tyr
145                 150                 155                 160

Leu Gly Asp Arg Phe Asn Arg Lys Val Ile Leu Ser Cys Gly Ile Phe
                165                 170                 175

Phe Trp Ser Ala Val Thr Phe Ser Ser Ser Phe Ile Pro Gln Gln Tyr
            180                 185                 190

Phe Trp Leu Leu Val Leu Ser Arg Gly Leu Val Gly Ile Gly Glu Ala
            195                 200                 205

Ser Tyr Ser Thr Ile Ala Pro Thr Ile Ile Gly Asp Leu Phe Thr Lys
            210                 215                 220

Asn Thr Arg Thr Leu Met Leu Ser Val Phe Tyr Phe Ala Ile Pro Leu
225                 230                 235                 240

Gly Ser Gly Leu Gly Tyr Ile Thr Gly Ser Ser Val Lys Gln Ala Phe
                245                 250                 255

Gly Asp Trp His Trp Ala Leu Arg Val Ser Pro Val Leu Gly Met Ile
            260                 265                 270

Thr Gly Thr Leu Ile Leu Ile Leu Val Pro Ala Thr Lys Arg Gly His
            275                 280                 285

Ala Asp Gln Leu Gly Asp Gln Leu Lys Ala Arg Thr Ser Trp Leu Arg
            290                 295                 300

Asp Met Lys Ala Leu Ile Arg Asn Arg Ser Tyr Val Phe Ser Ser Leu
305                 310                 315                 320
```

```
Ala Thr Ser Ala Val Ser Phe Ala Thr Gly Ala Leu Gly Met Trp Ile
            325                 330                 335

Pro Leu Tyr Leu His Arg Ala Gln Val Val Gln Lys Thr Ala Glu Thr
        340                 345                 350

Cys Asn Ser Pro Pro Cys Gly Ala Lys Asp Ser Leu Ile Phe Gly Ala
    355                 360                 365

Ile Thr Cys Phe Thr Gly Phe Leu Gly Val Val Thr Gly Ala Gly Ala
370                 375                 380

Thr Arg Trp Cys Arg Leu Lys Thr Gln Arg Ala Asp Pro Leu Val Cys
385                 390                 395                 400

Ala Val Gly Met Leu Gly Ser Ala Ile Phe Ile Cys Leu Ile Phe Val
            405                 410                 415

Ala Ala Lys Ser Ser Ile Val Gly Ala Tyr Ile Cys Ile Phe Val Gly
        420                 425                 430

Glu Thr Leu Leu Phe Ser Asn Trp Ala Ile Thr Ala Asp Ile Leu Met
    435                 440                 445

Tyr Val Val Ile Pro Thr Arg Arg Ala Thr Ala Val Ala Leu Gln Ser
450                 455                 460

Phe Thr Ser His Leu Leu Gly Asp Ala Gly Ser Pro Tyr Leu Ile Gly
465                 470                 475                 480

Phe Ile Ser Asp Leu Ile Arg Gln Ser Thr Lys Asp Ser Pro Leu Trp
            485                 490                 495

Glu Phe Leu Ser Leu Gly Tyr Ala Leu Met Leu Cys Pro Phe Val Val
        500                 505                 510

Val Leu Gly Gly Met Phe Phe Leu Ala Thr Ala Leu Phe Phe Val Ser
    515                 520                 525

Asp Arg Ala Arg Ala Glu Gln Gln Val Asn Gln Leu Ala Met Pro Pro
530                 535                 540

Ala Ser Val Lys Val
545
```

<210> SEQ ID NO 208
<211> LENGTH: 1650
<212> TYPE: DNA
<213> ORGANISM: Artificial Sequence
<220> FEATURE:
<223> OTHER INFORMATION: Homo sapiens

<400> SEQUENCE: 208

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca ccccggctgc     240
gcagctactg caaagggccc cggcgctcag cagcccaaac cggccagctt gggccgcggg     300
cggggggcag ccgccgccat cctcagcttg gcaacgtgc tcaactacct ggacaggtac     360
accgtggcag gcgtccttgc cgacatccag cagcactttg ggtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg cattttctt ctggtcggcc     540
gtcaccttct ccagctcctt cattccccag cagtacttct ggctgctggt cctgtcccgg     600
gggctggtgg gcatcgggga ggccagctac tccaccatcg cccccactat cattggcgac     660
ctcttcacca agaacacgcg tacgctcatg ctgtccgtct tctacttcgc catcccactg     720
```

| | |
|---|---:|
| ggcagtggcc tgggctacat tactggctcc agcgtgaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg ccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 209
<211> LENGTH: 1650
<212> TYPE: DNA
<213> ORGANISM: Artificial Sequence
<220> FEATURE:
<223> OTHER INFORMATION: Homo sapiens

<400> SEQUENCE: 209

| | |
|---|---:|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcta taaggcgggc cccgaccgga ccccccggca ccccggctgc | 240 |
| gcagctactg caaagggccc cggcgctcag cagcccaaac cggccagctt gggccgcggg | 300 |
| cgggggcag ccgccgccat cctcagcttg gcaacgtgc tcaactacct ggacaggtac | 360 |
| accgtggcag gcgtccttct ggccatccag cagcactttg gggtcaagga ccgaggcgcc | 420 |
| ggcctgctgc agtcagtgtt catctgtagc ttcatggtgg ctgccccat cttcggctac | 480 |
| ctgggcgacc gcttcaacag gaaggtgatt ctcagctgcg gcattttctt ctggtcggcc | 540 |
| gtcaccttct ccagctcctt cattcccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg ccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |

```
gggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650

<210> SEQ ID NO 210
<211> LENGTH: 1650
<212> TYPE: DNA
<213> ORGANISM: Artificial Sequence
<220> FEATURE:
<223> OTHER INFORMATION: Homo sapiens

<400> SEQUENCE: 210
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga cccccggca cccccggcac cccggctgc       240 gcagctactg caaagggccc cggcgctcag cagcccaaac cggccagctt gggccgcggg     300
cggggggcag ccgccgccat cctcagcttg ggcaacgtgc tcaactacct ggacaggtac     360
accgtggcag gcgtccttct ggacgcccag cagcactttg gggtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcatttttctt ctggtcggcc    540 gtcaccttct ccagctcctt cattcccag cagtacttct ggctgctggt cctgtcccgg      600
gggctggtgg gcatcgggga ggccagctac tccaccatcg ccccactat cattggcgac     660 ctcttcacca gaacacgcg tacgctcatg ctgtccgtct tctacttcgc catcccactg      720
ggcagtggcc tgggctacat tactggctcc agcgtgaagc aggcagccgg agactggcac      780
tgggcattgc gggtgtcccc tgtcctgggc atgatcacag gaacactcat cctcattctg      840
gtcccagcca ctaaaagggg tcatgccgac cagctcgggg accagctcaa ggcccggacc      900
tcatggctcc gagatatgaa ggccctgatt cgaaaccgca gctacgtctt ctcctccctg      960
gccacgtcgc tgtctccttc gccacgggg gccctgggca tgtggatccc gctctacctg    1020
caccgcgccc aagttgtgca agacagca gagacgtgca acagcccgcc ctgtggggcc       1080
aaggacagca tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga gttcctgagc    1500
```

| | |
|---|---|
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 211
<211> LENGTH: 1650
<212> TYPE: DNA
<213> ORGANISM: Artificial Sequence
<220> FEATURE:
<223> OTHER INFORMATION: Homo sapiens

<400> SEQUENCE: 211

| | |
|---|---|
| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga cccccggca ccccggcac ccccggctgc | 240 |
| gcagctactg caaagggccc cggcgctcag cagcccaaac cggccagctt gggccgcggg | 300 |
| cggggggcag ccgccgccat cctcagcttg ggcaacgtgc tcaactacct ggacaggtac | 360 |
| accgtggcag gcgtccttct ggacatcgcc cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca gaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca agacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 212
<211> LENGTH: 1650
<212> TYPE: DNA
<213> ORGANISM: Artificial Sequence
<220> FEATURE:
<223> OTHER INFORMATION: Homo sapiens

<400> SEQUENCE: 212

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca ccccggcac ccccggctgc      240
gcagctactg caaagggccc cggcgctcag cagcccaaac cggccagctt gggccgcggg     300
cggggggcag ccgccgccat cctcagcttg gcaacgtgc tcaactacct ggacaggtac      360
accgtggcag gcgtccttct ggacatccag gcccactttg gggtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcattttctt ctggtcggcc     540
gtcaccttct ccagctcctt cattccccag cagtacttct ggctgctggt cctgtcccgg     600
gggctggtgg gcatcgggga ggccagctac tccaccatcg cccccactat cattggcgac     660
ctcttcacca gaacacgcg tacgctcatg ctgtccgtct tctacttcgc catcccactg      720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca agagacagca gagacgtgca acagcccgcc ctgtggggcc    1080
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650
```

<210> SEQ ID NO 213
<211> LENGTH: 1650
<212> TYPE: DNA
<213> ORGANISM: Artificial Sequence
<220> FEATURE:
<223> OTHER INFORMATION: Homo sapiens

<400> SEQUENCE: 213

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca ccccggcac ccccggctgc      240
gcagctactg caaagggccc cggcgctcag cagcccaaac cggccagctt gggccgcggg     300
```

| | |
|---|---|
| cgggggggcag ccgccgccat cctcagcttg ggcaacgtgc tcaactacct ggacaggtac | 360 |
| accgtggcag gcgtccttct ggacatccag caggcctttg ggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

```
<210> SEQ ID NO 214
<211> LENGTH: 1650
<212> TYPE: DNA
<213> ORGANISM: Artificial Sequence
<220> FEATURE:
<223> OTHER INFORMATION: Homo sapiens

<400> SEQUENCE: 214
```

| | |
|---|---|
| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga cccccggca cccccggcac cccccggctgc | 240 |
| gcagctactg caaagggccc cggcgctcag cagcccaaac cggccagctt gggccgcggg | 300 |
| cgggggggcag ccgccgccat cctcagcttg ggcaacgtgc tcaactacct ggacaggtac | 360 |
| accgtggcag gcgtccttct ggacatccag cagcacgccg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |

```
ggcagtggcc tgggctacat tactggctcc agcgtgaagc aggcagccgg agactggcac      780
tgggcattgc gggtgtcccc tgtcctgggc atgatcacag gaacactcat cctcattctg      840
gtcccagcca ctaaaagggg tcatgccgac cagctcgggg accagctcaa ggcccggacc      900
tcatggctcc gagatatgaa ggccctgatt cgaaaccgca gctacgtctt ctcctccctg      960
gccacgtcgg ctgtctcctt cgccacgggg gccctgggca tgtggatccc gctctacctg     1020
caccgcgccc aagttgtgca gaagacagca gagacgtgca cagcccgcc ctgtggggcc      1080 aaggacagcc tcatctttgg ggccatcacc tgctttacgg gatttctggg cgtggtcacg     1140
ggggcaggag ccacgcgctg gtgccgcctg aagacccagc gggccgaccc actggtgtgt     1200
gccgtgggca tgctgggctc tgccatcttc atctgcctga tcttcgtggc tgccaagagc     1260
agcatcgtag gagcctatat ctgtatcttc gtcggggaga cgctgctgtt ttctaactgg     1320
gccatcactg cagacatcct catgtacgtg gtcatcccca cgcggcgcgc cactgccgtg     1380
gccttgcaga gcttcacctc ccacctgctg ggggacgccg ggagccccta cctcattggc     1440
tttatctcag acctgatccg ccagagcact aaggactccc cgctctggga gttcctgagc     1500
ctgggctacg cgctcatgct ctgccctttc gtcgtggtcc tgggcggcat gttcttcctc     1560
gccactgcgc tcttcttcgt cagcgaccgc gccagggctg agcagcaggt gaaccagctg     1620
gcgatgccgc ccgcatctgt gaaagtctga                                       1650
```

<210> SEQ ID NO 215
<211> LENGTH: 1650
<212> TYPE: DNA
<213> ORGANISM: Artificial Sequence
<220> FEATURE:
<223> OTHER INFORMATION: Homo sapiens

<400> SEQUENCE: 215

```
atgatgtgcc tggaatgcgc ctcggcggcg gcgggcggcg cggaggagga ggaggcggac       60
gcggagcggc ggcgccggcg ccgggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca ccccggctgc                 240
gcagctactg caaagggccc cggcgctcag cagcccaaac cggccagctt gggccgcggg     300
cggggggcag ccgccgccat cctcagcttg gcaacgtgc tcaactacct ggacaggtac     360
accgtggcag gcgtccttct ggacatccag cagcactttg ccgtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcattttctt ctggtcggcc     540
gtcaccttct ccagctcctt cattcccag cagtacttct ggctgctggt cctgtcccgg     600
gggctggtgg gcatcgggga ggccagctac tccaccatcg cccccactat cattggcgac     660
ctcttcacca gaacacgcg tacgctcatg ctgtccgtct tctacttcgc catcccactg     720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca gaagacagca gagacgtgca cagcccgcc ctgtggggcc     1080
```

| | |
|---|---|
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 216
<211> LENGTH: 1650
<212> TYPE: DNA
<213> ORGANISM: Artificial Sequence
<220> FEATURE:
<223> OTHER INFORMATION: Homo sapiens

<400> SEQUENCE: 216

| | |
|---|---|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga ccccccggca cccccggctgc | 240 |
| gcagctactg caaagggccc cggcgctcag cagcccaaac cggccagctt gggccgcggg | 300 |
| cgggggggcag ccgccgccat cctcagcttg gcaacgtgc tcaactacct ggacaggtac | 360 |
| accgtggcag gcgtccttct ggacatccag cagcactttg ggccaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ccagctgcg gcatttttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc ggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |

```
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650
```

<210> SEQ ID NO 217
<211> LENGTH: 1650
<212> TYPE: DNA
<213> ORGANISM: Artificial Sequence
<220> FEATURE:
<223> OTHER INFORMATION: Homo sapiens

<400> SEQUENCE: 217

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca cccccggcac ccccggctgc     240
gcagctactg caaagggccc cggcgctcag cagcccaaac cggccagctt gggccgcggg     300
cggggggcag ccgccgccat cctcagcttg ggcaacgtgc tcaactacct ggacaggtac     360
accgtggcag gcgtccttct ggacatccag cagcactttg gggtcgccga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcatttcttt ctggtcggcc     540
gtcaccttct ccagctcctt cattccccag cagtacttct ggctgctggt cctgtcccgg     600
gggctggtgg gcatcgggga ggccagctac tccaccatcg cccccactat cattggcgac     660
ctcttcacca gaacacgcg tacgctcatg ctgtccgtct tctacttcgc catcccactg     720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca gaagacagca gagacgtgca acagcccgcc ctgtggggcc    1080
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                    1650
```

<210> SEQ ID NO 218
<211> LENGTH: 1650
<212> TYPE: DNA
<213> ORGANISM: Artificial Sequence
<220> FEATURE:

<223> OTHER INFORMATION: Homo sapiens

<400> SEQUENCE: 218

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | ccccggcac | ccccggctgc | 240 |
| gcagctactg | caaagggccc | cggcgctcag | cagcccaaac | cggccagctt | gggccgcggg | 300 |
| cgggggggcag | ccgccgccat | cctcagcttg | ggcaacgtgc | tcaactacct | ggacaggtac | 360 |
| accgtggcag | gcgtccttct | ggacatccag | cagcactttg | gggtcaaggc | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | gcattttctt | ctggtcggcc | 540 |
| gtcaccttct | ccagctcctt | cattccccag | cagtacttct | ggctgctggt | cctgtcccgg | 600 |
| gggctggtgg | gcatcgggga | ggccagctac | tccaccatcg | ccccactat | cattggcgac | 660 |
| ctcttcacca | agaacacgcg | tacgctcatg | ctgtccgtct | tctacttcgc | catcccactg | 720 |
| ggcagtggcc | tgggctacat | tactggctcc | agcgtgaagc | aggcagccgg | agactggcac | 780 |
| tgggcattgc | gggtgtcccc | tgtcctgggc | atgatcacag | gaacactcat | cctcattctg | 840 |
| gtcccagcca | ctaaaagggg | tcatgccgac | cagctcgggg | accagctcaa | ggcccggacc | 900 |
| tcatggctcc | gagatatgaa | ggccctgatt | cgaaaccgca | gctacgtctt | ctcctccctg | 960 |
| gccacgtcgg | ctgtctcctt | cgccacgggg | gccctgggca | tgtggatccc | gctctacctg | 1020 |
| caccgcgccc | aagttgtgca | gaagacagca | gagacgtgca | acagcccgcc | ctgtggggcc | 1080 |
| aaggacagcc | tcatctttgg | ggccatcacc | tgctttacgg | gatttctggg | cgtggtcacg | 1140 |
| ggggcaggag | ccacgcgctg | gtgccgcctg | aagacccagc | gggccgaccc | actggtgtgt | 1200 |
| gccgtgggca | tgctgggctc | tgccatcttc | atctgcctga | tcttcgtggc | tgccaagagc | 1260 |
| agcatcgtag | gagcctatat | ctgtatcttc | gtcggggaga | cgctgctgtt | ttctaactgg | 1320 |
| gccatcactg | cagacatcct | catgtacgtg | gtcatcccca | cgcggcgcgc | cactgccgtg | 1380 |
| gccttgcaga | gcttcaccte | ccacctgctg | ggggacgccg | ggagcccta | cctcattggc | 1440 |
| tttatctcag | acctgatccg | ccagagcact | aaggactccc | cgctctggga | gttcctgagc | 1500 |
| ctgggctacg | cgctcatgct | ctgccctttc | gtcgtggtcc | tgggcggcat | gttcttcctc | 1560 |
| gccactgcgc | tcttcttcgt | cagcgaccgc | gccagggctg | agcagcaggt | gaaccagctg | 1620 |
| gcgatgccgc | ccgcatctgt | gaaagtctga | | | | 1650 |

<210> SEQ ID NO 219
<211> LENGTH: 1650
<212> TYPE: DNA
<213> ORGANISM: Artificial Sequence
<220> FEATURE:
<223> OTHER INFORMATION: Homo sapiens

<400> SEQUENCE: 219

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | ccccggcac | ccccggctgc | 240 |
| gcagctactg | caaagggccc | cggcgctcag | cagcccaaac | cggccagctt | gggccgcggg | 300 |

```
cgggggggcag ccgccgccat cctcagcttg ggcaacgtgc tcaactacct ggacaggtac       360
accgtggcag gcgtccttct ggacatccag cagcactttg gggtcaagga cgccggcgcc       420
ggcctgctgc agtcagtgtt catctgtagc ttcatggtgg ctgccccat cttcggctac        480 ctgggcgacc gcttcaacag gaaggtgatt ctcagctgcg gcattttctt ctggtcggcc       540
gtcaccttct ccagctcctt cattccccag cagtacttct ggctgctggt cctgtcccgg      600
gggctggtgg gcatcgggga ggccagctac tccaccatcg cccccactat cattggcgac      660
ctcttcacca gaacacgcg tacgctcatg ctgtccgtct tctacttcgc catcccactg       720
ggcagtggcc tgggctacat tactggctcc agcgtgaagc aggcagccgg agactggcac      780
tgggcattgc gggtgtcccc tgtcctgggc atgatcacag aacactcat cctcattctg       840 gtcccagcca ctaaaagggg tcatgccgac cagctcgggg accagctcaa ggcccggacc      900
tcatggctcc gagatatgaa ggccctgatt cgaaaccgca gctacgtctt ctcctccctg      960
gccacgtcgg ctgtctcctt cgccacgggg ccctgggca tgtggatccc gctctacctg      1020
caccgcgccc aagttgtgca agacacagca gagacgtgca acagcccgcc ctgtggggcc     1080
aaggacagcc tcatctttgg ggccatcacc tgctttacgg gatttctggg cgtggtcacg     1140
ggggcaggag ccacgcgctg gtgccgcctg aagacccagc gggccgaccc actggtgtgt     1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg     1320
gccatcactg cagacatcct catgtacgtg gtcatcccca cgcggcgcgc cactgccgtg    1380
gccttgcaga gcttcacctc ccacctgctg ggggacgccg ggagcccta cctcattggc      1440 tttatctcag acctgatccg ccagagcact aaggactccc cgctctggga gttcctgagc     1500
ctgggctacg cgctcatgct ctgcccttc gtcgtggtcc tgggcggcat gttcttcctc      1560
gccactgcgc tcttcttcgt cagcgaccgc gccagggctg agcagcaggt gaaccagctg      1620
gcgatgccgc ccgcatctgt gaaagtctga                                       1650
```

<210> SEQ ID NO 220
<211> LENGTH: 1650
<212> TYPE: DNA
<213> ORGANISM: Artificial Sequence
<220> FEATURE:
<223> OTHER INFORMATION: Homo sapiens

<400> SEQUENCE: 220

```
atgatgtgcc tggaatgcgc ctcggcggcg gcgggcggcg cggaggagga ggaggcggac        60
gcggagcggc ggcgccggcg ccggggggcg cagcgagggg ctggcggtag cggttgctgc       120
ggggcgcggg gcgcgggcgg cgctggagtc tcggccgcgg gcgatgaggt gcagacgctg       180
tcgggcagcg taaggcgggc cccgaccgga cccccggca ccccggcac cccggctgc         240 gcagctactg caaagggccc cggcgctcag cagcccaaac cggccagctt gggccgcggg      300 cgggggggcag ccgccgccat cctcagcttg ggcaacgtgc tcaactacct ggacaggtac      360
accgtggcag gcgtccttct ggacatccag cagcactttg gggtcaagga ccgagccgcc      420
ggcctgctgc agtcagtgtt catctgtagc ttcatggtgg ctgccccat cttcggctac       480 ctgggcgacc gcttcaacag gaaggtgatt ctcagctgcg gcattttctt ctggtcggcc      540
gtcaccttct ccagctcctt cattccccag cagtacttct ggctgctggt cctgtcccgg     600
gggctggtgg gcatcgggga ggccagctac tccaccatcg cccccactat cattggcgac     660
```

| | |
|---|---|
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca agagacagca gagacgtgca cagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 221
<211> LENGTH: 1650
<212> TYPE: DNA
<213> ORGANISM: Artificial Sequence
<220> FEATURE:
<223> OTHER INFORMATION: Homo sapiens

<400> SEQUENCE: 221

| | |
|---|---|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga cccccggca ccccggcac ccccggctgc | 240 |
| gcagctactg caaagggccc cggcgctcag cagcccaaac cggccagctt gggccgcggg | 300 |
| cggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt tcagctgcg gcattttctt ctggtcggcc | 540 |
| gtcaccttct ccagctcctt cattgcccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca agagacagca gagacgtgca cagcccgcc ctgtggggcc | 1080 |

```
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
tttatctcag acctgatccg ccagagcact aaggactccc cgctctggga gttcctgagc    1500
ctgggctacg cgctcatgct ctgcccttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                      1650

<210> SEQ ID NO 222
<211> LENGTH: 1650
<212> TYPE: DNA
<213> ORGANISM: Artificial Sequence
<220> FEATURE:
<223> OTHER INFORMATION: Homo sapiens

<400> SEQUENCE: 222
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcggcgg cgctggagtc tcggccgcgg gcgatgaggt gcagacgctg     180
tcgggcagcg taaggcgggc cccgaccgga cccccccggca cccccggctgc                240 gcagctactg caaagggccc cggcgctcag cagcccaaac cggccagctt gggccgcggg     300
cgggggcagg ccgccgccat cctcagcttg ggcaacgtgc tcaactacct ggacaggtac     360
accgtggcag gcgtccttct ggacatccag cagcactttg gggtcaagga ccgaggcgcc     420
ggcctgctgc agtcagtgtt catctgtagc ttcatggtgg ctgccccat cttcggctac     480 ctgggcgacc gcttcaacag gaaggtgatt ctcagctgcg gcattttctt ctggtcggcc     540
gtcaccttct ccagctcctt cattcccgcc cagtacttct ggctgctggt cctgtcccgg     600
gggctggtgg catcggggga ggccagctac tccaccatcg cccccactat cattggcgac     660
ctcttcacca gaacacgcg tacgctcatg ctgtccgtct tctacttcgc catcccactg     720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca gaagacagca gagacgtgca acagcccgcc ctgtggggcc    1080
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagccccta cctcattggc    1440
```

| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 223
<211> LENGTH: 1650
<212> TYPE: DNA
<213> ORGANISM: Artificial Sequence
<220> FEATURE:
<223> OTHER INFORMATION: Homo sapiens

<400> SEQUENCE: 223

| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcgccgcgg gcgatgaggt gcagacgctg | 180 |
| tcgggcagcg taaggcgggc cccgaccgga ccccccggca cccccggcac cccggctgc | 240 |
| gcagctactg caaagggccc cggcgctcag cagcccaaac cggccagctt gggccgcggg | 300 |
| cgggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg cattttctt ctggtcggcc | 540 |
| gtcaccttct ccagctcctt cattcccag gcctacttct ggctgctggt cctgtcccgg | 600 |
| gggctggtgg gcatcgggga ggccagctac tccaccatcg cccccactat cattggcgac | 660 |
| ctcttcacca gaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 224
<211> LENGTH: 1650
<212> TYPE: DNA
<213> ORGANISM: Artificial Sequence
<220> FEATURE:
<223> OTHER INFORMATION: Homo sapiens

<400> SEQUENCE: 224

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga cccccggca ccccggcac ccccggctgc      240
gcagctactg caaagggccc cggcgctcag cagcccaaac cggccagctt gggccgcggg     300
cggggggcag ccgccgccat cctcagcttg ggcaacgtgc tcaactacct ggacaggtac     360
accgtggcag gcgtccttct ggacatccag cagcactttg gggtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcattttctt ctggtcggcc     540
gtcaccttct ccagctcctt cattccccag caggccttct ggctgctggt cctgtcccgg     600
gggctggtgg gcatcgggga ggccagctac tccaccatcg ccccactat cattggcgac      660
ctcttcacca gaacacgcg tacgctcatg ctgtccgtct tctacttcgc catcccactg      720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca gaagacagca gagacgtgca acagcccgcc ctgtggggcc    1080
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagcccta cctcattggc    1440
tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650
```

<210> SEQ ID NO 225
<211> LENGTH: 1650
<212> TYPE: DNA
<213> ORGANISM: Artificial Sequence
<220> FEATURE:
<223> OTHER INFORMATION: Homo sapiens

<400> SEQUENCE: 225

```
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga cccccggca ccccggcac ccccggctgc      240
```

```
gcagctactg caaagggccc cggcgctcag cagcccaaac cggccagctt gggccgcggg      300
cggggggcag ccgccgccat cctcagcttg ggcaacgtgc tcaactacct ggacaggtac      360
accgtggcag gcgtccttct ggacatccag cagcactttg gggtcaagga ccgaggcgcc      420
ggcctgctgc agtcagtgtt catctgtagc ttcatggtgg ctgcccccat cttcggctac      480
ctgggcgacc gcttcaacag gaaggtgatt ctcagctgcg gcattttctt ctggtcggcc      540
gtcaccttct ccagctcctt cattccccag cagtacgcct ggctgctggt cctgtcccgg      600
gggctggtgg gcatcgggga ggccagctac tccaccatcg cccccactat cattggcgac      660
ctcttcacca agaacacgcg tacgctcatg ctgtccgtct tctacttcgc catcccactg      720
ggcagtggcc tgggctacat tactggctcc agcgtgaagc aggcagccgg agactggcac      780
tgggcattgc gggtgtcccc tgtcctgggc atgatcacag gaacactcat cctcattctg      840
gtcccagcca ctaaaagggg tcatgccgac cagctcgggg accagctcaa ggcccggacc      900
tcatggctcc gagatatgaa ggccctgatt cgaaaccgca gctacgtctt ctcctccctg      960
gccacgtcgg ctgtctcctt cgccacgggg gccctgggca tgtggatccc gctctacctg      1020
caccgcgccc aagttgtgca gaagacagca gagacgtgca acagcccgcc ctgtggggcc      1080
aaggacagcc tcatctttgg ggccatcacc tgctttacgg gatttctggg cgtggtcacg      1140
ggggcaggag ccacgcgctg gtgccgcctg aagacccagc gggccgaccc actggtgtgt      1200
gccgtgggca tgctgggctc tgccatcttc atctgcctga tcttcgtggc tgccaagagc      1260
agcatcgtag gagcctatat ctgtatcttc gtcggggaga cgctgctgtt ttctaactgg      1320
gccatcactg cagacatcct catgtacgtg gtcatcccca cgcggcgcgc cactgccgtg      1380
gccttgcaga gcttcacctc ccacctgctg ggggacgccg ggagccccta cctcattggc      1440
tttatctcag acctgatccg ccagagcact aaggactccc cgctctggga gttcctgagc      1500
ctgggctacg cgctcatgct ctgccctttc gtcgtggtcc tgggcggcat gttcttcctc      1560
gccactgcgc tcttcttcgt cagcgaccgc gccagggctg agcagcaggt gaaccagctg      1620
gcgatgccgc ccgcatctgt gaaagtctga      1650
```

<210> SEQ ID NO 226
<211> LENGTH: 1650
<212> TYPE: DNA
<213> ORGANISM: Artificial Sequence
<220> FEATURE:
<223> OTHER INFORMATION: Homo sapiens

<400> SEQUENCE: 226

```
atgatgtgcc tggaatgcgc ctcggcggcg gcgggcggcg cggaggagga ggaggcggac       60
gcggagcggc ggcgccggcg ccggggggcg cagcgagggg ctggcggtag cggttgctgc      120
ggggcgcggg gcgcgggcgg cgctggagtc tcggccgcgg gcgatgaggt gcagacgctg      180
tcgggcagcg taaggcgggc cccgaccgga ccccccggca ccccggctgc                 240
gcagctactg caaagggccc cggcgctcag cagcccaaac cggccagctt gggccgcggg      300
cggggggcag ccgccgccat cctcagcttg ggcaacgtgc tcaactacct ggacaggtac      360
accgtggcag gcgtccttct ggacatccag cagcactttg gggtcaagga ccgaggcgcc      420
ggcctgctgc agtcagtgtt catctgtagc ttcatggtgg ctgcccccat cttcggctac      480
ctgggcgacc gcttcaacag gaaggtgatt ctcagctgcg gcattttctt ctggtcggcc      540
gtcaccttct ccagctcctt cattccccag cagtacttcg ccctgctggt cctgtcccgg      600
gggctggtgg gcatcgggga ggccagctac tccaccatcg cccccactat cattggcgac      660
```

```
ctcttcacca agaacacgcg tacgctcatg ctgtccgtct tctacttcgc catcccactg    720
ggcagtggcc tgggctacat tactggctcc agcgtgaagc aggcagccgg agactggcac    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
gccacgtcgg ctgtctcctt cgccacgggg gccctgggca tgtggatccc gctctacctg   1020
caccgcgccc aagttgtgca agacagca gagacgtgca acagcccgcc ctgtgggggcc   1080 aaggacagca tcatctttgg ggccatcacc tgctttacgg gatttctggg cgtggtcacg   1140
ggggcaggag ccacgcgctg gtgccgcctg aagacccagc gggccgaccc actggtgtgt   1200
gccgtgggca tgctgggctc tgccatcttc atctgcctga tcttcgtggc tgccaagagc   1260
agcatcgtag gagcctatat ctgtatcttc gtcggggaga cgctgctgtt ttctaactgg   1320
gccatcactg cagacatcct catgtacgtg gtcatcccca cgcggcgcgc cactgccgtg   1380
gccttgcaga gcttcacctc ccacctgctg ggggacgccg ggagcccta cctcattggc   1440 tttatctcag acctgatccg ccagagcact aaggactccc cgctctggga gttcctgagc   1500
ctgggctacg cgctcatgct ctgccctttc gtcgtggtcc tgggcggcat gttcttcctc   1560
gccactgcgc tcttcttcgt cagcgaccgc gccagggctg agcagcaggt gaaccagctg   1620
gcgatgccgc ccgcatctgt gaaagtctga                                    1650

<210> SEQ ID NO 227
<211> LENGTH: 1650
<212> TYPE: DNA
<213> ORGANISM: Artificial Sequence
<220> FEATURE:
<223> OTHER INFORMATION: Homo sapiens

<400> SEQUENCE: 227
atgatgtgcc tggaatgcgc ctcggcggcg gcgggcggcg cggaggagga ggaggcggac     60
gcggagcggc ggcgccggcg ccggggggcg cagcgagggg ctggcggtag cggttgctgc    120
ggggcgcggg gcgcgggcgg cgctggagtc tcggccgcgg gcgatgaggt gcagacgctg    180
tcgggcagcg taaggcgggc cccgaccgga ccccccggca ccccggcac ccccggctgc    240 gcagctactg caaagggccc cggcgctcag cagcccaaac cggccagctt gggccgcggg    300 cgggggggcag ccgccgccat cctcagcttg gcaacgtgc tcaactacct ggacaggtac    360
accgtggcag gcgtccttct ggacatccag cagcactttg gggtcaagga ccgaggcgcc    420
ggcctgctgc agtcagtgtt catctgtagc ttcatggtgg ctgcccccat cttcggctac    480
ctgggcgacc gcttcaacag gaaggtgatt ctcagctgcg gcatttttctt ctggtcggcc    540 gtcaccttct ccagctcctt cattcccag cagtacttct gggccctggt cctgtcccgg    600
gggctggtgg gcatcgggga ggccagctac tccaccatcg ccccactat cattggcgac    660 ctcttcacca agaacacgcg tacgctcatg ctgtccgtct tctacttcgc catcccactg    720
ggcagtggcc tgggctacat tactggctcc agcgtgaagc aggcagccgg agactggcac    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
gccacgtcgg ctgtctcctt cgccacgggg gccctgggca tgtggatccc gctctacctg   1020
```

| | |
|---|---|
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcaccte ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 228
<211> LENGTH: 1650
<212> TYPE: DNA
<213> ORGANISM: Artificial Sequence
<220> FEATURE:
<223> OTHER INFORMATION: Homo sapiens

<400> SEQUENCE: 228

| | |
|---|---|
| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga ccccccggca ccccggcac cccggctgc | 240 |
| gcagctactg caaagggccc cggcgctcag cagcccaaac cggccagctt gggccgcggg | 300 |
| cgggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctggccgt cctgtcccgg | 600 |
| gggctggtgg catcggggga ggccagctac tccaccatcg cccccactat cattggcgac | 660 |
| ctcttcacca gaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcaccte ccacctgctg ggggacgccg ggagccccta cctcattggc | 1440 |

```
tttatctcag acctgatccg ccagagcact aaggactccc cgctctggga gttcctgagc    1500
ctgggctacg cgctcatgct ctgcccttcc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650

<210> SEQ ID NO 229
<211> LENGTH: 1650
<212> TYPE: DNA
<213> ORGANISM: Artificial Sequence
<220> FEATURE:
<223> OTHER INFORMATION: Homo sapiens

<400> SEQUENCE: 229
atgatgtgcc tggaatgcgc ctcggcggcg gcgggcggcg cggaggagga ggaggcggac      60
gcggagcggc ggcgccggcg ccggggggcg cagcgagggg ctggcggtag cggttgctgc     120
ggggcgcggg gcgcgggcgg cgctggagtc tcggccgcgg gcgatgaggt gcagacgctg     180
tcgggcagcg taaggcgggc cccgaccgga ccccccggca ccccggcac ccccggctgc      240 gcagctactg caaagggccc cggcgctcag cagcccaaac cggccagctt gggccgcggg     300 cgggggggcag ccgccgccat cctcagcttg ggcaacgtgc tcaactacct ggacaggtac    360
accgtggcag gcgtccttct ggacatccag cagcactttg gggtcaagga ccgaggcgcc     420
ggcctgctgc agtcagtgtt catctgtagc ttcatggtgg ctgcccccat cttcggctac     480
ctgggcgacc gcttcaacag gaaggtgatt ctcagctgcg gcattttctt ctggtcggcc     540
gtcaccttct ccagctcctt cattccccag cagtacttct ggctgctggc cctgtcccgg    600
gggctggtgg gcatcgggga ggccagctac tccaccatcg cccccactat cattggcgac     660
ctcttcacca gaacacgcg tacgctcatg ctgtccgtct tctacttcgc catcccactg     720
ggcagtggcc tgggctacat tactggctcc agcgtgaagc aggcagccgg agactggcac    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg   1020
caccgcgccc aagttgtgca gaagacagca gagacgtgca cagcccgcc ctgtggggcc     1080 aaggacagcc tcatctttgg ggccatcacc tgctttacgg gatttctggg cgtggtcacg   1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg   1380
gccttgcaga gcttcacctc ccacctgctg gggggacgccg ggagcccta cctcattggc    1440 tttatctcag acctgatccg ccagagcact aaggactccc cgctctggga gttcctgagc    1500
ctgggctacg cgctcatgct ctgcccttcc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                     1650

<210> SEQ ID NO 230
<211> LENGTH: 1650
<212> TYPE: DNA
```

<213> ORGANISM: Artificial Sequence
<220> FEATURE:
<223> OTHER INFORMATION: Homo sapiens

<400> SEQUENCE: 230

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | cccccggca | ccccggcac | cccggctgc | 240 |
| gcagctactg | caaagggccc | cggcgctcag | cagcccaaac | cggccagctt | gggccgcggg | 300 |
| cgggggcag | ccgccgccat | cctcagcttg | gcaacgtgc | tcaactacct | ggacaggtac | 360 |
| accgtggcag | gcgtccttct | ggacatccag | cagcactttg | gggtcaagga | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | gcattttctt | ctggtcggcc | 540 |
| gtcaccttct | ccagctcctt | cattcccag | cagtacttct | ggctgctggt | cgcctcccgg | 600 |
| gggctggtgg | gcatcgggga | ggccagctac | tccaccatcg | ccccactat | cattggcgac | 660 |
| ctcttcacca | agaacacgcg | tacgctcatg | ctgtccgtct | tctacttcgc | catcccactg | 720 |
| ggcagtggcc | tgggctacat | tactggctcc | agcgtgaagc | aggcagccgg | agactggcac | 780 |
| tgggcattgc | gggtgtcccc | tgtcctgggc | atgatcacag | gaacactcat | cctcattctg | 840 |
| gtcccagcca | ctaaaagggg | tcatgccgac | cagctcgggg | accagctcaa | ggcccggacc | 900 |
| tcatggctcc | gagatatgaa | ggccctgatt | cgaaaccgca | gctacgtctt | ctcctccctg | 960 |
| gccacgtcgg | ctgtctcctt | cgccacgggg | gccctgggca | tgtggatccc | gctctacctg | 1020 |
| caccgcgccc | aagttgtgca | gaagacagca | gagacgtgca | acagcccgcc | ctgtggggcc | 1080 |
| aaggacagcc | tcatctttgg | ggccatcacc | tgctttacgg | gatttctggg | cgtggtcacg | 1140 |
| ggggcaggag | ccacgcgctg | gtgccgcctg | aagacccagc | gggccgaccc | actggtgtgt | 1200 |
| gccgtgggca | tgctgggctc | tgccatcttc | atctgcctga | tcttcgtggc | tgccaagagc | 1260 |
| agcatcgtag | gagcctatat | ctgtatcttc | gtcggggaga | cgctgctgtt | ttctaactgg | 1320 |
| gccatcactg | cagacatcct | catgtacgtg | gtcatcccca | cgcggcgcgc | cactgccgtg | 1380 |
| gccttgcaga | gcttcacctc | ccacctgctg | ggggacgccg | ggagcccta | cctcattggc | 1440 |
| tttatctcag | acctgatccg | ccagagcact | aaggactccc | cgctctggga | gttcctgagc | 1500 |
| ctgggctacg | cgctcatgct | ctgccctttc | gtcgtggtcc | tgggcggcat | gttcttcctc | 1560 |
| gccactgcgc | tcttcttcgt | cagcgaccgc | gccagggctg | agcagcaggt | gaaccagctg | 1620 |
| gcgatgccgc | ccgcatctgt | gaaagtctga | | | | 1650 |

<210> SEQ ID NO 231
<211> LENGTH: 1650
<212> TYPE: DNA
<213> ORGANISM: Artificial Sequence
<220> FEATURE:
<223> OTHER INFORMATION: Homo sapiens

<400> SEQUENCE: 231

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccggggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | cccccggca | ccccggcac | cccggctgc | 240 |

```
gcagctactg caaagggccc cggcgctcag cagcccaaac cggccagctt gggccgcggg      300 cgggggggcag ccgccgccat cctcagcttg ggcaacgtgc tcaactacct ggacaggtac     360
accgtggcag gcgtccttct ggacatccag cagcactttg ggtcaagga ccgaggcgcc      420 ggcctgctgc agtcagtgtt catctgtagc ttcatggtgg ctgcccccat cttcggctac     480
ctgggcgacc gcttcaacag gaaggtgatt ctcagctgcg gcattttctt ctggtcggcc     540
gtcaccttct ccagctcctt cattcccag cagtacttct ggctgctggt cctgcccgg      600 gggctggtgg gcatcgggga ggccagctac tccaccatcg cccccactat cattggcgac     660
ctcttcacca agaacacgcg tacgctcatg ctgtccgtct tctacttcgc catcccactg     720
ggcagtggcc tgggctacat tactggctcc agcgtgaagc aggcagccgg agactggcac     780
tgggcattgc gggtgtcccc tgtcctgggc atgatcacag gaacactcat cctcattctg     840
gtcccagcca ctaaaagggg tcatgccgac cagctcgggg accagctcaa ggcccggacc     900
tcatggctcc gagatatgaa ggccctgatt cgaaaccgca gctacgtctt ctcctccctg     960
gccacgtcgg ctgtctcctt cgccacgggg gccctgggca tgtggatccc gctctacctg    1020
caccgcgccc aagttgtgca gaagacagca gagacgtgca cagcccgccc ctgtggggcc    1080
aaggacagcc tcatctttgg ggccatcacc tgctttacgg gatttctggg cgtggtcacg    1140
ggggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg gggacgccg ggagcccta cctcattggc    1440 tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                      1650
```

<210> SEQ ID NO 232
<211> LENGTH: 1650
<212> TYPE: DNA
<213> ORGANISM: Artificial Sequence
<220> FEATURE:
<223> OTHER INFORMATION: Homo sapiens

<400> SEQUENCE: 232

```
atgatgtgcc tggaatgcgc ctcggcggcg gcgggcggcg cggaggagga ggaggcggac      60
gcggagcggc ggcgccggcg ccgggggggcg cagcgagggg ctggcggtag cggttgctgc     120
ggggcgcggg gcgcgggcgg cgctggagtc tcggccgcgg gcgatgaggt gcagacgctg     180
tcgggcagct aaggcgggc cccgaccgga cccccggca cccccggcac ccccggctgc      240
gcagctactg caaagggccc cggcgctcag cagcccaaac cggccagctt gggccgcggg     300 cgggggggcag ccgccgccat cctcagcttg ggcaacgtgc tcaactacct ggacaggtac    360
accgtggcag gcgtccttct ggacatccag cagcactttg ggtcaagga ccgaggcgcc     420 ggcctgctgc agtcagtgtt catctgtagc ttcatggtgg ctgcccccat cttcggctac    480
ctgggcgacc gcttcaacag gaaggtgatt ctcagctgcg gcattttctt ctggtcggcc    540
gtcaccttct ccagctcctt cattcccag cagtacttct ggctgctggt cctgtccgcc    600
```

| | | |
|---|---|---|
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca agagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 233
<211> LENGTH: 1650
<212> TYPE: DNA
<213> ORGANISM: Artificial Sequence
<220> FEATURE:
<223> OTHER INFORMATION: Homo sapiens

<400> SEQUENCE: 233

| | | |
|---|---|---|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga ccccccggca cccccggctgc | 240 |
| gcagctactg caaagggccc cggcgctcag cagcccaaac cggccagctt gggccgcggg | 300 |
| cggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ccagctgcg gcattttctt ctggtcggcc | 540 |
| gtcaccttct ccagctcctt cattcccag cagtacttct ggctgctggt cctgtcccgg | 600 |
| gccctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |

| | |
|---|---|
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgccctttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 234
<211> LENGTH: 1650
<212> TYPE: DNA
<213> ORGANISM: Artificial Sequence
<220> FEATURE:
<223> OTHER INFORMATION: Homo sapiens

<400> SEQUENCE: 234

| | |
|---|---|
| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga cccccggca ccccggcac ccccggctgc | 240 |
| gcagctactg caaagggccc cggcgctcag cagcccaaac cggccagctt gggccgcggg | 300 |
| cgggggggcag ccgccgccat cctcagcttg ggcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattcccag cagtacttct ggctgctggt cctgtcccgg | 600 |
| ggggccgtgg gcatcgggga ggccagctac tccaccatcg cccccactat cattggcgac | 660 |
| ctcttcacca gaacacgcg tacgctcatg ctgtccgtct tctacttcgc catcccactg | 720 |
| ggcagtggcc tgggctacat tactggctcc agcgtgaagc aggcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |

| | |
|---|---|
| gccttgcaga gcttcacctc ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 235
<211> LENGTH: 1650
<212> TYPE: DNA
<213> ORGANISM: Artificial Sequence
<220> FEATURE:
<223> OTHER INFORMATION: Homo sapiens

<400> SEQUENCE: 235

| | |
|---|---|
| atgatgtgcc tggaatgcgc ctcggcggcg gcgggcggcg cggaggagga ggaggcggac | 60 |
| gcggagcggc ggcgccggcg ccgggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc ccgaccggga ccccccggca cccccggcac cccggctgc | 240 |
| gcagctactg caaagggccc cggcgctcag cagcccaaac cggccagctt gggccgcggg | 300 |
| cggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca gaacacgcg tacgctcatg ctgtccgtct tctacttcgc catcccactg | 720 |
| ggcagtggcc tgggctacat tactggctcc agcgccaagc aggcagccgg agactggcac | 780 |
| tgggcattgc gggtgtcccc tgtcctgggc atgatcacag aacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca agacacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg tcatcccca cgcggcgcgc cactgccgtg | 1380 |
| gccttgcaga gcttcacctc ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 236
<211> LENGTH: 1650

<212> TYPE: DNA
<213> ORGANISM: Artificial Sequence
<220> FEATURE:
<223> OTHER INFORMATION: Homo sapiens

<400> SEQUENCE: 236

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccgggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |
| tcgggcagcg | taaggcgggc | cccgaccgga | ccccccggca | ccccggcac | ccccggctgc | 240 |
| gcagctactg | caaagggccc | cggcgctcag | cagcccaaac | cggccagctt | gggccgcggg | 300 |
| cggggggcag | ccgccgccat | cctcagcttg | ggcaacgtgc | tcaactacct | ggacaggtac | 360 |
| accgtggcag | gcgtccttct | ggacatccag | cagcactttg | gggtcaagga | ccgaggcgcc | 420 |
| ggcctgctgc | agtcagtgtt | catctgtagc | ttcatggtgg | ctgcccccat | cttcggctac | 480 |
| ctgggcgacc | gcttcaacag | gaaggtgatt | ctcagctgcg | gcattttctt | ctggtcggcc | 540 |
| gtcaccttct | ccagctcctt | cattccccag | cagtacttct | ggctgctggt | cctgtcccgg | 600 |
| gggctggtgg | gcatcgggga | ggccagctac | tccaccatcg | ccccactat | cattggcgac | 660 |
| ctcttcacca | agaacacgcg | tacgctcatg | ctgtccgtct | tctacttcgc | catcccactg | 720 |
| ggcagtggcc | tgggctacat | tactggctcc | agcgtggccc | aggcagccgg | agactggcac | 780 |
| tgggcattgc | gggtgtcccc | tgtcctgggc | atgatcacag | gaacactcat | cctcattctg | 840 |
| gtcccagcca | ctaaaagggg | tcatgccgac | cagctcgggg | accagctcaa | ggcccggacc | 900 |
| tcatggctcc | gagatatgaa | ggccctgatt | cgaaaccgca | gctacgtctt | ctcctccctg | 960 |
| gccacgtcgg | ctgtctcctt | cgccacgggg | gccctgggca | tgtggatccc | gctctacctg | 1020 |
| caccgcgccc | aagttgtgca | gaagacagca | gagacgtgca | acagcccgcc | ctgtggggcc | 1080 |
| aaggacagcc | tcatctttgg | ggccatcacc | tgctttacgg | gatttctggg | cgtggtcacg | 1140 |
| ggggcaggag | ccacgcgctg | gtgccgcctg | aagacccagc | gggccgaccc | actggtgtgt | 1200 |
| gccgtgggca | tgctgggctc | tgccatcttc | atctgcctga | tcttcgtggc | tgccaagagc | 1260 |
| agcatcgtag | gagcctatat | ctgtatcttc | gtcggggaga | cgctgctgtt | ttctaactgg | 1320 |
| gccatcactg | cagacatcct | catgtacgtg | gtcatcccca | cgcggcgcgc | cactgccgtg | 1380 |
| gccttgcaga | gcttcacctc | ccacctgctg | ggggacgccg | ggagcccta | cctcattggc | 1440 |
| tttatctcag | acctgatccg | ccagagcact | aaggactccc | cgctctggga | gttcctgagc | 1500 |
| ctgggctacg | cgctcatgct | ctgccctttc | gtcgtggtcc | tgggcggcat | gttcttcctc | 1560 |
| gccactgcgc | tcttcttcgt | cagcgaccgc | gccagggctg | agcagcaggt | gaaccagctg | 1620 |
| gcgatgccgc | ccgcatctgt | gaaagtctga | | | | 1650 |

<210> SEQ ID NO 237
<211> LENGTH: 1650
<212> TYPE: DNA
<213> ORGANISM: Artificial Sequence
<220> FEATURE:
<223> OTHER INFORMATION: Homo sapiens

<400> SEQUENCE: 237

| | | | | | |
|---|---|---|---|---|---|
| atgatgtgcc | tggaatgcgc | ctcggcggcg | gcgggcggcg | cggaggagga | ggaggcggac | 60 |
| gcggagcggc | ggcgccggcg | ccgggggcg | cagcgagggg | ctggcggtag | cggttgctgc | 120 |
| ggggcgcggg | gcgcgggcgg | cgctggagtc | tcggccgcgg | gcgatgaggt | gcagacgctg | 180 |

| | |
|---|---|
| tcgggcagcg taaggcgggc cccgaccgga cccccggca ccccggcac ccccggctgc | 240 |
| gcagctactg caaagggccc cggcgctcag cagcccaaac cggccagctt gggccgcggg | 300 |
| cggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagg ccgcagccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga gctgctgtt ttctaactgg | 1320 |
| gccatcactg cagacatcct catgtacgtg gtcatcccca gcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc gctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 238
<211> LENGTH: 1650
<212> TYPE: DNA
<213> ORGANISM: Artificial Sequence
<220> FEATURE:
<223> OTHER INFORMATION: Homo sapiens

<400> SEQUENCE: 238

| | |
|---|---|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga cccccggca ccccggcac ccccggctgc | 240 |
| gcagctactg caaagggccc cggcgctcag cagcccaaac cggccagctt gggccgcggg | 300 |
| cggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |

```
gggctggtgg gcatcgggga ggccagctac tccaccatcg cccccactat cattggcgac    660
ctcttcacca agaacacgcg tacgctcatg ctgtccgtct tctacttcgc catcccactg    720
ggcagtggcc tgggctacat tactggctcc agcgtgaagc aggcagccgc cgactggcac    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
gccacgtcgg ctgtctcctt cgccacgggg gccctgggca tgtggatccc gctctacctg   1020
caccgcgccc aagttgtgca gaagacagca gagacgtgca cagcccgcc ctgtggggcc     1080 aaggacagcc tcatctttgg ggccatcacc tgctttacgg gatttctggg cgtggtcacg   1140
ggggcaggag ccacgcgctg gtgccgcctg aagacccagc gggccgaccc actggtgtgt   1200
gccgtgggca tgctgggctc tgccatcttc atctgcctga tcttcgtggc tgccaagagc   1260
agcatcgtag gagcctatat ctgtatcttc gtcggggaga cgctgctgtt ttctaactgg   1320
gccatcactg cagacatcct catgtacgtg gtcatcccca cgcggcgcgc cactgccgtg   1380
gccttgcaga gcttcacctc ccacctgctg ggggacgccg ggagcccta cctcattggc    1440 tttatctcag acctgatccg ccagagcact aaggactccc cgctctggga gttcctgagc   1500
ctgggctacg cgctcatgct ctgccctttc gtcgtggtcc tgggcggcat gttcttcctc   1560
gccactgcgc tcttcttcgt cagcgaccgc gccagggctg agcagcaggt gaaccagctg   1620
gcgatgccgc ccgcatctgt gaaagtctga                                    1650

<210> SEQ ID NO 239
<211> LENGTH: 1650
<212> TYPE: DNA
<213> ORGANISM: Artificial Sequence
<220> FEATURE:
<223> OTHER INFORMATION: Homo sapiens

<400> SEQUENCE: 239
atgatgtgcc tggaatgcgc ctcggcggcg gcgggcggcg cggaggagga ggaggcggac     60
gcggagcggc ggcgccggcg ccgggggggcg cagcgagggg ctggcggtag cggttgctgc   120
ggggcgcggg gcgcgggcgg cgctggagtc tcggccgcgg gcgatgaggt gcagacgctg   180
tcgggcagcg taaggcgggc cccgaccgga ccccccggca cccccggcac cccccggctgc   240 gcagctactg caaagggccc cggcgctcag cagcccaaac cggccagctt gggccgcggg   300 cgggggggcag ccgccgccat cctcagcttg gcaacgtgc tcaactacct ggacaggtac    360
accgtggcag gcgtccttct ggacatccag cagcactttg gggtcaagga ccgaggcgcc    420
ggcctgctgc agtcagtgtt catctgtagc ttcatggtgg ctgcccccat cttcggctac    480
ctgggcgacc gcttcaacag gaaggtgatt ctcagctgcg gcatttttctt ctggtcggcc    540 gtcaccttct ccagctcctt cattcccag cagtacttct ggctgctggt cctgtcccgg    600
gggctggtgg gcatcgggga ggccagctac tccaccatcg cccccactat cattggcgac    660
ctcttcacca agaacacgcg tacgctcatg ctgtccgtct tctacttcgc catcccactg    720
ggcagtggcc tgggctacat tactggctcc agcgtgaagc aggcagccgg agcctggcac   780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
```

| | |
|---|---|
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagccccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 240
<211> LENGTH: 1650
<212> TYPE: DNA
<213> ORGANISM: Artificial Sequence
<220> FEATURE:
<223> OTHER INFORMATION: Homo sapiens

<400> SEQUENCE: 240

| | |
|---|---|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga ccccccggca cccccggctgc | 240 |
| gcagctactg caaagggccc cggcgctcag cagcccaaac cggccagctt gggccgcggg | 300 |
| cgggggggcag ccgccgccat cctcagcttg gcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattccccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc aggcagccgg agacgcccac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg gccctgggca tgtggatccc gctctacctg | 1020 |
| caccgcgccc aagttgtgca gaagacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |

```
gccttgcaga gcttcacctc ccacctgctg ggggacgccg ggagcccta cctcattggc    1440 tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                      1650
```

<210> SEQ ID NO 241
<211> LENGTH: 1650
<212> TYPE: DNA
<213> ORGANISM: Artificial Sequence
<220> FEATURE:
<223> OTHER INFORMATION: Homo sapiens

<400> SEQUENCE: 241

```
atgatgtgcc tggaatgcgc ctcggcggcg gcgggcggcg cggaggagga ggaggcggac      60
gcggagcggc ggcgccggcg ccgggggggcg cagcgagggg ctggcggtag cggttgctgc    120
ggggcgcggg gcgcgggcgg cgctggagtc tcggccgcgg gcgatgaggt gcagacgctg    180
tcgggcagcg taaggcgggc cccgaccgga ccccccggca ccccggcac ccccggctgc      240 gcagctactg caaagggccc cggcgctcag cagcccaaac cggccagctt gggccgcggg    300 cgggggggcag ccgccgccat cctcagcttg gcaacgtgc tcaactacct ggacaggtac    360
accgtggcag gcgtccttct ggacatccag cagcactttg gggtcaagga ccgaggcgcc    420
ggcctgctgc agtcagtgtt catctgtagc ttcatggtgg ctgcccccat cttcggctac    480
ctgggcgacc gcttcaacag gaaggtgatt ctcagctgcg gcattttctt ctggtcggcc    540
gtcaccttct ccagctcctt cattccccag cagtacttct ggctgctggt cctgtcccgg    600
gggctggtgg gcatcgggga ggccagctac tccaccatcg cccccactat cattggcgac    660
ctcttcacca agaacacgcg tacgctcatg ctgtccgtct tctacttcgc catcccactg    720
ggcagtggcc tgggctacat tactggctcc agcgtgaagc aggcagccgg agactgggcc    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
gccacgtcgg ctgtctcctt cgccacgggg gccctgggca tgtggatccc gctctacctg   1020
caccgcgccc aagttgtgca gaagacagca gagacgtgca acagcccgcc ctgtggggcc   1080
aaggacagcc tcatctttgg ggccatcacc tgctttacgg gatttctggg cgtggtcacg   1140
ggggcaggag ccacgcgctg gtgccgcctg aagacccagc gggccgaccc actggtgtgt   1200
gccgtgggca tgctgggctc tgccatcttc atctgcctga tcttcgtggc tgccaagagc   1260
agcatcgtag gagcctatat ctgtatcttc gtcggggaga cgctgctgtt ttctaactgg   1320
gccatcactg cagacatcct catgtacgtg gtcatcccca cgcggcgcgc cactgccgtg   1380
gccttgcaga gcttcacctc ccacctgctg ggggacgccg ggagcccta cctcattggc    1440 tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                      1650
```

<210> SEQ ID NO 242

<211> LENGTH: 1650
<212> TYPE: DNA
<213> ORGANISM: Artificial Sequence
<220> FEATURE:
<223> OTHER INFORMATION: Homo sapiens

<400> SEQUENCE: 242

| | |
|---|---:|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |
| tcgggcagcg taaggcgggc cccgaccgga ccccccggca ccccggcac ccccggctgc | 240 |
| gcagctactg caaagggccc cggcgctcag cagcccaaac cggccagctt gggccgcggg | 300 |
| cgggggggcag ccgccgccat cctcagcttg ggcaacgtgc tcaactacct ggacaggtac | 360 |
| accgtggcag gcgtccttct ggacatccag cagcactttg gggtcaagga ccgaggcgcc | 420 |
| ggcctgctgc agtcagtgtt catctgtagc ttcatggtgg ctgcccccat cttcggctac | 480 |
| ctgggcgacc gcttcaacag gaaggtgatt ctcagctgcg gcattttctt ctggtcggcc | 540 |
| gtcaccttct ccagctcctt cattcccag cagtacttct ggctgctggt cctgtcccgg | 600 |
| gggctggtgg gcatcgggga ggccagctac tccaccatcg cccccactat cattggcgac | 660 |
| ctcttcacca agaacacgcg tacgctcatg ctgtccgtct tctacttcgc catcccactg | 720 |
| ggcagtggcc tgggctacat tactggctcc agcgtgaagc agttcgccgg agactggcac | 780 |
| tgggcattgc gggtgtcccc tgtcctgggc atgatcacag gaacactcat cctcattctg | 840 |
| gtcccagcca ctaaaagggg tcatgccgac cagctcgggg accagctcaa ggcccggacc | 900 |
| tcatggctcc gagatatgaa ggccctgatt cgaaaccgca gctacgtctt ctcctccctg | 960 |
| gccacgtcgg ctgtctcctt cgccacgggg ccctgggca tgtggatccc gctctacctg | 1020 |
| caccgcgccc aagttgtgca agacacagca gagacgtgca acagcccgcc ctgtggggcc | 1080 |
| aaggacagcc tcatctttgg ggccatcacc tgctttacgg gatttctggg cgtggtcacg | 1140 |
| ggggcaggag ccacgcgctg gtgccgcctg aagacccagc gggccgaccc actggtgtgt | 1200 |
| gccgtgggca tgctgggctc tgccatcttc atctgcctga tcttcgtggc tgccaagagc | 1260 |
| agcatcgtag gagcctatat ctgtatcttc gtcggggaga cgctgctgtt ttctaactgg | 1320 |
| gccatcactg cagacatcct catgtacgtg gtcatcccca cgcggcgcgc cactgccgtg | 1380 |
| gccttgcaga gcttcacctc ccacctgctg ggggacgccg ggagcccta cctcattggc | 1440 |
| tttatctcag acctgatccg ccagagcact aaggactccc cgctctggga gttcctgagc | 1500 |
| ctgggctacg cgctcatgct ctgcccttc gtcgtggtcc tgggcggcat gttcttcctc | 1560 |
| gccactgcgc tcttcttcgt cagcgaccgc gccagggctg agcagcaggt gaaccagctg | 1620 |
| gcgatgccgc ccgcatctgt gaaagtctga | 1650 |

<210> SEQ ID NO 243
<211> LENGTH: 1650
<212> TYPE: DNA
<213> ORGANISM: Artificial Sequence
<220> FEATURE:
<223> OTHER INFORMATION: Homo sapiens

<400> SEQUENCE: 243

| | |
|---|---:|
| atgatgtgcc tggaatgcgc ctcggcggcg gcgggcggcg cggaggagga ggaggcggac | 60 |
| gcggagcggc ggcgccggcg ccggggggcg cagcgagggg ctggcggtag cggttgctgc | 120 |
| ggggcgcggg gcgcgggcgg cgctggagtc tcggccgcgg gcgatgaggt gcagacgctg | 180 |

```
tcgggcagcg taaggcgggc cccgaccgga ccccccggca ccccggctgc    240
gcagctactg caaagggccc cggcgctcag cagcccaaac cggccagctt gggccgcggg    300 cgggggcag ccgccgccat cctcagcttg gcaacgtgc tcaactacct ggacaggtac    360
accgtggcag gcgtccttct ggacatccag cagcactttg gggtcaagga ccgaggcgcc    420
ggcctgctgc agtcagtgtt catctgtagc ttcatggtgg ctgcccccat cttcggctac    480
ctgggcgacc gcttcaacag gaaggtgatt ctcagctgcg gcattttctt ctggtcggcc    540
gtcaccttct ccagctcctt cattccccag cagtacttct ggctgctggt cctgtcccgg    600
gggctggtgg gcatcgggga ggccagctac tccaccatcg cccccactat cattggcgac    660
ctcttcacca agaacacgcg tacgctcatg ctgtccgtct tctacttcgc catcccactg    720
ggcagtggcc tgggctacat tactggctcc agcgtgaagc aggcattcgg agactggcac    780
tgggcattgc gggtgtcccc tgtcctgggc atgatcacag gaacactcat cctcattctg    840
gtcccagcca ctaaaagggg tcatgccgac cagctcgggg accagctcaa ggcccggacc    900
tcatggctcc gagatatgaa ggccctgatt cgaaaccgca gctacgtctt ctcctccctg    960
gccacgtcgg ctgtctcctt cgccacgggg gccctgggca tgtggatccc gctctacctg    1020
caccgcgccc aagttgtgca gaagacagca gagacgtgca acagcccgcc ctgtggggcc    1080
aaggacagcc tcatctttgg ggccatcacc tgctttacgg gatttctggg cgtggtcacg    1140 gggcaggag ccacgcgctg gtgccgcctg aagacccagc gggccgaccc actggtgtgt    1200
gccgtgggca tgctgggctc tgccatcttc atctgcctga tcttcgtggc tgccaagagc    1260
agcatcgtag gagcctatat ctgtatcttc gtcggggaga cgctgctgtt ttctaactgg    1320
gccatcactg cagacatcct catgtacgtg gtcatcccca cgcggcgcgc cactgccgtg    1380
gccttgcaga gcttcacctc ccacctgctg ggggacgccg ggagcccta cctcattggc    1440 tttatctcag acctgatccg ccagagcact aaggactccc cgctctggga gttcctgagc    1500
ctgggctacg cgctcatgct ctgccctttc gtcgtggtcc tgggcggcat gttcttcctc    1560
gccactgcgc tcttcttcgt cagcgaccgc gccagggctg agcagcaggt gaaccagctg    1620
gcgatgccgc ccgcatctgt gaaagtctga                                    1650
```

<210> SEQ ID NO 244
<211> LENGTH: 21
<212> TYPE: DNA
<213> ORGANISM: Artificial Sequence
<220> FEATURE:
<223> OTHER INFORMATION: primer

<400> SEQUENCE: 244
gatagactga tggggtgtt g                                              21

<210> SEQ ID NO 245
<211> LENGTH: 21
<212> TYPE: DNA
<213> ORGANISM: Artificial Sequence
<220> FEATURE:
<223> OTHER INFORMATION: Primer

<400> SEQUENCE: 245
gatagacaga tggggtgtt g                                              21

<210> SEQ ID NO 246
<211> LENGTH: 21
<212> TYPE: DNA

```
<213> ORGANISM: Artificial Sequence
<220> FEATURE:
<223> OTHER INFORMATION: Primer

<400> SEQUENCE: 246
gatagaccga tggggctgtt g                                              21

<210> SEQ ID NO 247
<211> LENGTH: 21
<212> TYPE: DNA
<213> ORGANISM: Artificial Sequence
<220> FEATURE:
<223> OTHER INFORMATION: Primer

<400> SEQUENCE: 247
gatagacaga tggggctgtt g                                              21

<210> SEQ ID NO 248
<211> LENGTH: 20
<212> TYPE: DNA
<213> ORGANISM: Artificial Sequence
<220> FEATURE:
<223> OTHER INFORMATION: Primer

<400> SEQUENCE: 248
ccatggacat cagtctcagc                                                20

<210> SEQ ID NO 249
<211> LENGTH: 19
<212> TYPE: DNA
<213> ORGANISM: Artificial Sequence
<220> FEATURE:
<223> OTHER INFORMATION: Primer

<400> SEQUENCE: 249
catggacatc aggctcagc                                                 19

<210> SEQ ID NO 250
<211> LENGTH: 19
<212> TYPE: DNA
<213> ORGANISM: Artificial Sequence
<220> FEATURE:
<223> OTHER INFORMATION: Primer

<400> SEQUENCE: 250
catggctgtc ctggtgctg                                                 19

<210> SEQ ID NO 251
<211> LENGTH: 19
<212> TYPE: DNA
<213> ORGANISM: Artificial Sequence
<220> FEATURE:
<223> OTHER INFORMATION: Primer

<400> SEQUENCE: 251
aatggctgtc ctggtgctg                                                 19

<210> SEQ ID NO 252
<211> LENGTH: 19
<212> TYPE: DNA
<213> ORGANISM: Artificial Sequence
<220> FEATURE:
<223> OTHER INFORMATION: Primer

<400> SEQUENCE: 252
catggctgtc ctggtgcta                                                 19
```

```
<210> SEQ ID NO 253
<211> LENGTH: 19
<212> TYPE: DNA
<213> ORGANISM: Artificial Sequence
<220> FEATURE:
<223> OTHER INFORMATION: Primer

<400> SEQUENCE: 253
catggatgtc ctggtgctg                                              19

<210> SEQ ID NO 254
<211> LENGTH: 19
<212> TYPE: DNA
<213> ORGANISM: Artificial Sequence
<220> FEATURE:
<223> OTHER INFORMATION: Primer

<400> SEQUENCE: 254
catggctgtc ctggcgctc                                              19

<210> SEQ ID NO 255
<211> LENGTH: 19
<212> TYPE: DNA
<213> ORGANISM: Artificial Sequence
<220> FEATURE:
<223> OTHER INFORMATION: Primer

<400> SEQUENCE: 255
catggctatc ctggtgctg                                              19

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
ccatgggatg gagccagatc                                             20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
ccatgggatg gatctgtatc                                             20

<210> SEQ ID NO 258
<211> LENGTH: 20
<212> TYPE: DNA
<213> ORGANISM: Artificial Sequence
<220> FEATURE:
<223> OTHER INFORMATION: Primer

<400> SEQUENCE: 258
ccatggacag gcttacttcc                                             20

<210> SEQ ID NO 259
<211> LENGTH: 20
<212> TYPE: DNA
<213> ORGANISM: Artificial Sequence
<220> FEATURE:
```

<223> OTHER INFORMATION: Primer

<400> SEQUENCE: 259
ccatggactt cagcatcagc                                           20

<210> SEQ ID NO 260
<211> LENGTH: 20
<212> TYPE: DNA
<213> ORGANISM: Artificial Sequence
<220> FEATURE:
<223> OTHER INFORMATION: Primer

<400> SEQUENCE: 260
ccatgtactt cagcatcagc                                           20

<210> SEQ ID NO 261
<211> LENGTH: 20
<212> TYPE: DNA
<213> ORGANISM: Artificial Sequence
<220> FEATURE:
<223> OTHER INFORMATION: Primer

<400> SEQUENCE: 261
ccatggactt caggctcagc                                           20

<210> SEQ ID NO 262
<211> LENGTH: 20
<212> TYPE: DNA
<213> ORGANISM: Artificial Sequence
<220> FEATURE:
<223> OTHER INFORMATION: Primer

<400> SEQUENCE: 262
ccatggactt caggctgaac                                           20

<210> SEQ ID NO 263
<211> LENGTH: 20
<212> TYPE: DNA
<213> ORGANISM: Artificial Sequence
<220> FEATURE:
<223> OTHER INFORMATION: Primer

<400> SEQUENCE: 263
ccatggaatg gagctgggtc                                           20

<210> SEQ ID NO 264
<211> LENGTH: 20
<212> TYPE: DNA
<213> ORGANISM: Artificial Sequence
<220> FEATURE:
<223> OTHER INFORMATION: Primer

<400> SEQUENCE: 264
ccatggaatg gaactgggtc                                           20

<210> SEQ ID NO 265
<211> LENGTH: 20
<212> TYPE: DNA
<213> ORGANISM: Artificial Sequence
<220> FEATURE:
<223> OTHER INFORMATION: Primer

<400> SEQUENCE: 265
catgaaatgc agctggatca                                           20

```
<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
catgaaaagc agctggatca                                              20

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
aacatggagt tggaattgag c                                            21

<210> SEQ ID NO 268
<211> LENGTH: 22
<212> TYPE: DNA
<213> ORGANISM: Artificial Sequence
<220> FEATURE:
<223> OTHER INFORMATION: Primer

<400> SEQUENCE: 268
catgaagttg agattgagct ta                                           22

<210> SEQ ID NO 269
<211> LENGTH: 21
<212> TYPE: DNA
<213> ORGANISM: Artificial Sequence
<220> FEATURE:
<223> OTHER INFORMATION: Primer

<400> SEQUENCE: 269
catggagttc agcatgatct g                                            21

<210> SEQ ID NO 270
<211> LENGTH: 20
<212> TYPE: DNA
<213> ORGANISM: Artificial Sequence
<220> FEATURE:
<223> OTHER INFORMATION: Primer

<400> SEQUENCE: 270
ccatggaatg gagctttgtc                                              20

<210> SEQ ID NO 271
<211> LENGTH: 21
<212> TYPE: DNA
<213> ORGANISM: Artificial Sequence
<220> FEATURE:
<223> OTHER INFORMATION: Primer

<400> SEQUENCE: 271
agatgagaat gctggttctt c                                            21

<210> SEQ ID NO 272
<211> LENGTH: 20
<212> TYPE: DNA
<213> ORGANISM: Artificial Sequence
<220> FEATURE:
<223> OTHER INFORMATION: Primer
```

<400> SEQUENCE: 272
ccatggattg tagctgggtc                                           20

<210> SEQ ID NO 273
<211> LENGTH: 19
<212> TYPE: DNA
<213> ORGANISM: Artificial Sequence
<220> FEATURE:
<223> OTHER INFORMATION: Primer

<400> SEQUENCE: 273
catggacacc aggctcagc                                            19

<210> SEQ ID NO 274
<211> LENGTH: 19
<212> TYPE: DNA
<213> ORGANISM: Artificial Sequence
<220> FEATURE:
<223> OTHER INFORMATION: Primer

<400> SEQUENCE: 274
catggctgcc ctggggctg                                            19

<210> SEQ ID NO 275
<211> LENGTH: 19
<212> TYPE: DNA
<213> ORGANISM: Artificial Sequence
<220> FEATURE:
<223> OTHER INFORMATION: Primer

<400> SEQUENCE: 275
catggctttc ctggggctg                                            19

<210> SEQ ID NO 276
<211> LENGTH: 19
<212> TYPE: DNA
<213> ORGANISM: Artificial Sequence
<220> FEATURE:
<223> OTHER INFORMATION: Primer

<400> SEQUENCE: 276
catggctgtg ctggtgttg                                            19

<210> SEQ ID NO 277
<211> LENGTH: 19
<212> TYPE: DNA
<213> ORGANISM: Artificial Sequence
<220> FEATURE:
<223> OTHER INFORMATION: Primer

<400> SEQUENCE: 277
gatggcggtg cagatttcc                                            19

<210> SEQ ID NO 278
<211> LENGTH: 20
<212> TYPE: DNA
<213> ORGANISM: Artificial Sequence
<220> FEATURE:
<223> OTHER INFORMATION: Primer

<400> SEQUENCE: 278
ccatggacag gctaacttcc                                           20

<210> SEQ ID NO 279
<211> LENGTH: 20

```
<212> TYPE: DNA
<213> ORGANISM: Artificial Sequence
<220> FEATURE:
<223> OTHER INFORMATION: Primer

<400> SEQUENCE: 279
ccatggaatg gggctgggtc                                                  20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
ccatgaagtc gtggctgaac                                                  20

<210> SEQ ID NO 281
<211> LENGTH: 20
<212> TYPE: DNA
<213> ORGANISM: Artificial Sequence
<220> FEATURE:
<223> OTHER INFORMATION: Primer

<400> SEQUENCE: 281
ccatgaagtc gtggctgaac                                                  20

<210> SEQ ID NO 282
<211> LENGTH: 19
<212> TYPE: DNA
<213> ORGANISM: Artificial Sequence
<220> FEATURE:
<223> OTHER INFORMATION: Primer

<400> SEQUENCE: 282
catgaaatgc agctgggtc                                                   19

<210> SEQ ID NO 283
<211> LENGTH: 21
<212> TYPE: DNA
<213> ORGANISM: Artificial Sequence
<220> FEATURE:
<223> OTHER INFORMATION: Primer

<400> SEQUENCE: 283
aacatggagt tggaactgag a                                                21

<210> SEQ ID NO 284
<211> LENGTH: 22
<212> TYPE: DNA
<213> ORGANISM: Artificial Sequence
<220> FEATURE:
<223> OTHER INFORMATION: Primer

<400> SEQUENCE: 284
caacatggaa ttggaactga ga                                               22

<210> SEQ ID NO 285
<211> LENGTH: 20
<212> TYPE: DNA
<213> ORGANISM: Artificial Sequence
<220> FEATURE:
<223> OTHER INFORMATION: Primer

<400> SEQUENCE: 285
```
catgatggct ccagttcaac                                                    20

<210> SEQ ID NO 286
<211> LENGTH: 20
<212> TYPE: DNA
<213> ORGANISM: Artificial Sequence
<220> FEATURE:
<223> OTHER INFORMATION: Primer

<400> SEQUENCE: 286
catgaactgg atccgccagc                                                    20

<210> SEQ ID NO 287
<211> LENGTH: 21
<212> TYPE: DNA
<213> ORGANISM: Artificial Sequence
<220> FEATURE:
<223> OTHER INFORMATION: Primer

<400> SEQUENCE: 287
atcatggatt ggttgtggac c                                                  21

<210> SEQ ID NO 288
<211> LENGTH: 20
<212> TYPE: DNA
<213> ORGANISM: Artificial Sequence
<220> FEATURE:
<223> OTHER INFORMATION: Primer

<400> SEQUENCE: 288
gtgctgtctt tgctgtcctg                                                    20

<210> SEQ ID NO 289
<211> LENGTH: 20
<212> TYPE: DNA
<213> ORGANISM: Artificial Sequence
<220> FEATURE:
<223> OTHER INFORMATION: Primer

<400> SEQUENCE: 289
catgatggct gcagttcaac                                                    20

<210> SEQ ID NO 290
<211> LENGTH: 20
<212> TYPE: DNA
<213> ORGANISM: Artificial Sequence
<220> FEATURE:
<223> OTHER INFORMATION: Primer

<400> SEQUENCE: 290
catgatggct gcacttcaac                                                    20

<210> SEQ ID NO 291
<211> LENGTH: 20
<212> TYPE: DNA
<213> ORGANISM: Artificial Sequence
<220> FEATURE:
<223> OTHER INFORMATION: Primer

<400> SEQUENCE: 291
catgatggca ccagttcaac                                                    20

<210> SEQ ID NO 292
<211> LENGTH: 20
<212> TYPE: DNA
<213> ORGANISM: Artificial Sequence

```
<220> FEATURE:
<223> OTHER INFORMATION: Primer

<400> SEQUENCE: 292
catgatggct ccagttcaac                                               20

<210> SEQ ID NO 293
<211> LENGTH: 22
<212> TYPE: DNA
<213> ORGANISM: Artificial Sequence
<220> FEATURE:
<223> OTHER INFORMATION: Primer

<400> SEQUENCE: 293
atggctccag ttcaactttt ag                                            22

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
catgatggct ccagtccagc                                               20

<210> SEQ ID NO 295
<211> LENGTH: 20
<212> TYPE: DNA
<213> ORGANISM: Artificial Sequence
<220> FEATURE:
<223> OTHER INFORMATION: Primer

<400> SEQUENCE: 295
caatgatgag tcctgcccag                                               20

<210> SEQ ID NO 296
<211> LENGTH: 23
<212> TYPE: DNA
<213> ORGANISM: Artificial Sequence
<220> FEATURE:
<223> OTHER INFORMATION: Primer

<400> SEQUENCE: 296
caatgatgag tcctgcccag ttc                                           23

<210> SEQ ID NO 297
<211> LENGTH: 22
<212> TYPE: DNA
<213> ORGANISM: Artificial Sequence
<220> FEATURE:
<223> OTHER INFORMATION: Primer

<400> SEQUENCE: 297
caatgatgag tcctgtccag tc                                            22

<210> SEQ ID NO 298
<211> LENGTH: 22
<212> TYPE: DNA
<213> ORGANISM: Artificial Sequence
<220> FEATURE:
<223> OTHER INFORMATION: Primer

<400> SEQUENCE: 298
caatgatgag tcctgtccag ac                                            22
```

```
<210> SEQ ID NO 299
<211> LENGTH: 23
<212> TYPE: DNA
<213> ORGANISM: Artificial Sequence
<220> FEATURE:
<223> OTHER INFORMATION: Primer

<400> SEQUENCE: 299
caatgatgat tcctgcccag ttc                                             23

<210> SEQ ID NO 300
<211> LENGTH: 21
<212> TYPE: DNA
<213> ORGANISM: Artificial Sequence
<220> FEATURE:
<223> OTHER INFORMATION: Primer

<400> SEQUENCE: 300
aatgatgatc ctgtttattc c                                               21

<210> SEQ ID NO 301
<211> LENGTH: 19
<212> TYPE: DNA
<213> ORGANISM: Artificial Sequence
<220> FEATURE:
<223> OTHER INFORMATION: Primer

<400> SEQUENCE: 301
gatgagtcct gtccagtcc                                                  19

<210> SEQ ID NO 302
<211> LENGTH: 20
<212> TYPE: DNA
<213> ORGANISM: Artificial Sequence
<220> FEATURE:
<223> OTHER INFORMATION: Primer

<400> SEQUENCE: 302
acatgggtgt gcccactcag                                                 20

<210> SEQ ID NO 303
<211> LENGTH: 20
<212> TYPE: DNA
<213> ORGANISM: Artificial Sequence
<220> FEATURE:
<223> OTHER INFORMATION: Primer

<400> SEQUENCE: 303
acatgggtgt ccccactcag                                                 20

<210> SEQ ID NO 304
<211> LENGTH: 20
<212> TYPE: DNA
<213> ORGANISM: Artificial Sequence
<220> FEATURE:
<223> OTHER INFORMATION: Primer

<400> SEQUENCE: 304
acatggctgt gcccactcag                                                 20

<210> SEQ ID NO 305
<211> LENGTH: 21
<212> TYPE: DNA
<213> ORGANISM: Artificial Sequence
<220> FEATURE:
<223> OTHER INFORMATION: Primer
```

```
<400> SEQUENCE: 305
aaatgaagtg gcctgttagg c                                      21

<210> SEQ ID NO 306
<211> LENGTH: 21
<212> TYPE: DNA
<213> ORGANISM: Artificial Sequence
<220> FEATURE:
<223> OTHER INFORMATION: Primer

<400> SEQUENCE: 306
aaatgaagtg gcctgtgagg c                                      21

<210> SEQ ID NO 307
<211> LENGTH: 21
<212> TYPE: DNA
<213> ORGANISM: Artificial Sequence
<220> FEATURE:
<223> OTHER INFORMATION: Primer

<400> SEQUENCE: 307
atgagggtgg ctgttcaatt c                                      21

<210> SEQ ID NO 308
<211> LENGTH: 20
<212> TYPE: DNA
<213> ORGANISM: Artificial Sequence
<220> FEATURE:
<223> OTHER INFORMATION: Primer

<400> SEQUENCE: 308
catgggtgtg cctactcatc                                        20

<210> SEQ ID NO 309
<211> LENGTH: 20
<212> TYPE: DNA
<213> ORGANISM: Artificial Sequence
<220> FEATURE:
<223> OTHER INFORMATION: Primer

<400> SEQUENCE: 309
catgaacgtg cccactcaac                                        20

<210> SEQ ID NO 310
<211> LENGTH: 20
<212> TYPE: DNA
<213> ORGANISM: Artificial Sequence
<220> FEATURE:
<223> OTHER INFORMATION: Primer

<400> SEQUENCE: 310
catgaatgtg cccactcaac                                        20

<210> SEQ ID NO 311
<211> LENGTH: 19
<212> TYPE: DNA
<213> ORGANISM: Artificial Sequence
<220> FEATURE:
<223> OTHER INFORMATION: Primer

<400> SEQUENCE: 311
atggacatga gggcccatg                                         19

<210> SEQ ID NO 312
```

-continued

```
<211> LENGTH: 19
<212> TYPE: DNA
<213> ORGANISM: Artificial Sequence
<220> FEATURE:
<223> OTHER INFORMATION: Primer

<400> SEQUENCE: 312
atggacatga gggtccatg                                                    19

<210> SEQ ID NO 313
<211> LENGTH: 20
<212> TYPE: DNA
<213> ORGANISM: Artificial Sequence
<220> FEATURE:
<223> OTHER INFORMATION: Primer

<400> SEQUENCE: 313
catggacatg agggcccata                                                   20

<210> SEQ ID NO 314
<211> LENGTH: 20
<212> TYPE: DNA
<213> ORGANISM: Artificial Sequence
<220> FEATURE:
<223> OTHER INFORMATION: Primer

<400> SEQUENCE: 314
catggacaag agggcccatg                                                   20

<210> SEQ ID NO 315
<211> LENGTH: 21
<212> TYPE: DNA
<213> ORGANISM: Artificial Sequence
<220> FEATURE:
<223> OTHER INFORMATION: Primer

<400> SEQUENCE: 315
atggaatcac aaactcaggc c                                                 21

<210> SEQ ID NO 316
<211> LENGTH: 21
<212> TYPE: DNA
<213> ORGANISM: Artificial Sequence
<220> FEATURE:
<223> OTHER INFORMATION: Primer

<400> SEQUENCE: 316
atggagtcat atactcgggt c                                                 21

<210> SEQ ID NO 317
<211> LENGTH: 21
<212> TYPE: DNA
<213> ORGANISM: Artificial Sequence
<220> FEATURE:
<223> OTHER INFORMATION: Primer

<400> SEQUENCE: 317
atggagtcac atactagggt c                                                 21

<210> SEQ ID NO 318
<211> LENGTH: 21
<212> TYPE: DNA
<213> ORGANISM: Artificial Sequence
<220> FEATURE:
<223> OTHER INFORMATION: Primer

<400> SEQUENCE: 318
```
atggaatcac atactcaggt c                                                 21

<210> SEQ ID NO 319
<211> LENGTH: 20
<212> TYPE: DNA
<213> ORGANISM: Artificial Sequence
<220> FEATURE:
<223> OTHER INFORMATION: Primer

<400> SEQUENCE: 319
gatggaatca caaacgcagg                                                   20

<210> SEQ ID NO 320
<211> LENGTH: 20
<212> TYPE: DNA
<213> ORGANISM: Artificial Sequence
<220> FEATURE:
<223> OTHER INFORMATION: Primer

<400> SEQUENCE: 320
gatggaatca cagacccagg                                                   20

<210> SEQ ID NO 321
<211> LENGTH: 21
<212> TYPE: DNA
<213> ORGANISM: Artificial Sequence
<220> FEATURE:
<223> OTHER INFORMATION: Primer

<400> SEQUENCE: 321
atgaggtgct ctttccagtt c                                                 21

<210> SEQ ID NO 322
<211> LENGTH: 22
<212> TYPE: DNA
<213> ORGANISM: Artificial Sequence
<220> FEATURE:
<223> OTHER INFORMATION: Primer

<400> SEQUENCE: 322
atgaagtttc ctgctcagtt tc                                                22

<210> SEQ ID NO 323
<211> LENGTH: 24
<212> TYPE: DNA
<213> ORGANISM: Artificial Sequence
<220> FEATURE:
<223> OTHER INFORMATION: Primer

<400> SEQUENCE: 323
atggattttc tggtgcaaat tttc                                              24

<210> SEQ ID NO 324
<211> LENGTH: 21
<212> TYPE: DNA
<213> ORGANISM: Artificial Sequence
<220> FEATURE:
<223> OTHER INFORMATION: Primer

<400> SEQUENCE: 324
ctatggattg ttgggtgcag a                                                 21

<210> SEQ ID NO 325
<211> LENGTH: 21
<212> TYPE: DNA

<213> ORGANISM: Artificial Sequence
<220> FEATURE:
<223> OTHER INFORMATION: Primer

<400> SEQUENCE: 325
caatggattt tcgggtgcag a                                              21

<210> SEQ ID NO 326
<211> LENGTH: 21
<212> TYPE: DNA
<213> ORGANISM: Artificial Sequence
<220> FEATURE:
<223> OTHER INFORMATION: Primer

<400> SEQUENCE: 326
caatggattt tcaggtgcag a                                              21

<210> SEQ ID NO 327
<211> LENGTH: 21
<212> TYPE: DNA
<213> ORGANISM: Artificial Sequence
<220> FEATURE:
<223> OTHER INFORMATION: Primer

<400> SEQUENCE: 327
catgaaaatg acgacacctg c                                              21

<210> SEQ ID NO 328
<211> LENGTH: 22
<212> TYPE: DNA
<213> ORGANISM: Artificial Sequence
<220> FEATURE:
<223> OTHER INFORMATION: Primer

<400> SEQUENCE: 328
atgagggtcc agattcagtt tc                                             22

<210> SEQ ID NO 329
<211> LENGTH: 22
<212> TYPE: DNA
<213> ORGANISM: Artificial Sequence
<220> FEATURE:
<223> OTHER INFORMATION: Primer

<400> SEQUENCE: 329
atgagggtcc agattcagtt tg                                             22

<210> SEQ ID NO 330
<211> LENGTH: 22
<212> TYPE: DNA
<213> ORGANISM: Artificial Sequence
<220> FEATURE:
<223> OTHER INFORMATION: Primer

<400> SEQUENCE: 330
atgagggtcc aggttcagtt tc                                             22

<210> SEQ ID NO 331
<211> LENGTH: 21
<212> TYPE: DNA
<213> ORGANISM: Artificial Sequence
<220> FEATURE:
<223> OTHER INFORMATION: Primer

<400> SEQUENCE: 331
atgagggtcc ctgttcaatt c                                              21

<210> SEQ ID NO 332
<211> LENGTH: 21
<212> TYPE: DNA
<213> ORGANISM: Artificial Sequence
<220> FEATURE:
<223> OTHER INFORMATION: Primer

<400> SEQUENCE: 332
atggagacag acagactcct g                                        21

<210> SEQ ID NO 333
<211> LENGTH: 21
<212> TYPE: DNA
<213> ORGANISM: Artificial Sequence
<220> FEATURE:
<223> OTHER INFORMATION: Primer

<400> SEQUENCE: 333
atggagacag acacactcct g                                        21

<210> SEQ ID NO 334
<211> LENGTH: 19
<212> TYPE: DNA
<213> ORGANISM: Artificial Sequence
<220> FEATURE:
<223> OTHER INFORMATION: Primer

<400> SEQUENCE: 334
catgctctcc ctagctcac                                           19

<210> SEQ ID NO 335
<211> LENGTH: 21
<212> TYPE: DNA
<213> ORGANISM: Artificial Sequence
<220> FEATURE:
<223> OTHER INFORMATION: Primer

<400> SEQUENCE: 335
atggtgttca tacctcagtt c                                        21

<210> SEQ ID NO 336
<211> LENGTH: 25
<212> TYPE: DNA
<213> ORGANISM: Artificial Sequence
<220> FEATURE:
<223> OTHER INFORMATION: Primer

<400> SEQUENCE: 336
gataggtgya ccatytrcct tccag                                    25

<210> SEQ ID NO 337
<211> LENGTH: 24
<212> TYPE: DNA
<213> ORGANISM: Artificial Sequence
<220> FEATURE:
<223> OTHER INFORMATION: Primer

<400> SEQUENCE: 337
atggcctgga yttcacttat actc                                     24

<210> SEQ ID NO 338
<211> LENGTH: 22
<212> TYPE: DNA
<213> ORGANISM: Artificial Sequence
<220> FEATURE:

```
<223> OTHER INFORMATION: Primer

<400> SEQUENCE: 338
atggcctgga ctcctctctt ct                                          22

<210> SEQ ID NO 339
<211> LENGTH: 25
<212> TYPE: DNA
<213> ORGANISM: Artificial Sequence
<220> FEATURE:
<223> OTHER INFORMATION: Primer

<400> SEQUENCE: 339
atgacctgta cttcactttt gctta                                       25

<210> SEQ ID NO 340
<211> LENGTH: 25
<212> TYPE: DNA
<213> ORGANISM: Artificial Sequence
<220> FEATURE:
<223> OTHER INFORMATION: Primer

<400> SEQUENCE: 340
atgacatgga ctctmctatt ccttg                                       25

<210> SEQ ID NO 341
<211> LENGTH: 23
<212> TYPE: DNA
<213> ORGANISM: Artificial Sequence
<220> FEATURE:
<223> OTHER INFORMATION: Primer

<400> SEQUENCE: 341
atggccttgg cctatcttct atc                                         23

<210> SEQ ID NO 342
<211> LENGTH: 22
<212> TYPE: DNA
<213> ORGANISM: Artificial Sequence
<220> FEATURE:
<223> OTHER INFORMATION: Primer

<400> SEQUENCE: 342
atggccagga taccccttct tt                                          22

<210> SEQ ID NO 343
<211> LENGTH: 27
<212> TYPE: DNA
<213> ORGANISM: Artificial Sequence
<220> FEATURE:
<223> OTHER INFORMATION: Primer

<400> SEQUENCE: 343
accatggact ctactattcc ttgcctt                                     27

<210> SEQ ID NO 344
<211> LENGTH: 26
<212> TYPE: DNA
<213> ORGANISM: Artificial Sequence
<220> FEATURE:
<223> OTHER INFORMATION: Primer

<400> SEQUENCE: 344
accatgactt gggctccact actcct                                      26
```

```
<210> SEQ ID NO 345
<211> LENGTH: 459
<212> TYPE: PRT
<213> ORGANISM: Artificial Sequence
<220> FEATURE:
<223> OTHER INFORMATION: Mouse IgG1 chimera antibody: heavy chain

<400> SEQUENCE: 345

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Ala Gly Leu Val
            20                  25                  30

Arg Pro Arg Thr Ser Val Arg Leu Ser Cys Lys Ile Ser Gly Asp Ser
        35                  40                  45

Ile Thr Ala Tyr Tyr Val His Phe Val Lys Gln Arg Pro Gly Gln Gly
    50                  55                  60

Leu Glu Trp Ile Gly Arg Ile Asp Pro Glu Asp Asp Ser Thr Lys Tyr
65                  70                  75                  80

Ser Glu Lys Phe Lys Asn Lys Ala Thr Leu Thr Ala Asp Val Ser Ser
                85                  90                  95

Ser Thr Ala Tyr Leu Ile Leu Ser Ser Leu Thr Ser Asp Asp Ser Ala
            100                 105                 110

Thr Tyr Phe Cys Ser Thr Leu Thr Gly Leu Asp Tyr Trp Gly Gln Gly
        115                 120                 125

Val Met Val Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Pro Ser Ser
        195                 200                 205

Thr Trp Pro Ser Glu Thr Val Thr Cys Asn Val Ala His Pro Ala Ser
    210                 215                 220

Ser Thr Lys Val Asp Lys Lys Ile Val Pro Arg Asp Cys Gly Cys Lys
225                 230                 235                 240

Pro Cys Ile Cys Thr Val Pro Glu Val Ser Ser Val Phe Ile Phe Pro
                245                 250                 255

Pro Lys Pro Lys Asp Val Leu Thr Ile Thr Leu Thr Pro Lys Val Thr
            260                 265                 270

Cys Val Val Val Asp Ile Ser Lys Asp Asp Pro Glu Val Gln Phe Ser
        275                 280                 285

Trp Phe Val Asp Asp Val Glu Val His Thr Ala Gln Thr Gln Pro Arg
    290                 295                 300

Glu Glu Gln Phe Asn Ser Thr Phe Arg Ser Val Ser Glu Leu Pro Ile
305                 310                 315                 320

Met His Gln Asp Trp Leu Asn Gly Lys Glu Phe Lys Cys Arg Val Asn
                325                 330                 335

Ser Ala Ala Phe Pro Ala Pro Ile Glu Lys Thr Ile Ser Lys Thr Lys
            340                 345                 350

Gly Arg Pro Lys Ala Pro Gln Val Tyr Thr Ile Pro Pro Pro Lys Glu
        355                 360                 365

Gln Met Ala Lys Asp Lys Val Ser Leu Thr Cys Met Ile Thr Asp Phe
```

```
                    370                 375                 380
Phe Pro Glu Asp Ile Thr Val Glu Trp Gln Trp Asn Gly Gln Pro Ala
385                 390                 395                 400

Glu Asn Tyr Lys Asn Thr Gln Pro Ile Met Asp Thr Asp Gly Ser Tyr
                405                 410                 415

Phe Val Tyr Ser Lys Leu Asn Val Gln Lys Ser Asn Trp Glu Ala Gly
            420                 425                 430

Asn Thr Phe Thr Cys Ser Val Leu His Glu Gly Leu His Asn His His
        435                 440                 445

Thr Glu Lys Ser Leu Ser His Ser Pro Gly Lys
    450                 455

<210> SEQ ID NO 346
<211> LENGTH: 233
<212> TYPE: PRT
<213> ORGANISM: Artificial Sequence
<220> FEATURE:
<223> OTHER INFORMATION: Mouse IgG1 chimera antibody: light chain

<400> SEQUENCE: 346

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Val Leu Ser
            20                  25                  30

Ala Ser Val Gly Asp Arg Val Thr Leu Ser Cys Lys Ala Ser Gln Ser
        35                  40                  45

Val His Asn Lys Leu Asp Trp Tyr Gln Gln Lys His Gly Glu Ala Pro
    50                  55                  60

Lys Leu Leu Ile Tyr Tyr Thr His Asn Leu Gln Thr Gly Ile Pro Ser
65                  70                  75                  80

Arg Phe Ser Gly Ser Gly Ser Gly Ser Asp Tyr Thr Leu Thr Ile Ser
                85                  90                  95

Ser Leu Arg Ala Glu Asp Val Ala Thr Tyr Tyr Cys Phe Gln Tyr Tyr
            100                 105                 110

Ser Gly Trp Thr Phe Gly Gly Gly Thr Lys Leu Glu Met Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 347
<211> LENGTH: 1380
<212> TYPE: DNA
<213> ORGANISM: Artificial Sequence
<220> FEATURE:
<223> OTHER INFORMATION: Expression vector of mouse IgG1 chimera
``` antibody: heavy chain

<400> SEQUENCE: 347

| | |
|---|---|
| atggaaaccg atacactgct gctgtgggtc ctgctgctgt gggtgccagg atccacaggc | 60 |
| gaagtccagc tgcagcagtc tggggctgga cttgtgagac ctaggacctc tgtgaggtta | 120 |
| tcttgcaaaa tttctggcga ttccattaca gcatattacg tgcactttgt gaaacaaagg | 180 |
| cctggacagg gtctggaatg gataggaaga attgatcctg aggatgatag tactaaatat | 240 |
| tctgagaagt tcaaaaacaa ggcgacactc actgcagatg tatcctccag cacagcctac | 300 |
| ctgattctca gcagcctgac ctctgacgac tctgcaacct attttgttc cactctgact | 360 |
| ggccttgatt actggggcca gggagtcatg gtcacggtct cctcagctaa aacgacaccc | 420 |
| ccatctgtct atccactggc ccctggatct gctgcccaaa ctaactccat ggtgaccctg | 480 |
| ggatgcctgg tcaagggcta tttccctgag ccagtgacag tgacctggaa ctctggatcc | 540 |
| ctgtccagcg gtgtgcacac cttcccagct gtcctgcagt ctgacctcta cactctgagc | 600 |
| agctcagtga ctgtcccctc cagcacctgg cccagcgaga ccgtcacctg caacgttgcc | 660 |
| cacccggcca gcagcaccaa ggtggacaag aaaattgtgc ccagggattg tggttgtaag | 720 |
| ccttgcatat gtacagtccc agaagtatca tctgtcttca tcttccccc aaagcccaag | 780 |
| gatgtgctca ccattactct gactcctaag gtcacgtgtg ttgtggtaga catcagcaag | 840 |
| gatgatcccg aggtccagtt cagctggttt gtagatgatg tggaggtgca cacagctcag | 900 |
| acgcaacccc gggaggagca gttcaacagc actttccgct cagtcagtga acttcccatc | 960 |
| atgcaccagg actggctcaa tggcaaggag ttcaaatgca gggtcaacag tgcagctttc | 1020 |
| cctgccccca tcgagaaaac catctccaaa accaaggca gaccgaaggc tccgcaggtg | 1080 |
| tacaccattc cacctcccaa ggagcagatg gccaaggata agtcagtct gacctgcatg | 1140 |
| ataacagact tcttccctga agacattact gtggagtggc agtggaatgg gcagccagcg | 1200 |
| gagaactaca gaacactca gcccatcatg gacacagatg gctcttactt cgtctacagc | 1260 |
| aagctcaatg tgcagaagag caactgggag gcaggaaata ctttcacctg ctctgtgtta | 1320 |
| catgagggcc tgcacaacca ccatactgag aagagcctct cccactctcc tggtaaatga | 1380 |

<210> SEQ ID NO 348
<211> LENGTH: 702
<212> TYPE: DNA
<213> ORGANISM: Artificial Sequence
<220> FEATURE:
<223> OTHER INFORMATION: Expression vector of mouse IgG1 chimera
      antibody: light chain

<400> SEQUENCE: 348

| | |
|---|---|
| atggaaaccg atactctgct gctgtgggtc ctgctgctgt gggtccctgg atccaccgga | 60 |
| gacatccaga tgacccagtc tccccccagtc ctgtctgcat ctgtgggaga cagagtcact | 120 |
| ctcagctgca agcaagtca gagtgttcat aacaagttag actggtatca gcaaaagcat | 180 |
| ggagaggctc cgaaactcct gatttattat acacacaatt tacaaacggg catcccatca | 240 |
| aggttcagtg gcagtggatc cggttcagat tacacactca ccatcagcag cctgcgggct | 300 |
| gaagatgttg ccacatatta ctgttttcaa tattacagtg gtggacgtt cggtggaggc | 360 |
| accaagctgg aaatgaaacg ggctgacgct gctcctacag tgtctatctt tccccctcg | 420 |
| agtgagcagc tgacctccgg aggagctagc gtggtgtgct tcctgaacaa cttctaccca | 480 |
| aaggacatca acgtgaagtg gaagatcgat ggctctgaga ggcagaacgg cgtgctgaat | 540 |

```
tcctggacag accaggattc caaggacagc acctattcta tgagctctac cctgacactg    600
accaaggatg agtacgagag acataattcc tatacctgtg aggcaaccca taaaacttca    660
acaagcccaa tcgtcaaatc cttcaatcgt aatgagtgct ga                       702
```

SPNS2 NEUTRALIZING ANTIBODY

CROSS REFERENCE TO RELATED APPLICATIONS

This application is a National Stage of International Application No. PCT/JP2019/015208, filed Apr. 5, 2019, claiming priority based on Japanese Patent Application No. 2018-073940, filed Apr. 6, 2018.

TECHNICAL FIELD

The present invention relates to an SPNS2 neutralizing antibody and, more specifically, to an SPNS2 neutralizing antibody which specifically binds to an SPNS2 of a vertebrate.

BACKGROUND ART

Sphingosine 1 phosphate (S1P) is a kind of phospholipid, and its precursor, sphingosine, is produced via excision from ceramide, which is a component of the cell membrane. In a cell, SP is produced via phosphorylation of sphingosine by sphingosine kinase (SphK1, SphK2) (Non-Patent Literature 1), and transmits various signals via five types of receptors (S1PR1, S1PR2, S1PR3, S1PR4, S1PR5). Analysis using S1PR1-defective mice showed that S1PR1 is involved in various physiological effects, including vascular formation, migration of lymphocytes, and contraction of cardiomyocytes (Non-Patent Literatures 2, 3, 4, and 5). Analysis using S1PR2-defective mice showed that S1PR2 is involved in various physiological effects, including neural excitation, maintenance of the inner ear structure, and vascular formation (Non-Patent Literatures 6, 7, and 8). Analysis using S1PR3-defective mice showed that S1PR3 is involved in heart rhythm, survival of cardiomyocytes, and vascular relaxation (Non-Patent Literatures 9, 10, and 11). Analysis using S1PR4-defective mice showed that S1PR4 is involved in differentiation of megakaryocytes and differentiation and activation of T cells (Non-Patent Literatures 12, 13, and 14). Analysis using S1PR5-defective mice showed that S1PR5 is involved in survival of oligodendrocytes and migration of NK cells (Non-Patent Literatures 15 and 16).

The S1P levels are 100 nM to 300 nM in blood and lymph, but are maintained low in lymphatic tissues and other tissues, at around 10 nM or less (Non-Patent Literatures 17 and 18). In the presence of high levels of S1P, S1PR1 receptors expressed by lymphocytes are internalized and prevented from reacting with extracellular S1P (Non-Patent Literature 19). In blood and lymph, lymphocytes are exposed to high levels of SP and S1PR1 is subject to internalization, resulting in migration of lymphocytes into lymphatic tissues. Since the extracellular SP level is kept low in lymphatic tissues, expression of S1PR1 is restored over time. As a result, lymphocytes start to migrate into lymph (Non-Patent Literatures 17 and 18). SP are mainly produced by erythrocytes, platelets, vascular endothelial cells, and lymphatic endothelial cells (Non-Patent Literature 20). Transport of S1P out of erythrocytes and platelets is associated with an ATP-dependent transporter, while transport of S1P out of vascular endothelial cells and lymphatic endothelial cells is associated with SLC (Solute Carriers)-like transporter SPNS2 (Non-Patent Literatures 21 to 27 and Patent Literature 1).

SPNS2 is a transporter involved in the transport of S1P, which is a member of the SLC family. SPNS2 exists on the surface of cell membrane, and has a domain which crosses the cell membrane multiple times (transmembrane domain). However, the number of times the transmembrane domain of SPNS2 crosses the cell membrane varies from 11 times (EMBL Accession No: Q8IVW8) to 12 times (Non-Patent Literature 28) depending on reports. The position of the transmembrane domain with respect to the entire amino acid sequence of SPNS2 and the number of amino acid residues included in the transmembrane domain also vary depending on softwares used for analysis.

SPNS2 is mainly expressed in vascular endothelial cells and lymphatic endothelial cells and transports S1P from inside to outside of the cells. Analysis using SPNS2-defective mice showed that a reduction in blood lymphocytes, a reduction in the level of inflammatory cytokines in alveolar lavage fluid of a pathological model of allergic hypersensitivity reaction of airway induced via OVA sensitization, and an improvement of the airway resistance value in a methacholine challenge airway resistance test. A reduction in thickening of skin was also observed in an oxazolone-induced atopic dermatitis model. In a DSS-induced enteritis model using SPNS2-defective mice, a loss of body weight was inhibited, and the pathological scores were also decreased. Similar results were also observed in an enteritis model induced via administration of oxazolone into the rectum. An experimental autoimmune encephalomyelitis model using SPNS2-defective mice exhibited a decrease in pathological scores and a decrease of inflammatory image in the cerebellum. A collagen-induced arthritis model using SPNS2-defective mice exhibited a reduction in the swelling of joints and a decrease in pathological scores (Non-Patent Literature 29). An experimental lungmetastasis model using SPNS2-defective mice, which was induced via intravenous administration of various tumor cells such as malignant melanoma cells, exhibited a significant decrease in the number of tumors metastasizing to the lung (Non-Patent Literature 30). Fingolimod, which is a drug modulating an S1P receptor signal, has an agonistic activity on the S1P receptor and causes internalization of the SP receptor. Administration of fingolimod inhibits the functions of S1PR1 to reduce the blood lymphocyte level and thereby exhibits immunosuppressive effect. Fingolimod is therefore used as a drug for treating multiple sclerosis (Non-Patent Literature 18). Non-clinical researches suggested its potential in the treatment of various immune diseases including rheumatoid arthritis (Non-Patent Literatures 31 and 32), autoimmune enteritis (Non-Patent Literature 33), asthma (Non-Patent Literature 34), systemic erythematosus (Non-Patent Literatures 35, 36, and 37), and rejection of an organ transplant (Non-Patent Literature 38). S1PR1 selective agonist, Ponesimod, improved the conditions of psoriasis in a phase 2 trial (Non-Patent Literature 39).

Fingolimod is an activator of S1P receptors except S1PR2, and used as a drug for treating multiple sclerosis (Non-Patent Literature 40). Fingolimod is known to cause bradyarrhythmia as a clinical side effect (Non-Patent Literatures 41 and 42). Cardiomyocytes express S1P receptors, via which fingolimod activates heterotrimeric G protein. Activated Gβγ protein then activates G protein-coupled inwardly-rectifying potassium channels (GIRKs) to cause transfer of potassium ions from outside to inside of the cells, which leads to hyperpolarization of the membrane and a decrease in the frequency of excitation of cardiomyocytes, resulting in a decrease in heart rate (Non-Patent Literature 43). Since this mechanism causing the side effect is a class effect of fingolimod (i.e., an effect common to all the drugs sharing the same mechanism of action), it is expected that no drug targeted at S1PR1 can escape this side effect. In fact, there are currently no S1P signal regulating drugs that can circumvent the risk of bradyarrhythmia (Non-Patent Literatures 44 and 45).

Malignant tumor (cancer) is a leading cause of death among Japanese. There are still no effective treatments for many types of cancer. While early-stage cancer may be completely cured via surgical removal, its prognosis is considerably worsened and therapeutic options therefor are limited once it develops distant metastasis.

Cancer treatments are typically carried out using drugs that have cytotoxic effects or cell-growth inhibitory effects on tumor cells and molecular targeted drugs that inhibit specific signals (Non-Patent Literature 46). Other treatments do not directly act on tumor cells, but activate autoimmunity and help it to eliminate tumor cells. CD8-positive T cells and NK cells have the capability to remove tumor cells (Non-Patent Literature 47). Chimeric antigen receptor T cells that have chimeric T cell receptors for novel antigens are shown to be effective in the treatment of cancer, suggesting that CD8-positive T cells to novel antigens play an important role in the protection against cancer (Non-Patent Literature 48). NK cells are also known to play an important role in protection from tumor cells. Various stresses such as abnormal growth rate of tumor cells cause stress-dependent molecules expressed at the membrane surface. NK cells recognize such stress-dependent ligand via their receptors and remove the abnormal cells from the body. An experiment shows that mice deficient in NK cells exhibited significantly reduced resistance to transplanted tumor cells, supporting the recognition that NK cells are also important cells having antitumor effects (Non-Patent Literature 49). Immunotherapeutic drugs, pembrolizumab and nivolumab, have recently become available as new treatment options for malignant melanoma. However, since the response rates to these treatments are only around 50%, there is still a demand for new therapeutic methods (Non-Patent Literatures 50 and 51). Analysis using SPNS2-defective mice showed a significant reduction in settlement of intravenously transfused malignant melanoma into lung and liver. This report suggests that an increase in the ratio of effector T cells to regulatory T cells resulted in improved antitumor effects of T cells. Another experiment in which CD8-positive T cells and NK cells were removed using antibodies showed that T cells and NK cells are responsible for the tumor metastasis inhibitory effect of SPNS2-defective mice. This report suggests that SPNS2 inhibitors can be used not only as drugs for autoimmune diseases but also as cancer therapeutic drugs, and are also expected to enhance the effect of existing cancer immunotherapeutic treatments (Non-Patent Literature 30).

Existing information indicates that SPNS2 inhibitors are expected as promising drugs for the treatment of autoimmune diseases and cancers. However, there are currently no SPNS2 inhibitors. Inhibitors of SLC transporters known so far are mostly low molecular compounds, which exhibit low target selectivity and tend to cause side effects. Compared to such low molecular compound inhibitors, antibody drugs have improved target specificity and exhibit less side effects due to off-target (Non-Patent Literature 52). However, there have been no reports of antibodies that can inhibit the ligand transport funtion of the SLC transporter. In addition, in order to develop a pharmaceutical drug using an antibody inhibiting the function of SPNS2 (SPNS2 neutralizing antibody), it is also necessary to meet the requirements that the antibody recognizes extracellular parts (loops) of SPNS2, and that the extracellular loops recognized by the antibody are essential for SPNS2 to play its functions. However, the prior art provides little information about the structure of SPNS2. The sites of SPNS2 corresponding to extracellular loops were not specified, and there is no information about the extracellular loops essential for the funtion of SPNS2. These hurdles make it difficult to obtain an SPNS2 neutralizing antibody that can be used as a pharmaceutical.

An anti-S1P antibody, Sonepcizumab, is currently being tested in a clinical trial for use in the treatment of kidney cancer. However, there has been no report so far that it exhibits adequate effect. It is also deemed that a large amount of such an antibody will be required to neutralize S1P present in blood and lymph. The inventors believe that an antibody inhibiting the function of SPNS2, which transports S1P to outside of the cells, would enable more efficient inhibition of the effects of SP in a smaller amount.

LIST OF CITATIONS

Patent Literature

[Patent Literature 1] JP5885154B

Non-Patent Literature

[Non-Patent Literature 1] Spiegel, S. and Milstien, S., Sphingosine-1-phosphate: an enigmatic signalling lipid. Nat Rev Mol Cell Biol. 2003; 4(5): p. 397-407.

[Non-Patent Literature 2] Liu, Y., et al., Edg-1, the G protein-coupled receptor for sphingosine-1-phosphate, is essential for vascular maturation. J Clin Invest. 2000; 106(8): p. 951-61.

[Non-Patent Literature 3] Allende, M L., et al., Expression of the sphingosine 1-phosphate receptor, S1P1, on T-cells controls thymic emigration. J Biol Chem. 2004 Apr. 9; 279(15): p. 15396-401.

[Non-Patent Literature 4] Means, C K., et al., S1P1 receptor localization confers selectivity for Gi-mediated cAMP and contractile responses. J Biol Chem. 2008 May 2; 283(18): p. 11954-63

[Non-Patent Literature 5] O'Sullivan, C. and Dev, K. K. The structure and function of the S1P1 receptor. Trends Pharmacol Sci. 2013; 34(7): p. 401-12.

[Non-Patent Literature 6] MacLennan, A. J., et al., An essential role for the H218/AGR16/Edg-5/LP(B2) sphingosine 1-phosphate receptor in neuronal excitability. Eur J Neurosci. 2001; 14(2): p. 203-9.

[Non-Patent Literature 7] MacLennan, A. J., et al., The S1P2 sphingosine 1-phosphate receptor is essential for auditory and vestibular function. Hear Res. 2006; 220(1-2): p. 38-48.

[Non-Patent Literature 8] Kono, M., et al., The sphingosine-1-phosphate receptors S1P1, S1P2, and S1P3 function coordinate lyduring embryonic angiogenesis. J Biol Chem. 2004; 279(28): p. 29367-73.

[Non-Patent Literature 9] Nofer, J. R., et al., HDLinduces NO-dependent vasorelaxation via the lysophospholipid receptor S1P3. J Clin Invest. 2004; 113(4): p. 569-81.

[Non-Patent Literature 10] Sanna, M. G., et al., Bitopic Sphingosine 1-Phosphate Receptor 3 (S1P3) Antagonist Rescue from Complete Heart Block: Pharmacological and Genetic Evidence for Direct S1P3 Regulation of Mouse Cardiac Conduction. Mol Pharmacol. 2016; 89(1): p. 176-86.

[Non-Patent Literature 11] Means, C. K., et al., Sphingosine 1-phosphate S1P2 and S1P3 receptor-mediated Akt activation protects against in vivo myocardial ischemia-reperfusion injury. Am J Physiol Heart Circ Physiol. 2007; 292(6): p. H2944-51.

[Non-Patent Literature 12] Golfier, S., et al., Shaping of terminal megakaryocyte differentiation and proplatelet development by sphingosine-1-phosphate receptor S1P4. FASEB J. 2010; 24(12): p. 4701-10.

[Non-Patent Literature 13] Wang, W., et al., Type 4 sphingosine 1-phosphate G protein-coupled receptor (S1P4) transduces S1P effects on T cell proliferation and cytokine secretion without signaling migration. FASEB J. 2005; 19(12): p. 1731-3.

[Non-Patent Literature 14] Schulze, T., et al., Sphingosine-1-phospate receptor 4 (S1P4) deficiency profoundly affects dendritic cell function and TH17-cell differentiation in a murine model. FASEB J. 2011; 25(11): p. 4024-36.

[Non-Patent Literature 15] Jaillard, C., et al., Edg8/S1P5: an oligodendroglial receptor with dual function on process retraction and cell survival. J Neurosci. 2005; 25(6): p. 1459-69.

[Non-Patent Literature 16] Jenne, C. N., et al., T-bet-dependent S1P5 expression in NK cells promotes egress from lymph nodes and bone marrow. J Exp Med. 2009; 206 (11): p. 2469-81.

[Non-Patent Literature 17] Lo, C. G., et al., Cyclical modulation of sphingosine-1-phosphate receptor 1 surface expression during lymphocyte recirculation and relationship to lymphoid organ transit. J Exp Med. 2005; 201(2): p. 291-301.

[Non-Patent Literature 18] Chiba K. A new therapeutic approach for autoimmune diseases by the sphingosine 1-phosphate receptor modulator, fingolimod (FTY720) Nihon Rinsho Meneki Gakkai Kaishi. 2009 April; 32(2): p. 92-101.

[Non-Patent Literature 19] Matloubian, M., et al., Lymphocyte egress from thymus and peripheral lymphoid organs is dependent on SP receptor 1. Nature. 2004; 427(6972): p. 355-60.

[Non-Patent Literature 20] Schwab, S. R. and Cyster, J. G., Finding a way out: lymphocyte egress from lymphoid organs. Nat Immunol. 2007; 8(12): p. 1295-301.

[Non-Patent Literature 21] Nagahashi, M., et al., Sphingosine-1-phosphate transporters as targets for cancer therapy. Biomed Res Int. 2014; 2014: p. 651727

[Non-Patent Literature 22] Osborne, N., et al., The spinster homolog, two of hearts, is required for sphingosine 1-phosphate signaling in zebrafish. Curr Biol. 2008 Dec. 9; 18(23): p. 1882-8.

[Non-Patent Literature 23] Kawahara, A., et al., The sphingolipid transporter Spns2 functions in migration of zebrafish myocardial precursors. Science. 2009; 323 (5913):524-7.

[Non-Patent Literature 24] Fukuhara, S., et al., The sphingosine-1-phosphate transporter Spns2 expressed on endothelial cells regulates lymphocyte trafficking in mice. J Clin Invest. 2012; 122(4): p. 1416-26.

[Non-Patent Literature 25] Nijnik, A., et al., The role of sphingosine-1-phosphate transporterSpns2 in immune system function. J Immunol. 2012; 189(1): p. 102-11.

[Non-Patent Literature 26] Hisano, Y., et al., Mouse SPNS2 functions as a sphingosine-1-phosphate transporterin vascular endothelial cells. PLoS One. 2012; 7(6): p. e38941.

[Non-Patent Literature 27] Nagahashi, M., et al., Spns2, a transporter of phosphorylated sphingoid bases, regulates their blood and lymph levels, and the lymphatic network. FASEB J. 2013; 27(3): p. 1001-11.

[Non-Patent Literature 28] Perland, E., et al., Characteristics of 29 novel atypical solute carriers of major facilitator superfamily type: evolutionary conservation, predicted structure and neuronal co-expression. Open Biol. 2017 September; 7(9). pii: 170142.

[Non-Patent Literature 29] Donoviel, M. S., et al., Spinster 2, a sphingosine-1-phosphate transporter, plays a critical role in inflammatory and autoimmune diseases. FASEB J. 2015; 29(12): p. 5018-28.

[Non-Patent Literature 30] van der Weyden, L., et al., Genome-widein vivo screen identifies novel host regulators of metastatic colonization. Nature. 2017; 541(7636): p. 233-236.

[Non-Patent Literature 31] Matsuura, M., et al., Effect of FTY720, a novel immunosuppressant, on adjuvant-induced arthritis in rats. Inflamm Res. 2000; 49(8): p. 404-10.

[Non-Patent Literature 32] Wang, F., et al., Reduction of CD4 positive T cells and improvement of pathological changes of collagen-induced arthritis by FTY720. Eur J Pharmacol. 2007; 573(1-3): p. 230-40.

[Non-Patent Literature 33] Deguchi, Y., et al., The SP receptor modulator FTY720 prevents the development of experimental colitis in mice. Oncol Rep. 2006; 16(4): p. 699-703.

[Non-Patent Literature 34] Idzko, M., et al., Local application of FTY720 to the lung abrogates experimental asthma by altering dendritic cell function. J Clin Invest. 2006; 116(11): p. 2935-44.

[Non-Patent Literature 35] Ando, S., et al., FTY720 exerts a survival advantage through the prevention of end-stage glomerular inflammation in lupus-prone BXSB mice. Biochem Biophys Res Commun. 2010; 394(3): p. 804-10.

[Non-Patent Literature 36] Okazaki, H., et al., Effects of FTY720 in MRL-lpr/lpr mice: therapeutic potential in systemic lupus erythematosus. J Rheumatol. 2002; 29(4): p. 707-16.

[Non-Patent Literature 37] Sui, M., et al., The sphingosine-1-phosphate receptor agonist FTY720 prevents the development of anti-glomerular basement membrane glomerulonephritis. Mol Biol Rep. 2012; 39(1): p. 389-97.

[Non-Patent Literature 38] Habicht, A., et al., Novel insights into the mechanism of action of FTY720 in a transgenic model of allograft rejection: implications for therapy of chronic rejection. J Immunol. 2006; 176(1): p. 36-42.

[Non-Patent Literature 39] D'Ambrosio, D., et l., Ponesimod, a selective S1P1 receptor modulator: a potential treatment for multiple sclerosis and other immune-mediated diseases. Ther Adv Chronic Dis. 2016; 7(1): p. 18-33.

[Non-Patent Literature 40] Brinkmann, V., et al., The immune modulator FTY720 targets sphingosine 1-phosphate receptors. J Biol Chem. 2002; 277(24): p. 21453-7.

[Non-Patent Literature 41] Kappos, L., et al., A placebo-controlled trial of oral fingolimod in relapsing multiple sclerosis. N Engl J Med. 2010; 362(5): p. 387-401.

[Non-Patent Literature 42] Cohen, J. A., et al., Oralfingolimod or intramuscular interferon for relapsing multiple sclerosis. N Engl J Med. 2010; 362(5): p. 402-15.

[Non-Patent Literature 43] Koyrakh, L., et al., The heart rate decrease caused by acute FTY720 administration is mediated by the G protein-gated potassium channel I. Am J Transplant. 2005; 5(3): p. 529-36.

[Non-Patent Literature 44] Hoch, M., et al., Effect of ponesimod, a selectiveS1P1 receptor modulator, on the QT interval in healthy individuals. Basic Clin Pharmacol Toxicol. 2015; 116(5): p. 429-37.

[Non-Patent Literature 45] Legangneux, E., et al., Cardiac Effects of Siponimod (BAF312) Re-initiation After Variable Periods of Drug Discontinuation in Healthy Subjects. Clin Ther. 2016; 38(3): p. 631-45.e1.

[Non-Patent Literature 46] Japanese Skin Cancer Society, "Guidelines for Medication of Malignant Melanoma", Version 1., 2016, Skin Cancer Vol. 32 No. 1 2017 [Japanese Document]

[Non-Patent Literature 47] Smyth, M. J., et al., NKG2Dfunction protects the host from tumor initiation. J Exp Med. 2005; 202(5): p. 583-8.

[Non-Patent Literature 48] Xia, A. L., et al., Chimericantigen receptor T (CAR-T) cell therapy for solid tumors: challenges and opportunities. Oncotarget. 2017; 8(52): p. 90521-90531.

[Non-Patent Literature 49] Kim, S., et al., In vivo natural killer cell activities revealed by natural killer cell-deficient mice. Proc Natl Acad Sci USA. 2000; 97(6): p. 2731-6.

[Non-Patent Literature 50] Robert, C., et al., Nivolumab in previously untreated melanoma without BRAF mutation. N Engl J Med. 2015; 372(4): p. 320-30.

[Non-Patent Literature 51] Schachter, J., et al., Pembrolizumabversus ipilimumab for advanced melanoma: final overall survival results of a multicentre, randomised, open-label phase 3 study (KEYNOTE-006). Lancet. 2017; 390(10105): p. 1853-1862.

[Non-Patent Literature 52] Mocsai, A., et al., What is the future of targeted therapy in rheumatology: biologics or small molecules?, BMC Med. 2014; 12: p. 43.

SUMMARY OF INVENTION

Problem to be Solved by the Invention

An objective of the present invention is to provide an SPNS2 neutralizing antibody or antibody fragment or a derivative thereof which specifically binds to SPNS2 of a vertebrate and thereby inhibits transport of S1P. Another objective of the present invention is to provide an antibody which inhibits migration of lymphocytes via SPNS2 and is effective in the treatment for autoimmune diseases or cancers.

Means to Solve the Problem

Aspects of the present invention include the following:

[1] An SPNS2 neutralizing antibody or antibody fragment or a derivative thereof, which specifically binds to SPNS2 of a vertebrate and thereby exhibits an activity to inhibit its transport of sphingosine-1-phosphate (S1P).

[2] An SPNS2 neutralizing antibody or antibody fragment or a derivative thereof according to [1], which exhibits an EC50 value of $1 \times 10^{-7}$ M or less measured by Cell-based Enzyme-Linked ImmunoSorbent Assay (ELISA) using SPNS2 expressing cells.

[3] An SPNS2 neutralizing antibody or antibody fragment or a derivative thereof according to [1] or [2], which inhibits the transport of S1P in SPNS2 expressing cells at an IC50 value of $1 \times 10^{-7}$ M or less.

[4] An SPNS2 neutralizing antibody or antibody fragment or a derivative thereof according to any one of [1] to [3], which binds to extracellular loop 1 (SEQ ID NO:3), extracellular loop 3 (SEQ ID NO:4), or extracellular loop 5 (SEQ ID NO:5) of SPNS2 to thereby inhibit the transport of S1P.

[5] An SPNS2 neutralizing antibody or antibody fragment or a derivative thereof according to [4], which binds to extracellular loop 1 (SEQ ID NO:3) or extracellular loop 5 (SEQ ID NO:5) of SPNS2 to thereby inhibit the transport of S1P.

[6] An SPNS2 neutralizing antibody or antibody fragment or a derivative thereof according to [4] or [5], which binds to an epitope comprising at least a partial sequence of extracellular loop 1 (SEQ ID NO:3) of SPNS2, or to a site in the vicinity thereof.

[7] An SPNS2 neutralizing antibody or antibody fragment or a derivative thereof according to [4] or [5], which binds to an epitope comprising at least a partial sequence of extracellular loop 3 (SEQ ID NO:4) of SPNS2, or to a site in the vicinity thereof.

[8] An SPNS2 neutralizing antibody or antibody fragment or a derivative thereof according to [4] or [5], which binds to an epitope comprising at least a partial sequence of extracellular loop 5 (SEQ ID NO:5) of SPNS2, or to a site in the vicinity thereof.

[9] An SPNS2 neutralizing antibody or antibody fragment or a derivative thereof according to any one of [1] to [8], wherein the SPNS2 is human SPNS2.

[10] An SPNS2 neutralizing antibody or antibody fragment or a derivative thereof according to any one of [1] to [9], which exhibits, when administered to a vertebrate, an activity to induce a decrease in the number of blood lymphocytes in the vertebrate.

[11] An SPNS2 neutralizing antibody or antibody fragment or a derivative thereof according to any one of [1] to [10], which is to be administered to a vertebrate at a frequency of once weekly or less.

[12] An SPNS2 neutralizing antibody or antibody fragment or a derivative thereof according to any one of [1] to [11], comprising:

(1) as a CDR-H1 sequence, the amino acid sequence defined in SEQ ID NO:98 or an amino acid sequence derived from the amino acid sequence defined in SEQ ID NO:98 via substitution, deletion, or addition of one or two amino acid residues;

as a CDR-H2 sequence, the amino acid sequence defined in SEQ ID NO:108 or SEQ ID NO:111 or an amino acid sequence derived from the amino acid sequence defined in SEQ ID NO:108 or SEQ ID NO:111 via substitution, deletion, or addition of one or two amino acid residues; and as a CDR-H3 sequence, the amino acid sequence defined in SEQ ID NO:120 or SEQ ID NO:123 or an amino acid sequence derived from the amino acid sequence defined in SEQ ID NO:120 or SEQ ID NO:123 via substitution, deletion, or addition of one or two amino acid residues;

(2) as a CDR-H1 sequence, the amino acid sequence defined in SEQ ID NO:101 or an amino acid sequence derived from the amino acid sequence defined in SEQ ID NO:101 via substitution, deletion, or addition of one or two amino acid residues;

as a CDR-H2 sequence, the amino acid sequence defined in SEQ ID NO:113 or an amino acid sequence derived from the amino acid sequence defined in SEQ ID NO:113 via substitution, deletion, or addition of one or two amino acid residues; and as a CDR-H3 sequence, the amino acid sequence defined in SEQ ID NO:124 or an amino acid sequence derived from the amino acid sequence defined in SEQ ID NO:124 via substitution, deletion, or addition of one or two amino acid residues;

(3) as a CDR-H1 sequence, the amino acid sequence defined in SEQ ID NO:103 or SEQ ID NO:105 or an amino acid sequence derived from the amino acid sequence defined in SEQ ID NO:103 or SEQ ID NO:105 via substitution, deletion, or addition of one or two amino acid residues;

as a CDR-H2 sequence, the amino acid sequence defined in SEQ ID NO:115 or SEQ ID NO:118 or an amino acid sequence derived from the amino acid sequence defined in SEQ ID NO:115 or SEQ ID NO:118 via substitution, deletion, or addition of one or two amino acid residues; and as a CDR-H3 sequence, the amino acid sequence defined in SEQ ID NO:126 or SEQ ID NO:127 or an amino acid sequence derived from the amino acid sequence defined in SEQ ID NO:126 or SEQ ID NO:127 via substitution, deletion, or addition of one or two amino acid residues;

(4) as a CDR-H1 sequence, the amino acid sequence defined in SEQ ID NO:100 or SEQ ID NO:106 or an amino acid sequence derived from the amino acid sequence defined in SEQ ID NO:100 or SEQ ID NO:106 via substitution, deletion, or addition of one or two amino acid residues;

as a CDR-H2 sequence, the amino acid sequence as defined in any one of SEQ ID NO:110, SEQ ID NO:112 or SEQ ID NO:117 or an amino acid sequence derived from the amino acid sequence as defined in any one of SEQ ID NO:110, SEQ ID NO:112 or SEQ ID NO:117 via substitution, deletion, or addition of one or two amino acid residues; and as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues;

(5) as a CDR-H1 sequence, the amino acid sequence defined in SEQ ID NO:99 or an amino acid sequence derived from the amino acid sequence defined in SEQ ID NO:99 via substitution, deletion, or addition of one or two amino acid residues;

as a CDR-H2 sequence, the amino acid sequence defined in SEQ ID NO:109 or an amino acid sequence derived from the amino acid sequence defined in SEQ ID NO:109 via substitution, deletion, or addition of one or two amino acid residues; and as a CDR-H3 sequence, the amino acid sequence defined in SEQ ID NO:121 or an amino acid sequence derived from the amino acid sequence defined in SEQ ID NO:121 via substitution, deletion, or addition of one or two amino acid residues;

(6) as a CDR-H1 sequence, the amino acid sequence defined in SEQ ID NO:102 or an amino acid sequence derived from the amino acid sequence defined in SEQ ID NO:102 via substitution, deletion, or addition of one or two amino acid residues;

as a CDR-H2 sequence, the amino acid sequence defined in SEQ ID NO:114 or an amino acid sequence derived from the amino acid sequence defined in SEQ ID NO:114 via substitution, deletion, or addition of one or two amino acid residues; and as a CDR-H3 sequence, the amino acid sequence defined in SEQ ID NO:125 or an amino acid sequence derived from the amino acid sequence defined in SEQ ID NO:125 via substitution, deletion, or addition of one or two amino acid residues; or (7) as a CDR-H1 sequence, the amino acid sequence defined in SEQ ID NO:104 or an amino acid sequence derived from the amino acid sequence defined in SEQ ID NO:104 via substitution, deletion, or addition of one or two amino acid residues;

as a CDR-H2 sequence, the amino acid sequence defined in SEQ ID NO:116 or an amino acid sequence derived from the amino acid sequence defined in SEQ ID NO:116 via substitution, deletion, or addition of one or two amino acid residues; and as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues.

[13] An SPNS2 neutralizing antibody or antibody fragment or a derivative thereof according to any one of [1] to [12], comprising:

(1) as a CDR-H1 sequence, an amino acid sequence having a homology of 80% or more to SEQ ID NO:98;

as a CDR-H2 sequence, an amino acid sequence having a homology of 88% or more to SEQ ID NO:108 or SEQ ID NO:111; and as a CDR-H3 sequence, an amino acid sequence having a homology of 83% or more to SEQ ID NO:120 or SEQ ID NO:123;

(2) as a CDR-H1 sequence, an amino acid sequence having a homology of 80% or more to SEQ ID NO:101;

as a CDR-H2 sequence, an amino acid sequence having a homology of 88% or more to SEQ ID NO:113; and as a CDR-H3 sequence, an amino acid sequence having a homology of 88% or more to SEQ ID NO:124;

(3) as a CDR-H1 sequence, an amino acid sequence having a homology of 80% or more to SEQ ID NO:103 or SEQ ID NO:105;

as a CDR-H2 sequence, an amino acid sequence having a homology of 89% or more to SEQ ID NO:115 or SEQ ID NO:118; and as a CDR-H3 sequence, an amino acid sequence having a homology of 85% or more to SEQ ID NO:126 or SEQ ID NO:127;

(4) as a CDR-H1 sequence, an amino acid sequence having a homology of 80% or more to SEQ ID NO:100 or SEQ ID NO:106;

as a CDR-H2 sequence, an amino acid sequence having a homology of 88% or more to any one of SEQ ID NO:110, SEQ ID NO:112 or SEQ ID NO:117; and as a CDR-H3 sequence, an amino acid sequence having a homology of 83% or more to SEQ ID NO:122;

(5) as a CDR-H1 sequence, an amino acid sequence having a homology of 80% or more to SEQ ID NO:99;

as a CDR-H2 sequence, an amino acid sequence having a homology of 88% or more to SEQ ID NO:109; and as a CDR-H3 sequence, an amino acid sequence having a homology of 80% or more to SEQ ID NO:121;

(6) as a CDR-H1 sequence, an amino acid sequence having a homology of 80% or more to SEQ ID NO:102;

as a CDR-H2 sequence, an amino acid sequence having a homology of 88% or more to SEQ ID NO:114; and as a CDR-H3 sequence, an amino acid sequence having a homology of 83% or more to SEQ ID NO:125; or (7) as a CDR-H1 sequence, an amino acid sequence having a homology of 80% or more to SEQ ID NO:104;

as a CDR-H2 sequence, an amino acid sequence having a homology of 88% or more to SEQ ID NO:116; and as a CDR-H3 sequence, an amino acid sequence having a homology of 83% or more to SEQ ID NO:122.

[14] An SPNS2 neutralizing antibody or antibody fragment or a derivative thereof according to any one of [1] to [13], comprising:

(1) as a CDR-H1 sequence, the amino acid sequence defined in SEQ ID NO:98;

as a CDR-H2 sequence, the amino acid sequence defined in SEQ ID NO:108 or the amino acid sequence derived from SEQ ID NO:108 via substitution of the 1st amino acid residue Thr with Ser; and as a CDR-H3 sequence, the amino acid sequence defined in SEQ ID NO:123 or an amino acid sequence derived from SEQ ID NO:123 via substitution of the 4th amino acid residue Ser with Thr;
(2) as a CDR-H1 sequence, the amino acid sequence defined in SEQ ID NO:101;
as a CDR-H2 sequence, the amino acid sequence defined in SEQ ID NO:113; and
as a CDR-H3 sequence, the amino acid sequence defined in SEQ ID NO:124;
(3) as a CDR-H1 sequence, the amino acid sequence defined in SEQ ID NO:105 or an amino acid sequence derived from SEQ ID NO:105 via substitution of the 1st amino acid residue Asp with Glu;
as a CDR-H2 sequence, the amino acid sequence defined in SEQ ID NO:115 or an amino acid sequence derived from SEQ ID NO:115 via substitution of the 9th amino acid residue Tyr with Ser and/or substitution of the 17th amino acid residue Val with Ile; and
as a CDR-H3 sequence the amino acid sequence defined in SEQ ID NO:126 or an amino acid sequence derived from SEQ ID NO:126 via substitution of the 9th amino acid residue Ser with Gly;
(4) as a CDR-H1 sequence, the amino acid sequence defined in SEQ ID NO:100 or an amino acid sequence derived from SEQ ID NO:100 via substitution of the 1st amino acid residue Arg with Ala;
as a CDR-H2 sequence, the amino acid sequence defined in SEQ ID NO:110 or an amino acid sequence derived from SEQ ID NO:110 via substitution of the 8th amino acid residue Thr with Ser and/or substitution of the 17th amino acid residue Asn with Lys; and
as a CDR-H3 sequence the amino acid sequence defined in SEQ ID NO:122;
(5) as a CDR-H1 sequence, the amino acid sequence defined in SEQ ID NO:99;
as a CDR-H2 sequence the amino acid sequence defined in SEQ ID NO:109; and
as a CDR-H3 sequence the amino acid sequence defined in SEQ ID NO:121;
(6) as a CDR-H1 sequence, the amino acid sequence defined in SEQ ID NO:102;
as a CDR-H2 sequence, the amino acid sequence defined in SEQ ID NO:114; and
as a CDR-H3 sequence, the amino acid sequence defined in SEQ ID NO:125; or
(7) as a CDR-H1 sequence, the amino acid sequence defined in SEQ ID NO:104;
as a CDR-H2 sequence, the amino acid sequence defined in SEQ ID NO:116; and
as a CDR-H3 sequence, the amino acid sequence defined in SEQ ID NO:122.
[15] An SPNS2 neutralizing antibody or antibody fragment or a derivative thereof according to any one of [1] to [14], comprising:
(1) as a CDR-H1 sequence, the amino acid sequence defined in SEQ ID NO:98;
as a CDR-H2 sequence, the amino acid sequence defined in SEQ ID NO:108; and
as a CDR-H3 sequence, the amino acid sequence defined in SEQ ID NO:120;
(2) as a CDR-H1 sequence, the amino acid sequence defined in SEQ ID NO:99;
as a CDR-H2 sequence, the amino acid sequence defined in SEQ ID NO:109; and
as a CDR-H3 sequence, the amino acid sequence defined in SEQ ID NO:121;
(3) as a CDR-H1 sequence, the amino acid sequence defined in SEQ ID NO:100;
as a CDR-H2 sequence, the amino acid sequence defined in SEQ ID NO:110; and
as a CDR-H3 sequence, the amino acid sequence defined in SEQ ID NO:122;
(4) as a CDR-H1 sequence, the amino acid sequence defined in SEQ ID NO:98;
as a CDR-H2 sequence, the amino acid sequence defined in SEQ ID NO:111; and
as a CDR-H3 sequence, the amino acid sequence defined in SEQ ID NO:123;
(5) as a CDR-H1 sequence, the amino acid sequence defined in SEQ ID NO:98;
as a CDR-H2 sequence the amino acid sequence defined in SEQ ID NO:108; and
as a CDR-H3 sequence, the amino acid sequence defined in SEQ ID NO:123;
(6) as a CDR-H1 sequence, the amino acid sequence defined in SEQ ID NO:100;
as a CDR-H2 sequence, the amino acid sequence defined in SEQ ID NO:112; and
as a CDR-H3 sequence, the amino acid sequence defined in SEQ ID NO:122;
(7) as a CDR-H1 sequence, the amino acid sequence defined in SEQ ID NO:101;
as a CDR-H2 sequence, the amino acid sequence defined in SEQ ID NO:113; and
as a CDR-H3 sequence, the amino acid sequence defined in SEQ ID NO:124;
(8) as a CDR-H1 sequence, the amino acid sequence defined in SEQ ID NO:102;
as a CDR-H2 sequence, the amino acid sequence defined in SEQ ID NO:114; and
as a CDR-H3 sequence, the amino acid sequence defined in SEQ ID NO:125;
(9) as a CDR-H1 sequence, the amino acid sequence defined in SEQ ID NO:103;
as a CDR-H2 sequence, the amino acid sequence defined in SEQ ID NO:115; and
as a CDR-H3 sequence, the amino acid sequence defined in SEQ ID NO:126;
(10) as a CDR-H1 sequence, the amino acid sequence defined in SEQ ID NO:104;
as a CDR-H2 sequence, the amino acid sequence defined in SEQ ID NO:116; and
as a CDR-H3 sequence, the amino acid sequence defined in SEQ ID NO:122;
(11) as a CDR-H1 sequence, the amino acid sequence defined in SEQ ID NO:105;
as a CDR-H2 sequence, the amino acid sequence defined in SEQ ID NO:115; and
as a CDR-H3 sequence, the amino acid sequence defined in SEQ ID NO:126;
(12) as a CDR-H1 sequence, the amino acid sequence defined in SEQ ID NO:106;
as a CDR-H2 sequence, the amino acid sequence defined in SEQ ID NO:117; and
as a CDR-H3 sequence, the amino acid sequence defined in SEQ ID NO:122; or
(13) as a CDR-H1 sequence, the amino acid sequence defined in SEQ ID NO:105;
as a CDR-H2 sequence, the amino acid sequence defined in SEQ ID NO:118; and
as a CDR-H3 sequence, the amino acid sequence defined in SEQ ID NO:127.

[16] An SPNS2 neutralizing antibody or antibody fragment or a derivative thereof according to any one of [1] to [11], comprising:
(1) as a CDR-L1 sequence, the amino acid sequence defined in SEQ ID NO:129 or SEQ ID NO:132 or an amino acid sequence derived from the amino acid sequence defined in SEQ ID NO:129 or SEQ ID NO:132 via substitution, deletion, or addition of one or two amino acid residues;
 as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and
 as a CDR-L3 sequence, the amino acid sequence as defined in any one of SEQ ID NO:149, SEQ ID NO:152 or SEQ ID NO:157 or an amino acid sequence derived from the amino acid sequence as defined in any one of SEQ ID NO:149, SEQ ID NO:152 or SEQ ID NO:157 via substitution, deletion, or addition of one or two amino acid residues;
(2) as a CDR-L1 sequence, the amino acid sequence defined in SEQ ID NO:134 or an amino acid sequence derived from the amino acid sequence defined in SEQ ID NO:134 via substitution, deletion, or addition of one or two amino acid residues;
 as a CDR-L2 sequence, the amino acid sequence defined in SEQ ID NO:142 or an amino acid sequence derived from the amino acid sequence defined in SEQ ID NO:142 via substitution, deletion, or addition of one or two amino acid residues; and
 as a CDR-L3 sequence, the amino acid sequence defined in SEQ ID NO:153 or an amino acid sequence derived from the amino acid sequence defined in SEQ ID NO:153 via substitution, deletion, or addition of one or two amino acid residues;
(3) as a CDR-L1 sequence, the amino acid sequence defined in SEQ ID NO:136 or an amino acid sequence derived from the amino acid sequence defined in SEQ ID NO:136 via substitution, deletion, or addition of one or two amino acid residues;
 as a CDR-L2 sequence, the amino acid sequence as defined in any one of SEQ ID NO:144, SEQ ID NO:146 or SEQ ID NO:147 or an amino acid sequence derived from the amino acid sequence as defined in any one of SEQ ID NO:144, SEQ ID NO:146 or SEQ ID NO:147 via substitution, deletion, or addition of one or two amino acid residues; and
 as a CDR-L3 sequence, the amino acid sequence defined in SEQ ID NO:155 or SEQ ID NO:158 or an amino acid sequence derived from the amino acid sequence defined in SEQ ID NO:155 or SEQ ID NO:158 via substitution, deletion, or addition of one or two amino acid residues;
(4) as a CDR-L1 sequence, the amino acid sequence as defined in any one of SEQ ID NO:131, SEQ ID NO:133 or SEQ ID NO:138 or an amino acid sequence derived from the amino acid sequence as defined in any one of SEQ ID NO:131, SEQ ID NO:133 or SEQ ID NO:138 via substitution, deletion, or addition of one or two amino acid residues;
 as a CDR-L2 sequence, the amino acid sequence defined in SEQ ID NO:141 or an amino acid sequence derived from the amino acid sequence defined in SEQ ID NO:141 via substitution, deletion, or addition of one or two amino acid residues; and
 as a CDR-L3 sequence, the amino acid sequence defined in SEQ ID NO:151 or an amino acid sequence derived from the amino acid sequence defined in SEQ ID NO:151 via substitution, deletion, or addition of one or two amino acid residues;
(5) as a CDR-L1 sequence, the amino acid sequence defined in SEQ ID NO:130 or an amino acid sequence derived from the amino acid sequence defined in SEQ ID NO:130 via substitution, deletion, or addition of one or two amino acid residues;
 as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and
 as a CDR-L3 sequence, the amino acid sequence defined in SEQ ID NO:150 or an amino acid sequence derived from the amino acid sequence defined in SEQ ID NO:150 via substitution, deletion, or addition of one or two amino acid residues;
(6) as a CDR-L1 sequence, the amino acid sequence defined in SEQ ID NO:135 or an amino acid sequence derived from the amino acid sequence defined in SEQ ID NO:135 via substitution, deletion, or addition of one or two amino acid residues;
 as a CDR-L2 sequence, the amino acid sequence defined in SEQ ID NO:143 or an amino acid sequence derived from the amino acid sequence defined in SEQ ID NO:143 via substitution, deletion, or addition of one or two amino acid residues; and
 as a CDR-L3 sequence, the amino acid sequence defined in SEQ ID NO:154 or an amino acid sequence derived from the amino acid sequence defined in SEQ ID NO:154 via substitution, deletion, or addition of one or two amino acid residues; or
(7) as a CDR-L1 sequence, the amino acid sequence defined in SEQ ID NO:137 or an amino acid sequence derived from the amino acid sequence defined in SEQ ID NO:137 via substitution, deletion, or addition of one or two amino acid residues;
 as a CDR-L2 sequence, the amino acid sequence defined in SEQ ID NO:145 or an amino acid sequence derived from the amino acid sequence defined in SEQ ID NO:145 via substitution, deletion, or addition of one or two amino acid residues; and
 as a CDR-L3 sequence, the amino acid sequence defined in SEQ ID NO:156 or an amino acid sequence derived from the amino acid sequence defined in SEQ ID NO:156 via substitution, deletion, or addition of one or two amino acid residues.
[17] An SPNS2 neutralizing antibody or antibody fragment or a derivative thereof according to any one of [1] to [11] and [16], comprising:
(1) as a CDR-L1 sequence, an amino acid sequence having a homology of 84% or more to SEQ ID NO:129 or SEQ ID NO:132;
 as a CDR-L2 sequence, an amino acid sequence having a homology of 85% or more to SEQ ID NO:140; and
 as a CDR-L3 sequence, an amino acid sequence having a homology of 88% or more to any one of SEQ ID NO:149, SEQ ID NO:152 or SEQ ID NO:157;
(2) as a CDR-L1 sequence, an amino acid sequence having a homology of 84% or more to SEQ ID NO:134;
 as a CDR-L2 sequence, an amino acid sequence having a homology of 85% or more to SEQ ID NO:142; and
 as a CDR-L3 sequence, an amino acid sequence having a homology of 88% or more to SEQ ID NO:153;
(3) as a CDR-L1 sequence, an amino acid sequence having a homology of 81% or more to SEQ ID NO:136;
 as a CDR-L2 sequence, an amino acid sequence having a homology of 85% or more to any one of SEQ ID NO:144, SEQ ID NO:146 or SEQ ID NO:147; and as a CDR-L3 sequence, an amino acid sequence having a homology of 88% or more to SEQ ID NO:155 or SEQ ID NO:158;
(4) as a CDR-L1 sequence, an amino acid sequence having a homology of 81% or more to any one of SEQ ID NO:131, SEQ ID NO:133 or SEQ ID NO:138;
as a CDR-L2 sequence, an amino acid sequence having a homology of 85% or more to SEQ ID NO:141; and
as a CDR-L3 sequence, an amino acid sequence having a homology of 88% or more to SEQ ID NO:151;
(5) as a CDR-L1 sequence, an amino acid sequence having a homology of 84% or more to SEQ ID NO:130;
as a CDR-L2 sequence, an amino acid sequence having a homology of 85% or more to SEQ ID NO:140; and
as a CDR-L3 sequence, an amino acid sequence having a homology of 88% or more to SEQ ID NO:150;
(6) as a CDR-L1 sequence, an amino acid sequence having a homology of 84% or more to SEQ ID NO:135;
as a CDR-L2 sequence, an amino acid sequence having a homology of 85% or more to SEQ ID NO:143; and
as a CDR-L3 sequence, an amino acid sequence having a homology of 88% or more to SEQ ID NO:154; or
(7) as a CDR-L1 sequence, an amino acid sequence having a homology of 81% or more to SEQ ID NO:137;
as a CDR-L2 sequence, an amino acid sequence having a homology of 85% or more to SEQ ID NO:145; and
as a CDR-L3 sequence, an amino acid sequence having a homology of 88% or more to SEQ ID NO:156.
[18] An SPNS2 neutralizing antibody or antibody fragment or a derivative thereof according to any one of [1] to [11], [16] and [17], comprising:
(1) as a CDR-L1 sequence, the amino acid sequence defined in SEQ ID NO:129 or an amino acid sequence derived from SEQ ID NO:129 via substitution of the 1st amino acid residue Thr with Lys and/or substitution of the 4th amino acid residue Ile with Thr;
as a CDR-L2 sequence, the amino acid sequence defined in SEQ ID NO:140; and
as a CDR-L3 sequence, the amino acid sequence defined in SEQ ID NO:149 or an amino acid sequence derived from SEQ ID NO:149 via substitution of the 5th amino acid residue Ser with Asn and/or substitution of the 7th amino acid residue Ile with Met;
(2) as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;
(3) as a CDR-L1 sequence, the amino acid sequence defined in SEQ ID NO:136;
as a CDR-L2 sequence, the amino acid sequence defined in SEQ ID NO:146 or an amino acid sequence derived from SEQ ID NO:146 via substitution of the 6th amino acid residue Ile with Met and/or substitution of the 7th amino acid residue Ser with Ala; and
as a CDR-L3 sequence, the amino acid sequence defined in SEQ ID NO:158 or an amino acid sequence derived from SEQ ID NO:158 via substitution of the 3rd amino acid residue Thr with Ser and/or substitution of the 5th amino acid residue Ser with Asn;
(4) as a CDR-L1 sequence, the amino acid sequence defined in SEQ ID NO:133 or an amino acid sequence derived from SEQ ID NO:133 via one or more selected from substitution of the 2nd amino acid residue Ala with Pro, substitution of the 5th amino acid residue Asn with Ser, and substitution of the 8th amino acid Ser with Asn;
as a CDR-L2 sequence, the amino acid sequence defined in SEQ ID NO:141; and
as a CDR-L3 sequence, the amino acid sequence defined in SEQ ID NO:151;
(5) as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;
(6) as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154; or
(7) as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156.
[19] An SPNS2 neutralizing antibody or antibody fragment or a derivative thereof according to any one of [1] to [11] and [16] to [18], comprising:
(1) as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;
(2) as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;
(3) as a CDR-L1 sequence, the amino acid sequence defined in SEQ ID NO:131;
as a CDR-L2 sequence, the amino acid sequence defined in SEQ ID NO:141; and
as a CDR-L3 sequence, the amino acid sequence defined in SEQ ID NO:151;
(4) as a CDR-L1 sequence, the amino acid sequence defined in SEQ ID NO:132;
as a CDR-L2 sequence, the amino acid sequence defined in SEQ ID NO:140; and
as a CDR-L3 sequence, the amino acid sequence defined in SEQ ID NO:152;
(5) as a CDR-L1 sequence, the amino acid sequence defined in SEQ ID NO:133;
as a CDR-L2 sequence, the amino acid sequence defined in SEQ ID NO:141; and
as a CDR-L3 sequence, the amino acid sequence defined in SEQ ID NO:151;
(6) as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;
(7) as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;

(8) as a CDR-L1 sequence, the amino acid sequence defined in SEQ ID NO:136;
as a CDR-L2 sequence, the amino acid sequence defined in SEQ ID NO:144; and
as a CDR-L3 sequence, the amino acid sequence defined in SEQ ID NO:155;
(9) as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;
(10) as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:157;
(11) as a CDR-L1 sequence, the amino acid sequence defined in SEQ ID NO:136;
as a CDR-L2 sequence, the amino acid sequence defined in SEQ ID NO:146; and
as a CDR-L3 sequence, the amino acid sequence defined in SEQ ID NO:158;
(12) as a CDR-L1 sequence, the amino acid sequence defined in SEQ ID NO:138;
as a CDR-L2 sequence, the amino acid sequence defined in SEQ ID NO:141; and
as a CDR-L3 sequence, the amino acid sequence defined in SEQ ID NO:151; or
(13) as a CDR-L1 sequence, the amino acid sequence defined in SEQ ID NO:136;
as a CDR-L2 sequence, the amino acid sequence defined in SEQ ID NO:147; and
as a CDR-L3 sequence, the amino acid sequence defined in SEQ ID NO:158.

[20]0An SPNS2 neutralizing antibody or antibody fragment or a derivative thereof according to any one of [1] to [19], comprising:

(1) as a CDR-H1 sequence, the amino acid sequence defined in SEQ ID NO:98 or an amino acid sequence derived from the amino acid sequence defined in SEQ ID NO:98 via substitution, deletion, or addition of one or two amino acid residues;
as a CDR-H2 sequence, the amino acid sequence defined in SEQ ID NO:108 or SEQ ID NO:111 or an amino acid sequence derived from the amino acid sequence defined in SEQ ID NO:108 or SEQ ID NO:111 via substitution, deletion, or addition of one or two amino acid residues;
as a CDR-H3 sequence, the amino acid sequence defined in SEQ ID NO:120 or SEQ ID NO:123 or an amino acid sequence derived from the amino acid sequence defined in SEQ ID NO:120 or SEQ ID NO:123 via substitution, deletion, or addition of one or two amino acid residues;
as a CDR-L1 sequence, the amino acid sequence defined in SEQ ID NO:129 or SEQ ID NO:132 or an amino acid sequence derived from the amino acid sequence defined in SEQ ID NO:129 or SEQ ID NO:132 via substitution, deletion, or addition of one or two amino acid residues;
as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and
as a CDR-L3 sequence, the amino acid sequence as defined in any one of SEQ ID NO:149, SEQ ID NO:152 or SEQ ID NO:157 or an amino acid sequence derived from the amino acid sequence as defined in any one of SEQ ID NO:149, SEQ ID NO:152 or SEQ ID NO:157 via substitution, deletion, or addition of one or two amino acid residues;

(2) as a CDR-H1 sequence, the amino acid sequence defined in SEQ ID NO:101 or an amino acid sequence derived from the amino acid sequence defined in SEQ ID NO:101 via substitution, deletion, or addition of one or two amino acid residues;
as a CDR-H2 sequence, the amino acid sequence defined in SEQ ID NO:113 or an amino acid sequence derived from the amino acid sequence defined in SEQ ID NO:113 via substitution, deletion, or addition of one or two amino acid residues;
as a CDR-H3 sequence, the amino acid sequence defined in SEQ ID NO:124 or an amino acid sequence derived from the amino acid sequence defined in SEQ ID NO:124 via substitution, deletion, or addition of one or two amino acid residues;
as a CDR-L1 sequence, the amino acid sequence defined in SEQ ID NO:134 or an amino acid sequence derived from the amino acid sequence defined in SEQ ID NO:134 via substitution, deletion, or addition of one or two amino acid residues;
as a CDR-L2 sequence, the amino acid sequence defined in SEQ ID NO:142 or an amino acid sequence derived from the amino acid sequence defined in SEQ ID NO:142 via substitution, deletion, or addition of one or two amino acid residues; and
as a CDR-L3 sequence, the amino acid sequence defined in SEQ ID NO:153 or an amino acid sequence derived from the amino acid sequence defined in SEQ ID NO:153 via substitution, deletion, or addition of one or two amino acid residues;

(3) as a CDR-H1 sequence, the amino acid sequence defined in SEQ ID NO:103 or SEQ ID NO:105 or an amino acid sequence derived from the amino acid sequence defined in SEQ ID NO:103 or SEQ ID NO:105 via substitution, deletion, or addition of one or two amino acid residues;
as a CDR-H2 sequence, the amino acid sequence defined in SEQ ID NO:115 or SEQ ID NO:118 or an amino acid sequence derived from the amino acid sequence defined in SEQ ID NO:115 or SEQ ID NO:118 via substitution, deletion, or addition of one or two amino acid residues;
as a CDR-H3 sequence, the amino acid sequence defined in SEQ ID NO:126 or SEQ ID NO:127 or an amino acid sequence derived from the amino acid sequence defined in SEQ ID NO:126 or SEQ ID NO:127 via substitution, deletion, or addition of one or two amino acid residues;
as a CDR-L1 sequence, the amino acid sequence defined in SEQ ID NO:136 or an amino acid sequence derived from the amino acid sequence defined in SEQ ID NO:136 via substitution, deletion, or addition of one or two amino acid residues;
as a CDR-L2 sequence, the amino acid sequence as defined in any one of SEQ ID NO:144, SEQ ID NO:146 or SEQ ID NO:147 or an amino acid sequence derived from the amino acid sequence as defined in any one of SEQ ID NO:144, SEQ ID NO:146 or SEQ ID NO:147 via substitution, deletion, or addition of one or two amino acid residues; and
as a CDR-L3 sequence, the amino acid sequence defined in SEQ ID NO:155 or SEQ ID NO:158 or an amino acid sequence derived from the amino acid sequence defined in SEQ ID NO:155 or SEQ ID NO:158 via substitution, deletion, or addition of one or two amino acid residues;

(4) as a CDR-H1 sequence, the amino acid sequence defined in SEQ ID NO:100 or SEQ ID NO:106 or an amino acid sequence derived from the amino acid sequence defined in SEQ ID NO:100 or SEQ ID NO:106 via substitution, deletion, or addition of one or two amino acid residues;

as a CDR-H2 sequence, the amino acid sequence as defined in any one of SEQ ID NO:110, SEQ ID NO:112 or SEQ ID NO:117 or an amino acid sequence derived from the amino acid sequence as defined in any one of SEQ ID NO:110, SEQ ID NO:112 or SEQ ID NO:117 via substitution, deletion, or addition of one or two amino acid residues;

as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues;

as a CDR-L1 sequence, the amino acid sequence as defined in any one of SEQ ID NO:131, SEQ ID NO:133 or SEQ ID NO:138 or an amino acid sequence derived from the amino acid sequence as defined in any one of SEQ ID NO:131, SEQ ID NO:133 or SEQ ID NO:138 via substitution, deletion, or addition of one or two amino acid residues;

as a CDR-L2 sequence, the amino acid sequence defined in SEQ ID NO:141 or an amino acid sequence derived from the amino acid sequence defined in SEQ ID NO:141 via substitution, deletion, or addition of one or two amino acid residues; and as a CDR-L3 sequence, the amino acid sequence defined in SEQ ID NO:151 or an amino acid sequence derived from the amino acid sequence defined in SEQ ID NO:151 via substitution, deletion, or addition of one or two amino acid residues;

(5) as a CDR-H1 sequence, the amino acid sequence defined in SEQ ID NO:99 or an amino acid sequence derived from the amino acid sequence defined in SEQ ID NO:99 via substitution, deletion, or addition of one or two amino acid residues;

as a CDR-H2 sequence, the amino acid sequence defined in SEQ ID NO:109 or an amino acid sequence derived from the amino acid sequence defined in SEQ ID NO:109 via substitution, deletion, or addition of one or two amino acid residues;

as a CDR-H3 sequence, the amino acid sequence defined in SEQ ID NO:121 or an amino acid sequence derived from the amino acid sequence defined in SEQ ID NO:121 via substitution, deletion, or addition of one or two amino acid residues;

as a CDR-L1 sequence, the amino acid sequence defined in SEQ ID NO:130 or an amino acid sequence derived from the amino acid sequence defined in SEQ ID NO:130 via substitution, deletion, or addition of one or two amino acid residues;

as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and as a CDR-L3 sequence, the amino acid sequence defined in SEQ ID NO:150 or an amino acid sequence derived from the amino acid sequence defined in SEQ ID NO:150 via substitution, deletion, or addition of one or two amino acid residues;

(6) as a CDR-H1 sequence, the amino acid sequence defined in SEQ ID NO:102 or an amino acid sequence derived from the amino acid sequence defined in SEQ ID NO:102 via substitution, deletion, or addition of one or two amino acid residues;

as a CDR-H2 sequence, the amino acid sequence defined in SEQ ID NO:114 or an amino acid sequence derived from the amino acid sequence defined in SEQ ID NO:114 via substitution, deletion, or addition of one or two amino acid residues;

as a CDR-H3 sequence, the amino acid sequence defined in SEQ ID NO:125 or an amino acid sequence derived from the amino acid sequence defined in SEQ ID NO:125 via substitution, deletion, or addition of one or two amino acid residues;

as a CDR-L1 sequence, the amino acid sequence defined in SEQ ID NO:135 or an amino acid sequence derived from the amino acid sequence defined in SEQ ID NO:135 via substitution, deletion, or addition of one or two amino acid residues;

as a CDR-L2 sequence, the amino acid sequence defined in SEQ ID NO:143 or an amino acid sequence derived from the amino acid sequence defined in SEQ ID NO:143 via substitution, deletion, or addition of one or two amino acid residues; and as a CDR-L3 sequence, the amino acid sequence defined in SEQ ID NO:154 or an amino acid sequence derived from the amino acid sequence defined in SEQ ID NO:154 via substitution, deletion, or addition of one or two amino acid residues; or (7) as a CDR-H1 sequence, the amino acid sequence defined in SEQ ID NO:104 or an amino acid sequence derived from the amino acid sequence defined in SEQ ID NO:104 via substitution, deletion, or addition of one or two amino acid residues;

as a CDR-H2 sequence, the amino acid sequence defined in SEQ ID NO:116 or an amino acid sequence derived from the amino acid sequence defined in SEQ ID NO:116 via substitution, deletion, or addition of one or two amino acid residues;

as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues;

as a CDR-L1 sequence, the amino acid sequence defined in SEQ ID NO:137 or an amino acid sequence derived from the amino acid sequence defined in SEQ ID NO:137 via substitution, deletion, or addition of one or two amino acid residues;

as a CDR-L2 sequence, the amino acid sequence defined in SEQ ID NO:145 or an amino acid sequence derived from the amino acid sequence defined in SEQ ID NO:145 via substitution, deletion, or addition of one or two amino acid residues; and as a CDR-L3 sequence, the amino acid sequence defined in SEQ ID NO:156 or an amino acid sequence derived from the amino acid sequence defined in SEQ ID NO:156 via substitution, deletion, or addition of one or two amino acid residues.

[21] An SPNS2 neutralizing antibody or antibody fragment or a derivative thereof according to any one of [1] to [20], comprising:

(1) as a CDR-H1 sequence, an amino acid sequence having a homology of 80% or more to SEQ ID NO:98;

as a CDR-H2 sequence, an amino acid sequence having a homology of 88% or more to SEQ ID NO:108 or SEQ ID NO:111;

as a CDR-H3 sequence, an amino acid sequence having a homology of 83% or more to SEQ ID NO:120 or SEQ ID NO:123;

as a CDR-L1 sequence, an amino acid sequence having a homology of 84% or more to SEQ ID NO:129 or SEQ ID NO:132;

as a CDR-L2 sequence, an amino acid sequence having a homology of 85% or more to SEQ ID NO:140; and
as a CDR-L3 sequence, an amino acid sequence having a homology of 88% or more to any one of SEQ ID NO:149, SEQ ID NO:152 or SEQ ID NO:157;
(2) as a CDR-H1 sequence, an amino acid sequence having a homology of 80% or more to SEQ ID NO:101;
as a CDR-H2 sequence, an amino acid sequence having a homology of 88% or more to SEQ ID NO:113;
as a CDR-H3 sequence, an amino acid sequence having a homology of 88% or more to SEQ ID NO:124;
as a CDR-L1 sequence, an amino acid sequence having a homology of 84% or more to SEQ ID NO:134;
as a CDR-L2 sequence, an amino acid sequence having a homology of 85% or more to SEQ ID NO:142; and
as a CDR-L3 sequence, an amino acid sequence having a homology of 88% or more to SEQ ID NO:153;
(3) as a CDR-H1 sequence, an amino acid sequence having a homology of 80% or more to SEQ ID NO:103 or SEQ ID NO:105;
as a CDR-H2 sequence, an amino acid sequence having a homology of 89% or more to SEQ ID NO:115 or SEQ ID NO:118;
as a CDR-H3 sequence, an amino acid sequence having a homology of 85% or more to SEQ ID NO:126 or SEQ ID NO:127;
as a CDR-L1 sequence, an amino acid sequence having a homology of 81% or more to SEQ ID NO:136;
as a CDR-L2 sequence, an amino acid sequence having a homology of 85% or more to any one of SEQ ID NO:144, SEQ ID NO:146 or SEQ ID NO:147; and
as a CDR-L3 sequence, an amino acid sequence having a homology of 88% or more to SEQ ID NO:155 or SEQ ID NO:158;
(4) as a CDR-H1 sequence, an amino acid sequence having a homology of 80% or more to SEQ ID NO:100 or SEQ ID NO:106;
as a CDR-H2 sequence, an amino acid sequence having a homology of 88% or more to any one of SEQ ID NO:110, SEQ ID NO:112 or SEQ ID NO:117;
as a CDR-H3 sequence, an amino acid sequence having a homology of 83% or more to SEQ ID NO:122;
as a CDR-L1 sequence, an amino acid sequence having a homology of 81% or more to any one of SEQ ID NO:131, SEQ ID NO:133 or SEQ ID NO:138;
as a CDR-L2 sequence, an amino acid sequence having a homology of 85% or more to SEQ ID NO:141; and
as a CDR-L3 sequence, an amino acid sequence having a homology of 88% or more to SEQ ID NO:151;
(5) as a CDR-H1 sequence, an amino acid sequence having a homology of 80% or more to SEQ ID NO:99;
as a CDR-H2 sequence, an amino acid sequence having a homology of 88% or more to SEQ ID NO:109;
as a CDR-H3 sequence, an amino acid sequence having a homology of 80% or more to SEQ ID NO:121;
as a CDR-L1 sequence, an amino acid sequence having a homology of 84% or more to SEQ ID NO:130;
as a CDR-L2 sequence, an amino acid sequence having a homology of 85% or more to SEQ ID NO:140; and
as a CDR-L3 sequence, an amino acid sequence having a homology of 88% or more to SEQ ID NO:150;
(6) as a CDR-H1 sequence, an amino acid sequence having a homology of 80% or more to SEQ ID NO:102;
as a CDR-H2 sequence, an amino acid sequence having a homology of 88% or more to SEQ ID NO:114;
as a CDR-H3 sequence, an amino acid sequence having a homology of 83% or more to SEQ ID NO:125;
as a CDR-L1 sequence, an amino acid sequence having a homology of 84% or more to SEQ ID NO:135;
as a CDR-L2 sequence, an amino acid sequence having a homology of 85% or more to SEQ ID NO:143; and
as a CDR-L3 sequence, an amino acid sequence having a homology of 88% or more to SEQ ID NO:154; or
(7) as a CDR-H1 sequence, an amino acid sequence having a homology of 80% or more to SEQ ID NO:104;
as a CDR-H2 sequence, an amino acid sequence having a homology of 88% or more to SEQ ID NO:116;
as a CDR-H3 sequence, an amino acid sequence having a homology of 83% or more to SEQ ID NO:122;
as a CDR-L1 sequence, an amino acid sequence having a homology of 81% or more to SEQ ID NO:137;
as a CDR-L2 sequence, an amino acid sequence having a homology of 85% or more to SEQ ID NO:145; and
as a CDR-L3 sequence, an amino acid sequence having a homology of 88% or more to SEQ ID NO:156.
[22] An SPNS2 neutralizing antibody or antibody fragment or a derivative thereof according to any one of [1] to [21], comprising:
(1) as a CDR-H1 sequence, the amino acid sequence defined in SEQ ID NO:98;
as a CDR-H2 sequence, the amino acid sequence defined in SEQ ID NO:108 or the amino acid sequence derived from SEQ ID NO:108 via substitution of the 1st amino acid residue Thr with Ser;
as a CDR-H3 sequence, the amino acid sequence defined in SEQ ID NO:123 or an amino acid sequence derived from SEQ ID NO:123 via substitution of the 4th amino acid residue Ser with Thr;
as a CDR-L1 sequence, the amino acid sequence defined in SEQ ID NO:129 or an amino acid sequence derived from SEQ ID NO:129 via substitution of the 1st amino acid residue Thr with Lys and/or substitution of the 4th amino acid residue Ile with Thr;
as a CDR-L2 sequence, the amino acid sequence defined in SEQ ID NO:140; and
as a CDR-L3 sequence, the amino acid sequence defined in SEQ ID NO:149 or an amino acid sequence derived from SEQ ID NO:149 via substitution of the 5th amino acid residue Ser with Asn and/or substitution of the 7th amino acid residue Ile with Met;
(2) as a CDR-H1 sequence, the amino acid sequence defined in SEQ ID NO:101;
as a CDR-H2 sequence, the amino acid sequence defined in SEQ ID NO:113;
as a CDR-H3 sequence, the amino acid sequence defined in SEQ ID NO:124;
as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;
(3) as a CDR-H1 sequence, the amino acid sequence defined in SEQ ID NO:105 or an amino acid sequence derived from SEQ ID NO:105 via substitution of the 1st amino acid residue Asp with Glu;
as a CDR-H2 sequence, the amino acid sequence defined in SEQ ID NO:115 or an amino acid sequence derived from SEQ ID NO:115 via substitution of the 9th amino acid residue Tyr with Ser and/or substitution of the 17th amino acid residue Val with Ile;

as a CDR-H3 sequence, the amino acid sequence defined in SEQ ID NO:126 or an amino acid sequence derived from SEQ ID NO:126 via substitution of the 9th amino acid residue Ser with Gly;

as a CDR-L1 sequence, the amino acid sequence defined in SEQ ID NO:136;

as a CDR-L2 sequence, the amino acid sequence defined in SEQ ID NO:146 or an amino acid sequence derived from SEQ ID NO:146 via substitution of the 6th amino acid residue Ile with Met and/or substitution of the 7th amino acid residue Ser with Ala; and as a CDR-L3 sequence, the amino acid sequence defined in SEQ ID NO:158 or an amino acid sequence derived from SEQ ID NO:158 via substitution of the 3rd amino acid residue Thr with Ser and/or substitution of the 5th amino acid residue Ser with Asn;

(4) as a CDR-H1 sequence, the amino acid sequence defined in SEQ ID NO:100 or an amino acid sequence derived from SEQ ID NO:100 via substitution of the 1st amino acid residue Arg with Ala;

as a CDR-H2 sequence, the amino acid sequence defined in SEQ ID NO:110 or an amino acid sequence derived from SEQ ID NO:110 via substitution of the 8th amino acid residue Thr with Ser and/or substitution of the 17th amino acid residue Asn with Lys;

as a CDR-H3 sequence, the amino acid sequence defined in SEQ ID NO:122;

as a CDR-L1 sequence, the amino acid sequence defined in SEQ ID NO:133 or an amino acid sequence derived from SEQ ID NO:133 via one or more selected from substitution of the 2nd amino acid residue Ala with Pro, substitution of the 5th amino acid residue Asn with Ser, and substitution of the 8th amino acid Ser with Asn;

as a CDR-L2 sequence, the amino acid sequence defined in SEQ ID NO:141; and as a CDR-L3 sequence, the amino acid sequence defined in SEQ ID NO:151;

(5) as a CDR-H1 sequence, the amino acid sequence defined in SEQ ID NO:99;

as a CDR-H2 sequence, the amino acid sequence defined in SEQ ID NO:109;

as a CDR-H3 sequence, the amino acid sequence defined in SEQ ID NO:121;

as a CDR-L1 sequence, the amino acid sequence defined in SEQ ID NO:130;

as a CDR-L2 sequence, the amino acid sequence defined in SEQ ID NO:140; and as a CDR-L3 sequence, the amino acid sequence defined in SEQ ID NO:150;

(6) as a CDR-H1 sequence, the amino acid sequence defined in SEQ ID NO:102;

as a CDR-H2 sequence, the amino acid sequence defined in SEQ ID NO:114;

as a CDR-H3 sequence, the amino acid sequence defined in SEQ ID NO:125;

as a CDR-L1 sequence, the amino acid sequence defined in SEQ ID NO:135;

as a CDR-L2 sequence, the amino acid sequence defined in SEQ ID NO:143; and as a CDR-L3 sequence, the amino acid sequence defined in SEQ ID NO:154; or (7) as a CDR-H1 sequence, the amino acid sequence defined in SEQ ID NO:104;

as a CDR-H2 sequence, the amino acid sequence defined in SEQ ID NO:116;

as a CDR-H3 sequence, the amino acid sequence defined in SEQ ID NO:122;

as a CDR-L1 sequence, the amino acid sequence defined in SEQ ID NO:137;

as a CDR-L2 sequence, the amino acid sequence defined in SEQ ID NO:145; and as a CDR-L3 sequence, the amino acid sequence defined in SEQ ID NO:156.

[23] An SPNS2 neutralizing antibody or antibody fragment or a derivative thereof according to any one of [1] to [22], comprising:

(1) as a CDR-H1 sequence, the amino acid sequence defined in SEQ ID NO:98;

as a CDR-H2 sequence, the amino acid sequence defined in SEQ ID NO:108;

as a CDR-H3 sequence, the amino acid sequence defined in SEQ ID NO:120;

as a CDR-L1 sequence, the amino acid sequence defined in SEQ ID NO:129;

as a CDR-L2 sequence, the amino acid sequence defined in SEQ ID NO:140; and as a CDR-L3 sequence, the amino acid sequence defined in SEQ ID NO:149;

(2) as a CDR-H1 sequence, the amino acid sequence defined in SEQ ID NO:99;

as a CDR-H2 sequence, the amino acid sequence defined in SEQ ID NO:109;

as a CDR-H3 sequence, the amino acid sequence defined in SEQ ID NO:121;

as a CDR-L1 sequence, the amino acid sequence defined in SEQ ID NO:130;

as a CDR-L2 sequence, the amino acid sequence defined in SEQ ID NO:140; and as a CDR-L3 sequence, the amino acid sequence defined in SEQ ID NO:150;

(3) as a CDR-H1 sequence, the amino acid sequence defined in SEQ ID NO:100;

as a CDR-H2 sequence, the amino acid sequence defined in SEQ ID NO:110;

as a CDR-H3 sequence, the amino acid sequence defined in SEQ ID NO:122;

as a CDR-L1 sequence, the amino acid sequence defined in SEQ ID NO:131;

as a CDR-L2 sequence, the amino acid sequence defined in SEQ ID NO:141; and as a CDR-L3 sequence, the amino acid sequence defined in SEQ ID NO:151;

(4) as a CDR-H1 sequence, the amino acid sequence defined in SEQ ID NO:98;

as a CDR-H2 sequence, the amino acid sequence defined in SEQ ID NO:111;

as a CDR-H3 sequence, the amino acid sequence defined in SEQ ID NO:123;

as a CDR-L1 sequence, the amino acid sequence defined in SEQ ID NO:132;

as a CDR-L2 sequence, the amino acid sequence defined in SEQ ID NO:140; and as a CDR-L3 sequence, the amino acid sequence defined in SEQ ID NO:152;

(5) as a CDR-H1 sequence, the amino acid sequence defined in SEQ ID NO:98;

as a CDR-H2 sequence, the amino acid sequence defined in SEQ ID NO:108;

as a CDR-H3 sequence, the amino acid sequence defined in SEQ ID NO:123;

as a CDR-L1 sequence, the amino acid sequence defined in SEQ ID NO:129;

as a CDR-L2 sequence, the amino acid sequence defined in SEQ ID NO:140; and as a CDR-L3 sequence, the amino acid sequence defined in SEQ ID NO:149;
(6) as a CDR-H1 sequence, the amino acid sequence defined in SEQ ID NO:100;
as a CDR-H2 sequence, the amino acid sequence defined in SEQ ID NO:112;
as a CDR-H3 sequence, the amino acid sequence defined in SEQ ID NO:122;
as a CDR-L1 sequence, the amino acid sequence defined in SEQ ID NO:133;
as a CDR-L2 sequence, the amino acid sequence defined in SEQ ID NO:141; and
as a CDR-L3 sequence, the amino acid sequence defined in SEQ ID NO:151;
(7) as a CDR-H1 sequence, the amino acid sequence defined in SEQ ID NO:101;
as a CDR-H2 sequence, the amino acid sequence defined in SEQ ID NO:113;
as a CDR-H3 sequence, the amino acid sequence defined in SEQ ID NO:124;
as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;
(8) as a CDR-H1 sequence, the amino acid sequence defined in SEQ ID NO:102;
as a CDR-H2 sequence, the amino acid sequence defined in SEQ ID NO:114;
as a CDR-H3 sequence, the amino acid sequence defined in SEQ ID NO:125;
as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;
(9) as a CDR-H1 sequence, the amino acid sequence defined in SEQ ID NO:103;
as a CDR-H2 sequence, the amino acid sequence defined in SEQ ID NO:115;
as a CDR-H3 sequence, the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:144; and
as a CDR-L3 sequence, the amino acid sequence defined in SEQ ID NO:155;
(10) as a CDR-H1 sequence, the amino acid sequence defined in SEQ ID NO:104;
as a CDR-H2 sequence, the amino acid sequence defined in SEQ ID NO:116;
as a CDR-H3 sequence, the amino acid sequence defined in SEQ ID NO:122;
as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO: 156;
(11) as a CDR-H1 sequence, the amino acid sequence defined in SEQ ID NO:98;
as a CDR-H2 sequence the amino acid sequence defined in SEQ ID NO:108;
as a CDR-H3 sequence the amino acid sequence defined in SEQ ID NO:123;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:157;
(12) as a CDR-H1 sequence, the amino acid sequence defined in SEQ ID NO:105;
as a CDR-H2 sequence the amino acid sequence defined in SEQ ID NO:115;
as a CDR-H3 sequence the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:146; and
as a CDR-L3 sequence, the amino acid sequence defined in SEQ ID NO:158;
(13) as a CDR-H1 sequence, the amino acid sequence defined in SEQ ID NO:106;
as a CDR-H2 sequence the amino acid sequence defined in SEQ ID NO:117;
as a CDR-H3 sequence the amino acid sequence defined in SEQ ID NO:122;
as a CDR-L1 sequence, the amino acid sequence defined in SEQ ID NO:138;
as a CDR-L2 sequence, the amino acid sequence defined in SEQ ID NO:141; and
as a CDR-L3 sequence, the amino acid sequence defined in SEQ ID NO:151; or
(14) as a CDR-H1 sequence, the amino acid sequence defined in SEQ ID NO:105;
as a CDR-H2 sequence the amino acid sequence defined in SEQ ID NO:118;
as a CDR-H3 sequence the amino acid sequence defined in SEQ ID NO:127;
as a CDR-L1 sequence, the amino acid sequence defined in SEQ ID NO:136;
as a CDR-L2 sequence, the amino acid sequence defined in SEQ ID NO:147; and
as a CDR-L3 sequence, the amino acid sequence defined in SEQ ID NO:158.

[24] An SPNS2 neutralizing antibody or antibody fragment or a derivative thereof according to any one of [1] to [23], further comprising a framework sequence of an immunoglobulin.

[25] An SPNS2 neutralizing antibody or antibody fragment or a derivative thereof according to [24], wherein the framework sequence of an immunoglobulin is a framework sequence of each class of an immunoglobulin of a human or a non-human animal comprising a monkey, a mouse or a rat.

[26] An SPNS2 neutralizing antibody or antibody fragment or a derivative thereof according to any one of [1] to [15] and [20] to [25], comprising, as a heavy chain variable region, an amino acid sequence having a homology of 90% or more to a sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62.

[27] An SPNS2 neutralizing antibody or antibody fragment or a derivative thereof according to any one of [1] to [15] and [20] to [26], comprising, as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62, or an amino acid sequence derived via substitution, deletion, or addition of one or more amino acid residues from an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62.

[28] An SPNS2 neutralizing antibody or antibody fragment or a derivative thereof according to any one of [1] to [15] and [20] to [27], comprising, as a heavy chain variable region,
(1) the amino acid sequence defined in SEQ ID NO:42 or an amino acid sequence derived from SEQ ID NO:42 via one or more substitutions selected from the group consisting of: substitution of the 1st (Kabat No.: H1) amino acid residue Glu with Ala, substitution of the 6th (Kabat No.: H6) amino acid residue Gly with Glu, substitution of the 23rd (Kabat No.: H23) amino acid residue Glu with Ala, substitution of the 43rd (Kabat No.: H43) amino acid residue Lys with Arg, substitution of the 50th (Kabat No.: H50) amino acid residue Thr with Ser, substitution of the 75th (Kabat No.: H74) amino acid residue Ala with Thr, substitution of the 76th (Kabat No.: H75) amino acid residue Arg with Lys, substitution of the 78th (Kabat No.: H77) amino acid residue Thr with Ile, substitution of the 80th (Kabat No.: H79) amino acid residue Ser with Tyr, substitution of the 97th (Kabat No.: H93) amino acid residue Ala with Thr, and substitution of the 102nd (Kabat No.: H98) amino acid residue Ser with Thr;
(2) the amino acid sequence defined in SEQ ID NO:46 or an amino acid sequence derived from SEQ ID NO:46 via substitution of the 82nd (Kabat No.: H81) amino acid residue Gln with Lys;
(3) the amino acid sequence defined in SEQ ID NO:58 or an amino acid sequence derived from SEQ ID NO:58 via one or more substitutions selected from the group consisting of: substitution of the 13th (Kabat No.: H13) amino acid residue Gln with Arg, substitution of the 23rd (Kabat No.: H23) amino acid residue Ala with Ser, substitution of the 31st (Kabat No.: H31) amino acid residue Asp with Glu, 49th (Kabat No.: H49) amino acid residue Ala with Gly, substitution of the 58th (Kabat No.: H55) amino acid residue Tyr with Ser, substitution of the 66th (Kabat No.: H63) amino acid residue Val with Ile, substitution of the 79th (Kabat No.: H76) amino acid residue Arg with Ser, substitution of the 86th (Kabat No.: H82A) amino acid residue Phe with Tyr or Asn, substitution of the 100th (Kabat No.: H94) amino acid residue Ser with Arg, substitution of the 109th (Kabat No.: H100C) amino acid residue Ser with Gly, substitution of the and 117th (Kabat No.: H105) amino acid residue His with Gln;
(4) the amino acid sequence defined in SEQ ID NO:44 or an amino acid sequence derived from SEQ ID NO:44 via one or more substitutions selected from the group consisting of: 3rd (Kabat No.: H3) amino acid residue Gln with His, substitution of the 10th (Kabat No.: H10) amino acid residue Glu with Ala or Gly, substitution of the 16th (Kabat No.: H16) amino acid residue Thr with Ala, substitution of the 19th (Kabat No.: H19) amino acid residue Lys with Arg, substitution of the 24th (Kabat No.: H24) amino acid residue Val with Ile, substitution of the 30th (Kabat No.: H30) amino acid residue Thr with Ser, substitution of the 31st (Kabat No.: H31) amino acid residue Arg with Ala, substitution of the 57th (Kabat No.: H56) amino acid residue Thr with Ser, substitution of the 66th (Kabat No.: H65) amino acid residue Lys with Asn, substitution of the 67th (Kabat No.: H66) amino acid residue Lys with Arg, substitution of the 74th (Kabat No.: H73) amino acid residue Ala with Val, substitution of the 77th (Kabat No.: H76) amino acid residue Asn with Asp or Ser, substitution of the 80th (Kabat No.: H79) amino acid residue Tyr with Ser, substitution of the 83rd (Kabat No.: H82) amino acid residue Phe with Leu, substitution of the 85th (Kabat No.: H82B) amino acid residue Gly with Ser, substitution of the 89th (Kabat No.: H85) amino acid residue Glu with Asp, substitution of the and 91st (Kabat No.: H87) amino acid residue Thr with Ser; or
(5) an amino acid sequence selected from SEQ ID NO:36, SEQ ID NO:48, and SEQ ID NO:52.

[29] An SPNS2 neutralizing antibody or antibody fragment or a derivative thereof according to any one of [1] to [15] and [20] to [28], comprising, as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62.

[30] An SPNS2 neutralizing antibody or antibody fragment or a derivative thereof according to any one of [1] to [11] and [16] to [25], comprising, as a light chain variable region, an amino acid sequence having a homology of 90% or more to a sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

[31] An SPNS2 neutralizing antibody or antibody fragment or a derivative thereof according to any one of [1] to [11], [16] to [25], and [30], comprising, as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, or an amino acid sequence derived via substitution, deletion, or addition of one or more amino acid residues from an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

[32] An SPNS2 neutralizing antibody or antibody fragment or a derivative thereof according to any one of [1] to [11], [16] to [25], [30], and [31], comprising, as a light chain variable region,
(1) the amino acid sequence defined in SEQ ID NO:88 or an amino acid sequence derived from SEQ ID NO:88 via one or more substitutions selected from the group consisting of: the 23rd (Kabat No.: L24) amino acid residue Thr with Lys, substitution of the 26th (Kabat No.: L27) amino acid residue Ile with Thr, substitution of the 38th (Kabat No.: L37) amino acid residue Lys with Gln, substitution of the 48th (Kabat No.: L47) amino acid residue Met with Leu, substitution of the 80th (Kabat No.: L77) amino acid residue Asn with Ser, substitution of the 86th (Kabat No.: L83) amino acid residue Glu with Gly, substitution of the 96th (Kabat No.: L93) amino acid residue Ser with Asn, substitution of the 98th (Kabat No.: L95) amino acid residue Met with Ile, substitution of the 102nd (Kabat No.: L99) amino acid residue Gly with Ala, substitution of the and 106th (Kabat No.: L103) amino acid residue Lys with Thr or Gln;

(2) the amino acid sequence defined in SEQ ID NO:78 or an amino acid sequence derived from SEQ ID NO:78 via substitution of the 48th (Kabat No.: L47) amino acid residue Leu with Met and/or substitution of the 106th (Kabat No.: L103) amino acid residue Lys with Thr;
(3) the amino acid sequence defined in SEQ ID NO:90 or an amino acid sequence derived from SEQ ID NO:90 via one or more substitutions selected from the group consisting of: the 9th (Kabat No.: L9) amino acid residue Ala with Pro, substitution of the 39th (Kabat No.: L39) amino acid residue Lys with Arg, substitution of the 42nd (Kabat No.: L42) amino acid residue Gly with Glu, substitution of the 55th (Kabat No.: L55) amino acid residue Ile with Met, substitution of the 56th (Kabat No.: L56) amino acid residue Ser with Ala, substitution of the 72nd (Kabat No.: L72) amino acid residue Thr with Ile, substitution of the 74th (Kabat No.: L74) amino acid residue Arg with Ser, substitution of the 91st (Kabat No.: L91) amino acid residue Thr with Ser, substitution of the 93rd (Kabat No.: L93) amino acid residue Ser with Asn, substitution of the 100th (Kabat No.: L100) amino acid residue Ser with Pro, substitution of the 103rd (Kabat No.: L103) amino acid residue Arg with Lys, substitution of the and 106th (Kabat No.: L106) amino acid residue Ile with Val;
(4) the amino acid sequence defined in SEQ ID NO:76 or an amino acid sequence derived from SEQ ID NO:76 via one or more substitutions selected from the group consisting of: the 13th (Kabat No.: L13) amino acid residue Thr with Ala, substitution of the 22nd (Kabat No.: L22) amino acid residue Arg with Ser, substitution of the 25th (Kabat No.: L25) amino acid residue Ala with Pro, substitution of the 28th (Kabat No.: L28) amino acid residue Asn with Ser, substitution of the 31st (Kabat No.: L31) amino acid residue Ser with Asn, substitution of the 69th (Kabat No.: L69) amino acid residue Thr with Ser, substitution of the 79th (Kabat No.: L79) amino acid residue Gln with Arg, substitution of the and 80th (Kabat No.: L80) amino acid residue Pro with Ala,
(5) an amino acid sequence selected from SEQ ID NO:68, SEQ ID NO:80, or SEQ ID NO:84.
[33] An SPNS2 neutralizing antibody or antibody fragment or a derivative thereof according to any one of [1] to [11], [16] to [25], and [30] to [32], comprising, as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.
[34] An SPNS2 neutralizing antibody or antibody fragment or a derivative thereof according to any one of [1] to [33], comprising:
as a heavy chain variable region, an amino acid sequence having a homology of 90% or more to a sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62; and
as a light chain variable region, an amino acid sequence having a homology of 90% or more to a sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

[35] An SPNS2 neutralizing antibody or antibody fragment or a derivative thereof according to any one of [1] to [34], comprising:
as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62, or an amino acid sequence derived via substitution, deletion, or addition of one or more amino acid residues from an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62; and
as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, or an amino acid sequence derived via substitution, deletion, or addition of one or more amino acid residues from an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.
[36] An SPNS2 neutralizing antibody or antibody fragment or a derivative thereof according to any one of [1] to [35], comprising:
(1) as a heavy chain variable region, the amino acid sequence defined in SEQ ID NO:42 or an amino acid sequence derived from SEQ ID NO:42 via one or more substitutions selected from the group consisting of: substitution of the 1st (Kabat No.: H1) amino acid residue Glu with Ala, substitution of the 6th (Kabat No.: H6) amino acid residue Gly with Glu, substitution of the 23rd (Kabat No.: H23) amino acid residue Glu with Ala, substitution of the 43rd (Kabat No.: H43) amino acid residue Lys with Arg, substitution of the 50th (Kabat No.: H50) amino acid residue Thr with Ser, substitution of the 75th (Kabat No.: H74) amino acid residue Ala with Thr, substitution of the 76th (Kabat No.: H75) amino acid residue Arg with Lys, substitution of the 78th (Kabat No.: H77) amino acid residue Thr with Ile, substitution of the 80th (Kabat No.: H79) amino acid residue Ser with Tyr, substitution of the 97th (Kabat No.: H93) amino acid residue Ala with Thr, and 102nd (Kabat No.: H98) amino acid residue Ser with Thr; and
as a light chain variable region, the amino acid sequence defined in SEQ ID NO:88 or an amino acid sequence derived from SEQ ID NO:88 via one or more substitutions selected from the group consisting of: substitution of the 23rd (Kabat No.: L24) amino acid residue Thr with Lys, substitution of the 26th (Kabat No.: L27) amino acid residue Ile with Thr, substitution of the 38th (Kabat No.: L37) amino acid residue Lys with Gln, substitution of the 48th (Kabat No.: L47) amino acid residue Met with Leu, substitution of the 80th (Kabat No.: L77) amino acid residue Asn with Ser, substitution of the 86th (Kabat No.: L83) amino acid residue Glu with Gly, substitution of the 96th (Kabat No.: L93) amino acid residue Ser with Asn, substitution of the 98th (Kabat No.: L95) amino acid residue Met with Ile, substitution of the 102nd (Kabat No.: L99) amino acid residue Gly with Ala, substitution of the and 106th (Kabat No.: L103) amino acid residue Lys with Thr or Gln;

(2) as a heavy chain variable region, the amino acid sequence defined in SEQ ID NO:46 or an amino acid sequence derived from SEQ ID NO:46 via substitution of the 82nd (Kabat No.: H81) amino acid residue Gln with Lys; and
as a light chain variable region, the amino acid sequence defined in SEQ ID NO:78 or an amino acid sequence derived from SEQ ID NO:78 via substitution of the 48th (Kabat No.: L47) amino acid residue Leu with Met and/or substitution of the 106th (Kabat No.: L103) amino acid residue Lys with Thr;
(3) as a heavy chain variable region, the amino acid sequence defined in SEQ ID NO:58 or an amino acid sequence derived from SEQ ID NO:58 via one or more substitutions selected from the group consisting of: substitution of the 13th (Kabat No.: H13) amino acid residue Gln with Arg, substitution of the 23rd (Kabat No.: H23) amino acid residue Ala with Ser, substitution of the 31st (Kabat No.: H31) amino acid residue Asp with Glu, substitution of the 49th (Kabat No.: H49) amino acid residue Ala with Gly, substitution of the 58th (Kabat No.: H55) amino acid residue Tyr with Ser, substitution of the 66th (Kabat No.: H63) amino acid residue Val with Ile, substitution of the 79th (Kabat No.: H76) amino acid residue Arg with Ser, substitution of the 86th (Kabat No.: H82A) amino acid residue Phe with Tyr or Asn, substitution of the 100th (Kabat No.: H94) amino acid residue Ser with Arg, substitution of the 109th (Kabat No.: H100C) amino acid residue Ser with Gly, substitution of the and 117th (Kabat No.: H105) amino acid residue His with Gln; and
as a light chain variable region, the amino acid sequence defined in SEQ ID NO:90 or an amino acid sequence derived from SEQ ID NO:90 via one or more substitutions selected from the group consisting of: substitution of the 9th (Kabat No.: L9) amino acid residue Ala with Pro, substitution of the 39th (Kabat No.: L39) amino acid residue Lys with Arg, substitution of the 42nd (Kabat No.: L42) amino acid residue Gly with Glu, substitution of the 55th (Kabat No.: L55) amino acid residue Ile with Met, substitution of the 56th (Kabat No.: L56) amino acid residue Ser with Ala, substitution of the 72nd (Kabat No.: L72) amino acid residue Thr with Ile, substitution of the 74th (Kabat No.: L74) amino acid residue Arg with Ser, substitution of the 91st (Kabat No.: L91) amino acid residue Thr with Ser, substitution of the 93rd (Kabat No.: L93) amino acid residue Ser with Asn, substitution of the 100th (Kabat No.: L100) amino acid residue Ser with Pro, substitution of the 103rd (Kabat No.: L103) amino acid residue Arg with Lys, substitution of the and 106th (Kabat No.: L106) amino acid residue Ile with Val;
(4) as a heavy chain variable region, the amino acid sequence defined in SEQ ID NO:44 or an amino acid sequence derived from SEQ ID NO:44 via one or more substitutions selected from the group consisting of: substitution of the 3rd (Kabat No.: H3) amino acid residue Gln with His, substitution of the 10th (Kabat No.: H10) amino acid residue Glu with Ala or Gly, substitution of the 16th (Kabat No.: H16) amino acid residue Thr with Ala, substitution of the 19th (Kabat No.: H19) amino acid residue Lys with Arg, substitution of the 24th (Kabat No.: H24) amino acid residue Val with Ile, substitution of the 30th (Kabat No.: H30) amino acid residue Thr with Ser, substitution of the 31st (Kabat No.: H31) amino acid residue Arg with Ala, substitution of the 57th (Kabat No.: H56) amino acid residue Thr with Ser, substitution of the 66th (Kabat No.: H65) amino acid residue Lys with Asn, substitution of the 67th (Kabat No.: H66) amino acid residue Lys with Arg, substitution of the 74th (Kabat No.: H73) amino acid residue Ala with Val, substitution of the 77th (Kabat No.: H76) amino acid residue Asn with Asp or Ser, substitution of the 80th (Kabat No.: H79) amino acid residue Tyr with Ser, substitution of the 83rd (Kabat No.: H82) amino acid residue Phe with Leu, substitution of the 85th (Kabat No.: H82B) amino acid residue Gly with Ser, substitution of the 89th (Kabat No.: H85) amino acid residue Glu with Asp, substitution of the and 91st (Kabat No.: H87) amino acid residue Thr with Ser; and
as a light chain variable region, the amino acid sequence defined in SEQ ID NO:76 or an amino acid sequence derived from SEQ ID NO:76 via one or more substitutions selected from the group consisting of: substitution of the 13th (Kabat No.: L13) amino acid residue Thr with Ala, substitution of the 22nd (Kabat No.: L22) amino acid residue Arg with Ser, substitution of the 25th (Kabat No.: L25) amino acid residue Ala with Pro, substitution of the 28th (Kabat No.: L28) amino acid residue Asn with Ser, substitution of the 31st (Kabat No.: L31) amino acid residue Ser with Asn, substitution of the 69th (Kabat No.: L69) amino acid residue Thr with Ser, substitution of the 79th (Kabat No.: L79) amino acid residue Gln with Arg, substitution of the and 80th (Kabat No.: L80) amino acid residue Pro with Ala; or
(5) as a heavy chain variable region, an amino acid sequence selected from SEQ ID NO:36, SEQ ID NO:48, or SEQ ID NO:52; and
as a light chain variable region, an amino acid sequence selected from SEQ ID NO:68, SEQ ID NO:80, and SEQ ID NO:84.

[37] An SPNS2 neutralizing antibody or antibody fragment or a derivative thereof according to any one of [1] to [36], comprising:
as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62,
as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

[38] An SPNS2 neutralizing antibody or antibody fragment or a derivative thereof according to any one of [1] to [37], which competitively binds to SPNS2 with an SPNS2 neutralizing antibody or antibody fragment or a derivative thereof comprising:
(1) as a heavy chain variable region, the amino acid sequence defined in SEQ ID NO:34 and, as a light chain variable region, the amino acid sequence defined in SEQ ID NO:66;
(2) as a heavy chain variable region, the amino acid sequence defined in SEQ ID NO:36 and, as a light chain variable region, the amino acid sequence defined in SEQ ID NO:68;
(3) as a heavy chain variable region, the amino acid sequence defined in SEQ ID NO:38 and, as a light chain variable region, the amino acid sequence defined in SEQ ID NO:70;
(4) as a heavy chain variable region, the amino acid sequence defined in SEQ ID NO:40 and, as a light chain variable region, the amino acid sequence defined in SEQ ID NO:72;

(5) as a heavy chain variable region, the amino acid sequence defined in SEQ ID NO:42 and, as a light chain variable region, the amino acid sequence defined in SEQ ID NO:74;
(6) as a heavy chain variable region, the amino acid sequence defined in SEQ ID NO:44 and, as a light chain variable region, the amino acid sequence defined in SEQ ID NO:76;
(7) as a heavy chain variable region, the amino acid sequence defined in SEQ ID NO:46 and, as a light chain variable region, the amino acid sequence defined in SEQ ID NO:78;
(8) as a heavy chain variable region, the amino acid sequence defined in SEQ ID NO:48 and, as a light chain variable region, the amino acid sequence defined in SEQ ID NO:80;
(9) as a heavy chain variable region, the amino acid sequence defined in SEQ ID NO:50 and, as a light chain variable region, the amino acid sequence defined in SEQ ID NO:82;
(10) as a heavy chain variable region, the amino acid sequence defined in SEQ ID NO:52 and, as a light chain variable region, the amino acid sequence defined in SEQ ID NO:84;
(11) as a heavy chain variable region, the amino acid sequence defined in SEQ ID NO:54 and, as a light chain variable region, the amino acid sequence defined in SEQ ID NO:86;
(12) as a heavy chain variable region, the amino acid sequence defined in SEQ ID NO:56 and, as a light chain variable region, the amino acid sequence defined in SEQ ID NO:88;
(13) as a heavy chain variable region, the amino acid sequence defined in SEQ ID NO:58 and, as a light chain variable region, the amino acid sequence defined in SEQ ID NO:90;
(14) as a heavy chain variable region, the amino acid sequence defined in SEQ ID NO:60 and, as a light chain variable region, the amino acid sequence defined in SEQ ID NO:92; or
(15) as a heavy chain variable region, the amino acid sequence defined in SEQ ID NO:62 and, as a light chain variable region, the amino acid sequence defined in SEQ ID NO:94.

[39] An SPNS2 neutralizing antibody or antibody fragment or a derivative thereof according to any one of [1] to [38], comprising:
(1) as a heavy chain variable region, the amino acid sequence defined in SEQ ID NO:34 and, as a light chain variable region, the amino acid sequence defined in SEQ ID NO:66;
(2) as a heavy chain variable region, the amino acid sequence defined in SEQ ID NO:36 and, as a light chain variable region, the amino acid sequence defined in SEQ ID NO:68;
(3) as a heavy chain variable region, the amino acid sequence defined in SEQ ID NO:38 and, as a light chain variable region, the amino acid sequence defined in SEQ ID NO:70;
(4) as a heavy chain variable region, the amino acid sequence defined in SEQ ID NO:40 and, as a light chain variable region, the amino acid sequence defined in SEQ ID NO:72;
(5) as a heavy chain variable region, the amino acid sequence defined in SEQ ID NO:42 and, as a light chain variable region, the amino acid sequence defined in SEQ ID NO:74;
(6) as a heavy chain variable region, the amino acid sequence defined in SEQ ID NO:44 and, as a light chain variable region, the amino acid sequence defined in SEQ ID NO:76;
(7) as a heavy chain variable region, the amino acid sequence defined in SEQ ID NO:46 and, as a light chain variable region, the amino acid sequence defined in SEQ ID NO:78;
(8) as a heavy chain variable region, the amino acid sequence defined in SEQ ID NO:48 and, as a light chain variable region, the amino acid sequence defined in SEQ ID NO:80;
(9) as a heavy chain variable region, the amino acid sequence defined in SEQ ID NO:50 and, as a light chain variable region, the amino acid sequence defined in SEQ ID NO:82;
(10) as a heavy chain variable region, the amino acid sequence defined in SEQ ID NO:52 and, as a light chain variable region, the amino acid sequence defined in SEQ ID NO:84;
(11) as a heavy chain variable region, the amino acid sequence defined in SEQ ID NO:54 and, as a light chain variable region, the amino acid sequence defined in SEQ ID NO:86;
(12) as a heavy chain variable region, the amino acid sequence defined in SEQ ID NO:56 and, as a light chain variable region, the amino acid sequence defined in SEQ ID NO:88;
(13) as a heavy chain variable region, the amino acid sequence defined in SEQ ID NO:58 and, as a light chain variable region, the amino acid sequence defined in SEQ ID NO:90;
(14) as a heavy chain variable region, the amino acid sequence defined in SEQ ID NO:60 and, as a light chain variable region, the amino acid sequence defined in SEQ ID NO:92; or
(15) as a heavy chain variable region, the amino acid sequence defined in SEQ ID NO:62 and, as a light chain variable region, the amino acid sequence defined in SEQ ID NO:94.

[40] An SPNS2 neutralizing antibody or antibody fragment or a derivative thereof according to any one of [1] to [39], further comprising, as a constant region, a constant region of each class of an immunoglobulin of a human or a non-human animal comprising a mouse, a rat, or a monkey.

[41] A nucleic acid molecule comprising a polynucleotide sequence encoding an SPNS2 neutralizing antibody or antibody fragment or a derivative thereof according to any one of [1] to [40].

[42] A cloning vector or expression vector comprising at least one nucleic acid molecule according to [41].

[43] A recombinant cell prepared via introduction of a vector according to [42] into a host cell.

[44] A process of producing an SPNS2 neutralizing antibody or antibody fragment or a derivative thereof according to any one of [1] to [40], comprising: culturing a recombinant cell according to [43]; and purifying the resultant SPNS2 neutralizing antibody or antibody fragment or a derivative thereof.

[45] A pharmaceutical composition comprising an SPNS2 neutralizing antibody or antibody fragment or a derivative thereof according to any one of [1] to [40], a nucleic acid molecule according to [41], a vector according to [42], or a recombinant cell according to [43].

[46] A pharmaceutical composition according to [45], for use in the treatment, suppression, or prevention of cancer or autoimmune disease of a vertebrate.

[47] A pharmaceutical composition according to [45] or [46], further comprising a pharmaceutically acceptable diluent and/or carrier and/or other additive.

[48] A pharmaceutical composition according to any one of [45] to [47], further comprising an additional active ingredient other than the SPNS2 neutralizing antibody or antibody fragment or a derivative thereof according to any one of [1] to [40], the nucleic acid molecule according to [41], the vector according to [42], or the recombinant cell according to [43].

[49] A pharmaceutical composition according to [48], wherein the active ingredient is selected from the group consisting of azelastine, oxatomide, mequitazine, fexofenadine, epinastine, ebastine, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorcyclizine, cyproheptadine, mesalazine, interferon beta 1b, interferon beta 1a, fingolimod hydrochloride, natalizumab, glatiramer acetate, dimethyl fumarate, and apremilast.

[50] A pharmaceutical composition according to [48], wherein the active ingredient is selected from the group consisting of corticosteroid, antiemetic, ondansetron hydrochloride, granisetron hydrochloride, metroclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesic, ibuprofen, naproxen, choline magnesium trisalicylate, oxycodone hydrochloride, anti-angiogenics, antithrombotics, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative, farnesyl protein transferase inhibitor, $\alpha v\beta 3$ inhibitor, $\alpha v\beta 5$ inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

[51] An SPNS2 neutralizing antibody or antibody fragment or a derivative thereof according to any one of [1] to [40], which is a Fab, scFv, Diabody or bispecific antibody, or a derivative thereof.

Advantageous Effects of Invention

The SPNS2 neutralizing antibody or antibody fragment or a derivative thereof according to the present invention specifically binds to SPNS2 of a vertebrate and thereby exhibits the effects of improving autoimmune diseases and anti-cancer effects, etc.

BRIEF DESCRIPTION OF DRAWINGS

FIG. 2-1 shows an alignment of the amino acid sequences of SPNS2s derived from guinea pig (*Cavia porcellus*; SEQ ID NO: 32), mouse (*Mus musculus*; SEQ ID NO: 19), rat (*Rattus norvegicus*; SEQ ID NO: 33), monkey (*Macaca mulatta*; SEQ ID NO: 31) and human (*Homo sapiens*; SEQ ID NO: 1).

FIG. 2-2 shows an alignment of the amino acid sequences of SPNS2s derived from guinea pig (*Cavia porcellus*; SEQ ID NO: 32), mouse (*Mus musculus*; SEQ ID NO: 19), rat (*Rattus norvegicus*; SEQ ID NO: 33), monkey (*Macaca mulatta*; SEQ ID NO: 31) and human (*Homo sapiens*; SEQ ID NO: 1).

FIG. 9-1 is a table showing homologies of the amino acid sequences of heavy chain variable regions between 15 clones of SPNS2 neutralizing antibodies.

FIG. 9-2 is a table showing homologies of the amino acid sequences of light chain variable regions between 15 clones of SPNS2 neutralizing antibodies.

FIG. 10-1 illustrates the results of phylogenetic tree analysis the amino acid sequences of heavy chain variable regions between SPNS2 neutralizing antibodies.

FIG. 10-2 illustrates the results of phylogenetic tree analysis the amino acid sequences of light chain variable regions between SPNS2 neutralizing antibodies.

FIG. 11-1-1 shows an alignment of the amino acid sequences of heavy chain variable regions derived from one of the groups into which the 15 clones of SPNS2 neutralizing antibodies are categorized, with reference to Kabat Numbers.

FIG. 11-1-2 shows an alignment of the amino acid sequences of light chain variable regions derived from one of the groups into which the 15 clones of SPNS2 neutralizing antibodies are categorized, with reference to Kabat Numbers.

FIG. 11-2-1 shows an alignment of the amino acid sequences of heavy chain variable regions derived from one of the groups into which the 15 clones of SPNS2 neutralizing antibodies are categorized, with reference to Kabat Numbers.

FIG. 11-2-2 shows an alignment of the amino acid sequences of light chain variable regions derived from one of the groups into which the 15 clones of SPNS2 neutralizing antibodies are categorized, with reference to Kabat Numbers.

FIG. 11-3-1 shows an alignment of the amino acid sequences of heavy chain variable regions derived from one of the groups into which the 15 clones of SPNS2 neutralizing antibodies are categorized, with reference to Kabat Numbers.

FIG. 11-3-2 shows an alignment of the amino acid sequences of light chain variable regions derived from one of the groups into which the 15 clones of SPNS2 neutralizing antibodies are categorized, with reference to Kabat Numbers.

FIG. 11-4-1 shows an alignment of the amino acid sequences of heavy chain variable regions derived from one of the groups into which the 15 clones of SPNS2 neutralizing antibodies are categorized, with reference to Kabat Numbers.

FIG. 11-4-2 shows an alignment of the amino acid sequences of light chain variable regions derived from one of the groups into which the 15 clones of SPNS2 neutralizing antibodies are categorized, with reference to Kabat Numbers.

FIG. 11-5-1 shows an alignment of the amino acid sequences of heavy chain variable regions derived from one of the groups into which the 15 clones of SPNS2 neutralizing antibodies are categorized, with reference to Kabat Numbers.

FIG. 11-5-2 shows an alignment of the amino acid sequences of light chain variable regions derived from one of the groups into which the 15 clones of SPNS2 neutralizing antibodies are categorized, with reference to Kabat Numbers.

DESCRIPTION OF EMBODIMENTS

Figure 1:
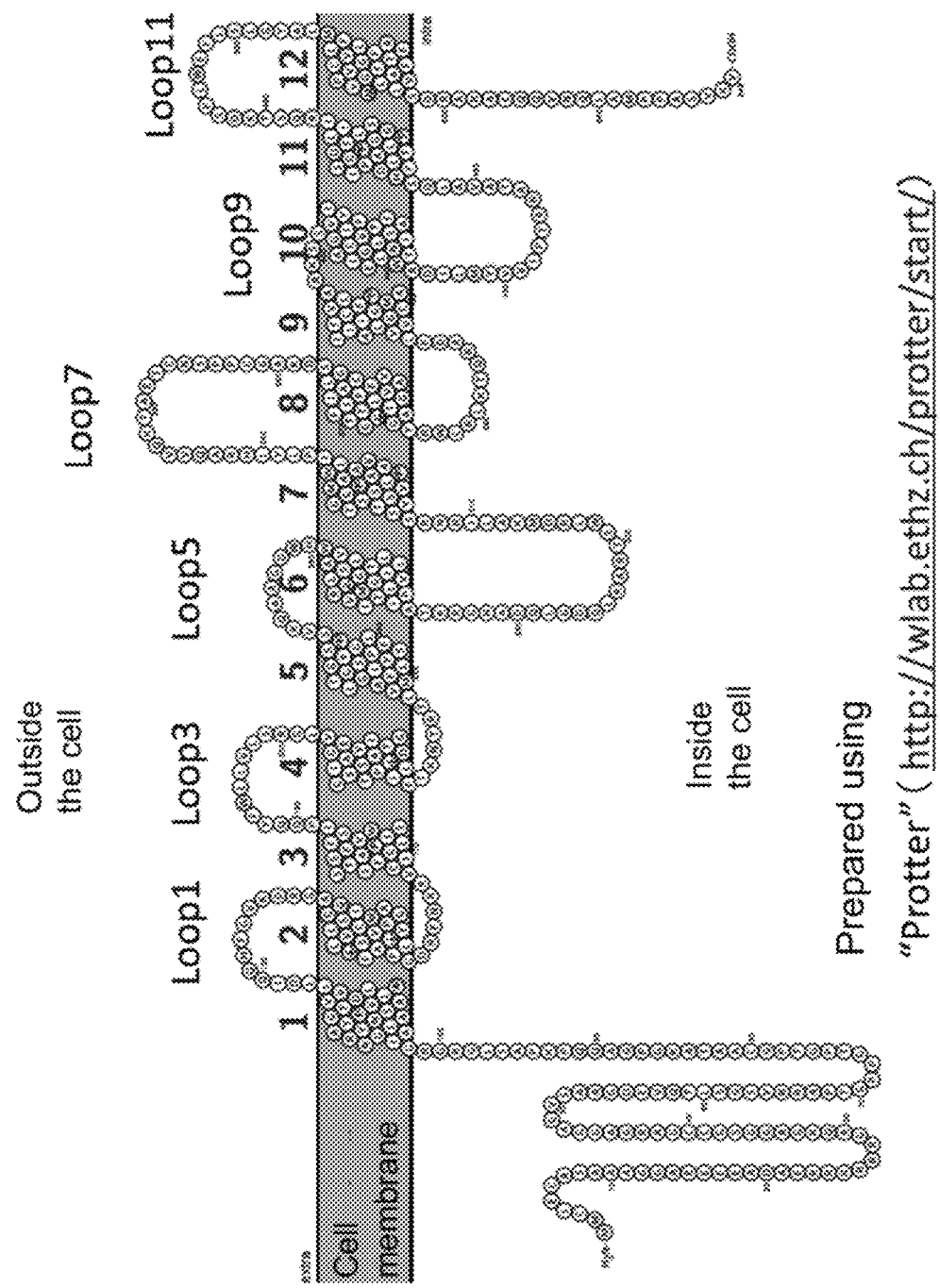
FIG. 1 schematically illustrates the structure of human SPNS2.

The present invention will now be described based on specific embodiments. These embodiments should not be construed to limit the scope of the invention. All references, including patent publications, unexamined patent publications, and non-patent publications cited in this specification, can be incorporated by reference in their entirety for all purposes.

S1P refers to sphingosine-1-phosphate/phosphoric acid. SP is an in vivo ligand having an agonist activity that binds to a S1P receptor described later to incorporate a cytoskeletal change, an anti-apoptosis or a proliferation signal into cells. Five subtypes of the SP receptor are known, that is, S1PR1, S1PR2, S1PR3, S1PR4 and S1PR5. The present specification mainly includes the behavior related to the lymphocyte migration of S1P through S1PR1, or may include the behaviors of all SP receptors when the behaviors or diseases mediated with SP are studied.

S1P is one of phospholipids and is known to function as a bioactive lipid in many species. S1P is mainly produced by erythrocytes, platelets, vascular endothelium, and lymphatic endothelial cells. ATP-dependent transporter is involved when S1P is transported from erythrocytes and platelets to the outside of the cells, while SPNS2 of SLC transporter is involved when S1P is transported from the vascular endothelium and lymphatic endothelial cells to the outside of the cells.

S1P is produced by phosphorylating sphingosine, which is a precursor of S1P cleaved from ceramide that is a cell membrane constituent, with a sphingosine kinase (SphK1, SphK2).

[SPNS2]

SPNS2 (Spinster homolog 2) is a membrane transporter protein localized in the cell membrane and refers to a protein having S1P transporter activity among proteins having a homology of 85% or more with SEQ ID NO: 1. Many vertebrate species are known to possess SPNS2 protein, which includes human (SEQ ID NO: 1), monkey (SEQ ID NO: 31), mouse (SEQ ID NO: 19), rat (SEQ ID NO: 33), and guinea pig (SEQ ID No. 32). In addition, the amino acid sequences of SPNS2 in human and other species can be retrieved from databases such as NCBI and EMBL. For example, the amino acid sequence of human SPNS2 protein shown in SEQ ID NO: 1 can be referred to by, for example, NCBI accession number: NP 001118230 and EMBL accession number: Q8IVW8. Throughout the specification, the term "SPNS2" indicates SPNS2 protein unless otherwise specified. SPNS2 is a protein having multiple transmembrane domains, which is believed to be an eleven-pass or twelve-pass transmembrane protein based on the structure of related transporter proteins and the analytical results by the recent prediction program of transmembrane domains. Although the function of each amino acid region constituting the structure of SPNS2 has not been confirmed to date, SPNS2 has been already identified to be a transporter to transfer S1P from the inside of the cells to the outside of the cells because S1P in the culture supernatant increases by the overexpression of SPNS2 in cultured cells.

SPNS2 is a transporter having a major facilitator superfamily domain from the characteristics of the amino acid sequence and is believed to be an eleven-pass or twelve-pass transmembrane protein. In this SPNS2, partial polypeptide chains are built extracellularly and intracellularly in an exposed form like thread seams, and the portion of the polypeptide chain exposed extracellularly or intracellularly is called a loop. The presence of N-terminal and C-terminal polypeptide chains of SPNS2 inside the cells was confirmed in Example 4. This result suggests that SPNS2 protein has an even number of transmembrane domains and thus is a twelve-pass transmembrane protein. If SPNS2 protein is a twelve-pass transmembrane protein, its structure is composed of the sections called, in sequence from the N-terminal side, a N-terminal intracellular region, a transmembrane [46] region 1, an extracellular loop 1, a transmembrane region 2, an intracellular loop 2, a transmembrane domain 3, an extracellular loop 3, a transmembrane domain 4, an intracellular loop 4, a transmembrane domain 5, an extracellular loop 5, a transmembrane domain 6, an intracellular loop 6, a transmembrane region 7, an extracellular loop 7, a transmembrane region 8, an intracellular loop 8, a transmembrane region 9, an extracellular loop 9, a transmembrane region 10, an intracellular loop 10, a transmembrane region 11, an extracellular loop 11, a transmembrane region 12, and a C-terminal intracellular region. (FIG. 1)

Conventional techniques cannot identify which parts of amino acid sequence in the structure of SPNS2 correspond to each of transmembrane region, intracellular loop sequence, and extracellular loop sequence. In the present invention, in addition to the prediction of the transmembrane region in Example 4, the binding site of an anti-SPNS2 antibody in the present invention was analyzed for SPNS2 in which the FLAG sequence was inserted into the extracellular loop sequence in Example 10, and an epitope of the anti-SPNS2 antibody was determined by replacing each amino acid in the extracellular loop sequence of Example 11 with alanine (Ala) or phenylalanine (Phe), and the structure of extracellular loop sequence was analyzed. The results confirmed that the extracellular loop 1 sequence of human SPNS2 corresponds to an amino acid sequence comprising at least leucine (Leu or L) at position 127 to glycine (Gly or G) at position 139 from the N-terminal of SEQ ID NO: 1, the extracellular loop 3 sequence corresponds to an amino acid sequence comprising glutamine (Gln or Q) at position 190 to arginine (Arg or R) at position 200 from the N-terminal of SEQ ID NO: 1, and the extracellular loop 5 sequence corresponds to an amino acid sequence comprising valine (Val or V) at position 252 to histidine (His or H) at position 260 from the N-terminal of SEQ ID NO: 1. In addition, as shown in FIG. 2, the amino acid sequences of SPNS2 has high preservability among species other than human, and in particular, SPNS2s of human, monkey, mouse, rat and guinea pig have the same sequence in extracellular loop 1, extracellular loop 3 and extracellular loop 5.

SPNS2 is known to mainly express in vascular endothelium and lymphatic endothelium, and SPNS2 is involved in the transfer of lymphocytes through the extracellular transport of S1P. S1P transport function can be evaluated using the amount of SW in the culture supernatant of cultured cells with overexpressed SPNS2 as an index. The SPNS2 expressing-cells can be used for the analysis of binding properties of antibodies and the study of S1P transport functions.

[SPNS2 Neutralizing Antibody]

An antibody is a glycoprotein comprising at least two heavy (H) chains and two light (L) chains interconnected through disulfide bonds. Each heavy chain comprises a heavy chain variable region (abbreviated as VH) and a heavy chain constant region, and the heavy chain constant region contains three domains, CH1, CH2 and CH3. Each light chain comprises a light chain variable region (abbreviated as VL) and a light chain constant region. The light chain constant region contains one domain, CL. The light chain constant region has two chains called a λ chain and a κ chain. The heavy chain constant region has a γ chain, a μ chain, an α chain, a δ chain, and an ε chain, and has isotypes of antibodies called IgG, IgM, IgA, IgD and IgE, respectively, depending on the difference in the heavy chain. The VH and VL regions are further divided into four regions (FR-1, FR-2, FR-3, FR-4) having higher preservability called framework regions (FR) and three regions (CDR-1, CDR-2, CDR-3) called complementarity determining regions (CDR). The VH region comprises three CDRs and four FRs, in detail, a sequence of FR-1, CDR-1 (CDR-H1), FR-2, CDR-2 (CDR-H2), FR-3, CDR-3 (CDR-H3), and FR4 from the amino terminal to the carboxy terminal. The VL region comprises three CDRs and four FRs, in detail, a sequence of FR-1, CDR-1 (CDR-L1), FR-2, CDR-2 (CDR-L2), FR-3, CDR-3 (CDR-L3), and FR4 from the amino terminal to the carboxy terminal. The variable regions of the heavy and light chains contain binding domains that interact with an antigen.

The antibody of the present invention may be a fragment and/or derivative of an antibody. Examples of the fragment of the antibody include F (ab') 2, Fab, and Fv. Examples of the derivative of the antibody include an antibody in which an amino acid mutation is artificially incorporated in the constant region, an antibody in which the domain configuration of the constant region is modified, an antibody in the form having two or more Fc fragments per molecule, an antibody composed of only a heavy chain or only a light chain, a sugar chain modified antibody, a bispecific antibody, an antibody conjugate combined with an antibody or a fragment compound of an antibody or a protein other than antibodies, an antibody enzyme, a nanobody, a tandem scFv fragment, a bispecific tandem scFv fragment, a diabody, and a VHH body. In the present invention, the term "antibody" simply includes a fragment and/or a derivative of an antibody unless otherwise specified.

In addition, a monoclonal antibody generally refers to an antibody molecule given by a clone derived from a single antibody producing cell, and a single type of antibody molecule containing a combination of VH and VL consisting of a specific amino acid sequence. A monoclonal antibody can yield a nucleic acid molecule having a gene sequence encoding an amino acid of a protein in the antibody, and can also produce an antibody through genetic engineering with such a nucleic acid molecule. Those skilled in the art highly recognize the techniques for the modification to improve the binding property or specificity of the antibody with genetic information, such as H chain, L chain, variable regions thereof and CDR sequence, and the production of antibodies having a structure suitable for use as therapeutic agents by modifying antibodies from a mouse type to a human type. A human monoclonal antibody can be also produced with a transgenic animal into which a human antibody gene can be introduced as an animal that sensitizes an antigen. As a method which does not require sensitization to animals, a phage library (human antibody phage display) expressing an antigen binding region of a human antibody or a part thereof is used to give a binding antibody and a phage clone consisting of a specific amino acid sequence, thereby those skilled in the art can appropriately use the technique of producing a human antibody from the information (see, for example, a review by Taketo Tanaka et al., Keio J. Med., Volume 60, pp 37-46). Similar to the technique for the human antibody, those skilled in the art can also design an antibody to be administered to animals other than humans by appropriately using amino acid sequence information of CDRs and the variable regions.

The specificity of an antibody indicates that a high antigen-antibody reaction occurs between an antibody and a specific antigen. Those skilled in the art can determine the antigen-antibody reaction by appropriately selecting binding measurement in a solid phase or liquid phase systems. Examples of such methods include enzyme-linked immunosorbent assay (ELISA), enzyme immunoassay (EIA), surface plasmon resonance (SPR), fluorescence resonance energy transfer (FRET), and luminescence resonance energy transfer (LRET). Before such binding between antigen and antibody is measured, the antibody and/or antigen may be labeled with, for example, an enzyme, a fluorescent substance, a luminescent substance, or a radioisotope, and then the antigen-antibody reaction may be detected by a method suitable for the physical and/or chemical properties of the labeled substance.

The SPNS2 neutralizing antibody of the present invention has an S1P transport inhibitory activity to SPNS2. The SPNS2 neutralizing antibody strongly bound to the specific domain of SPNS2 in the present invention has an in vitro S1P transport inhibitory activity to SPNS2. Specifically, the SPNS2 neutralizing antibody is added to SPNS2 expressing-cells as described in Examples 12 and 13, and the S1P transport inhibitory activity of SPNS2 neutralizing antibody is determined by measuring S1P concentration in the culture supernatant.

Although S1P receptor agonist, fingolimod, causes bradyarrhythmia, the SPNS2 neutralizing antibody of the present invention is believed to have no S1PR1 agonist activity and thereby expected not to trigger the bradyarrhythmia.

Analysis using SPNS2-deficient mice has been reported that the SPNS2 neutralizing antibody can remarkably reduce the colonization of malignant melanoma transferred intravenously into the lungs and liver. This report indicates that the SPNS2 neutralizing antibody is available for not only an autoimmune disease but also a remedy for cancer, and furthermore can be expected to enhance the activity of an existing cancer immunotherapy.

In conclusion, the SPNS2 neutralizing antibody of the present invention is a potential drug for the treatment, suppression, or prevention of various diseases associated with the S1P receptor signal, and can overcome bradyarrhythmia that is a problem caused by the S1P receptor agonist and prolong the half-life in blood. The analytical results show that SPNS2 is a twelve-pass transmembrane protein and consist of, in sequence from N-terminal side, an extracellular loop 1 sequence (SEQ ID NO: 3), an extracellular loop 3 sequence (SEQ ID NO: 4), an extracellular loop 5 sequence (SEQ ID NO: 5), an extracellular loop 7 sequence (SEQ ID NO: 6), extracellular loop 9 sequence (SEQ ID NO: 7), and extracellular loop 11 sequence (SEQ ID NO: 8). Six mutant genes (SEQ ID NOs: 161, 163, 165, 167, 169, 171) were constructed, in which FLAG sequences were inserted into extracellular loops 1, 3, 5, 7, 9 and 11, respectively. Transiently expressing-cells were produced as described in Example 10 by introducing an expressing plasmid in which the mutant gene was inserted into the cells and giving an extracellular loop 1 mutant (SEQ ID NO: 160), an extracellular loop 3 mutant (SEQ ID NO: 162), an extracellular loop 5 mutant (SEQ ID NO: 164), an extracellular loop 7 mutant (SEQ ID NO: 166), an extracellular loop 9 mutant (SEQ ID NO: 168) and extracellular loop 11 mutant (SEQ ID NO: 170), and the reactivity of the antibodies was then measured by flow cytometry. The expressing-cells of each extracellular loop mutant were analyzed by flow cytometry using an antibody that can recognize the FLAG sequence. The analytical results demonstrate that the extracellular loop 3 mutant and the extracellular loop 9 mutant were not stained, and the other mutants were exposed outside the cells. As a result, the binding site of each anti-SPNS2 antibody was determined based on the binding reactivity shown in Table 7 (Example 10).

Since the SPNS2 neutralizing antibody bound to the extracellular loops 1 and 5, a mutant in which amino acids were substituted was produced in the extracellular loops 1 and 5, and also in the extracellular loop 3 which did not express in FLAG sequence inserted mutant in order to further restrict the binding site. An alanine mutant in the extracellular loop 1 (leucine substitute L127A at position 127 of SEQ ID NO: 1 (SEQ ID NO: 172), aspartic acid substitute D128A at position 128 (SEQ ID NO: 173), isoleuce substitute I129A at position 129 (SEQ ID NO: 174), glutamine substitute Q130A at position 130 (SEQ ID NO: 175), glutamine substitute Q131A at position 131 (SEQ ID NO: 176), histidine substitute H132A at position 132 (SEQ ID NO: 177), phenylalanine substitute F133A at position 133 (SEQ ID NO: 178), glycine substitute G134A at position 134 (SEQ ID NO: 179), valine substitute V135A at position 135 (SEQ ID NO: 180), lysine substitute K136A at position 136 (SEQ ID NO: 181), aspartic acid substitute D137A at position 137 (SEQ ID NO: 182), arginine substitute R138A at position 138 (SEQ ID NO: 183), and glycine substitute G139A at position 139 (SEQ ID NO: 184)); an alanine mutant in the extracellular loop 3 (proline substitute P189A at position 189 of SEQ ID NO: 1 (SEQ ID NO: 185), glutamine substitute Q190A at position 190 (SEQ ID NO: 186), glutamine substitute Q191A at position 191 (SEQ ID NO: 187), tyrosine substitute Y192A at position 192 (SEQ ID NO: 188), phenylalanine substitute F193A at position 193 (SEQ ID NO: 189), tryptophan substitute W194A at position 194 (SEQ ID NO: 190), leucine substitute L195A at position 195 (SEQ ID NO: 191), leucine substitute L196A at position 196 (SEQ ID NO: 192), valine substitute V197A at position 197 (SEQ ID NO: 193), leucine substitute L198A at position 198 (SEQ ID NO: 194), serine substitute S199A at position 199 (SEQ ID NO: 195), arginine substitute R200A at position 200 (SEQ ID NO: 196), glycine substitute G201A at position 201 (SEQ ID NO: 197), and leucine substitute L202A at position 202 (SEQ ID NO: 198)); and an alanine or phenylalanine mutant in the extracellular loop 5 (valine substitute V252A at position 252 of SEQ ID NO: 1 (SEQ ID NO: 199), lysine substitute K253A at position 253 (SEQ ID NO: 200), glutamine substitute Q254A at position 254 (SEQ ID NO: 201), alanine substitute A255F at position 255 (SEQ ID NO: 206), alanine substitute A256F at position 256 (SEQ ID NO: 207), glycine substitute G257A at position 257 (SEQ ID NO: 202), aspartic acid substitute D258A at position 258 (SEQ ID NO: 203), tryptophan substitute W259A at position 259 (SEQ ID NO: 204), histidine substitute H260A at position 260 (SEQ ID NO: 205)) were used to produce the expressing-cells as described in Example 11 and then determine an essential amino acid in the antigen-antibody reaction of SPNS2 neutralizing antibodies. As a result, a decrease in binding ability was observed in each substitute from leucine at position 127 to glycine at position 139 of SEQ ID NO: 1 in the extracellular loop 1, in each substitute from glutamine at position 190 to arginine at position 200 of SEQ ID NO: 1 in the extracellular loop 3, and in each substitute from valine at position 252 to histidine at position 260 of SEQ ID NO: 1 in the extracellular loop 5.

Among the antibodies produced in Examples 5 and 6, 15 clones of an antibody having the binding ability to SPNS2 and S1P production inhibitory activity of the cells bound to any of the extracellular loop 1, the extracellular loop 3 and the extracellular loop 5. Accordingly, at least a part of sequences in the extracellular loop 1, the extracellular loop 3 and the extracellular loop 5 was exposed outside the cells. In particular, the exposed sequence in the extracellular loop 1 included at least from Leu at position 1 (Leu at position 127 of SEQ ID NO: 1) to Gly at position 13 (Gly at position 139 of SEQ ID NO: 1) from N-terminal of SEQ ID NO: 3, the exposed sequence in the extracellular loop 3 included at least from Gln at position 2 (Gln at position 190 of SEQ ID NO: 1) to Arg at position 12 (Arg at position 200 of SEQ ID NO: 1) from the N-terminal of SEQ ID NO: 4, and the exposed sequence in the extracellular loop 5 included at least from Val at position 1 (Val at position 252 of SEQ ID NO: 1) to His at position 9 (His at position 260 of SEQ ID NO: 1) from the N-terminal of SEQ ID NO: 5. In addition, the antibody that inhibits the S1P transport of SPNS2 is believed to bind to the extracellular loop 1, the extracellular loop 3 or the extracellular loop 5 to restrain a structural change necessary for the S1P transport.

Accordingly, the SPNS2 neutralizing antibody of the present invention has an amino acid sequence to be an epitope in the extracellular loop of SPNS2. In particular, the SPNS2 neutralizing antibody of the present invention can bind to the extracellular loop 1, the extracellular loop 3 or the extracellular loop 5 of SPNS2. The SPNS2 neutralizing antibody of the present invention can bind to preferably an amino acid sequence at position 1 to 13 from the N-terminal of SEQ ID NO: 3 or a partial sequence thereof, an amino acid sequence at position 2 to 12 from the N-terminal of SEQ ID NO: 4 or a partial sequence thereof, or an amino acid sequence at position 1 to 9 from the N-terminal of SEQ ID NO: 5 or a partial sequence thereof.

The SPNS2 neutralizing antibody of the present invention may has any sequence that specifically binds to SPNS2 of a vertebrate and has an inhibitory effect of S1P transport function in SPNS2.

However, in the embodiment of the SPNS2 neutralizing antibody of the present invention, each CDR sequence preferably has a specific amino acid sequence as specifically described below. In the present invention, the term "identity" in the amino acid sequence indicates the proportion of amino acid residues that are identical, and the term "homology or similarity" indicates the proportion of amino acid residues that are identical or similar. Homology and identity can be determined by, for example, a BLAST method (default condition of PBLAST in NCBI). For example, the expression of "homology of 80% or more" obviously includes that of "identity of 80% or more", including "homology of 100%" and "identity of 100%".

The phrase "similar amino acid residue" indicates an amino acid residue having side chains with similar chemical properties (e.g., electric charge or hydrophobicity). Examples of similar amino acid residues include:
1) amino acid residues having aliphatic side chains: glycine (Gly or G), alanine (Ala or A), valine (Val or V), leucine (Leu or L), and isoleucine (Ile or I) residues;
2) amino acid residues having aliphatic hydroxyl side chains: serine (Ser or S) and threonine (Thr or T) residues;
3) amino acid residues having amide-containing side chains: asparagine (Asn or N) and glutamine (Gln or Q) residues;
4) amino acid residues having aromatic side chains: phenylalanine (Phe or F), tyrosine (Tyr or Y), and tryptophan (Trp or W) residues;
5) amino acid residues having basic side chains: lysine (Lys or K), arginine (Arg or R), and histidine (His or H) residues;
6) amino acid residues having acidic side chains: aspartic acid (Asp or D) and glutamic acid (Glu or E) residues; and
7) amino acid residues having sulfur-containing side chains: cysteine (Cys or C) and methionine (Met or M) residues.

An embodiment of the SPNS2 neutralizing antibody according to the present invention is an antibody containing a heavy chain variable region having a feature of at least any one of (1) to (3) below:
(1) having, as a CDR-H1 sequence, an amino acid sequence having a homology of 80% or more to an amino acid sequence selected from SEQ ID NO:98, SEQ ID NO:99, SEQ ID NO:100, SEQ ID NO:101, SEQ ID NO:102, SEQ ID NO:103, SEQ ID NO:104, SEQ ID NO:105 or SEQ ID NO:106;
(2) having, as a CDR-H2 sequence, an amino acid sequence having a homology of 88% or more to an amino acid sequence selected from SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117 or SEQ ID NO:118; and
(3) having, as a CDR-H3 sequence, an amino acid sequence having a homology of 80% or more to an amino acid sequence selected from SEQ ID NO:120, SEQ ID NO:121, SEQ ID NO:122, SEQ ID NO:123, SEQ ID NO:124, SEQ ID NO:125, SEQ ID NO:126 or SEQ ID NO:127.

The embodiment of the SPNS2 neutralizing antibody metioned above should preferably contain a heavy chain variable region having CDRs 1, 2 and 3 that satisfy any one of the features (1) to (7) below:
(1) having, as a CDR-H1 sequence, an amino acid sequence having a homology of 80% or more to SEQ ID NO:98;
  as a CDR-H2 sequence, an amino acid sequence having a homology of 88% or more to SEQ ID NO:108 or SEQ ID NO:111; and
  as a CDR-H3 sequence, an amino acid sequence having a homology of 83% or more to SEQ ID NO:120 or SEQ ID NO:123;
(2) having, as a CDR-H1 sequence, an amino acid sequence having a homology of 80% or more to SEQ ID NO:101;
  as a CDR-H2 sequence, an amino acid sequence having a homology of 88% or more to SEQ ID NO:113; and
  as a CDR-H3 sequence, an amino acid sequence having a homology of 88% or more to SEQ ID NO:124;
(3) having, as a CDR-H1 sequence, an amino acid sequence having a homology of 80% or more to SEQ ID NO:103 or SEQ ID NO:105;
  as a CDR-H2 sequence, an amino acid sequence having a homology of 89% or more to SEQ ID NO:115 or SEQ ID NO:118; and
  as a CDR-H3 sequence, an amino acid sequence having a homology of 85% or more to SEQ ID NO:126 or SEQ ID NO:127;
(4) having, as a CDR-H1 sequence, an amino acid sequence having a homology of 80% or more to SEQ ID NO:100 or SEQ ID NO:106;
  as a CDR-H2 sequence, an amino acid sequence having a homology of 88% or more to any one of SEQ ID NO:110, SEQ ID NO:112 or SEQ ID NO:117; and
  as a CDR-H3 sequence, an amino acid sequence having a homology of 83% or more to SEQ ID NO:122;
(5) having, as a CDR-H1 sequence, an amino acid sequence having a homology of 80% or more to SEQ ID NO:104;
  as a CDR-H2 sequence, an amino acid sequence having a homology of 88% or more to SEQ ID NO:116; and
  as a CDR-H3 sequence, an amino acid sequence having a homology of 83% or more to SEQ ID NO:122;
(6) having, as a CDR-H1 sequence, an amino acid sequence having a homology of 80% or more to SEQ ID NO:99;
  as a CDR-H2 sequence, an amino acid sequence having a homology of 88% or more to SEQ ID NO:109; and
  as a CDR-H3 sequence, an amino acid sequence having a homology of 80% or more to SEQ ID NO:121; and
(7) having, as a CDR-H1 sequence, an amino acid sequence having a homology of 80% or more to SEQ ID NO:102;
  as a CDR-H2 sequence, an amino acid sequence having a homology of 88% or more to SEQ ID NO:114; and
  as a CDR-H3 sequence, an amino acid sequence having a homology of 83% or more to SEQ ID NO:125.

Another embodiment of the SPNS2 neutralizing antibody according to the present invention is an antibody containing a heavy chain variable region that satisfies any one of the features (1) to (7) below:
(1) having, as a CDR-H1 sequence, the amino acid sequence defined in SEQ ID NO:98 or an amino acid sequence derived from SEQ ID NO:98 via substitution, deletion, or addition of one or two amino acid residues;
  as a CDR-H2 sequence, the amino acid sequence defined in SEQ ID NO:108 or SEQ ID NO:111 or an amino acid sequence derived from SEQ ID NO:108 or SEQ ID NO:111 via substitution, deletion, or addition of one or two amino acid residues; and
  as a CDR-H3 sequence, the amino acid sequence defined in SEQ ID NO:120 or SEQ ID NO:123 or an amino acid sequence derived from SEQ ID NO:120 or SEQ ID NO:123 via substitution, deletion, or addition of one or two amino acid residues.
(2) having, as a CDR-H1 sequence, the amino acid sequence defined in SEQ ID NO:101 or an amino acid sequence derived from SEQ ID NO:101 via substitution, deletion, or addition of one or two amino acid residues;
  as a CDR-H2 sequence, the amino acid sequence defined in SEQ ID NO:113 or an amino acid sequence derived from SEQ ID NO:113 via substitution, deletion, or addition of one or two amino acid residues; and
  as a CDR-H3 sequence, the amino acid sequence defined in SEQ ID NO:124 or an amino acid sequence derived from SEQ ID NO:124 via substitution, deletion, or addition of one or two amino acid residues;
(3) having, as a CDR-H1 sequence, the amino acid sequence defined in SEQ ID NO:103 or SEQ ID NO:105 or an amino acid sequence derived from SEQ ID NO:103 or SEQ ID NO:105 via substitution, deletion, or addition of one or two amino acid residues;

as a CDR-H2 sequence, the amino acid sequence defined in SEQ ID NO:115 or SEQ ID NO:118 or an amino acid sequence derived from SEQ ID NO:115 or SEQ ID NO:118 via substitution, deletion, or addition of one or two amino acid residues; and as a CDR-H3 sequence, the amino acid sequence defined in SEQ ID NO:126 or SEQ ID NO:127 or an amino acid sequence derived from SEQ ID NO:126 or SEQ ID NO:127 via substitution, deletion, or addition of one or two amino acid residues;

(4) having, as a CDR-H1 sequence, the amino acid sequence defined in SEQ ID NO:100 or SEQ ID NO:106 or an amino acid sequence derived from SEQ ID NO:100 or SEQ ID NO:106 via substitution, deletion, or addition of one or two amino acid residues;

as a CDR-H2 sequence, the amino acid sequence as defined in any one of SEQ ID NO:110, SEQ ID NO:112 or SEQ ID NO:117 or an amino acid sequence derived from any one of SEQ ID NO:110, SEQ ID NO:112 or SEQ ID NO:117 via substitution, deletion, or addition of one or two amino acid residues; and as a CDR-H3 sequence, the amino acid sequence defined in SEQ ID NO:122 or an amino acid sequence derived from SEQ ID NO:122 via substitution, deletion, or addition of one or two amino acid residues;

(5) having, as a CDR-H1 sequence, the amino acid sequence defined in SEQ ID NO:99 or an amino acid sequence derived from SEQ ID NO:99 via substitution, deletion, or addition of one or two amino acid residues;

as a CDR-H2 sequence, the amino acid sequence defined in SEQ ID NO:109 or an amino acid sequence derived from SEQ ID NO:109 via substitution, deletion, or addition of one or two amino acid residues; and as a CDR-H3 sequence, the amino acid sequence defined in SEQ ID NO:121 or an amino acid sequence derived from SEQ ID NO:121 via substitution, deletion, or addition of one or two amino acid residues;

(6) having, as a CDR-H1 sequence, the amino acid sequence defined in SEQ ID NO:102 or an amino acid sequence derived from SEQ ID NO:102 via substitution, deletion, or addition of one or two amino acid residues;

as a CDR-H2 sequence, the amino acid sequence defined in SEQ ID NO:114 or an amino acid sequence derived from SEQ ID NO:114 via substitution, deletion, or addition of one or two amino acid residues; and as a CDR-H3 sequence, the amino acid sequence defined in SEQ ID NO:125 or an amino acid sequence derived from SEQ ID NO:125 via substitution, deletion, or addition of one or two amino acid residues; and (7) having, as a CDR-H1 sequence, the amino acid sequence defined in SEQ ID NO:104 or an amino acid sequence derived from SEQ ID NO:104 via substitution, deletion, or addition of one or two amino acid residues;

as a CDR-H2 sequence, the amino acid sequence defined in SEQ ID NO:116 or an amino acid sequence derived from SEQ ID NO:116 via substitution, deletion, or addition of one or two amino acid residues; and as a CDR-H3 sequence, the amino acid sequence defined in SEQ ID NO:122 or an amino acid sequence derived from SEQ ID NO:122 via substitution, deletion, or addition of one or two amino acid residues.

The embodiment of the SPNS2 neutralizing antibody metioned above should preferably contain a heavy chain variable region having CDRs 1, 2 and 3 that satisfy any one of the features (1) to (7) below:

(1) having, as a CDR-H1 sequence, the amino acid sequence defined in SEQ ID NO:98;

as a CDR-H2 sequence, the amino acid sequence defined in SEQ ID NO:108 or the amino acid sequence derived from SEQ ID NO:108 via substitution of the 1st amino acid residue Thr with Ser; and as a CDR-H3 sequence, the amino acid sequence defined in SEQ ID NO:123 or an amino acid sequence derived from SEQ ID NO:123 via substitution of the 4th amino acid residue Ser with Thr;

(2) having, as a CDR-H1 sequence, the amino acid sequence defined in SEQ ID NO:101;

as a CDR-H2 sequence, the amino acid sequence defined in SEQ ID NO:113; and as a CDR-H3 sequence, the amino acid sequence defined in SEQ ID NO:124;

(3) having, as a CDR-H1 sequence, the amino acid sequence defined in SEQ ID NO:105 or an amino acid sequence derived from SEQ ID NO:105 via substitution of the 1st amino acid residue Asp with Glu;

as a CDR-H2 sequence, the amino acid sequence defined in SEQ ID NO:115 or an amino acid sequence derived from SEQ ID NO:115 via substitution of the 9th amino acid residue Tyr with Ser and/or substitution of the 17th amino acid residue Val with Ile; and as a CDR-H3 sequence, the amino acid sequence defined in SEQ ID NO:126 or an amino acid sequence derived from SEQ ID NO:126 via substitution of the 9th amino acid residue Ser with Gly;

(4) having, as a CDR-H1 sequence, the amino acid sequence defined in SEQ ID NO:100 or an amino acid sequence derived from SEQ ID NO:100 via substitution of the 1st amino acid residue Arg with Ala;

as a CDR-H2 sequence, the amino acid sequence defined in SEQ ID NO:110 or an amino acid sequence derived from SEQ ID NO:110 via substitution of the 8th amino acid residue Tyr with Ser and/or substitution of the 17th amino acid residue Asn with Lys; and as a CDR-H3 sequence, the amino acid sequence defined in SEQ ID NO:122;

(5) having, as a CDR-H1 sequence, the amino acid sequence defined in SEQ ID NO:104;

as a CDR-H2 sequence, the amino acid sequence defined in SEQ ID NO:116; and as a CDR-H3 sequence, the amino acid sequence defined in SEQ ID NO:122;

(6) having, as a CDR-H1 sequence, the amino acid sequence defined in SEQ ID NO:99;

as a CDR-H2 sequence, the amino acid sequence defined in SEQ ID NO:109; and as a CDR-H3 sequence, the amino acid sequence defined in SEQ ID NO:121; or (7) having, as a CDR-H1 sequence, the amino acid sequence defined in SEQ ID NO:102;

as a CDR-H2 sequence, the amino acid sequence defined in SEQ ID NO:114; and as a CDR-H3 sequence, the amino acid sequence defined in SEQ ID NO:125.

The embodiment of the SPNS2 neutralizing antibody metioned above should more preferably contain a heavy chain variable region having CDRs 1, 2 and 3 that satisfy any one of the features (1) to (13) below:

(1) having, as a CDR-H1 sequence, the amino acid sequence defined in SEQ ID NO:98;
as a CDR-H2 sequence, the amino acid sequence defined in SEQ ID NO:108; and
as a CDR-H3 sequence, the amino acid sequence defined in SEQ ID NO:120;
(2) having, as a CDR-H1 sequence, the amino acid sequence defined in SEQ ID NO:99;
as a CDR-H2 sequence, the amino acid sequence defined in SEQ ID NO:109; and
as a CDR-H3 sequence, the amino acid sequence defined in SEQ ID NO:121;
(3) having, as a CDR-H1 sequence, the amino acid sequence defined in SEQ ID NO:100;
as a CDR-H2 sequence, the amino acid sequence defined in SEQ ID NO:110; and
as a CDR-H3 sequence, the amino acid sequence defined in SEQ ID NO:122;
(4) having, as a CDR-H1 sequence, the amino acid sequence defined in SEQ ID NO:98;
as a CDR-H2 sequence, the amino acid sequence defined in SEQ ID NO:111; and
as a CDR-H3 sequence, the amino acid sequence defined in SEQ ID NO:123;
(5) having, as a CDR-H1 sequence, the amino acid sequence defined in SEQ ID NO:98;
as a CDR-H2 sequence, the amino acid sequence defined in SEQ ID NO:108; and
as a CDR-H3 sequence, the amino acid sequence defined in SEQ ID NO:123;
(6) having, as a CDR-H1 sequence, the amino acid sequence defined in SEQ ID NO:100;
as a CDR-H2 sequence, the amino acid sequence defined in SEQ ID NO:112; and
as a CDR-H3 sequence, the amino acid sequence defined in SEQ ID NO:122;
(7) having, as a CDR-H1 sequence, the amino acid sequence defined in SEQ ID NO:101;
as a CDR-H2 sequence, the amino acid sequence defined in SEQ ID NO:113; and
as a CDR-H3 sequence, the amino acid sequence defined in SEQ ID NO:124;
(8) having, as a CDR-H1 sequence, the amino acid sequence defined in SEQ ID NO:102;
as a CDR-H2 sequence, the amino acid sequence defined in SEQ ID NO:114; and
as a CDR-H3 sequence, the amino acid sequence defined in SEQ ID NO:125;
(9) having, as a CDR-H1 sequence, the amino acid sequence defined in SEQ ID NO:103;
as a CDR-H2 sequence, the amino acid sequence defined in SEQ ID NO:115; and
as a CDR-H3 sequence, the amino acid sequence defined in SEQ ID NO:126;
(10) having, as a CDR-H1 sequence, the amino acid sequence defined in SEQ ID NO:104;
as a CDR-H2 sequence, the amino acid sequence defined in SEQ ID NO:116; and
as a CDR-H3 sequence, the amino acid sequence defined in SEQ ID NO:122;
(11) having, as a CDR-H1 sequence, the amino acid sequence defined in SEQ ID NO:105;
as a CDR-H2 sequence, the amino acid sequence defined in SEQ ID NO:115; and
as a CDR-H3 sequence, the amino acid sequence defined in SEQ ID NO:126;
(12) having, as a CDR-H1 sequence, the amino acid sequence defined in SEQ ID NO:106;
as a CDR-H2 sequence, the amino acid sequence defined in SEQ ID NO:117; and
as a CDR-H3 sequence, the amino acid sequence defined in SEQ ID NO:122;
(13) having, as a CDR-H1 sequence, the amino acid sequence defined in SEQ ID NO:105;
as a CDR-H2 sequence, the amino acid sequence defined in SEQ ID NO:118; and
as a CDR-H3 sequence, the amino acid sequence defined in SEQ ID NO:127.

An embodiment of the SPNS2 neutralizing antibody according to the present invention is an antibody containing a light chain variable region having a feature of at least any one of (1) to (3) below:
(1) having, as a CDR-L1 sequence, an amino acid sequence having a homology of 81% or more to an amino acid sequence selected from SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137 or SEQ ID NO:138;
(2) having, as a CDR-L2 sequence, an amino acid sequence having a homology of 85% or more to an amino acid sequence selected from SEQ ID NO:140, SEQ ID NO:141, SEQ ID NO:142, SEQ ID NO:143, SEQ ID NO:144, SEQ ID NO:145, SEQ ID NO:146, or SEQ ID NO:147; and
(3) having, as a CDR-L3 sequence, an amino acid sequence having a homology of 88% or more to an amino acid sequence selected from SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157 or SEQ ID NO:158.

The embodiment of the SPNS2 neutralizing antibody mentioned above should preferably contain a light chain variable region having CDRs 1, 2 and 3 that satisfy any one of the features (1) to (7) below:
(1) having, as a CDR-L1 sequence, an amino acid sequence having a homology of 84% or more to SEQ ID NO:129 or SEQ ID NO:132;
as a CDR-L2 sequence, an amino acid sequence having a homology of 85% or more to SEQ ID NO:140; and
as a CDR-L3 sequence, an amino acid sequence having a homology of 88% or more to any one of SEQ ID NO:149, SEQ ID NO:152 or SEQ ID NO:157;
(2) having, as a CDR-L1 sequence, an amino acid sequence having a homology of 84% or more to SEQ ID NO:134;
as a CDR-L2 sequence, an amino acid sequence having a homology of 85% or more to SEQ ID NO:142; and
as a CDR-L3 sequence, an amino acid sequence having a homology of 88% or more to SEQ ID NO:153;
(3) having, as a CDR-L1 sequence, an amino acid sequence having a homology of 81% or more to SEQ ID NO:136;
as a CDR-L2 sequence, an amino acid sequence having a homology of 85% or more to any one of SEQ ID NO:144, SEQ ID NO:146 or SEQ ID NO:147; and
as a CDR-L3 sequence, an amino acid sequence having a homology of 88% or more to SEQ ID NO:155 or SEQ ID NO:158;
(4) having, as a CDR-L1 sequence, an amino acid sequence having a homology of 81% or more to any one of SEQ ID NO:131, SEQ ID NO:133 or SEQ ID NO:138;
as a CDR-L2 sequence, an amino acid sequence having a homology of 85% or more to SEQ ID NO:141; and
as a CDR-L3 sequence, an amino acid sequence having a homology of 88% or more to SEQ ID NO:151;
(5) having, as a CDR-L1 sequence, an amino acid sequence having a homology of 81% or more to SEQ ID NO:137;

as a CDR-L2 sequence, an amino acid sequence having a homology of 85% or more to SEQ ID NO:145; and as a CDR-L3 sequence, an amino acid sequence having a homology of 88% or more to SEQ ID NO:156;

(6) having, as a CDR-L1 sequence, an amino acid sequence having a homology of 84% or more to SEQ ID NO:130;

as a CDR-L2 sequence, an amino acid sequence having a homology of 85% or more to SEQ ID NO:140; and as a CDR-L3 sequence, an amino acid sequence having a homology of 88% or more to SEQ ID NO:150;

(7) having, as a CDR-L1 sequence, an amino acid sequence having a homology of 84% or more to SEQ ID NO:135;

as a CDR-L2 sequence, an amino acid sequence having a homology of 85% or more to SEQ ID NO:143; and as a CDR-L3 sequence, an amino acid sequence having a homology of 88% or more to SEQ ID NO:154.

Another embodiment of the SPNS2 neutralizing antibody according to the present invention is an antibody containing a light chain variable region that satisfies any one of the features (1) to (7) below:

(1) having, as a CDR-L1 sequence, the amino acid sequence defined in SEQ ID NO:129 or SEQ ID NO:132 or an amino acid sequence derived from SEQ ID NO:129 or SEQ ID NO:132 via substitution, deletion, or addition of one or two amino acid residues;

as a CDR-L2 sequence, the amino acid sequence defined in SEQ ID NO:140 or an amino acid sequence derived from SEQ ID NO:140 via substitution, deletion, or addition of one or two amino acid residues; and as a CDR-L3 sequence, the amino acid sequence as defined in any one of SEQ ID NO:149, SEQ ID NO:152 or SEQ ID NO:157 or an amino acid sequence derived from SEQ ID NO:149, SEQ ID NO:152 or SEQ ID NO:157 via substitution, deletion, or addition of one or two amino acid residues;

(2) having, as a CDR-L1 sequence, the amino acid sequence defined in SEQ ID NO:134 or an amino acid sequence derived from SEQ ID NO:134 via substitution, deletion, or addition of one or two amino acid residues;

as a CDR-L2 sequence, the amino acid sequence defined in SEQ ID NO:142 or an amino acid sequence derived from SEQ ID NO:142 via substitution, deletion, or addition of one or two amino acid residues; and as a CDR-L3 sequence, the amino acid sequence defined in SEQ ID NO:153 or an amino acid sequence derived from SEQ ID NO:153 via substitution, deletion, or addition of one or two amino acid residues;

(3) having, as a CDR-L1 sequence, the amino acid sequence defined in SEQ ID NO:136 or an amino acid sequence derived from SEQ ID NO:136 via substitution, deletion, or addition of one or two amino acid residues;

as a CDR-L2 sequence, the amino acid sequence as defined in any one of SEQ ID NO:144, SEQ ID NO:146 or SEQ ID NO:147 or an amino acid sequence derived from any one of SEQ ID NO:144, SEQ ID NO:146 or SEQ ID NO:147 via substitution, deletion, or addition of one or two amino acid residues; and as a CDR-L3 sequence, the amino acid sequence defined in SEQ ID NO:155 or SEQ ID NO:158 or an amino acid sequence derived from SEQ ID NO:155 or SEQ ID NO:158 via substitution, deletion, or addition of one or two amino acid residues;

(4) having, as a CDR-L1 sequence, the amino acid sequence as defined in any one of SEQ ID NO:131, SEQ ID NO:133 or SEQ ID NO:138 or an amino acid sequence derived from any one of SEQ ID NO:131, SEQ ID NO:133 or SEQ ID NO:138 via substitution, deletion, or addition of one or two amino acid residues;

as a CDR-L2 sequence, the amino acid sequence defined in SEQ ID NO:141 or an amino acid sequence derived from SEQ ID NO:141 via substitution, deletion, or addition of one or two amino acid residues; and as a CDR-L3 sequence, the amino acid sequence defined in SEQ ID NO:151 or an amino acid sequence derived from SEQ ID NO:151 via substitution, deletion, or addition of one or two amino acid residues;

(5) having, as a CDR-L1 sequence, the amino acid sequence defined in SEQ ID NO:130 or an amino acid sequence derived from SEQ ID NO:130 via substitution, deletion, or addition of one or two amino acid residues;

as a CDR-L2 sequence, the amino acid sequence defined in SEQ ID NO:140 or an amino acid sequence derived from SEQ ID NO:140 via substitution, deletion, or addition of one or two amino acid residues; and as a CDR-L3 sequence, the amino acid sequence defined in SEQ ID NO:150 or an amino acid sequence derived from SEQ ID NO:150 via substitution, deletion, or addition of one or two amino acid residues;

(6) having, as a CDR-L1 sequence, the amino acid sequence defined in SEQ ID NO:135 or an amino acid sequence derived from SEQ ID NO:135 via substitution, deletion, or addition of one or two amino acid residues;

as a CDR-L2 sequence, the amino acid sequence defined in SEQ ID NO:143 or an amino acid sequence derived from SEQ ID NO:143 via substitution, deletion, or addition of one or two amino acid residues; and as a CDR-L3 sequence, the amino acid sequence defined in SEQ ID NO:154 or an amino acid sequence derived from SEQ ID NO:154 via substitution, deletion, or addition of one or two amino acid residues;

(7) having, as a CDR-L1 sequence, the amino acid sequence defined in SEQ ID NO:137 or an amino acid sequence derived from SEQ ID NO:137 via substitution, deletion, or addition of one or two amino acid residues;

as a CDR-L2 sequence, the amino acid sequence defined in SEQ ID NO:145 or an amino acid sequence derived from SEQ ID NO:145 via substitution, deletion, or addition of one or two amino acid residues; and as a CDR-L3 sequence, the amino acid sequence defined in SEQ ID NO:156 or an amino acid sequence derived from SEQ ID NO:156 via substitution, deletion, or addition of one or two amino acid residues.

The embodiment of the SPNS2 neutralizing antibody should preferably contain a light chain variable region that satisfies any one of the features (1) to (7) below:

(1) having, as a CDR-L1 sequence, the amino acid sequence defined in SEQ ID NO:129 or an amino acid sequence derived from SEQ ID NO:129 via substitution of the 1st amino acid residue Thr with Lys and/or substitution of the 4th amino acid residue Ile with Thr;

as a CDR-L2 sequence, the amino acid sequence defined in SEQ ID NO:140; and as a CDR-L3 sequence, the amino acid sequence defined in SEQ ID NO:149 or an amino acid sequence derived from SEQ ID NO:149 via substitution of the 5th amino acid residue Ser with Asn and/or substitution of the 7th amino acid residue Ile with Met;

(2) having, as a CDR-L1 sequence, the amino acid sequence defined in SEQ ID NO:134;

as a CDR-L2 sequence, the amino acid sequence defined in SEQ ID NO:142; and as a CDR-L3 sequence, the amino acid sequence defined in SEQ ID NO:153;
(3) having, as a CDR-L1 sequence, the amino acid sequence defined in SEQ ID NO:136;
as a CDR-L2 sequence, the amino acid sequence defined in SEQ ID NO:146 or an amino acid sequence derived from SEQ ID NO:146 via substitution of the 6th amino acid residue Ile with Met and/or substitution of the 7th amino acid residue Ser with Ala; and
as a CDR-L3 sequence, the amino acid sequence defined in SEQ ID NO:158 or an amino acid sequence derived from SEQ ID NO:158 via substitution of the 3rd amino acid residue Thr with Ser and/or substitution of the 5th amino acid residue Ser with Asn;
(4) having, as a CDR-L1 sequence, the amino acid sequence defined in SEQ ID NO:133 or an amino acid sequence derived from SEQ ID NO:133 via one or more selected from substitution of the 2nd amino acid residue Ala with Pro, substitution of the 5th amino acid residue Asn with Ser, and substitution of the 8th amino acid Ser with Asn;
as a CDR-L2 sequence, the amino acid sequence defined in SEQ ID NO:141; and
as a CDR-L3 sequence, the amino acid sequence defined in SEQ ID NO:151; or
(5) having, as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;
(6) having, as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;
(7) having, as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154.

The embodiment of the SPNS2 neutralizing antibody mentioned above should more preferably contain a light chain variable region having CDRs 1, 2 and 3 that satisfy any one of the features (1) to (13) below:
(1) having, as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;
(2) having, as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;
(3) having, as a CDR-L1 sequence, the amino acid sequence defined in SEQ ID NO:131;
as a CDR-L2 sequence, the amino acid sequence defined in SEQ ID NO:141; and
as a CDR-L3 sequence, the amino acid sequence defined in SEQ ID NO:151;
(4) having, as a CDR-L1 sequence, the amino acid sequence defined in SEQ ID NO:132;
as a CDR-L2 sequence, the amino acid sequence defined in SEQ ID NO:140; and
as a CDR-L3 sequence, the amino acid sequence defined in SEQ ID NO:152;
(5) having, as a CDR-L1 sequence, the amino acid sequence defined in SEQ ID NO:133;
as a CDR-L2 sequence, the amino acid sequence defined in SEQ ID NO:141; and
as a CDR-L3 sequence, the amino acid sequence defined in SEQ ID NO:151;
(6) having, as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;
(7) having, as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;
(8) having, as a CDR-L1 sequence, the amino acid sequence defined in SEQ ID NO:136;
as a CDR-L2 sequence, the amino acid sequence defined in SEQ ID NO:144; and
as a CDR-L3 sequence, the amino acid sequence defined in SEQ ID NO:155;
(9) having, as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;
(10) having, as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:157;
(11) having, as a CDR-L1 sequence, the amino acid sequence defined in SEQ ID NO:136;
as a CDR-L2 sequence, the amino acid sequence defined in SEQ ID NO:146; and
as a CDR-L3 sequence, the amino acid sequence defined in SEQ ID NO:158;
(12) having, as a CDR-L1 sequence, the amino acid sequence defined in SEQ ID NO:138;
as a CDR-L2 sequence, the amino acid sequence defined in SEQ ID NO:141; and
as a CDR-L3 sequence, the amino acid sequence defined in SEQ ID NO:151;
(13) having, as a CDR-L1 sequence, the amino acid sequence defined in SEQ ID NO:136;
as a CDR-L2 sequence, the amino acid sequence defined in SEQ ID NO:147; and
as a CDR-L3 sequence, the amino acid sequence defined in SEQ ID NO:158.

An embodiment of the SPNS2 neutralizing antibody according to the present invention is an antibody containing a heavy chain variable region satisfying at least one of features (1) to (3) below and a light chain variable region satisfying at least one of features (4) to (6) below:
(1) the heavy chain variable region has, as a CDR-H1 sequence, an amino acid sequence having a homology of 80% or more to an amino acid sequence selected from SEQ ID NO:98, SEQ ID NO:99, SEQ ID NO:100, SEQ ID NO:101, SEQ ID NO:102, SEQ ID NO:103, SEQ ID NO:104, SEQ ID NO:105 or SEQ ID NO:106;

(2) the heavy chain variable region has, as a CDR-H2 sequence, an amino acid sequence having a homology of 88% or more to an amino acid sequence selected from SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117 or SEQ ID NO:118;

(3) the heavy chain variable region has, as a CDR-H3 sequence, an amino acid sequence having a homology of 80% or more to an amino acid sequence selected from SEQ ID NO:120, SEQ ID NO:121, SEQ ID NO:122, SEQ ID NO:123, SEQ ID NO:124, SEQ ID NO:125, SEQ ID NO:126 or SEQ ID NO:127;

(4) the light chain variable region has, as a CDR-L1 sequence, an amino acid sequence having a homology of 81% or more to an amino acid sequence selected from SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137 or SEQ ID NO:138;

(5) the light chain variable region has, as a CDR-L2 sequence, an amino acid sequence having a homology of 85% or more to an amino acid sequence selected from SEQ ID NO:140, SEQ ID NO:141, SEQ ID NO:142, SEQ ID NO:143, SEQ ID NO:144, SEQ ID NO:145, SEQ ID NO:146 or SEQ ID NO:147; and (6) the light chain variable region has, as a CDR-L3 sequence, an amino acid sequence having a homology of 88% or more to an amino acid sequence selected from SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157 or SEQ ID NO:158.

The anti-SPNS2 antibody according to this embodiment should preferably contain CDRs 1, 2, and 3 of the heavy chain variable region and CDRs 1, 2 and 3 of the light chain variable region that satisfy any one of the features (1) to (7) below:

(1) having, as a CDR-H1 sequence, an amino acid sequence having a homology of 80% or more to SEQ ID NO:98;
as a CDR-H2 sequence, an amino acid sequence having a homology of 88% or more to SEQ ID NO:108 or SEQ ID NO:111;
as a CDR-H3 sequence, an amino acid sequence having a homology of 83% or more to SEQ ID NO:120 or SEQ ID NO:123;
as a CDR-L1 sequence, an amino acid sequence having a homology of 84% or more to SEQ ID NO:129 or SEQ ID NO:132;
as a CDR-L2 sequence, an amino acid sequence having a homology of 85% or more to SEQ ID NO:140; and
as a CDR-L3 sequence, an amino acid sequence having a homology of 88% or more to any one of SEQ ID NO:149, SEQ ID NO:152 or SEQ ID NO:157;

(2) having, as a CDR-H1 sequence, an amino acid sequence having a homology of 80% or more to SEQ ID NO:101;
as a CDR-H2 sequence, an amino acid sequence having a homology of 88% or more to SEQ ID NO:113;
as a CDR-H3 sequence, an amino acid sequence having a homology of 88% or more to SEQ ID NO:124;
as a CDR-L1 sequence, an amino acid sequence having a homology of 84% or more to SEQ ID NO:134;
as a CDR-L2 sequence, an amino acid sequence having a homology of 85% or more to SEQ ID NO:142; and
as a CDR-L3 sequence, an amino acid sequence having a homology of 88% or more to SEQ ID NO:153;

(3) having, as a CDR-H1 sequence, an amino acid sequence having a homology of 80% or more to SEQ ID NO:103 or SEQ ID NO:105;
as a CDR-H2 sequence, an amino acid sequence having a homology of 89% or more to SEQ ID NO:115 or SEQ ID NO:118;
as a CDR-H3 sequence, an amino acid sequence having a homology of 85% or more to SEQ ID NO:126 or SEQ ID NO:127;
as a CDR-L1 sequence, an amino acid sequence having a homology of 81% or more to SEQ ID NO:136;
as a CDR-L2 sequence, an amino acid sequence having a homology of 85% or more to any one of SEQ ID NO:144, SEQ ID NO:146 or SEQ ID NO:147; and
as a CDR-L3 sequence, an amino acid sequence having a homology of 88% or more to SEQ ID NO:155 or SEQ ID NO:158;

(4) having, as a CDR-H1 sequence, an amino acid sequence having a homology of 80% or more to SEQ ID NO:100 or SEQ ID NO:106;
as a CDR-H2 sequence, an amino acid sequence having a homology of 88% or more to any one of SEQ ID NO:110, SEQ ID NO:112 or SEQ ID NO:117;
as a CDR-H3 sequence, an amino acid sequence having a homology of 83% or more to SEQ ID NO:122;
as a CDR-L1 sequence, an amino acid sequence having a homology of 81% or more to any one of SEQ ID NO:131, SEQ ID NO:133 or SEQ ID NO:138;
as a CDR-L2 sequence, an amino acid sequence having a homology of 85% or more to SEQ ID NO:141; and
as a CDR-L3 sequence, an amino acid sequence having a homology of 88% or more to SEQ ID NO:151;

(5) having, as a CDR-H1 sequence, an amino acid sequence having a homology of 80% or more to SEQ ID NO:104;
as a CDR-H2 sequence, an amino acid sequence having a homology of 88% or more to SEQ ID NO:116;
as a CDR-H3 sequence, an amino acid sequence having a homology of 83% or more to SEQ ID NO:122;
as a CDR-L1 sequence, an amino acid sequence having a homology of 81% or more to SEQ ID NO:137;
as a CDR-L2 sequence, an amino acid sequence having a homology of 85% or more to SEQ ID NO:145; and
as a CDR-L3 sequence, an amino acid sequence having a homology of 88% or more to SEQ ID NO:156;

(6) having, as a CDR-H1 sequence, an amino acid sequence having a homology of 80% or more to SEQ ID NO:99;
as a CDR-H2 sequence, an amino acid sequence having a homology of 88% or more to SEQ ID NO:109;
as a CDR-H3 sequence, an amino acid sequence having a homology of 80% or more to SEQ ID NO:121;
as a CDR-L1 sequence, an amino acid sequence having a homology of 84% or more to SEQ ID NO:130;
as a CDR-L2 sequence, an amino acid sequence having a homology of 85% or more to SEQ ID NO:140; and
as a CDR-L3 sequence, an amino acid sequence having a homology of 88% or more to SEQ ID NO:150; and (7) having, as a CDR-H1 sequence, an amino acid sequence having a homology of 80% or more to SEQ ID NO:102;
as a CDR-H2 sequence, an amino acid sequence having a homology of 88% or more to SEQ ID NO:114;
as a CDR-H3 sequence, an amino acid sequence having a homology of 83% or more to SEQ ID NO:125;
as a CDR-L1 sequence, an amino acid sequence having a homology of 84% or more to SEQ ID NO:135;

as a CDR-L2 sequence, an amino acid sequence having a homology of 85% or more to SEQ ID NO:143; and as a CDR-L3 sequence, an amino acid sequence having a homology of 88% or more to SEQ ID NO:154.

Another embodiment of the SPNS2 neutralizing antibody according to the present invention is an antibody containing CDRs 1, 2, and 3 of the heavy chain variable region and CDRs 1, 2 and 3 of the light chain variable region that satisfy any one of the features (1) to (7) below:

(1) having, as a CDR-H1 sequence, the amino acid sequence defined in SEQ ID NO:98 or an amino acid sequence derived from SEQ ID NO:98 via substitution, deletion, or addition of one or two amino acid residues;

as a CDR-H2 sequence, the amino acid sequence defined in SEQ ID NO:108 or SEQ ID NO:111 or an amino acid sequence derived from SEQ ID NO:108 or SEQ ID NO:111 via substitution, deletion, or addition of one or two amino acid residues;

as a CDR-H3 sequence, the amino acid sequence defined in SEQ ID NO:120 or SEQ ID NO:123 or an amino acid sequence derived from SEQ ID NO:120 or SEQ ID NO:123 via substitution, deletion, or addition of one or two amino acid residues;

as a CDR-L1 sequence, the amino acid sequence defined in SEQ ID NO:129 or SEQ ID NO:132 or an amino acid sequence derived from SEQ ID NO:129 or SEQ ID NO:132 via substitution, deletion, or addition of one or two amino acid residues;

as a CDR-L2 sequence, the amino acid sequence defined in SEQ ID NO:140 or an amino acid sequence derived from SEQ ID NO:140 via substitution, deletion, or addition of one or two amino acid residues; and as a CDR-L3 sequence, the amino acid sequence as defined in any one of SEQ ID NO:149, SEQ ID NO:152 or SEQ ID NO:157 or an amino acid sequence derived from any one of SEQ ID NO:149, SEQ ID NO:152 or SEQ ID NO:157 via substitution, deletion, or addition of one or two amino acid residues;

(2) having, as a CDR-H1 sequence, the amino acid sequence defined in SEQ ID NO:101 or an amino acid sequence derived from SEQ ID NO:101 via substitution, deletion, or addition of one or two amino acid residues;

as a CDR-H2 sequence, the amino acid sequence defined in SEQ ID NO:113 or an amino acid sequence derived from SEQ ID NO:113 via substitution, deletion, or addition of one or two amino acid residues;

as a CDR-H3 sequence, the amino acid sequence defined in SEQ ID NO:124 or an amino acid sequence derived from SEQ ID NO:124 via substitution, deletion, or addition of one or two amino acid residues;

as a CDR-L1 sequence, the amino acid sequence defined in SEQ ID NO:134 or an amino acid sequence derived from SEQ ID NO:134 via substitution, deletion, or addition of one or two amino acid residues;

as a CDR-L2 sequence, the amino acid sequence defined in SEQ ID NO:142 or an amino acid sequence derived from SEQ ID NO:142 via substitution, deletion, or addition of one or two amino acid residues; and as a CDR-L3 sequence, the amino acid sequence defined in SEQ ID NO:153 or an amino acid sequence derived from SEQ ID NO:153 via substitution, deletion, or addition of one or two amino acid residues;

(3) having, as a CDR-H1 sequence, the amino acid sequence defined in SEQ ID NO:103 or SEQ ID NO:105 or an amino acid sequence derived from SEQ ID NO:103 or SEQ ID NO:105 via substitution, deletion, or addition of one or two amino acid residues;

as a CDR-H2 sequence, the amino acid sequence defined in SEQ ID NO:115 or SEQ ID NO:118 or an amino acid sequence derived from SEQ ID NO:115 or SEQ ID NO:118 via substitution, deletion, or addition of one or two amino acid residues; and as a CDR-H3 sequence, the amino acid sequence defined in SEQ ID NO:126 or SEQ ID NO:127 or an amino acid sequence derived from SEQ ID NO:126 or SEQ ID NO:127 via substitution, deletion, or addition of one or two amino acid residues;

as a CDR-L1 sequence, the amino acid sequence defined in SEQ ID NO:136 or an amino acid sequence derived from SEQ ID NO:136 via substitution, deletion, or addition of one or two amino acid residues;

as a CDR-L2 sequence, the amino acid sequence as defined in any one of SEQ ID NO:144, SEQ ID NO:146 or SEQ ID NO:147 or an amino acid sequence derived from any one of SEQ ID NO:144, SEQ ID NO:146 or SEQ ID NO:147 via substitution, deletion, or addition of one or two amino acid residues; and as a CDR-L3 sequence, the amino acid sequence defined in SEQ ID NO:155 or SEQ ID NO:158 or an amino acid sequence derived from SEQ ID NO:155 or SEQ ID NO:158 via substitution, deletion, or addition of one or two amino acid residues;

(4) having, as a CDR-H1 sequence, the amino acid sequence defined in SEQ ID NO:100 or SEQ ID NO:106 or an amino acid sequence derived from SEQ ID NO:100 or SEQ ID NO:106 via substitution, deletion, or addition of one or two amino acid residues;

as a CDR-H2 sequence, the amino acid sequence as defined in any one of SEQ ID NO:110, SEQ ID NO:112 or SEQ ID NO:117 or an amino acid sequence derived from any one of SEQ ID NO:110, SEQ ID NO:112 or SEQ ID NO:117 via substitution, deletion, or addition of one or two amino acid residues; and as a CDR-H3 sequence, the amino acid sequence defined in SEQ ID NO:122 or an amino acid sequence derived from SEQ ID NO:122 via substitution, deletion, or addition of one or two amino acid residues;

as a CDR-L1 sequence, the amino acid sequence as defined in any one of SEQ ID NO:131, SEQ ID NO:133 or SEQ ID NO:138 or an amino acid sequence derived from any one of SEQ ID NO:131, SEQ ID NO:133 or SEQ ID NO:138 via substitution, deletion, or addition of one or two amino acid residues;

as a CDR-L2 sequence, the amino acid sequence defined in SEQ ID NO:141 or an amino acid sequence derived from SEQ ID NO:141 via substitution, deletion, or addition of one or two amino acid residues; and as a CDR-L3 sequence, the amino acid sequence defined in SEQ ID NO:151 or an amino acid sequence derived from SEQ ID NO:151 via substitution, deletion, or addition of one or two amino acid residues;

(5) having, as a CDR-H1 sequence, the amino acid sequence defined in SEQ ID NO:99 or an amino acid sequence derived from SEQ ID NO:99 via substitution, deletion, or addition of one or two amino acid residues;

as a CDR-H2 sequence, the amino acid sequence defined in SEQ ID NO:109 or an amino acid sequence derived from SEQ ID NO:109 via substitution, deletion, or addition of one or two amino acid residues; and as a CDR-H3 sequence, the amino acid sequence defined in SEQ ID NO:121 or an amino acid sequence derived from SEQ ID NO:121 via substitution, deletion, or addition of one or two amino acid residues;

as a CDR-L1 sequence, the amino acid sequence defined in SEQ ID NO:130 or an amino acid sequence derived from SEQ ID NO:130 via substitution, deletion, or addition of one or two amino acid residues;

as a CDR-L2 sequence, the amino acid sequence defined in SEQ ID NO:140 or an amino acid sequence derived from SEQ ID NO:140 via substitution, deletion, or addition of one or two amino acid residues; and as a CDR-L3 sequence, the amino acid sequence defined in SEQ ID NO:150 or an amino acid sequence derived from SEQ ID NO:150 via substitution, deletion, or addition of one or two amino acid residues;

(6) having, as a CDR-H1 sequence, the amino acid sequence defined in SEQ ID NO:102 or an amino acid sequence derived from SEQ ID NO:102 via substitution, deletion, or addition of one or two amino acid residues;

as a CDR-H2 sequence, the amino acid sequence defined in SEQ ID NO:114 or an amino acid sequence derived from SEQ ID NO:114 via substitution, deletion, or addition of one or two amino acid residues; and as a CDR-H3 sequence, the amino acid sequence defined in SEQ ID NO:125 or an amino acid sequence derived from SEQ ID NO:125 via substitution, deletion, or addition of one or two amino acid residues;

as a CDR-L1 sequence, the amino acid sequence defined in SEQ ID NO:135 or an amino acid sequence derived from SEQ ID NO:135 via substitution, deletion, or addition of one or two amino acid residues;

as a CDR-L2 sequence, the amino acid sequence defined in SEQ ID NO:143 or an amino acid sequence derived from SEQ ID NO:143 via substitution, deletion, or addition of one or two amino acid residues; and as a CDR-L3 sequence, the amino acid sequence defined in SEQ ID NO:154 or an amino acid sequence derived from SEQ ID NO:154 via substitution, deletion, or addition of one or two amino acid residues; and (7) having, as a CDR-H1 sequence, the amino acid sequence defined in SEQ ID NO:104 or an amino acid sequence derived from SEQ ID NO:104 via substitution, deletion, or addition of one or two amino acid residues;

as a CDR-H2 sequence, the amino acid sequence defined in SEQ ID NO:116 or an amino acid sequence derived from SEQ ID NO:116 via substitution, deletion, or addition of one or two amino acid residues; and as a CDR-H3 sequence, the amino acid sequence defined in SEQ ID NO:122 or an amino acid sequence derived from SEQ ID NO:122 via substitution, deletion, or addition of one or two amino acid residues;

as a CDR-L1 sequence, the amino acid sequence defined in SEQ ID NO:137 or an amino acid sequence derived from SEQ ID NO:137 via substitution, deletion, or addition of one or two amino acid residues;

as a CDR-L2 sequence, the amino acid sequence defined in SEQ ID NO:145 or an amino acid sequence derived from SEQ ID NO:145 via substitution, deletion, or addition of one or two amino acid residues; and as a CDR-L3 sequence, the amino acid sequence defined in SEQ ID NO:156 or an amino acid sequence derived from SEQ ID NO:156 via substitution, deletion, or addition of one or two amino acid residues.

The anti-SPNS2 antibody according to this embodiment should preferably contain CDRs 1, 2, and 3 of the heavy chain variable region and CDRs 1, 2 and 3 of the light chain variable region that satisfy any one of the features (1) to (7) below:

(1) having, as a CDR-H1 sequence, the amino acid sequence defined in SEQ ID NO:98;

as a CDR-H2 sequence, the amino acid sequence defined in SEQ ID NO:108 or the amino acid sequence derived from SEQ ID NO:108 via substitution of the 1st amino acid residue Thr with Ser;

as a CDR-H3 sequence, the amino acid sequence defined in SEQ ID NO:123 or an amino acid sequence derived from SEQ ID NO:123 via substitution of the 4th amino acid residue Ser with Thr;

as a CDR-L1 sequence, the amino acid sequence defined in SEQ ID NO:129 or an amino acid sequence derived from SEQ ID NO:129 via substitution of the 1st amino acid residue Thr with Lys and/or substitution of the 4th amino acid residue Ile with Thr;

as a CDR-L2 sequence, the amino acid sequence defined in SEQ ID NO:140; and as a CDR-L3 sequence, the amino acid sequence defined in SEQ ID NO:149 or an amino acid sequence derived from SEQ ID NO:149 via substitution of the 5th amino acid residue Ser with Asn and/or substitution of the 7th amino acid residue Ile with Met;

(2) having, as a CDR-H1 sequence, the amino acid sequence defined in SEQ ID NO:101;

as a CDR-H2 sequence, the amino acid sequence defined in SEQ ID NO:113;

as a CDR-H3 sequence, the amino acid sequence defined in SEQ ID NO:124;

as a CDR-L1 sequence, the amino acid sequence defined in SEQ ID NO:134;

as a CDR-L2 sequence, the amino acid sequence defined in SEQ ID NO:142; and as a CDR-L3 sequence, the amino acid sequence defined in SEQ ID NO:153;

(3) having, as a CDR-H1 sequence, the amino acid sequence defined in SEQ ID NO:105 or an amino acid sequence derived from SEQ ID NO:105 via substitution of the 1st amino acid residue Asp with Glu;

as a CDR-H2 sequence, the amino acid sequence defined in SEQ ID NO:115 or an amino acid sequence derived from SEQ ID NO:115 via substitution of the 9th amino acid residue Tyr with Ser and/or substitution of the 17th amino acid residue Val with Ile;

as a CDR-H3 sequence, the amino acid sequence defined in SEQ ID NO:126 or an amino acid sequence derived from SEQ ID NO:126 via substitution of the 9th amino acid residue Ser with Gly;

as a CDR-L1 sequence, the amino acid sequence defined in SEQ ID NO:136;

as a CDR-L2 sequence, the amino acid sequence defined in SEQ ID NO:146 or an amino acid sequence derived from SEQ ID NO:146 via substitution of the 6th amino acid residue Ile with Met and/or substitution of the 7th amino acid residue Ser with Ala; and as a CDR-L3 sequence, the amino acid sequence defined in SEQ ID NO:158 or an amino acid sequence derived from SEQ ID NO:158 via substitution of the 3rd amino acid residue Thr with Ser and/or substitution of the 5th amino acid residue Ser with Asn;

(4) having, as a CDR-H1 sequence, the amino acid sequence defined in SEQ ID NO:100 or an amino acid sequence derived from SEQ ID NO:100 via substitution of the 1st amino acid residue Arg with Ala;

as a CDR-H2 sequence, the amino acid sequence defined in SEQ ID NO:110 or an amino acid sequence derived from SEQ ID NO:110 via substitution of the 8th amino acid residue Thr with Ser and/or substitution of the 17th amino acid residue Asn with Lys;

as a CDR-H3 sequence, the amino acid sequence defined in SEQ ID NO:122;
as a CDR-L1 sequence, the amino acid sequence defined in SEQ ID NO:133 or an amino acid sequence derived from SEQ ID NO:133 via one or more substitutions selected from substitution of the 2nd amino acid residue Ala with Pro, substitution of the 5th amino acid residue Asn with Ser, and substitution of the 8th amino residue acid Ser with Asn;
as a CDR-L2 sequence, the amino acid sequence defined in SEQ ID NO:141; and
as a CDR-L3 sequence, the amino acid sequence defined in SEQ ID NO:151;
(5) having, as a CDR-H1 sequence, the amino acid sequence defined in SEQ ID NO:104;
as a CDR-H2 sequence, the amino acid sequence defined in SEQ ID NO:116;
as a CDR-H3 sequence, the amino acid sequence defined in SEQ ID NO:122;
as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;
(6) having, as a CDR-H1 sequence, the amino acid sequence defined in SEQ ID NO:99;
as a CDR-H2 sequence, the amino acid sequence defined in SEQ ID NO:109;
as a CDR-H3 sequence, the amino acid sequence defined in SEQ ID NO:121;
as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150; and
(7) having, as a CDR-H1 sequence, the amino acid sequence defined in SEQ ID NO:102;
as a CDR-H2 sequence, the amino acid sequence defined in SEQ ID NO:114;
as a CDR-H3 sequence, the amino acid sequence defined in SEQ ID NO:125;
as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;
The anti-SPNS2 antibody according to this embodiment should more preferably contain CDRs 1, 2, and 3 of the heavy chain variable region and CDRs 1, 2 and 3 of the light chain variable region that satisfy any one of the features (1) to (14) below:
(1) having, as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:120;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;
(2) having, as a CDR-H1 sequence, the amino acid sequence defined in SEQ ID NO:99;
as a CDR-H2 sequence, the amino acid sequence defined in SEQ ID NO:109;
as a CDR-H3 sequence, the amino acid sequence defined in SEQ ID NO:121;
as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;
(3) having, as a CDR-H1 sequence, the amino acid sequence defined in SEQ ID NO:100;
as a CDR-H2 sequence, the amino acid sequence defined in SEQ ID NO:110;
as a CDR-H3 sequence, the amino acid sequence defined in SEQ ID NO:122;
as a CDR-L1 sequence, the amino acid sequence defined in SEQ ID NO:131;
as a CDR-L2 sequence, the amino acid sequence defined in SEQ ID NO:141; and
as a CDR-L3 sequence, the amino acid sequence defined in SEQ ID NO:151;
(4) having, as a CDR-H1 sequence, the amino acid sequence defined in SEQ ID NO:98;
as a CDR-H2 sequence, the amino acid sequence defined in SEQ ID NO:111;
as a CDR-H3 sequence, the amino acid sequence defined in SEQ ID NO:123;
as a CDR-L1 sequence, the amino acid sequence defined in SEQ ID NO:132;
as a CDR-L2 sequence, the amino acid sequence defined in SEQ ID NO:140; and
as a CDR-L3 sequence, the amino acid sequence defined in SEQ ID NO:152;
(5) having, as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:123;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;
(6) having, as a CDR-H1 sequence, the amino acid sequence defined in SEQ ID NO:100;
as a CDR-H2 sequence, the amino acid sequence defined in SEQ ID NO:112;
as a CDR-H3 sequence, the amino acid sequence defined in SEQ ID NO:122;
as a CDR-L1 sequence, the amino acid sequence defined in SEQ ID NO:133;
as a CDR-L2 sequence, the amino acid sequence defined in SEQ ID NO:141; and
as a CDR-L3 sequence, the amino acid sequence defined in SEQ ID NO:151;
(7) having, as a CDR-H1 sequence, the amino acid sequence defined in SEQ ID NO:101;
as a CDR-H2 sequence, the amino acid sequence defined in SEQ ID NO:113;
as a CDR-H3 sequence, the amino acid sequence defined in SEQ ID NO:124;
as a CDR-L1 sequence, the amino acid sequence defined in SEQ ID NO:134;

as a CDR-L2 sequence, the amino acid sequence defined in SEQ ID NO:142; and
as a CDR-L3 sequence, the amino acid sequence defined in SEQ ID NO:153;
(8) having, as a CDR-H1 sequence, the amino acid sequence defined in SEQ ID NO:102;
as a CDR-H2 sequence, the amino acid sequence defined in SEQ ID NO:114;
as a CDR-H3 sequence, the amino acid sequence defined in SEQ ID NO:125;
as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;
(9) having, as a CDR-H1 sequence, the amino acid sequence defined in SEQ ID NO:103;
as a CDR-H2 sequence, the amino acid sequence defined in SEQ ID NO:115;
as a CDR-H3 sequence, the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:144; and
as a CDR-L3 sequence, the amino acid sequence defined in SEQ ID NO:155;
(10) having, as a CDR-H1 sequence, the amino acid sequence defined in SEQ ID NO:104;
as a CDR-H2 sequence, the amino acid sequence defined in SEQ ID NO:116;
as a CDR-H3 sequence, the amino acid sequence defined in SEQ ID NO:122;
as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;
(11) having, as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:123;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:157;
(12) having, as a CDR-H1 sequence, the amino acid sequence defined in SEQ ID NO:105;
as a CDR-H2 sequence, the amino acid sequence defined in SEQ ID NO:115;
as a CDR-H3 sequence, the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:146; and
as a CDR-L3 sequence, the amino acid sequence defined in SEQ ID NO:158;
(13) having, as a CDR-H1 sequence, the amino acid sequence defined in SEQ ID NO:106;
as a CDR-H2 sequence, the amino acid sequence defined in SEQ ID NO:117;
as a CDR-H3 sequence, the amino acid sequence defined in SEQ ID NO:122;
as a CDR-L1 sequence, the amino acid sequence defined in SEQ ID NO:138;
as a CDR-L2 sequence, the amino acid sequence defined in SEQ ID NO:141; and
as a CDR-L3 sequence, the amino acid sequence defined in SEQ ID NO:151;
(14) having, as a CDR-H1 sequence, the amino acid sequence defined in SEQ ID NO:105;
as a CDR-H2 sequence, the amino acid sequence defined in SEQ ID NO:118;
as a CDR-H3 sequence, the amino acid sequence defined in SEQ ID NO:127;
as a CDR-L1 sequence, the amino acid sequence defined in SEQ ID NO:136;
as a CDR-L2 sequence, the amino acid sequence defined in SEQ ID NO:147; and
as a CDR-L3 sequence, the amino acid sequence defined in SEQ ID NO:158;

An embodiment of the SPNS2 neutralizing antibody according to the present invention is an antibody containing a heavy chain variable region having an amino acid sequence having a homology of 80% or more, preferably 90% or more, more preferably 95% or more to a sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62.

Another embodiment of the SPNS2 neutralizing antibody according to the present invention is an antibody containing a heavy chain variable region having an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62, or an amino acid sequence derived from an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, and SEQ ID NO:62, via substitution, deletion, or addition of one or more amino acid residues, preferably via substitution, deletion, or addition of one or more amino acid residues in the 1st to 17th positions of the sequence.

The SPNS2 neutralizing antibody according to this embodiment should preferably contain, as a heavy chain variable region that satisfy any one of the features (1) to (5) below:

(1) having, the amino acid sequence defined in SEQ ID NO:42; or an amino acid sequence derived from SEQ ID NO:42 via one or more substitution selected from the group consisting of substitution of the 1st (Kabat No.: H1) amino acid residue with an amino acid residue other than Glu, substitution of the 6th (Kabat No.: H6) amino acid residue with an amino acid residue other than Gly, substitution of the 23rd (Kabat No.: H23) amino acid residue with an amino acid residue other than Glu, substitution of the 43rd (Kabat No.: H43) amino acid residue with an amino acid residue other than Lys, substitution of the 50th (Kabat No.: H50) amino acid residue with an amino acid residue other than Thr, substitution of the 75th (Kabat No.: H74) amino acid residue with an amino acid residue other than Ala, substitution of the 76th (Kabat No.: H75) amino acid residue with an amino acid residue other than Arg, substitution of the 78th (Kabat No.: H77) amino acid residue with an amino acid residue other than Thr, substitution of the 80th (Kabat No.: H79) amino acid residue with an amino acid residue other than Ser, substitution of the 97th (Kabat No.: H93) amino acid residue with an amino acid residue other than Ala, and substitution of the 102nd (Kabat No.: H98) amino acid residue with an amino acid residue other than Ser;

(2) having, the amino acid sequence defined in SEQ ID NO:46 or an amino acid sequence derived from SEQ ID NO:46 via substitution of the 82nd (Kabat No.: H81) amino acid residue with an amino acid residue other than Gln;

(3) having, the amino acid sequence defined in SEQ ID NO:58 or an amino acid sequence derived from SEQ ID NO:58 via one or more substitution selected from the group consisting of substitution of the 13th (Kabat No.: H13) amino acid residue with an amino acid residue other than Gln, substitution of the 23rd (Kabat No.: H23) amino acid residue with an amino acid residue other than Ala, substitution of the 31st (Kabat No.: H31) amino acid residue with an amino acid residue other than Asp, substitution of the 49th (Kabat No.: H49) amino acid residue with an amino acid residue other than Ala, substitution of the 58th (Kabat No.: H55) amino acid residue with an amino acid residue other than Tyr, substitution of the 66th (Kabat No.: H63) amino acid residue with an amino acid residue other than Val, substitution of the 79th (Kabat No.: H76) amino acid residue with an amino acid residue other than Arg, substitution of the 86th (Kabat No.: H82A) amino acid residue with an amino acid residue other than Phe, substitution of the 100th (Kabat No.: H94) amino acid residue with an amino acid residue other than Ser, substitution of the 109th (Kabat No.: H100C) amino acid residue with an amino acid residue other than Ser, and substitution of the and 117th (Kabat No.: H105) amino acid residue with an amino acid residue other than His;

(4) having, the amino acid sequence defined in SEQ ID NO:44 or an amino acid sequence derived from SEQ ID NO:44 via one or more substitution selected from the group consisting of substitution of the 3rd (Kabat No.: H3) amino acid residue with an amino acid residue other than Gln, substitution of the 10th (Kabat No.: H10) amino acid residue with an amino acid residue other than Glu, substitution of the 16th (Kabat No.: H16) amino acid residue with an amino acid residue other than Thr, substitution of the 19th (Kabat No.: H19) amino acid residue with an amino acid residue other than Lys, substitution of the 24th (Kabat No.: H24) amino acid residue with an amino acid residue other than Val, substitution of the 30th (Kabat No.: H30) amino acid residue with an amino acid residue other than Thr, substitution of the 31st (Kabat No.: H31) amino acid residue with an amino acid residue other than Arg, substitution of the 57th (Kabat No.: H56) amino acid residue with an amino acid residue other than Thr, substitution of the 66th (Kabat No.: H65) amino acid residue with an amino acid residue other than Lys, substitution of the 67th (Kabat No.: H66) amino acid residue with an amino acid residue other than Lys, substitution of the 74th (Kabat No.: H73) amino acid residue with an amino acid residue other than Ala, substitution of the 77th (Kabat No.: H76) amino acid residue with an amino acid residue other than Asn, substitution of the 80th (Kabat No.: H79) amino acid residue with an amino acid residue other than Tyr, substitution of the 83rd (Kabat No.: H82) amino acid residue with an amino acid residue other than Phe, substitution of the 85th (Kabat No.: H82B) amino acid residue with an amino acid residue other than Gly, substi- tution of the 89th (Kabat No.: H85) amino acid residue with an amino acid residue other than Glu, and substitution of the and 91st (Kabat No.: H87) amino acid residue with an amino acid residue other than Thr; and (5) having, an amino acid sequence selected from SEQ ID NO:52, SEQ ID NO:36, or SEQ ID NO:48.

The SPNS2 neutralizing antibody according to this embodiment should more preferably contain, as a heavy chain variable region that satisfy any one of the features (1) to (5) below:

(1) having, the amino acid sequence defined in SEQ ID NO:42 or an amino acid sequence derived from SEQ ID NO:42 via one or more substitutions selected from the group consisting of: substitution of the 1st (Kabat No.: H1) amino acid residue Glu with Ala, substitution of the 6th (Kabat No.: H6) amino acid residue Gly with Glu, substitution of the 23rd (Kabat No.: H23) amino acid residue Glu with Ala, substitution of the 43rd (Kabat No.: H43) amino acid residue Lys with Arg, substitution of the 50th (Kabat No.: H50) amino acid residue Thr with Ser, substitution of the 75th (Kabat No.: H74) amino acid residue Ala with Thr, substitution of the 76th (Kabat No.: H75) amino acid residue Arg with Lys, substitution of the 78th (Kabat No.: H77) amino acid residue Thr with Ile, substitution of the 80th (Kabat No.: H79) amino acid residue Ser with Tyr, substitution of the 97th (Kabat No.: H93) amino acid residue Ala with Thr, and substitution of the 102nd (Kabat No.: H98) amino acid residue Ser with Thr;

(2) having, the amino acid sequence defined in SEQ ID NO:46 or an amino acid sequence derived from SEQ ID NO:46 via substitution of the 82nd (Kabat No.: H81) amino acid residue Gln with Lys;

(3) having, the amino acid sequence defined in SEQ ID NO:58 or an amino acid sequence derived from SEQ ID NO:58 via one or more substitutions selected from the group consisting of: substitution of the 13th (Kabat No.: H13) amino acid residue Gln with Arg, substitution of the 23rd (Kabat No.: H23) amino acid residue Ala with Ser, substitution of the 31st (Kabat No.: H31) amino acid residue Asp with Glu, 49th (Kabat No.: H49) amino acid residue Ala with Gly, substitution of the 58th (Kabat No.: H55) amino acid residue Tyr with Ser, substitution of the 66th (Kabat No.: H63) amino acid residue Val with Ile, substitution of the 79th (Kabat No.: H76) amino acid residue Arg with Ser, substitution of the 86th (Kabat No.: H82A) amino acid residue Phe with Tyr or Asn, substitution of the 100th (Kabat No.: H94) amino acid residue Ser with Arg, substitution of the 109th (Kabat No.: H100C) amino acid residue Ser with Gly, and substitution of the 117th (Kabat No.: H105) amino acid residue His with Gln;

(4) having, the amino acid sequence defined in SEQ ID NO:44 or an amino acid sequence derived from SEQ ID NO:44 via one or more substitutions selected from the group consisting of: substitution of the 3rd (Kabat No.: H3) amino acid residue Gln with His, substitution of the 10th (Kabat No.: H10) amino acid residue Glu with Ala or Gly, substitution of the 16th (Kabat No.: H16) amino acid residue Thr with Ala, substitution of the 19th (Kabat No.: H19) amino acid residue Lys with Arg, substitution of the 24th (Kabat No.: H24) amino acid residue Val with Ile, substitution of the 30th (Kabat No.: H30) amino acid residue Thr with Ser, substitution of the 31st (Kabat No.: H31) amino acid residue Arg with Ala, substitution of the 57th (Kabat No.: H56) amino acid residue Thr with Ser, substitution of the 66th (Kabat No.: H65) amino acid residue Lys with Asn, substitution of the 67th (Kabat No.: H66) amino acid residue Lys with Arg, substitution of the 74th (Kabat No.: H73) amino acid residue Ala with Val, substitution of the 77th (Kabat No.: H76) amino acid residue Asn with Asp or Ser, substitution of the 80th (Kabat No.: H79) amino acid residue Tyr with Ser, substitution of the 83rd (Kabat No.: H82) amino acid residue Phe with Leu, substitution of the 85th (Kabat No.: H82B) amino acid residue Gly with Ser, substitution of the 89th (Kabat No.: H85) amino acid residue Glu with Asp, and substitution of the 91st (Kabat No.: H87) amino acid residue Thr with Ser; and (5) having, an amino acid sequence selected from SEQ ID NO:52, SEQ ID NO:36, or SEQ ID NO:48.

The SPNS2 neutralizing antibody according to this embodiment should more preferably contain, as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 or SEQ ID NO:62.

An embodiment of the SPNS2 neutralizing antibody according to the present invention is an antibody containing a light chain variable region having an amino acid sequence having a homology of 80% or more, preferably 90% or more, more preferably 95% or more to a sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO:94.

Another embodiment of the SPNS2 neutralizing antibody according to the present invention is an antibody containing a light chain variable region having an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, or an amino acid sequence derived from an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, via substitution, deletion, or addition of one or more amino acid residues, preferably via substitution, deletion, or addition of one or more amino acid residues in the 1st to 12th positions of the sequence.

The SPNS2 neutralizing antibody according to this embodiment should preferably contain, as a light chain variable region that satisfy any one of the features (1) to (5) below:

(1) having, the amino acid sequence defined in SEQ ID NO:88 or an amino acid sequence derived from SEQ ID NO:88 via one or more substitutions selected from the group consisting of: substitution of the 23rd (Kabat No.: L24) amino acid residue with an amino acid residue other than Thr, substitution of the 26th (Kabat No.: L27) amino acid residue with an amino acid residue other than Ile, substitution of the 38th (Kabat No.: L37) amino acid residue with an amino acid residue other than Lys, substitution of the 48th (Kabat No.: L47) amino acid residue with an amino acid residue other than Met, substitution of the 80th (Kabat No.: L77) amino acid residue with an amino acid residue other than Asn, substitution of the 86th (Kabat No.: L83) amino acid residue with an amino acid residue other than Glu, substitution of the 96th (Kabat No.: L93) amino acid residue with an amino acid residue other than Ser, substitution of the 98th (Kabat No.: L95) amino acid residue with an amino acid residue other than Met, substitution of the 102nd (Kabat No.: L99) amino acid residue with an amino acid residue other than Gly, and substitution of the 106th (Kabat No.: L103) amino acid residue with an amino acid residue other than Lys;

(2) having, the amino acid sequence defined in SEQ ID NO:78 or an amino acid sequence derived from SEQ ID NO:78 via substitution of the 48th (Kabat No.: L47) amino acid residue with an amino acid residue other than Leu and/or substitution of the 106th (Kabat No.: L103) amino acid residue with an amino acid residue other than Lys;

(3) having, the amino acid sequence defined in SEQ ID NO:90 or an amino acid sequence derived from SEQ ID NO:90 via substitution of 9th (Kabat No.: L9) amino acid residue with an amino acid residue other than Ala, substitution of the 39th (Kabat No.: L39) amino acid residue with an amino acid residue other than Lys, substitution of the 42nd (Kabat No.: L42) amino acid residue with an amino acid residue other than Gly, substitution of the 55th (Kabat No.: L55) amino acid residue with an amino acid residue other than Ile, substitution of the 56th (Kabat No.: L56) amino acid residue with an amino acid residue other than Ser, substitution of the 72nd (Kabat No.: L72) amino acid residue with an amino acid residue other than Thr, substitution of the 74th (Kabat No.: L74) amino acid residue with an amino acid residue other than Arg, substitution of the 91st (Kabat No.: L91) amino acid residue with an amino acid residue other than Thr, substitution of the 93rd (Kabat No.: L93) amino acid residue with an amino acid residue other than Ser, substitution of the 100th (Kabat No.: L100) amino acid residue with an amino acid residue other than Ser, substitution of the 103rd (Kabat No.: L103) amino acid residue with an amino acid residue other than Arg, and substitution of the 106th (Kabat No.: L106) amino acid residue with an amino acid residue other than Ile;

(4) having, the amino acid sequence defined in SEQ ID NO:76 or an amino acid sequence derived from SEQ ID NO:76 via one or more substitutions selected from the group consisting of: substitution of the 13th (Kabat No.: L13) amino acid residue with an amino acid residue other than Thr, substitution of the 22nd (Kabat No.: L22) amino acid residue with an amino acid residue other than Arg, substitution of the 25th (Kabat No.: L25) amino acid residue with an amino acid residue other than Ala, substitution of the 28th (Kabat No.: L28) amino acid residue with an amino acid residue other than Asn, substitution of the 31st (Kabat No.: L31) amino acid residue with an amino acid residue other than Ser, substitution of the 69th (Kabat No.: L69) amino acid residue with an amino acid residue other than Thr, substitution of the 79th (Kabat No.: L79) amino acid residue with an amino acid residue other than Gln, and substitution of the 80th (Kabat No.: L80) amino acid residue with an amino acid residue other than Pro; and (5) having, an amino acid sequence selected from SEQ ID NO:84, SEQ ID NO:68, or SEQ ID NO:80.

The SPNS2 neutralizing antibody according to this embodiment should more preferably contain, as a light chain variable region that satisfy any one of the features (1) to (5) below:

(1) having, the amino acid sequence defined in SEQ ID NO:88 or an amino acid sequence derived from SEQ ID NO:88 via one or more substitutions selected from the group consisting of: substitution of the 23rd (Kabat No.: L24) amino acid residue Thr with Lys, substitution of the 26th (Kabat No.: L27) amino acid residue Ile with Thr, substitution of the 38th (Kabat No.: L37) amino acid residue Lys with Gln, substitution of the 48th (Kabat No.: L47) amino acid residue Met with Leu, substitution of the 80th (Kabat No.: L77) amino acid residue Asn with Ser, substitution of the 86th (Kabat No.: L83) amino acid residue Glu with Gly, substitution of the 96th (Kabat No.: L93) amino acid residue Ser with Asn, substitution of the 98th (Kabat No.: L95) amino acid residue Met with Ile, substitution of the 102nd (Kabat No.: L99) amino acid residue Gly with Ala, substitution of the and 106th (Kabat No.: L103) amino acid residue Lys with Thr or Gln;

(2) having, the amino acid sequence defined in SEQ ID NO:78 or an amino acid sequence derived from SEQ ID NO:78 via substitution of the 48th (Kabat No.: L47) amino acid residue Leu with Met and/or substitution of the 106th (Kabat No.: L103) amino acid residue Lys with Thr;

(3) having, the amino acid sequence defined in SEQ ID NO:90 or an amino acid sequence derived from SEQ ID NO:90 via one or more substitutions selected from the group consisting of: substitution of the 9th (Kabat No.: L9) amino acid residue Ala with Pro, substitution of the 39th (Kabat No.: L39) amino acid residue Lys with Arg, substitution of the 42nd (Kabat No.: L42) amino acid residue Gly with Glu, substitution of the 55th (Kabat No.: L55) amino acid residue Ile with Met, substitution of the 56th (Kabat No.: L56) amino acid residue Ser with Ala, substitution of the 72nd (Kabat No.: L72) amino acid residue Thr with Ile, substitution of the 74th (Kabat No.: L74) amino acid residue Arg with Ser, substitution of the 91st (Kabat No.: L91) amino acid residue Thr with Ser, substitution of the 93rd (Kabat No.: L93) amino acid residue Ser with Asn, substitution of the 100th (Kabat No.: L100) amino acid residue Ser with Pro, substitution of the 103rd (Kabat No.: L103) amino acid residue Arg with Lys, substitution of the and 106th (Kabat No.: L106) amino acid residue Ile with Val;

(4) having, the amino acid sequence defined in SEQ ID NO:76 or an amino acid sequence derived from SEQ ID NO:76 via one or more substitutions selected from the group consisting of: substitution of the 13th (Kabat No.: L13) amino acid residue Thr with Ala, substitution of the 22nd (Kabat No.: L22) amino acid residue Arg with Ser, substitution of the 25th (Kabat No.: L25) amino acid residue Ala with Pro, substitution of the 28th (Kabat No.: L28) amino acid residue Asn with Ser, substitution of the 31st (Kabat No.: L31) amino acid residue Ser with Asn, substitution of the 69th (Kabat No.: L69) amino acid residue Thr with Ser, substitution of the 79th (Kabat No.: L79) amino acid residue Gln with Arg, substitution of the and 80th (Kabat No.: L80) amino acid residue Pro with Ala; and (5) having, an amino acid sequence selected from SEQ ID NO:84, SEQ ID NO:68, or SEQ ID NO:80.

The SPNS2 neutralizing antibody according to this embodiment should more preferably contain, as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

An embodiment of the SPNS2 neutralizing antibody according to the present invention is an antibody containing, as a heavy chain variable region, an amino acid sequence having a homology of 80% or more, preferably 90% or more, more preferably 95% or more to a sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62 and, as a light chain variable region, an amino acid sequence having a homology of 80% or more, preferably 90% or more, more preferably 95% or more to a sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94.

Another embodiment of the SPNS2 neutralizing antibody according to the present invention is an antibody containing:

as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62, or an amino acid sequence derived from an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 and SEQ ID NO:62, via substitution, deletion, or addition of one or more amino acid residues, preferably via substitution, deletion, or addition of one or more amino acid residues in the 1st to 17th positions of the sequence; and as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, or an amino acid sequence derived from an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94, via substitution, deletion, or addition of one or more amino acid residues, preferably via substitution, deletion, or addition of one or more amino acid residues in the 1st to 12nd positions of the sequence.

The SPNS2 neutralizing antibody according to this embodiment should preferably contain, as a heavy chain variable region and a light chain variable region that satisfy any one of the features (1) to (5) below:

(1) as a heavy chain variable region, the amino acid sequence defined in SEQ ID NO:42 or an amino acid sequence derived from SEQ ID NO:42 via one or more substitutions selected from the group consisting of: substitution of the 1st (Kabat No.: H1) amino acid residue with an amino acid other than Glu, substitution of the 6th (Kabat No.: H6) amino acid residue with an amino acid other than Gly, substitution of the 23rd (Kabat No.: H23) amino acid residue with an amino acid other than Glu, substitution of the 43rd (Kabat No.: H43) amino acid residue with an amino acid other than Lys, substitution of the 50th (Kabat No.: H50) amino acid residue with an amino acid other than Thr, substitution of the 75th (Kabat No.: H74) amino acid residue with an amino acid other than Ala, substitution of the 76th (Kabat No.: H75) amino acid residue with an amino acid other than Arg, substitution of the 78th (Kabat No.: H77) amino acid residue with an amino acid other than Thr, substitution of the 80th (Kabat No.: H79) amino acid residue with an amino acid other than Ser, substitution of the 97th (Kabat No.: H93) amino acid residue with an amino acid other than Ala, and substitution of the 102nd (Kabat No.: H98) amino acid residue with an amino acid other than Ser, and as a light chain variable region, the amino acid sequence defined in SEQ ID NO:88 or an amino acid sequence derived from SEQ ID NO:88 via one or more substitutions selected from the group consisting of: substitution of the 23rd (Kabat No.: L24) amino acid residue with an amino acid other than Thr, substitution of the 26th (Kabat No.: L27) amino acid residue with an amino acid other than Ile, substitution of the 38th (Kabat No.: L37) amino acid residue with an amino acid other than Lys, substitution of the 48th (Kabat No.: L47) amino acid residue with an amino acid other than Met, substitution of the 80th (Kabat No.: L77) amino acid residue Asn with Ser, substitution of 86th (Kabat No.: L83) amino acid residue with an amino acid other than Glu, substitution of the 96th (Kabat No.: L93) amino acid residue with an amino acid other than Ser, substitution of the 98th (Kabat No.: L95) amino acid residue with an amino acid other than Met, substitution of the 102nd (Kabat No.: L99) amino acid residue with an amino acid other than Gly, and substitution of the 106th (Kabat No.: L103) amino acid residue with an amino acid other than Lys;

(2) as a heavy chain variable region, the amino acid sequence defined in SEQ ID NO:46 or an amino acid sequence derived from SEQ ID NO:46 via substitution of the 82nd (Kabat No.: H81) amino acid residue with an amino acid other than Gln, and as a light chain variable region, the amino acid sequence defined in SEQ ID NO:78 or an amino acid sequence derived from SEQ ID NO:78 via substitution of the 48th (Kabat No.: L47) amino acid residue with an amino acid other than Leu and/or substitution of the 106th (Kabat No.: L103) amino acid residue with an amino acid other than Lys;

(3) as a heavy chain variable region, the amino acid sequence defined in SEQ ID NO:58 or an amino acid sequence derived from SEQ ID NO:58 via one or more substitutions selected from the group consisting of: substitution of the 13th (Kabat No.: H13) amino acid residue with an amino acid other than Gln, substitution of the 23rd (Kabat No.: H23) amino acid residue with an amino acid other than Ala, substitution of the 31st (Kabat No.: H31) amino acid residue with an amino acid other than Asp, substitution of the 49th (Kabat No.: H49) amino acid residue with an amino acid other than Ala, substitution of the 58th (Kabat No.: H55) amino acid residue with an amino acid other than Tyr, substitution of the 66th (Kabat No.: H63) amino acid residue with an amino acid other than Val, substitution of the 79th (Kabat No.: H76) amino acid residue with an amino acid other than Arg, substitution of the 86th (Kabat No.: H82A) amino acid residue with an amino acid other than Phe, substitution of the 100th (Kabat No.: H94) amino acid residue with an amino acid other than Ser, substitution of the 109th (Kabat No.: H100C) amino acid residue with an amino acid other than Ser, and substitution of the 117th (Kabat No.: H105) amino acid residue with an amino acid other than His, and as a light chain variable region, the amino acid sequence defined in SEQ ID NO:90 or an amino acid sequence derived from SEQ ID NO:90 via one or more substitutions selected from the group consisting of: substitution of the 9th (Kabat No.: L9) amino acid residue with an amino acid other than Ala, substitution of the 39th (Kabat No.: L39) amino acid residue with an amino acid other than Lys, substitution of the 42nd (Kabat No.: L42) amino acid residue with an amino acid other than Gly, substitution of the 55th (Kabat No.: L55) amino acid residue with an amino acid other than Ile, substitution of the 56th (Kabat No.: L56) amino acid residue with an amino acid other than Ser, substitution of the 72nd (Kabat No.: L72) amino acid residue with an amino acid other than Thr, substitution of the 74th (Kabat No.: L74) amino acid residue with an amino acid other than Arg, substitution of the 91st (Kabat No.: L91) amino acid residue with an amino acid other than Thr, substitution of the 93rd (Kabat No.: L93) amino acid residue with an amino acid other than Ser, substitution of the 100th (Kabat No.: L100) amino acid residue with an amino acid other than Ser, substitution of the 103rd (Kabat No.: L103) amino acid residue with an amino acid other than Arg, and substitution of the 106th (Kabat No.: L106) amino acid residue with an amino acid other than Ile;

(4) as a heavy chain variable region, the amino acid sequence defined in SEQ ID NO:44 or an amino acid sequence derived from SEQ ID NO:44 via one or more substitutions selected from the group consisting of: substitution of the 3rd (Kabat No.: H3) amino acid residue with an amino acid other than Gln, substitution of the 10th (Kabat No.: H10) amino acid residue with an amino acid other than Glu, substitution of the 16th (Kabat No.: H16) amino acid residue with an amino acid other than Thr, substitution of the 19th (Kabat No.: H19) amino acid residue with an amino acid other than Lys, substitution of the 24th (Kabat No.: H24) amino acid residue with an amino acid other than Val, substitution of the 30th (Kabat No.: H30) amino acid residue with an amino acid other than Thr, substitution of the 31st (Kabat No.: H31) amino acid residue with an amino acid other than Arg, substitution of the 57th (Kabat No.: H56) amino acid residue with an amino acid other than Thr, substitution of the 66th (Kabat No.: H65) amino acid residue with an amino acid other than Lys, substitution of the 67th (Kabat No.: H66) amino acid residue with an amino acid other than Lys, substitution of the 74th (Kabat No.: H73) amino acid residue with an amino acid other than Ala, substitution of the 77th (Kabat No.: H76) amino acid residue with an amino acid other than Asn, substitution of the 80th (Kabat No.: H79) amino acid residue with an amino acid other than Tyr, substitution of the 83rd (Kabat No.: H82) amino acid residue with an amino acid other than Phe, substitution of the 85th (Kabat No.: H82B) amino acid residue with an amino acid other than Gly, substitution of the 89th (Kabat No.: H85) amino acid residue with an amino acid other than Glu, and substitution of the 91st (Kabat No.: H87) amino acid residue with an amino acid other than Thr, and as a light chain variable region, the amino acid sequence defined in SEQ ID NO:76 or an amino acid sequence derived from SEQ ID NO:76 via one or more substitutions selected from the group consisting of: substitution of the 13th (Kabat No.: L13) amino acid residue with an amino acid other than Thr, substitution of the 22nd (Kabat No.: L22) amino acid residue with an amino acid other than Arg, substitution of the 25th (Kabat No.: L25) amino acid residue with an amino acid other than Ala, substitution of the 28th (Kabat No.: L28) amino acid residue with an amino acid other than Asn, substitution of the 31st (Kabat No.: L31) amino acid residue with an amino acid other than Ser, substitution of the 69th (Kabat No.: L69) amino acid residue with an amino acid other than Thr, substitution of the 79th (Kabat No.: L79) amino acid residue with an amino acid other than Gln, and substitution of the 80th (Kabat No.: L80) amino acid residue with an amino acid other than Pro; and (5) as a heavy chain variable region, an amino acid sequence selected from SEQ ID NO:52, SEQ ID NO:36, or SEQ ID NO:48, and as a light chain variable region, an amino acid sequence selected from SEQ ID NO:84, SEQ ID NO:68, or SEQ ID NO:80.

The SPNS2 neutralizing antibody according to this embodiment should more preferably contain, as a heavy chain variable region and a light chain variable region that satisfy any one of the features (1) to (5) below:
(1) as a heavy chain variable region, the amino acid sequence defined in SEQ ID NO:42 or an amino acid sequence derived from SEQ ID NO:42 via one or more substitutions selected from the group consisting of: substitution of the 1st (Kabat No.: H1) amino acid residue Glu with Ala, substitution of the 6th (Kabat No.: H6) amino acid residue Gly with Glu, substitution of the 23rd (Kabat No.: H23) amino acid residue Glu with Ala, substitution of the 43rd (Kabat No.: H43) amino acid residue Lys with Arg, substitution of the 50th (Kabat No.: H50) amino acid residue Thr with Ser, substitution of the 75th (Kabat No.: H74) amino acid residue Ala with Thr, substitution of the 76th (Kabat No.: H75) amino acid residue Arg with Lys, substitution of the 78th (Kabat No.: H77) amino acid residue Thr with Ile, substitution of the 80th (Kabat No.: H79) amino acid residue Ser with Tyr, substitution of the 97th (Kabat No.: H93) amino acid residue Ala with Thr, and substitution of the 102nd (Kabat No.: H98) amino acid residue Ser with Thr, and as a light chain variable region, the amino acid sequence defined in SEQ ID NO:88 or an amino acid sequence derived from SEQ ID NO:88 via one or more substitutions selected from the group consisting of: substitution of the 23rd (Kabat No.: L24) amino acid residue Thr with Lys, substitution of the 26th (Kabat No.: L27) amino acid residue Ile with Thr, substitution of the 38th (Kabat No.: L37) amino acid residue Lys with Gln, substitution of the 48th (Kabat No.: L47) amino acid residue Met with Leu, substitution of the 80th (Kabat No.: L77) amino acid residue Asn with Ser, substitution of the 86th (Kabat No.: L83) amino acid residue Glu with Gly, substitution of the 96th (Kabat No.: L93) amino acid residue Ser with Asn, substitution of the 98th (Kabat No.: L95) amino acid residue Met with Ile, substitution of the 102nd (Kabat No.: L99) amino acid residue Gly with Ala, and substitution of the 106th (Kabat No.: L103) amino acid residue Lys with Thr or Gln;
(2) as a heavy chain variable region, the amino acid sequence defined in SEQ ID NO:46 or an amino acid sequence derived from SEQ ID NO:46 via substitution of the 82nd (Kabat No.: H81) amino acid residue Gln with Lys, and as a light chain variable region, the amino acid sequence defined in SEQ ID NO:78 or an amino acid sequence derived from SEQ ID NO:78 via substitution of the 48th (Kabat No.: L47) amino acid residue Leu with Met and/or substitution of the 106th (Kabat No.: L103) amino acid residue Lys with Thr;
(3) as a heavy chain variable region, the amino acid sequence defined in SEQ ID NO:58 or an amino acid sequence derived from SEQ ID NO:58 via one or more substitutions selected from the group consisting of: substitution of the 13th (Kabat No.: H13) amino acid residue Gln with Arg, substitution of the 23rd (Kabat No.: H23) amino acid residue Ala with Ser, substitution of the 31st (Kabat No.: H31) amino acid residue Asp with Glu, 49th (Kabat No.: H49) amino acid residue Ala with Gly, substitution of the 58th (Kabat No.: H55) amino acid residue Tyr with Ser, substitution of the 66th (Kabat No.: H63) amino acid residue Val with Ile, substitution of the 79th (Kabat No.: H76) amino acid residue Arg with Ser, substitution of the 86th (Kabat No.: H82A) amino acid residue Phe with Tyr or Asn, substitution of the 100th (Kabat No.: H94) amino acid residue Ser with Arg, substitution of the 109th (Kabat No.: H100C) amino acid residue Ser with Gly, and substitution of the 117th (Kabat No.: H105) amino acid residue His with Gln, and as a light chain variable region, the amino acid sequence defined in SEQ ID NO:90 or an amino acid sequence derived from SEQ ID NO:90 via one or more substitutions selected from the group consisting of: substitution of the 9th (Kabat No.: L9) amino acid residue Ala with Pro, substitution of the 39th (Kabat No.: L39) amino acid residue Lys with Arg, substitution of the 42nd (Kabat No.: L42) amino acid residue Gly with Glu, substitution of the 55th (Kabat No.: L55) amino acid residue Ile with Met, substitution of the 56th (Kabat No.: L56) amino acid residue Ser with Ala, substitution of the 72nd (Kabat No.: L72) amino acid residue Thr with Ile, substitution of the 74th (Kabat No.: L74) amino acid residue Arg with Ser, substitution of the 91st (Kabat No.: L91) amino acid residue Thr with Ser, substitution of the 93rd (Kabat No.: L93) amino acid residue Ser with Asn, substitution of the 100th (Kabat No.: L100) amino acid residue Ser with Pro, substitution of the 103rd (Kabat No.: L103) amino acid residue Arg with Lys, and substitution of the 106th (Kabat No.: L106) amino acid residue Ile with Val;
(4) as a heavy chain variable region, the amino acid sequence defined in SEQ ID NO:44 or an amino acid sequence derived from SEQ ID NO:44 via one or more substitutions selected from the group consisting of: substitution of the 3rd (Kabat No.: H3) amino acid residue Gln with His, substitution of the 10th (Kabat No.: H10) amino acid residue Glu with Ala or Gly, substitution of the 16th (Kabat No.: H16) amino acid residue Thr with Ala, substitution of the 19th (Kabat No.: H19) amino acid residue Lys with Arg, substitution of the 24th (Kabat No.: H24) amino acid residue Val with Ile, substitution of the 30th (Kabat No.: H30) amino acid residue Thr with Ser, substitution of the 31st (Kabat No.: H31) amino acid residue Arg with Ala, substitution of the 57th (Kabat No.: H56) amino acid residue Thr with Ser, substitution of the 66th (Kabat No.: H65) amino acid residue Lys with Asn, substitution of the 67th (Kabat No.: H66) amino acid residue Lys with Arg, substitution of the 74th (Kabat No.: H73) amino acid residue Ala with Val, substitution of the 77th (Kabat No.: H76) amino acid residue Asn with Asp or Ser, substitution of the 80th (Kabat No.: H79) amino acid residue Tyr with Ser, substitution of the 83rd (Kabat No.: H82) amino acid residue Phe with Leu, substitution of the 85th (Kabat No.: H82B) amino acid residue Gly with Ser, substitution of the 89th (Kabat No.: H85) amino acid residue Glu with Asp, and substitution of the 91st (Kabat No.: H87) amino acid residue Thr with Ser, and as a light chain variable region, the amino acid sequence defined in SEQ ID NO:76 or an amino acid sequence derived from SEQ ID NO:76 via one or more substitutions selected from the group consisting of: substitution of the 13th (Kabat No.: L13) amino acid residue Thr with Ala, substitution of the 22nd (Kabat No.: L22) amino acid residue Arg with Ser, substitution of the 25th (Kabat No.: L25) amino acid residue Ala with Pro, substitution of the 28th (Kabat No.: L28) amino acid residue Asn with Ser, substitution of the 31st (Kabat No.: L31) amino acid residue Ser with Asn, substitution of the 69th (Kabat No.: L69) amino acid residue Thr with Ser, substitution of the 79th (Kabat No.: L79) amino acid residue Gln with Arg, and substitution of the 80th (Kabat No.: L80) amino acid residue Pro with Ala; and
(5) as a heavy chain variable region, an amino acid sequence selected from SEQ ID NO:52, SEQ ID NO:36, or SEQ ID NO:48, and as a light chain variable region, an amino acid sequence selected from SEQ ID NO:84, SEQ ID NO:68, or SEQ ID NO:80.

The SPNS2 neutralizing antibody according to this embodiment should more preferably contain, as a heavy chain variable region, an amino acid sequence selected from SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60 or SEQ ID NO:62 and, as a light chain variable region, an amino acid sequence selected from SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO:94.

An embodiment of the SPNS2 neutralizing antibody according to the present invention is an antibody:

(1) comprising, as a heavy chain variable region, the amino acid sequence defined in SEQ ID NO:34 and, as a light chain variable region, the amino acid sequence defined in SEQ ID NO:66.
(2) comprising, as a heavy chain variable region, the amino acid sequence defined in SEQ ID NO:36 and, as a light chain variable region, the amino acid sequence defined in SEQ ID NO:68.
(3) comprising, as a heavy chain variable region, the amino acid sequence defined in SEQ ID NO:38 and, as a light chain variable region, the amino acid sequence defined in SEQ ID NO:70.
(4) comprising, as a heavy chain variable region, the amino acid sequence defined in SEQ ID NO:40 and, as a light chain variable region, the amino acid sequence defined in SEQ ID NO:72.
(5) comprising, as a heavy chain variable region, the amino acid sequence defined in SEQ ID NO:42 and, as a light chain variable region, the amino acid sequence defined in SEQ ID NO:74.
(6) comprising, as a heavy chain variable region, the amino acid sequence defined in SEQ ID NO:44 and, as a light chain variable region, the amino acid sequence defined in SEQ ID NO:76.
(7) comprising, as a heavy chain variable region, the amino acid sequence defined in SEQ ID NO:46 and, as a light chain variable region, the amino acid sequence defined in SEQ ID NO:78.
(8) comprising, as a heavy chain variable region, the amino acid sequence defined in SEQ ID NO:48 and, as a light chain variable region, the amino acid sequence defined in SEQ ID NO:80.
(9) comprising, as a heavy chain variable region, the amino acid sequence defined in SEQ ID NO:50 and, as a light chain variable region, the amino acid sequence defined in SEQ ID NO:82.
(10) comprising, as a heavy chain variable region, the amino acid sequence defined in SEQ ID NO:52 and, as a light chain variable region, the amino acid sequence defined in SEQ ID NO:84.
(11) comprising, as a heavy chain variable region, the amino acid sequence defined in SEQ ID NO:54 and, as a light chain variable region, the amino acid sequence defined in SEQ ID NO:86.
(12) comprising, as a heavy chain variable region, the amino acid sequence defined in SEQ ID NO:56 and, as a light chain variable region, the amino acid sequence defined in SEQ ID NO:88.
(13) comprising, as a heavy chain variable region, the amino acid sequence defined in SEQ ID NO:58 and, as a light chain variable region, the amino acid sequence defined in SEQ ID NO:90.
(14) comprising, as a heavy chain variable region, the amino acid sequence defined in SEQ ID NO:60 and, as a light chain variable region, the amino acid sequence defined in SEQ ID NO:92.
(15) comprising, as a heavy chain variable region, the amino acid sequence defined in SEQ ID NO:62 and, as a light chain variable region, the amino acid sequence defined in SEQ ID NO:94.

Examples of the method of identifying each sequence of CDR-H1, CDR-H2, CDR-H3, CDR-L1, CDR-L2, or CDR-L3 in the antibody include a Kabat method (Kabat et al., The Journal of Immunology, 1991, Vol. 147, No. 5, pp. 1709-1719) and a Chothia method (Al-Lazikani et al., Journal of Molecular Biology, 1997, Vol. 273, No. 4, pp. 927-948). These methods are technically common for those skilled in the art, and the outline of the method is available from, for example, the Internet website of Dr. Andrew C.R. Martin's Group (bioinforg.uk/abs/).

The immunoglobulin that is the antibody of the present invention has preferably a framework sequence in each class of vertebrate immunoglobulin, and in particular, preferably a framework sequence in each class of the immunoglobulin of human or non-human animal including mouse or rat.

Through appropriate combination of the amino acid sequences of each framework region and/or each constant region in the heavy and light chains of the human antibody with the amino acid sequences of each CDR and/or each variable region in the heavy chain and light chains as described above, those skilled in the art can design a humanized SPNS2 neutralizing antibody of the present invention. The amino acid sequence of each framework region and/or each constant region in the heavy and light chains of the humanized antibody can be selected from, for example, each class of human IgG, IgA, IgM, IgE, IgD or mutants thereof.

In the SPNS2 neutralizing antibody of the present invention, the antibody of the present invention or antigen-binding fragment thereof is preferably a human IgG class or a mutant thereof, a human IgG4 subclass or a human IgG1 subclass or mutants thereof. In one example, a stabilized IgG4 constant region contains proline at position 241 of the hinge region in the Kabat system. This position corresponds to position 228 of the hinge region based on the EU numbering system (by Kabat et al.) and the sequence of protein in immunological interest (Washington D.C. United States, Department of Health and Human Services 2001, and Edelman et al., Proc. Natl. Acad. Sci USA, 63, 78-85, 1969). A residue in human IgG4 is generally serine, and can be induced to stabilize by replacing serine with proline. In one example, the incorporation of N297A mutation in the constant region of IgG1 can decrease the binding ability to Fc receptors and/or the anchoring ability of complements as much as possible.

[Competitive Binding]

Antibodies competitively binding to the SPNS2 neutralizing antibody and SPNS2 of the present invention are also included in the scope of the present invention. In the present invention, the term "competitive binding" indicates a phenomenon in which the binding of one antibody to an antigen is inhibited due to the binding of the other antibody to the antigen under the coexisting condition of multiple types of monoclonal antibodies and the antigen. In general, a specific amount (concentration) of one monoclonal antibody can be measured by determining an additive amount (concentration) of the other monoclonal antibody that the amount of one monoclonal antibody bound to the antigen decreases as the amount (concentration) of the other monoclonal antibody increases. The inhibitory activity can be expressed by an $IC_{50}$ or Ki value. The monoclonal antibody that competitively binds to the SPNS2 neutralizing antibody of the present invention refers to the antibody having an $IC_{50}$ value of usually 1000 nM or less, preferably 100 nM or less, more preferably 10 nM or less when an antigen-antibody binding is detected using the SPNS2 neutralizing antibody, for example, the SPNS2 neutralizing antibody at 10 nM. In the measurement of the competitive binding, an antibody to be used is labeled with, for example, an enzyme, a fluorescent substance, a luminescent substance, and a radioactive isotope, and can be measured through the detection by the method suitable for the physical and/or chemical properties of the labeled substances.

[Method for Producing SPNS2 Neutralizing Antibody]

The antibodies of the present invention can be produced by known processes to those skilled in the art. The antibody of the present invention is a polyclonal antibody or a monoclonal antibody (Milstein et al., Nature (England) published on Oct. 6, 1983, Volume 305 No. 5934, pp. 537-540). For example, the polyclonal antibody can be produced from SPNS2 of SEQ ID NO: 1 expressing-cells or a peptide as an antigen comprising the amino acid sequence SEQ ID NO: 3, SEQ ID NO: 4, SEQ ID NO: 5, SEQ ID NO: 6, SEQ ID NO: 7, or SEQ ID NO: 8. Alternatively, nucleotides of SPNS2 of SEQ ID NO: 2 is administered to the muscle or subcutaneously in a mammal to express and sensitize an antigen in the animal to be sensitized and then the polyclonal antibody can be recovered from the serum of the sensitized animal. When a peptide is used as an antigen, the antigen can be used in the form bound to, for example, a carrier protein such as BSA or KLH, and polylysine.

The monoclonal antibody of the present invention can be given through the following steps: administering the nucleotide of SPNS2 of SEQ ID NO: 2 to the animal to produce the antigen in the body of the animal; removing immune cells from the mammal sensitized with the produced antigen to yield hybridomas by cell fusion with myeloma cells; and cloning the hybridomas to recover the monoclonal antibody from the culture of the hybridomas. A method of producing such a monoclonal antibody is described in Example 6. Example of the monoclonal antibody produced by the method include, but is not limited to, a monoclonal antibody having the VH amino acid sequence of SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 and SEQ ID NO: 62, and the VL amino acid sequence of SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, and SEQ ID NO:94.

The resultant monoclonal antibody can also comprise a nucleic acid molecule having a gene sequence encoding an amino acid of a protein of the antibody. A method of producing such a gene sequence is described in Example 8. Examples of the monoclonal antibody produced by the method include, but is not limited to, a gene encoding the VH amino acid sequence of SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, and SEQ ID NO: 63, and a gene encoding the VL amino acid sequence of SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, and SEQ ID NO:95.

A genetically engineered antibody can be also produced with such a nucleic acid molecule. The techniques relating to genetic information on the antibody are useful for the modification of the H chain and the L chain and variable regions thereof using the information, such as CDR sequences to improve, for example, the binding ability and specificity of the antibody, and the production of the antibody having a structure suitable for therapeutic agents by converting the antibody from an animal, such as a mouse to a humanized antibody. These techniques are widely known to those skilled in the art. Alternatively, a human monoclonal antibody can be yielded using a non-human-transgenic animal that sensitizes the antigen into which a human antibody gene is introduced. Meanwhile, those skilled in the art can also apply a method that requires no sensitization to animals to produce a human antibody using a phage library (a human antibody phage display) expressing the variable region of human antibody or a part thereof to give a phage clone consisting of an antibody or a specific amino acid sequence that specifically binds to the corresponding antigen (see, for example, a review by Taketo Tanaka et al., Keio J. Med., Volume 60, pp 37-46).

In one method of producing the monoclonal antibody described above, a hybridoma that can produce each desired antibody is cultured, and the antibody is then purified and removed from the supernatant of the resultant cultured hybridoma by a conventional process. In another method, a gene encoding an antibody from a hybridoma that produces a desired antibody and a phage clone given by a human antibody phage display, more specifically, a gene encoding a heavy chain and/or a light chain of an immunoglobulin is derived, and a vector for expressing the gene is prepared and introduced into a host cell (e.g., a mammalian cell, an insect cell, a microorganism) to allow the antibody to be produced. In this case, those skilled in the art can genetically modify to introduce a desired trait into the genes encoding the heavy chain and/or the light chain of the immunoglobulin, and produce humanized antibodies, antibody chimeric proteins, small molecule antibodies and scaffold antibodies using the structure information relating to the variable region in the heavy chain and/or the light chain of the immunoglobulin or the CDR region through known techniques. In addition, an improvement in antibody performance and the avoidance of side effects can be appropriately achieved by techniques that include the structural modification of the constant region in the antibody or the sugar chain portion in the antibody, which is widely known to those skilled in the art.

The SPNS2 neutralizing antibody of the present invention can be produced through the techniques widely known to those skilled in the art. Specifically, the SPNS2 neutralizing antibody of the present invention is usually a monoclonal antibody (Milstein et al., Nature, 1983, Vol. 305, No. 5934, pp. 537-540), and such a monoclonal antibody can be manufactured by, for example, the following procedures:

For example, a nucleic acid molecule is produced, which encodes the amino acid sequence of a heavy chain and/or a light chain of an immunoglobulin of the SPNS2 neutralizing antibody in the present invention. In this procedure, a vector or a plasmid containing the nucleic acid molecule may be prepared by introducing such a nucleic acid molecule into various vectors or plasmids. A host cell is then transformed with the nucleic acid molecules, vectors, or plasmids described above. Examples of the host cells include eukaryotic cells such as mammalian cells, insect cells, yeast cells or plant cells, and bacterial cells. The transformed host cell is cultured under an appropriate condition to produce an SPNS2 neutralizing antibody of the present invention, and the resultant SPNS2 neutralizing antibody may be isolated from the host cell as needed. Various techniques used in these procedures are well known to those skilled in the art.

The monoclonal antibody can be also manufactured by the following process involving sensitization to animals: A non-human-transgenic animal into which a human antibody gene is introduced is used as an animal to sensitize an antigen, and SPNS2 and/or a partial peptide thereof, for example, is sensitized. Immune cells are removed from the animal and fused with, for example, myeloma cells by cell fusion to give a hybridoma. The hybridoma is then cloned and the antibody can be purified and recovered from the resultant culture supernatant of the hybridoma by a conventional method. A method of producing such a monoclonal antibody is disclosed in, for example, WO2013/180238.

Another technique can be also applied to produce a humanized antibody. The technique comprises: producing a phage clone consist of an antibody that specifically binds to the corresponding antigen and a specific amino acid sequence using a phage library (a human antibody phage display) that expresses the variable region of a desired humanized antibody or a part thereof; and producing the humanized antibody based on the information of the phage clone (for example, see a review of Taketo Tanaka et al., The Keio Journal of Medicine, Vol. 60, pp. 37-46).

In this case, those skilled in the art can produce, for example, an antibody chimeric protein, a low molecular weight antibody, and a scaffold antibody by the modification of the gene encoding the heavy chain and/or the light chain of the immunoglobulin to introduce a desired trait and the use of the structural information of the variable region or the CDR region of the immunoglobulin heavy chain and/or light chain through a known technique. In addition, the improvement in antibody performance and the avoidance of side effects can be appropriately achieved by the techniques that include the modification of the structure of the constant region in the antibody and the sugar chain portion in the antibody, which is widely known to those skilled in the art.

[Medicament Containing SPNS2 Neutralizing Antibody]

The SPNS2 neutralizing antibody of the present invention is available for drugs for the suppression of progress, recurrence, or metastasis of, the treatment of, or the prevention of S1P-related conditions or diseases caused by the behavior to S1P receptors. Specifically, examples of the diseases caused by S1P-related conditions or the behavior to SP receptors, include autoimmune diseases, such as multiple sclerosis, rheumatoid arthritis, psoriasis, ulcerative colitis, Crohn's disease, systemic erythematosus, lupus nephritis, asthma, atopic dermatitis, transplant rejection, systemic ankylosis, type 1 diabetes, optic neuritis, uveitis, cerebral apoplexy, schizophrenia, amyotrophic lateral sclerosis, dermatomyositis, polymyositis, pulmonary fibrosis, Hashimoto's thyroiditis, myasthenia gravis, autoimmune thyroiditis, and Behcet's disease, and the diseases that the SPNS2 neutralizing antibody can be expected as a remedy for cancer, such as neuroblastoma, rhabdomyosarcoma, osteosarcoma, childhood cancer, ovarian cancer, pancreatic cancer, breast cancer, prostate cancer, bone cancer, lung cancer, colorectal cancer, cervical cancer, synovial sarcoma, bladder cancer, stomach cancer, Wilms tumor, metastatic carcinoid and blood vessel diarrhea associated with aggressive intestinal peptide-secreting tumor, vipoma, Verner-Morrison syndrome, Beckwith-Wiedemann syndrome, kidney cancer, renal cell carcinoma, transitional cell carcinoma, Ewing's sarcoma, leukemia, acute lymphoblastic leukemia, brain tumor, glioblastoma, nonglioblastoma brain tumor, meningioma, pituitary adenoma, vestibular schwannoma, undifferentiated neuroectodermal tumor, medulloblastoma, astrocytoma, oligodendroglioma, ventricle ependymoma, and choroid plexiform papilloma. In particular, the SPNS2 neutralizing antibody of the present invention is preferably available for a drug for the prevention or the suppression of a cancer metastasis and/or the recurrence of multiple sclerosis. In addition, the SPNS2 neutralizing antibody of the present invention is superior in the effect that heart rate does not vary upon administration.

The medicament containing the SPNS2 neutralizing antibody of the present invention is formulated in the form of a pharmaceutical composition containing a pharmaceutically acceptable carrier and/or other additives in addition to the SPNS2 neutralizing antibody of the present invention. Formulation with pharmaceutically acceptable carriers and/or other additives may be based on the method described, for example, in "Remington: The Science and Practice of Pharmacy, 20 th EDITION" by Lippincott Williams & Wilkins, 2000 from University of the Sciences in Philadelphia. One form of such a drug may be a solution or its lyophilized form prepared by dissolving, suspending or emulsifying in a sterile aqueous liquid or oily liquid. Examples of the solvent for the solution include distilled water for injection and physiological saline in an aqueous solution. Suitable solubilizing agents, such as alcohol (e.g., ethanol), polyalcohol (e.g., propylene glycol, polyethylene glycol), and nonionic surfactants (e.g., polysorbate 80, polyoxyethylene hardened castor oil 50) may be combined when an osmotic pressure regulating agent (for example, D-glucose, D-sorbitol, D-mannitol, and sodium chloride) is added to the aqueous solution. The oily liquid such as sesame oil and soybean oil may be used as a solvent, and a solubilizing agent such as benzyl benzoate, and benzyl alcohol may be combined. Such a formulation may appropriately contain additives comprising a buffer (e.g., a phosphate buffer, an acetate buffer), a soothing agent (e.g., benzalkonium chloride, procaine hydrochloride), a stabilizer (e.g., human serum albumin, polyethylene glycol), a preservative (e.g., ascorbic acid, erythorbic acid and salt thereof), a coloring agent (e.g., copper chlorophyll, β-carotene, food red No. 2, food blue No. 1), an antiseptic (e.g., paraoxybenzoic acid ester, phenol, benzethonium chloride, benzalkonium chloride), a thickening agent (e.g., hydroxypropyl cellulose, carboxymethyl cellulose and salt thereof), a stabilizing agent (e.g., human serum albumin, mannitol, sorbitol), and scenting agents (e.g., menthol and, citrus fragrances).

Examples of other dosage form of the drug include solid agents, such as powder, tablets, granules, capsules, pills, suppositories and troches. Solid agents to be administered in the form of oral formulations may contain additives, such as excipients (e.g., crystalline cellulose, lactose, and starch), lubricants (e.g., magnesium stearate and talc), bonding agents (e.g., hydroxypropyl cellulose, hydroxypropylmethyl cellulose, and macrogol), and disintegrating agents (e.g., starch, and carboxymethyl cellulose calcium). Further additives, such as preservatives (e.g., benzyl alcohol, chlorobutanol, methyl parahydroxybenzoate, and propyl parahydroxybenzoate), antioxidants, coloring agents, and sweetening agents, can be used as needed. In a further embodiment, drugs for the application to mucous membrane may contain additives, such as adhesives, adhesion enhancers, thickeners, thickening agents (e.g., mucin, agar, gelatin, pectin, carrageenan, sodium alginate, locust bean gum, xanthan gum, tragacanth gum, arabic gum, chitosan, pullulan, waxy starch, sucralfate, cellulose (e.g., hydroxypropylmethyl cellulose, polyglycerin fatty acid ester, alkyl (meth) acrylate copolymer or salts thereof, and polyglycerin fatty acid ester)) in order to mainly impart, for example, adsorbing and retaining properties to the mucous membranes. However, it should be appreciated that those skilled in the art can also appropriately select any other form of the drugs to be administered to the living body, solvent and additive.

The medicament containing the SPNS2 neutralizing antibody of the present invention may contain other known drugs (active ingredients) in addition to the SPNS2 neutralizing antibody of the present invention. Alternatively, the drug containing the SPNS2 neutralizing antibody of the present invention may be combined with other known drugs into a kit. Examples of the active ingredients to be combined with the SPNS2 neutralizing antibody include immunosuppressive agents and analogs thereof, anticancer agents and analogs thereof, SPNS2 neutralizing antibodies and analogs thereof, azelastine, oxatomide, mequitazine, fexofenadine, epinastine, ebastine, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorocyclizine, cyproheptadine, mesalazine, interferon β1b, interferon β1a, fingolimod hydrochloride, natalizumab, glatiramer acetate, dimethyl fumarate, aprelimilast corticosteroid, antiemetics, ondansetron hydrochloride, granisetron hydrochloride, metoclopramide, domperidone, haloperidol, cyclizine, lorazepam, prochlorperazine, dexamethazone, levomepromazine, tropisetron, cancer vaccines, GM-CSF inhibitors, GM-CSF DNA vaccines, cell based vaccines, dendritic cell vaccines, recombinant virus vaccines, heat shock protein (HSP) vaccines, allogeneic tumor vaccines, autologous tumor vaccines, analgesics, ibuprofen, naproxen, choline magnesium trisalicylate, oxycodone hydrochloride, antiangiogenic agents, antithrombotics, anti-PD-1 antibodies, nivolumab, pembrolizumab, atezolizumab, anti-CTLA4 antibodies, ipilimumab, anti-CD20 antibodies, rituximab, anti-HER2 antibody, trastuzumab, anti-CCR4 antibodies, mogamulizumab, anti-VEGF antibodies, bevacizumab, anti-VEGF receptor antibodies, soluble VEGF receptor fragments, anti-TWEAK antibodies, anti-TWEAK receptor antibodies, soluble TWEAK receptor fragments, AMG 706, AMG 386, antiproliferative drugs, farnesyl protein transferase inhibitors, αvβ3 inhibitors, αvβ5 inhibitors, p53 inhibitors, Kit receptor inhibitors, ret receptor inhibitors, PDGFR inhibitors, growth hormone secretion inhibitors, angiopoietin inhibitors, tumor infiltrating macrophage inhibitors, c-fms inhibitors, anti-c-fms antibodies, CSF-1 inhibitors, anti-CSF-1 antibodies, soluble c-fms fragments, pegvisomant, gemcitabine, panitumumab, irinotecan, and SN-38. A dose of the drug other than the formulated SPNS2 neutralizing antibody can be administered in a dose used for ordinary therapy, and can be increased or decreased depending on the situations.

The drug in the present invention can be administered parenterally to ameliorate symptoms. One example of the parenteral administration is nasal preparation in the form of a solution, a suspension, or a solid. Another example of the parenteral administration is injection. Examples of the injection agents include subcutaneous agents, intravenous agents, intravenous drip agents, intramuscular agents, intracerebroventricular agents, and intraperitoneal agents. Examples of the other dosage form for parenteral administration include suppository agents, sublingual agents, transdermal agents, and transmucosal administration agents other than nasal preparation. Topically intravascular administration is also available in the form that contained in or applied to a stent or intravascular obturator.

A dose of the drug in the present invention varies depending on age, sex, body weight, and symptom of the patient, therapeutic effect, administrative method, treatment time, and type of active ingredient contained in the pharmaceutical composition. In general, the does per an adult can be administered with a main agent in a range of 1 mg to 1 g, preferably 0.1 mg to 300 mg, once every 1 to 4 weeks or once every 1 to 2 months. Since the dose and the number of administrations varies depending on various conditions, an amount and frequency less than the above dosages and times may be sufficient, or those exceeding the above ranges may be required in some cases. In conclusion, the drug of the present invention is medicinal in a short administrative period.

EXAMPLES

[Example 1] Gene Cloning

The full-length cDNA encoding human SPNS2 was amplified by PCR with KOD-Plus-Ver. 2 (Toyobo Life Science, KOD-211) from a commercially available human cDNA template (Human MTC Panel II Takara Bio, 636743).

A reaction solution (50 μL) containing commercially available human cDNA (1 μL), a sense primer (1.5 μL) (SEQ ID NO: 9), an anti-sense primer (1.5 μL) (SEQ ID NO: 10), 10×PCR buffer (5 μL) for KOD-Plus, 2 mM dNTP mix (4 μL), 25 mM $MgSO_4$ (2 μL), and KOD DNA polymerase (1 μL) was subjected to 30 thermal cycles each consisting of 10 seconds at 98° C., 30 seconds at 58° C., and two minutes at 68° C. The amplicon by the PCR was inserted into a cloning vector pCR Blunt II-TOPO using a Zero Blunt TOPO PCR Cloning Kit (Thermo Fisher Scientific, K280020). The sequence was analyzed with an ABI3100 DNA sequencer. A cDNA encoding full-length human SPNS2 was isolated. The sequence represented by SEQ ID NO: 2 indicates the base sequence of the human SPNS2 gene, and the sequence represented by SEQ ID NO: 1 indicates the amino acid sequence of the human SPNS2 protein.

A fragment prepared by digestion of pCR Blunt II-TOPO containing cDNA of the human SPNS2 at HindIII, NotI was inserted into the HindIII and NotI sites of the multicloning site of the pcDNA5/FRT (Thermo Fisher Scientific, V601020).

The human SphK1 was amplified by PCR with KOD-Plus Ver. 2 (Toyobo Life Science, KOD-211) using a cDNA clone library (Open biosystems, MHS1010-7507992) as a template.

A reaction solution (50 μL) containing a commercially available human cDNA (1 μL), a sense primer (1.5 μL) (SEQ ID NO: 11), an anti-sense primer (1.5 μL) (SEQ ID NO: 12), a 10×PCR buffer (5 μL) for KOD-Plus, 2 mM dNTP mix(4 μL), 25 mM $MgSO_4$ (2 μL), and a KOD DNA polymerase (1 μL) was subjected to 30 thermal cycles each consisting of 10 seconds at 98°, 30 seconds at 58° C., and two minutes at 68° C. The amplicon by the PCR was inserted into the cloning vector pCR Blunt II-TOPO using a Zero Blunt TOPO PCR Cloning Kit. The sequence was analyzed with an ABI3100

DNA sequencer. A cDNA encoding full-length human SphK1 was isolated. The sequence represented by SEQ ID NO: 14 indicates the base sequence of the human SphK1 gene, and the sequence represented by SEQ ID NO: 13 indicates the amino acid sequence of the human SphK1 protein.

A fraction prepared by digestion of pCR Blunt II-TOPO containing cDNA of the human SphK1 at EcoRI and NotI was inserted into the EcoRI and NotI sites of the multicloning site of the pIRESpuro 3(Takara Bio Inc., 631619).

The human S1PR3 was amplified by PCR with KOD-Plus Ver. 2 (Toyobo Life Science, KOD-211) using commercially available human cDNA (Human MTC Panel II Takara Bio Inc., 636743) as a template.

A reaction solution (50 µL) containing a commercially available human cDNA (1 µL), a sense primer (1.5 µL) (SEQ ID NO: 15), an anti-sense primer (1.5 µL) (SEQ ID NO: 16), a 10×PCR buffer (5 µL) for KOD-Plus, 2 mM dNTP mix (4 mM $MgSO_4$ (2 µL), and a KOD DNA polymerase (1 µL) was subjected to 30 thermal cycles each consisting of 10 seconds at 98°, 30 seconds at 58° C., and two minutes at 68° C. The amplicon by the PCR was inserted into the cloning vector pCR Blunt II-TOPO using a Zero Blunt TOPO PCR Cloning Kit. The sequence was analyzed with an ABI3100 DNA sequencer. A cDNA encoding full-length human S1PR3 was isolated. The sequence represented by SEQ ID NO: 18 indicates the base sequence of the human S1PR3 gene, and the sequence represented by SEQ ID NO: 17 indicates the amino acid sequence of the human S1PR3 protein.

A fraction prepared by digestion of pCR Blunt II-TOPO containing cDNA of the human S1PR3 with EcoRI and NotI was inserted into the EcoRI and NotI sites of the multicloning site of the pIRESpuro 3(Takara Bio Inc., 631619).

The artificially synthesized DNA sequence of the mouse SPNS2 was inserted into the HindIII and NotI sites of the multicloning site of the pcDNA5/FRT (Thermo Fisher Scientific, V601020). The sequence represented by SEQ ID NO: 20 indicates the base sequence of the mouse SPNS2 gene, and the sequence represented by SEQ ID NO: 19 indicates the amino acid sequence of the mouse SPNS2 protein.

[Example 2] Preparation of Stable Expression Cells

A pIRESpuro3 expression vector incorporating a human SphK1 gene was introduced by a lipofection method to prepare stable human SphK1 expression cell strain in a selective medium containing puromycin. As human and mouse SPNS2expression cells, a pcDNA5/FRT expression vector incorporating human and mouse SPNS2 genes and a Flp-Recombinase expression vector, pOG44 (Thermo Fisher Scientific, V600520) are introduced into human SphK1 stable expression Flp-in 293 cells (Thermo Fisher Scientific, R75007) by a lipofection method to produce a stable expression cell line on a hygromycin containing selective culture medium. A pIRESpuro3 expression vector incorporating human S1PR3 gene was introduced to CHO cells by a lipofection method, and human S1PR3 stable expression cells were produced on a puromycin containing selective culture medium. The resulting stable transfectant was subjected to Cell ELISA and S1P production inhibitory evaluations.

[Example 3] Evaluation of Function of Stable Expression Cell

Figure 3:
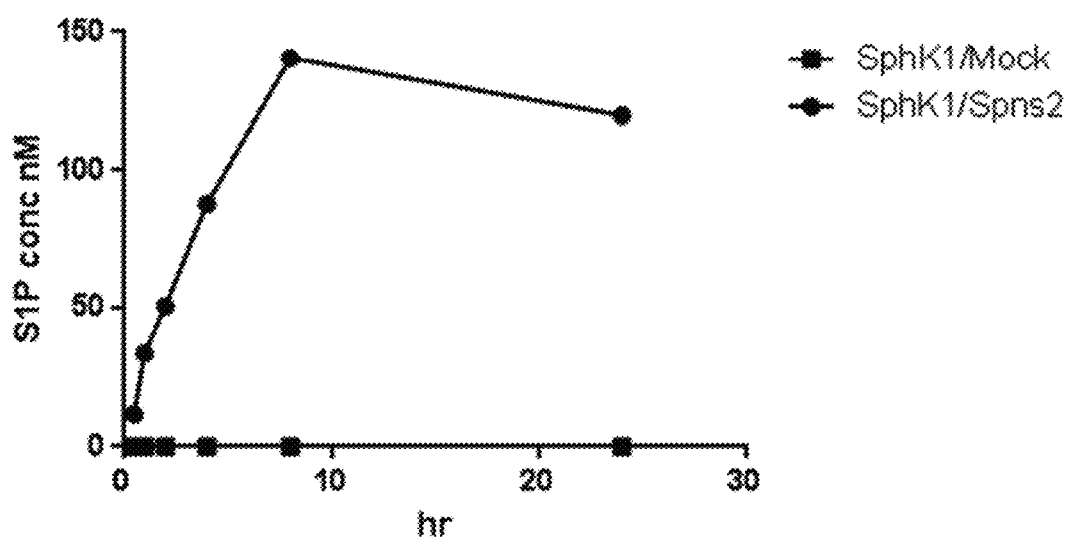
FIG. 3 is a graph showing measurement results of S1P production by a human SPNS2 and SphK1 double stable expression cell line.

The S1P in biological samples has usually been quantitatively determined by mass spectroscopy. A human SPNS2 and SphK1 double stable expression cell line or a Mock vector (pcDNA5/FRT) and SphK1 double stable expression cell line were seeded in a density of 2 mL/well (8×10$^5$ cells/well) on a poly D lysine coat 6-well plate (Corning, 356413) and were incubated overnight. The next day, the culture supernatant was removed from the human SPNS2 and SphK1 double stable expression cell line or the Mock vector (pcDNA5/FRT) and SphK1 double stable expression cell line, and the culture medium was replaced with DMEM containing 1% BSA, and 200 µL of supernatant was recovered after 0.5, 1, 2, 4, 8, and 24 hours. Each recovered supernatant (50 µL) was diluted with methanol (150 µL) containing 100 nM internal standard (C17-S1P Avanti Polar Lipids, 860641P), the solution was thoroughly agitated in a vortex mixer, and then protein was removed by centrifugation at 12000 rpm for 5 min. The resulting supernatant was subjected to mass spectrometry (Shimadzu LCMS-8030). S1P was detected with the parent ion at m/z: 380.15 and a fragment ion at m/z: 264.30, the internal standard C17-S1P was detected with the parent ion at m/z: 366.20 and a fragment ion at m/z: 250.25. The conditions of liquid chromatography are as follows: Solution A (0.1% formic acid), solution B (0.1% formic acid containing MeCN/MeOH 3:1), HPLC column (Shimadzu Luna C8 (2) 3.0 µm 30 mm×4.60 mm, 00A-4248-E0), injection volume: 60 µL, temperature of the sample cooler: 10° C., temperature of the column oven: 40° C., and flow rate: 1 mL/min. As an eluent, 60% solution B was fed for 2 minutes 50 seconds, the concentration of the solution B was increased to 98% for 10 seconds, 98% solution B was fed for 1 minute 50 seconds, and the 60% solution B was fed for 1 minute 10 seconds. The area of the target peak in each run was determined. A higher amount of S1P is observed in the culture supernatant of the human SPNS2 and SphK1 double stable expression cell line compared to the Mock vector introduced cell (FIG. 3).

[Example 4] Confirmation of Localization of N Terminal and C Terminal

Although the SLC transporter is usually a twelve-pass transmembrane protein, the detailed domain structure of SPNS2 is not clear. According to the prediction using a transmembrane region predicting program TMHMM (cbs.dtu.dk/services/TMHMM/) server, it is predicted that 11 transmembrane domains are present. A SPNS2 construct in which FLAG sequences are added to the N terminals and the C terminal was prepared to investigate the localization of the N terminals and the C terminals. FLAG sequences were added to the N terminals and the C terminals of the cDNA sequence of a human SPNS2 template inserted into pcDNA5/FRT by PCR. In the PCR, a reaction solution (50 µL) containing human SPNS2 inserted into pcDNA5/FRT (1 µL), a sense primer for N-terminal FLAG addition (1.5 µL) (SEQ ID NO: 23) and an antisense primer for N-terminal FLAG addition (1.5 µL) (SEQ ID NO: 24) or a sense primer for C-terminal FLAG addition (1.5 µL) (SEQ ID NO: 25) and an antisense primer for C-terminal FLAG addition (1.5 µL) (SEQ ID NO: 26), 10×PCR buffer for KOD-Plus (5 µL), 2 mM dNTP mix (4 µL), 25 mM MgSO4 (2 µL), and a KOD DNA polymerase (1 µL) was subjected to 30 thermal cycles each consisting of 10 seconds at 98° C., 30 seconds at 58° C., and 2 minutes for 68° C. The amplicon by the PCR was inserted into the cloning vector pCR Blunt II-TOPO using a Zero Blunt TOPO PCR Cloning Kit. The human SPNS2 cDNA sequence with the added FLAG tag sequence was spliced out and was inserted into the EcoRI site and the NotI site in the multicloning site of pIRESpuro3 (Takara Bio Inc., 631619). HEK293T cells were seeded in a density of 0.5 mL/well (1×10$^5$ cells/well on a poly D lysine coat 24-well plate (Corning, 354470) overnight. The next day, a pIRE-Spuro 3 expression vector into which a SPNS2 gene having an added FLAG sequence was incorporated was introduced by a lipofection method and cultivated overnight. The next day, the resultant was stained with an anti-FLAG antibody (Sigma-Aldrich, F1804) after membrane permeabilization or without membrane permeabilization.

Details of method without membrane permeabilization: After the culture medium was removed and the well was washed with PBS, the anti-FLAG antibody was diluted with PBS containing 3% BSA and 0.2% Serum into 10 µg/mL and the diluted antibody was added to the well in a volume of 200 µL/well, and reacted for one hour at room temperature. After washing of the well with PBS two times, a 1 µg/mL diluted solution of Alexa 488 anti-mouse IgG (Thermo Fisher Scientific, A-11001) in PBS containing 3% BSA and 0.2% Serum was added to the well in a volume of 200 µL/well, and was reacted for one hour at room temperature. After the well was washed with PBS two times, it was observed with a fluorescent microscope.

Details of the membrane permeabilization: After the culture medium was removed and the well was washed with PBS, 4% paraformaldehyde was added and the well was allowed to stand for 5 minutes at room temperature. After removal of 4% paraformaldehyde, PBS containing 0.5% TritonX-100 was added and the well was allowed to stand for 15 minutes at room temperature, and the solution was removed. After addition of PBS containing 3% BSA and 0.2% Serum, the well was allowed to stand for 30 minutes at room temperature, and the well was washed with PBS. A 10 µg/mL anti-FLAG antibody diluted in PBS containing 3% BSA and 0.2% Serum was added to the well in a volume of 200 µL/well and was reacted to one hour at room temperature. After the well was washed with PBS two times, a 1 µg/mL diluted Alexa 488 anti-mouse IgG (Thermo Fisher Scientific, A-11001) solution in PBS containing 3% BSA and 0.2% Serum and 2 µg/mL Hoechst 33342 solution (Dojindo Laboratories, 346-07951) were added in a volume of 200 µL/well, and reacted with one hour at room temperature. After the well was washed with PBS two times, the well was observed with a fluorescent microscope. The FLAG signals were observed under membrane permeabilization conditions in both the N terminal and C terminal.

Figure 4:
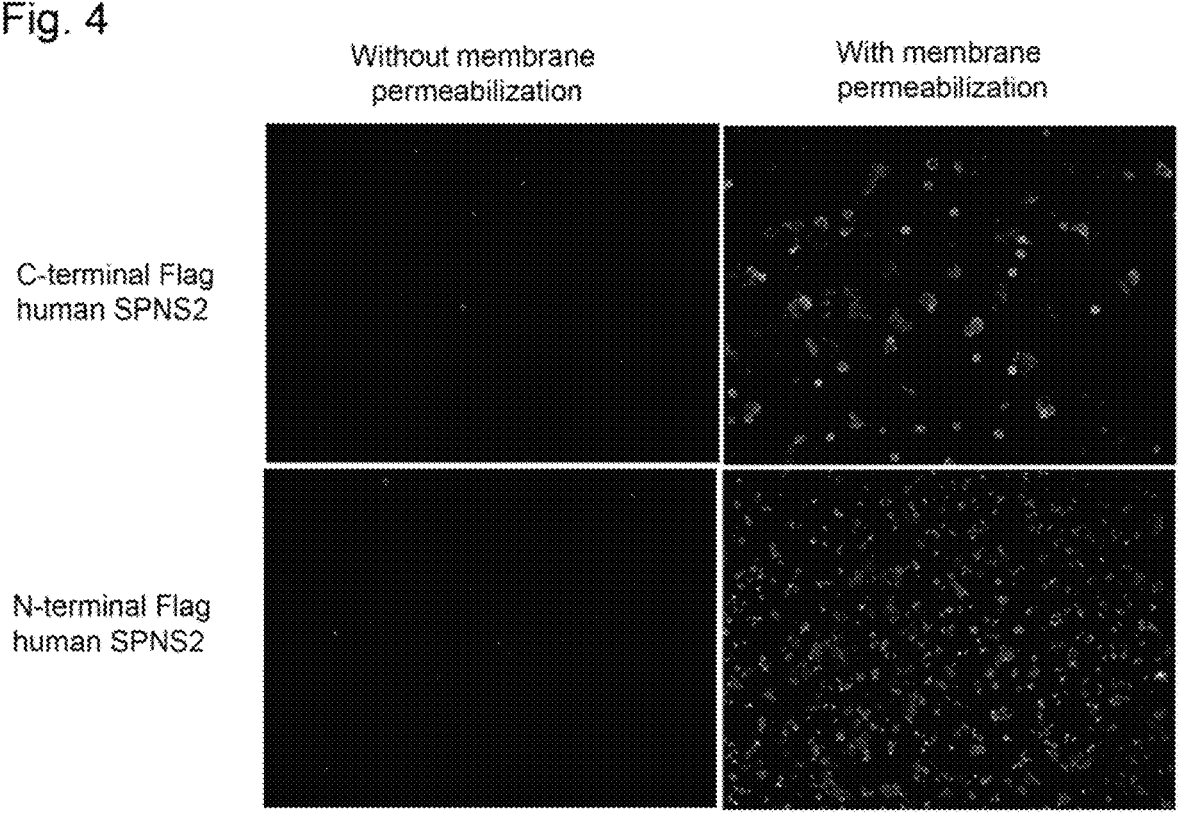
FIG. 4 shows images of immunostained SPNS2 expressing cells to which FLAG was added at the N terminal and C terminal.

The results demonstrate the existence of the N terminal and C terminal in the cell (FIG. 4). These results suggest that SPNS2 has an even number of transmembrane domains. The domain closest to the N terminal that did not forecasted to be a transmembrane region by TMHMM among transmembrane domains forecasted using a SOUSI (harrier.nagahama-i-bio.ac.jp/sosui/) server was added as the first transmembrane domain to a presumptive extracellular domain (FIGS. 1 and 2).

[Example 5] Preparation of Rat Anti-Human SPNS2 Antibody

The gene sequence of human SPNS2 was incorporated into the EcoRI and NotI sites of pIRESpuro3 (Takara Bio Inc., 631619). An EndoFree Plasmid Giga Kit (QIAGEN) was used for preparation of a large amount of human SPNS2 expression vector.

A female SLC/wister rat (Japan SLC, Inc.) was used for immunization. An expression vector of pIRESpuro3 into which human SPNS2 was incorporated was injected into the rat anterior tibial muscle. This site was subjected to in vivo electroporation with two needle electrodes in ECM 830 (BTX). After the in vivo electroporation process was repeated four times every two weeks, a human SPNS2 and SphK1 double stable expression cell line was administered into the abdominal cavity. Three days later, the spleen of the rat was collected to be used in preparation of hybridoma.

[Example 6] Production Hybridoma Producing Rat Monoclonal Antibody

The rat monoclonal antibody can be prepared by a hybridoma process by Kohler et al (Nature 256:495-497, 1975). A rat was immunized using the DNA plasmid and expression cells of human SPNS2, and lymphocyte collected from the rat and a mouse myeloma cell line (P3U1) were fused by electrical cell fusion. In detail, 1.8×10$^7$ P3U1 cells and rat lymphocytes were suspended in 700 µL of ECF buffer (0.3 M mannitol, 10 mM CaCl$_2$), 10 mM MgCl$_2$, and 1 mg/mL BSA), a cycle of AC voltage of 30 V for 10 s and three cycles of DC voltage of 350 V for 30 µs were applied across electrodes with a gap of 2 mm in a cell fusion unit (ECFG21, Nepa Gene CO., Ltd.) to fuse the cells. The hybridoma was selected from the fused cells using a culture medium containing hypoxanthine, aminopterin, and aminopterin. The binding ability was evaluated by Cell ELISA using human SPNS2 and human SphK1 double stable expression Flp-in 293 cells in the hybridoma culture solution. The depression ability of production of S1P (neutralization activity) was evaluated using the supernatants of 108 clones having binding ability, and wells containing positive hybridoma having neutralization activity were selected. In this process, one negative clone having only binding ability was also obtained. The hybridoma contained in a positive well was subjected to single clone isolation by limiting dilution. The monoclonal antibody was purified from the single clone positive hybridoma culture solution using a Protein G Sepharose 4 Fast Flow (GE Healthcare, 17061801). The concentration of the purified antibody was determined from the absorbance at 280 nm using a Nanodrop spectrophotometer (ND-1000, Thermo Fisher Scientific). The binding ability to SPNS2 was evaluated and the depression ability of production of S1P was reevaluated with this monoclonal antibody. Twenty-five SPNS2 neutralized antibody clones were found.

[Example 7] Determination of Antibody Isotype

The isotypes of the anti-SPNS2 antibody were determined by ELISA using antibodies specific to the isotypes of the anti-SPNS2 antibody. 1 µg/mL diluted anti-rat IgG antibody (Southern Biotech, 3051-01) in PBS was added to a 96-well plate (Nunc, MaxiSorp) in a volume of 50 µL/well, and allowed to stand overnight at 4° C. In the ELISA, the 96-well plate was replaced with 3% BSA/PBS. Anti-SPNS2 antibody was diluted into 1 µg/mL with 3% BSA/PBS, and the dilution was added to the 96-well plate onto which the anti-rat IgG antibody is immobilized in a volume of 30 µL/well, and reacted for one hour at room temperature. After washing with rinse solution (PBS containing 0.05% Tween 20), antibodies specifically reacting with various isotypes of the rat IgG, an anti-rat IgG1 antibody-ALP conjugate (Southern Biotech, 3061-04), an anti-rat IgG2a antibody-ALP conjugate (Southern Biotech, 3065-04), an anti-rat IgG2b antibody-ALP conjugate (Southern Biotech, 3070-04), an anti-rat IgG2c antibody-ALP conjugate (Southern Biotech, 3075-04), an anti-rat Kappa antibody-ALP conjugate (Southern Biotech, 3090-04), and an anti-rat IgM antibody-ALP conjugate (Southern Biotech, 3090-04) were diluted into 1000 folds using 3% BSA/PBS, and the diluted solutions were added to the respective wells in a volume of 30 μL/well, and reacted for 1 hour. The substrate (PNPP) was added in a volume of 100 μL/well, and reacted for two hours at room temperature to determine the absorbance at 405-550 nm. The absorbance at 405-550 nm was used to evaluate the binding activity. Regarding the lambda light chain, the antibody not reactive with the kappa chain was determined to be a lambda chain. Table 1 shows various isotypes of the antibody.

added to the RNA solution, the mixture was heated for 90 minutes at 42° C. and 10 minutes at 70° C. The resulting product was diluted into 10 folds with $dH_2O$ and the diluted solution was used as a template in the PCR. In the 5'RACE PCR, 2×Tks Gflex buffer (25 μL), Tks Gflex DNA polymerase (1 μL), 10×UPM (5 μL), an antisense primer (1 μL) (SEQ ID NO: 247), and 10-folded diluted 5'RACE cDNA (2.5 μL) were diluted with water into final 50 μL. The cDNA of the antibody was amplified by a 25-cycle PCR each consisting of 10 seconds at 94° C., 10 seconds at 55° C., one minute at 68° C.

TABLE 1

| Antibody No. | Subclass | Light chain | ELISA Absorbance | | | | | |
|---|---|---|---|---|---|---|---|---|
| | | | IgG1 | IgG2a | IgG2b | IgG2c | κ | IgM |
| 18-0211B | IgG2b | λ | 0.1603 | 0.1575 | 0.7407 | 0.1749 | 0.1579 | 0.1883 |
| 33-0503E | IgG2b | λ | 0.1579 | 0.167 | 0.6808 | 0.1557 | 0.1552 | 0.1765 |
| 37-0511F | IgG2b | κ | 0.1589 | 0.1579 | 1.3829 | 0.1659 | 2.0599 | 0.161 |
| 49-0703G | IgG2b | λ | 0.1591 | 0.1608 | 0.7926 | 0.1576 | 0.1568 | 0.158 |
| 50-0704C | IgG2b | λ | 0.1696 | 0.168 | 0.7901 | 0.156 | 0.1544 | 0.1956 |
| 53-0707E | IgG2b | κ | 0.1619 | 0.1581 | 1.0539 | 0.1552 | 1.2792 | 0.1591 |
| 64-0807A | IgG2b | λ | 0.1586 | 0.1694 | 0.856 | 0.1567 | 0.1621 | 0.1589 |
| 65-0810G | IgG2b | λ | 0.1567 | 0.1637 | 0.5565 | 0.1566 | 0.1586 | 0.157 |
| 80-1104A | IgG2b | κ | 0.1771 | 0.1579 | 1.0565 | 0.1581 | 1.1302 | 0.1565 |
| 82-1109A | IgG2b | κ | 0.1663 | 0.1589 | 0.6523 | 0.1583 | 1.2417 | 0.1567 |
| 83-1110B | IgG2b | κ | 0.1644 | 0.1621 | 0.7535 | 0.1447 | 0.8393 | 0.1563 |
| 84-1111F | IgG2b | λ | 0.1569 | 0.1565 | 0.7551 | 0.1593 | 0.1551 | 0.1556 |
| 89-1207D | IgG2b | λ | 0.1573 | 0.1575 | 0.6402 | 0.1667 | 0.1727 | 0.1812 |
| 93-1310F | IgG2b | κ | 0.158 | 0.1666 | 1.0835 | 0.1603 | 0.6212 | 0.1668 |
| 94-1311E | IgG2b | κ | 0.1555 | 0.1585 | 1.1911 | 0.1594 | 1.4322 | 0.2049 |
| 96-1403F | IgG2b | κ | 0.1619 | 0.1626 | 0.7646 | 0.1551 | 1.0745 | 0.1598 |

[Example 8] Determination of Antibody Sequence

The total RNA was extracted from the hybridoma producing the anti-SPNS2 antibody with an RNeasy Mini Kit (Qiagen, 74106) in accordance with the attached manual. After the determination of the RNA concentration by photometry, cDNA was prepared from Total RNA (1 μg) with an Omniscript RT Kit (Qiagen, 205113) in accordance with the attached manual. A gene encoding the variable region of the antibody was amplified using the produced cDNA as a template by PCR using the Tks Gflex DNA polymerase (Takara Bio Inc., R060A).

A reaction solution (50 μL) containing the cDNA prepared as above (1 μL), 1 μM primer set (12.5 μL, Table 2), 2×Gflex PCR buffer (25 μL) ($Mg^{2+}$, dNTP plus), a Tks Gflex DNA polymerase (1 μL) was subjected to 30 thermal cycles each consisting of 10 seconds at 98° C., 10 seconds at 55° C., and 30 seconds at 68° C.

Table 2 shows the sequence of the primer contained in the primer set used in identification of the antibody gene of the hybridoma clone. Table 3 shows the combination of the primers used in identification of the antibody gene of each hybridoma clone. Among the clones shown in Table 3, some of the clones not amplified with the primer set was amplified by a 5'RACE process using a SMARTer (trade mark) RACE 5'/3' Kit (Takara Bio Inc., 634858). The total RNA (1 μg) was mixed with a 5'-CDS primer A (1 μL), and the mixture was diluted in $dH_2O$ into 11 μL and was heated for 3 minutes at 72° C., 2 minutes at 42° C., and then 2 minutes at 4° C. After 5×First-Strand Buffer (4 μL), 100 mM DTT (0.5 μL), 20 mM dNTP (1 μL), SMARTer II Oligonucleotide (1 μL), Rnase Inhibitor (0.5 μL), SMART Scribe Rtase (2 μL) were The PCR product was inserted into a cloning vector using a Zero Blunt TOPO PCR Cloning Kit (Thermo Fisher Scientific, K280020) in accordance with the attached manual. After transformation into *E. coli* DH5α Competent Cells (Takara Bio Inc., 9057), the sample was seeded onto an agar culture medium containing kanamycin. After the clone was selected, the base sequence of the inserted cDNA was determined using a primer for determining a base sequence (SEQ ID NO: 21). Tables 4 and 5 show the base sequence and the amino acid sequence of the variable region of each anti-SPNS2 antibody.

TABLE 2

| Primer set | |
|---|---|
| Primer set | Primer sequence |
| Set 1 | SEQ ID NO: 244 to SEQ ID NO: 260 |
| Set 2 | SEQ ID NO: 244 to SEQ ID NO: 247 and SEQ ID NO: 261 to SEQ ID NO: 272 |
| Set 3 | SEQ ID NO: 244 to SEQ ID NO: 247 and SEQ ID NO: 273 to SEQ ID NO: 287 |
| Set 4 | SEQ ID NO: 288 to SEQ ID NO: 311 |
| Set 5 | SEQ ID NO: 288 and SEQ ID NO: 312 to SEQ ID NO: 335 |
| Set 6 | SEQ ID NO: 336 to SEQ ID NO: 344 |
| Set 7 | SEQ ID NO: 288 and SEQ ID NO: 312 to SEQ ID NO: 323 |
| Set 8 | SEQ ID NO: 288 and SEQ ID NO: 324 to SEQ ID NO: 335 |
| Set 9 | SEQ ID NO: 288, SEQ ID NO: 312 to SEQ ID NO: 331, SEQ ID NO: 334, and SEQ ID NO: 335 |

TABLE 3

Cloning primer set of variable region

| | Cloning primer set of variable region of heavy chain | Cloning primer set of variable region of light chain |
|---|---|---|
| 18-0211B | Set 2 | Set 6 |
| 33-0503E | Set 2 | Set 6 |
| 37-0511F | Set 2 | Set 4 |
| 49-0703G | Set 1 | Set 6 |
| 50-0704C | Set 1 | Set 6 |
| 53-0707E | Set 2 | Set 4 |
| 64-0807A | Set 1 | Set 6 |
| 65-0810G | Set 1 | Set 6 |
| 80-1104A | 5'RACE | Set 9 |
| 83-1110B | Set 2 | Set 4 |
| 84-1111F | Set 1 | Set 6 |
| 89-1207D | Set 1 | Set 6 |
| 93-1310F | 5'RACE | Set 9 |
| 94-1311E | Set 2 | Set 4 |
| 96-1403F | 5'RACE | Set 9 |
| 82-1109A | Set 2 | Set 5 |

TABLE 4

DNAbase sequence of variable region

| Antibody No. | Heavy chain/light chain | SEQ ID NO: |
|---|---|---|
| 18-0211B | Heavy chain | 35 |
| 33-0503E | Heavy chain | 37 |
| 37-0511F | Heavy chain | 39 |
| 49-0703G | Heavy chain | 41 |
| 50-0704C | Heavy chain | 43 |
| 53-0707E | Heavy chain | 45 |
| 64-0807A | Heavy chain | 47 |
| 65-0810G | Heavy chain | 49 |
| 80-1104A | Heavy chain | 51 |
| 83-1110B | Heavy chain | 53 |
| 84-1111F | Heavy chain | 55 |
| 89-1207D | Heavy chain | 57 |
| 93-1310F | Heavy chain | 59 |
| 94-1311E | Heavy chain | 61 |
| 96-1403F | Heavy chain | 63 |
| 82-1109A | Heavy chain | 65 |
| 18-0211B | Light chain | 67 |
| 33-0503E | Light chain | 69 |
| 37-0511F | Light chain | 71 |
| 49-0703G | Light chain | 73 |
| 50-0704C | Light chain | 75 |
| 53-0707E | Light chain | 77 |
| 64-0807A | Light chain | 79 |
| 65-0810G | Light chain | 81 |
| 80-1104A | Light chain | 83 |
| 83-1110B | Light chain | 85 |
| 84-1111F | Light chain | 87 |
| 89-1207D | Light chain | 89 |
| 93-1310F | Light chain | 91 |
| 94-1311E | Light chain | 93 |
| 96-1403F | Light chain | 95 |
| 82-1109A | Light chain | 97 |

TABLE 5

Amino acid sequence of variable region

| Antibody No. | Heavy chain/light chain | SEQ ID NO: |
|---|---|---|
| 18-0211B | Heavy chain | 34 |
| 33-0503E | Heavy chain | 36 |
| 37-0511F | Heavy chain | 38 |
| 49-0703G | Heavy chain | 40 |
| 50-0704C | Heavy chain | 42 |
| 53-0707E | Heavy chain | 44 |
| 64-0807A | Heavy chain | 46 |
| 65-0810G | Heavy chain | 48 |
| 80-1104A | Heavy chain | 50 |
| 83-1110B | Heavy chain | 52 |
| 84-1111F | Heavy chain | 54 |
| 89-1207D | Heavy chain | 56 |
| 93-1310F | Heavy chain | 58 |
| 94-1311E | Heavy chain | 60 |
| 96-1403F | Heavy chain | 62 |
| 82-1109A | Heavy chain | 64 |
| 18-0211B | Light chain | 66 |
| 33-0503E | Light chain | 68 |
| 37-0511F | Light chain | 70 |
| 49-0703G | Light chain | 72 |
| 50-0704C | Light chain | 74 |
| 53-0707E | Light chain | 76 |
| 64-0807A | Light chain | 78 |
| 65-0810G | Light chain | 80 |
| 80-1104A | Light chain | 82 |
| 83-1110B | Light chain | 84 |
| 84-1111F | Light chain | 86 |
| 89-1207D | Light chain | 88 |
| 93-1310F | Light chain | 90 |
| 94-1311E | Light chain | 92 |
| 96-1403F | Light chain | 94 |
| 82-1109A | Light chain | 96 |

[Example 9] Binding Activity to SPNS2 (Cell ELISA)

The binding activity of the anti-SPNS2 antibody to human SPNS2 and mouse SPNS2 was investigated by Cell ELISA using SPNS2-expressing cells.

Human and mouse SPNS2 and human SphK1 double stable expression Flp-in 293 cells were added to a poly D lysine coat 96-well plate (Corning, 356461) in a density of $1 \times 10^5$ cells/well and was cultivated overnight, and then the culture medium was removed. An anti-SPNS2 antibody solution was adjusted into 20 μg/mL using 0.2% FBS/3% BSA/PBS, and 0.2% FBS/3% BSA/PBS (60 μL) was added to the antibody diluted solution (20 μL) to prepare seven-step diluted solutions by four fold serial dilution. Each diluted solution of the anti-SPNS2 antibody was added in a volume of 30 μL/well, and reacted for about one hour at room temperature. The antibody solution was removed, and the residue was washed with PBS containing 0.05% Tween 20 (PBS-T) two times, and fixed for about ten minutes at room temperature using 10% buffered formalin (Mildform (Trade mark) 10NM, Wako). After washing with PBS-T one time, a 5000-fold diluted solution of anti-rat IgG antibody HRP conjugate (Southern Biotech, 3030-05) in 0.2% FBS/3% BSA/PBS was added to each well (30 μL), and reacted for about one hour at room temperature. After washing with PBS-T four times, a substrate (TMB; 3, 3', 5, 5'-tetramethylbenzidin) was added to each well (100 μL) to initiate the reaction. After 20 minutes, 2N sulfuric acid was added to each well (100 μL), and absorbance at 450 nm and 550 nm was measured. Table 6 shows maximum absorbance, Emax and the logarithmic value of the concentration representing 50% absorbance to the absorbance at the highest concentration of each antibody. Each antibody bound to human SPNS2 and mouse SPNS2.

TABLE 6

|  | Human SPNS2 | | Mouse SPNS2 | |
| --- | --- | --- | --- | --- |
|  | Emax | pEC50 (M) | Emax | pEC50 (M) |
| 18-0211B | 1.72 | 8.589 | 1.606 | 8.374 |
| 33-0503E | 2.031 | 8.117 | 2.199 | 7.657 |
| 37-0511F | 1.35 | 8.195 | 1.293 | 8.005 |
| 49-0703G | 1.767 | 8.418 | 1.672 | 8.085 |
| 50-0704C | 1.824 | 8.148 | 1.896 | 7.75 |
| 53-0707E | 1.618 | 7.872 | 1.433 | 7.823 |
| 64-0807A | 1.828 | 8.069 | 1.876 | 7.831 |
| 65-0810G | 1.7 | 8.361 | 1.543 | 8.153 |
| 80-1104A | 1.829 | 8.47 | 1.607 | 8.317 |
| 83-1110B | 1.6 | 8.322 | 1.588 | 8.166 |
| 84-1111F | 1.675 | 8.752 | 1.549 | 8.65 |
| 89-1207D | 2.027 | 7.97 | 1.847 | 7.721 |
| 93-1310F | 1.644 | 8.565 | 1.607 | 8.294 |
| 94-1311E | 1.61 | 8.344 | 1.516 | 8.2 |
| 96-1403F | 1.859 | 7.765 | 1.784 | 7.423 |
| 82-1109A | 1.658 | 7.828 | 1.286 | 7.833 |

[Example 10] Analysis of Binding Site of Anti-SPNS2 Antibody (Flow Cytometry)

In order to identify the binding site of the anti-SPNS2 antibody to SPNS2, the binding abilities of the anti-SPNS2 antibodies to mutants of human SPNS2 in which a FLAG tag sequence (SEQ ID NO: 22) was inserted into a sequence of its extracellular loops were measured.

In specific, the following four mutants in which a FLAG tag sequence was inserted into the extracellular loop sequence of the human SPNS2 were prepared.
Mutant 1 (SEQ ID NO: 160) that mutates the extracellular loop 1 sequence (SEQ ID NO: 3) of the human SPNS2.
Mutant 2 (SEQ ID NO: 164) that mutates the extracellular loop 5 sequence (SEQ ID NO: 5) of the human SPNS2.
Mutant 3 (SEQ ID NO: 166) that mutates the extracellular loop 7 sequence (SEQ ID NO: 6) of the human SPNS2.
Mutant 4 (SEQ ID NO: 170) that mutates the extracellular loop 11 sequence (SEQ ID NO: 8) of the human SPNS2.

pcDNA5/FRT (Thermo Fisher Scientific, V601020) into which genes (SEQ ID NOs: 161, 165, 167, and 171) of Mutants 1 to 4 of SPNS2 were incorporated were introduced to HEK293 cells by a lipofection process. After the lipofection, the HEK 293 cells cultivated overnight were recovered from the culture dishes, and reacted with a cell staining buffer (BioLegend, 420201) containing an anti-FLAG antibody (Sigma-Aldrich, F1804) and an anti-SPNS2 antibody each in a volume of 20 μg/mL for 30 minutes at room temperature. After washing with a cell staining buffer one time, the anti-FLAG antibody was detected with an anti-mouse IgG-Alexa 647 conjugate antibody, and the anti-SPNS2 antibody was detected with an anti-rat IgG-FITC conjugate antibody with flow cytometer BD LSR Fortessa (Becton Dickinson). The binding ability to each mutant was evaluated with the ratio of the FITC-positive cell rate to the Alexa 647-positive cell rate. In Table 7, symbol (+) indicates a ratio of less than 0.1, symbol (±) indicates a ratio of 0.1 or more and less than 0.5, and symbol (−) indicate a ratio of 0.5 or more.

TABLE 7

|  | Loop 1 | Loop 5 | Loop 7 | Loop 11 |
| --- | --- | --- | --- | --- |
| 18-0211B | + | + | − | − |
| 33-0503E | + | + | − | − |
| 37-0511F | + | + | ± | − |

TABLE 7-continued

|  | Loop 1 | Loop 5 | Loop 7 | Loop 11 |
| --- | --- | --- | --- | --- |
| 49-0703G | + | + | − | − |
| 50-0704C | + | + | − | − |
| 53-0707E | + | + | ± | − |
| 64-0807A | + | + | − | − |
| 65-0810G | + | + | − | − |
| 80-1104A | + | − | − | − |
| 83-1110B | + | + | − | − |
| 84-1111F | + | + | − | − |
| 89-1207D | + | + | − | − |
| 93-1310F | + | − | − | − |
| 94-1311E | + | + | − | − |
| 96-1403F | + | ± | − | − |
| 82-1109A | − | − | + | + |

Each antibody primarily bound to the extracellular loop 1 sequence and the extracellular loop 5 sequence. The antibody having SPNS2 neutralizing activity primarily bound to the extracellular loop 1 sequence and the extracellular loop 5 sequence, while the antibody not having neutralizing activity bound to the extracellular loop 7 sequence and the extracellular loop 11 sequence. These results demonstrate that identification of the extracellular loop 1 sequence and the extracellular loop 5 sequence are essential for the confirmation of SPNS2 neutralizing activity. The antibody 82-1109A having no SPNS2 inhibitory activity has CDR-H1 (SEQ ID NO: 107), CDR-H2 (SEQ ID NO: 119), CDR-H3 (SEQ ID NO: 128), CDR-L1 (SEQ ID NO: 139), CDR-L2 (SEQ ID NO: 148), and CDR-L3 (SEQ ID NO: 159) and does not bind to the extracellular loop 1 sequence or the extracellular loop 5 sequence.

[Example 11] Determination of Epitope of SPNS2 Neutralizing Antibody

In order to determine the binding site in more detail, mutants having a substituted amino acid were prepared on the extracellular loops 1 and 5 to which the SPNS2 neutralizing antibody binds and the extracellular loop 3, which was a mutant into which a FLAG sequence was inserted and the anti-FLAG antibody of which did not show the reactivity. The following mutants and replacements were prepared: An alanine mutant of the extracellular loop 1 (in SEQ ID NO: 1, the 127-th site, leucine replacement L127A (SEQ ID NO: 172), the 128-th site, aspartic acid replacement D128A (SEQ ID NO: 173), 129-th site, isoleucine replacement I129A (SEQ ID NO: 174), 130-th site, glutamine replacement Q130A (SEQ ID NO: 175), 131-st site, glutamine replacement Q131A (SEQ ID NO: 176), 132-nd site, histidine replacement H132A (SEQ ID NO: 177), 133-rd site, phenylalanine replacement F133A (SEQ ID NO: 178), 134-th site, glycine replacement G134A (SEQ ID NO: 179), 135-th site, valine replacement V135A (SEQ ID NO: 180), 136-th site, lysine replacement K136A (SEQ ID NO: 181), 137-th site, aspartic acid replacement D137A (SEQ ID NO: 182), 138-th site, arginine replacement R138A (SEQ ID NO: 183), 139-th site, and glycine replacement G139A (SEQ ID NO: 184)); an alanine mutant of the extracellular loop 3 (in SEQ ID NO: 1, 189-th site, proline replacement P189A (SEQ ID NO: 185), 190-th site, glutamine replacement Q190A (SEQ ID NO: 186), 191-st site, glutamine replacement Q191A (SEQ ID NO: 187), 192-nd site, tyrosine replacement Y192A (SEQ ID NO: 188), 193-rd site, phenylalanine replacement F193A (SEQ ID NO: 189), 194-th site, tryptophan replacement W194A (SEQ ID NO: 190), 195-th site, leucine replacement L195A (SEQ ID NO: 191), 196-th site, leucine replacement L196A (SEQ ID NO: 192), 197-th site, valine replacement V197A (SEQ ID NO: 193), 198-th site, leucine replacement L198A (SEQ ID NO: 194), 199-th site, serine replacement S199A (SEQ ID NO: 195), 200-th site, arginine replacement R200A (SEQ ID NO: 196), 201-st site, glycine replacement G201A (SEQ ID NO: 197), and 202-nd site, leucine replacement L202A (SEQ ID NO: 198)); and an alanine or phenylalanine mutant of the extracellular loop 5 (in SEQ ID NO: 1, 252-nd site, valine replacement V252A (SEQ ID NO: 199), 253-rd site, lysine replacement K253A (SEQ ID NO: 200), 254-th site, glutamine replacement Q254A (SEQ ID NO: 201), 255-th site, alanine replacement A255F (SEQ ID NO: 206), 256-th site, alanine replacement A256F (SEQ ID NO: 207), 257-th site, glycine replacement G257A (SEQ ID NO: 202), 258-th site, aspartic acid replacement D258A (SEQ ID NO: 203), 259-th site, tryptophan replacement W259A (SEQ ID NO: 204), and 260-th site, histidine replacement H260A(SEQ ID NO: 205)). The following genes were artificially synthesized: gene of the L127A mutant (SEQ ID NO: 208), gene of the D128A mutant (SEQ ID NO: 209), the gene of the I129A mutant (SEQ ID NO: 210), gene of the Q130A mutant (SEQ ID NO: 211), gene of the Q131A mutant (SEQ ID NO: 212), gene of the H132A mutant (SEQ ID NO: 213), gene of the F133A mutant (SEQ ID NO: 214), gene of the G134A mutant (SEQ ID NO: 215), gene of the V135A mutant (SEQ ID NO: 216), gene of the K136A mutant (SEQ ID NO: 217), gene of the D137A mutant (SEQ ID NO: 218), gene of the R138A mutant (SEQ ID NO: 219), gene of the G139A mutant (SEQ ID NO: 220), gene of the P189A mutant (SEQ ID NO: 221), gene of the Q190A mutant (SEQ ID NO: 222), gene of the Q191A mutant (SEQ ID NO: 223), gene of the Y192A mutant (SEQ ID NO: 224), F193A mutant (SEQ ID NO: 225), gene of the W194A mutant (SEQ ID NO: 226), gene of the L195A mutant (SEQ ID NO: 227), gene of the L196A mutant (SEQ ID NO: 228), gene of the V197A mutant (SEQ ID NO: 229), gene of the L198A mutant (SEQ ID NO: 230), gene of the S199A mutant (SEQ ID NO: 231), gene of the R200A mutant (SEQ ID NO: 232), gene of the G201A mutant (SEQ ID NO: 233), gene of the L202A mutant (SEQ ID NO: 234), gene of the V252A mutant (SEQ ID NO: 235), gene of the K253A mutant (SEQ ID NO: 236), gene of the Q254A mutant (SEQ ID NO: 237), gene of the A255F mutant (SEQ ID NO: 242), gene of the A256F mutant (SEQ ID NO: 243), gene of the G257A mutant (SEQ ID NO: 238), gene of the D258A mutant (SEQ ID NO: 239), gene of the W259A mutant (SEQ ID NO: 240), and gene of the H260A mutant (SEQ ID NO: 241). pcDNA5/FRT (Thermo Fisher Scientific, V601020) was introduced in which the gene of one of the 36 amino acid mutant of SPNS2 was incorporated into HEK293T cells by a lipofection method. The HEK293T cells cultivated overnight after the lipofection was recovered from the culture dishes, and reacted for 30 minutes at room temperature in suspension of a cell staining buffer (BioLegend, 420201) containing anti-SPNS2 antibody (20 µg/mL). After washing with a cell staining buffer one time, the anti-SPNS2 antibody was detected with an anti-rat IgG-FITC conjugate antibody, and measured with flow cytometer BD LSR Fortessa (Becton, Dickinson). From the data, the ratio of {(rate of cells positive to SPNS2 neutralizing antibody to each mutant)/(rate of cells positive to anti-SPNS2 antibody 82-1109A to each mutant)}/{(rate of cells positive to each SPNS2 neutralizing antibody to native type)/(rate of cells positive to anti-SPNS2 antibody 82-1109A to native type)} was calculated. In Table 8, symbol (+) indicates a ratio of 0.8 or more representing no change in bonding amount, symbol (±) indicates a ratio of 0.5 or more and less than 0.8 representing a decrease in bonding amount, and symbol (−) indicate a ratio of less than 0.5 indicating a significant decrease in bonding amount.

TABLE 8

|  | L127A | D128A | I129A | Q130A | Q131A | H132A | F133A | G134A | V135A | K136A |
|---|---|---|---|---|---|---|---|---|---|---|
| 18-0211B | + | + | ± | − | + | + | ± | ± | + | − |
| 33-0503E | ± | + | ± | + | ± | + | ± | ± | + | − |
| 37-0511F | + | − | ± | + | + | + | ± | ± | + | + |
| 49-0703G | + | + | ± | − | + | + | − | + | + | − |
| 50-0704C | + | + | ± | − | + | + | − | ± | + | − |
| 53-0707E | + | − | + | + | + | + | ± | ± | + | + |
| 64-0807A | + | ± | ± | + | − | + | ± | − | + | − |
| 65-0810G | + | + | − | + | − | ± | − | + | + | − |
| 80-1104A | + | + | + | + | + | ± | ± | + | + | − |
| 83-1110B | + | ± | + | + | + | + | + | + | + | + |
| 84-1111F | + | ± | + | + | ± | + | ± | ± | + | ± |
| 89-1207D | + | + | + | ± | + | + | ± | + | + | − |
| 93-1310F | + | + | + | + | + | ± | − | + | + | − |
| 94-1311E | + | ± | + | + | + | + | + | + | + | + |
| 96-1403F | + | + | + | + | + | ± | − | + | + | − |

|  | D137A | R138A | G139A | P189A | Q190A | Q191A | Y192A | F193A |
|---|---|---|---|---|---|---|---|---|
| 18-0211B | ± | + | + | + | + | + | + | + |
| 33-0503E | ± | + | + | + | + | + | + | + |
| 37-0511F | + | + | + | + | + | + | + | + |
| 49-0703G | ± | + | + | + | + | + | + | + |
| 50-0704C | ± | + | + | + | + | + | + | + |
| 53-0707E | + | + | + | + | + | + | + | + |
| 64-0807A | + | + | + | + | + | + | + | + |
| 65-0810G | + | + | + | + | + | + | + | ± |
| 80-1104A | + | ± | + | + | + | + | + | ± |
| 83-1110B | + | ± | + | + | + | + | + | + |
| 84-1111F | + | + | + | + | + | + | + | + |
| 89-1207D | ± | ± | + | + | + | + | + | + |

TABLE 8-continued

| | | | | | | | | |
|---|---|---|---|---|---|---|---|---|
| 93-1310F | ± | ± | + | + | − | + | + | ± |
| 94-1311E | ± | + | + | + | + | + | + | + |
| 96-1403F | + | ± | ± | + | − | + | + | ± |

| | W194A | L195A | L196A | V197A | L198A | S199A | F200A | G201A | L202A | V252A |
|---|---|---|---|---|---|---|---|---|---|---|
| 18-0211B | + | + | + | + | + | + | ± | + | + | + |
| 33-0503E | + | + | + | + | + | + | − | + | + | ± |
| 37-0511F | + | + | + | + | + | + | ± | + | + | + |
| 49-0703G | + | + | + | + | + | + | − | + | + | ± |
| 50-0704C | + | + | + | + | + | + | ± | + | + | + |
| 53-0707E | + | + | + | + | + | + | ± | + | + | + |
| 64-0807A | + | + | + | + | + | + | ± | + | + | + |
| 65-0810G | + | + | − | + | + | + | − | + | + | ± |
| 80-1104A | + | + | + | + | + | + | + | + | + | + |
| 83-1110B | + | + | + | + | + | + | + | + | + | + |
| 84-1111F | + | + | + | + | + | + | + | + | + | + |
| 89-1207D | + | + | + | + | + | + | ± | + | + | + |
| 93-1310F | + | + | + | + | + | + | + | + | + | + |
| 94-1311E | + | + | + | + | + | + | + | + | + | + |
| 96-1403F | + | + | + | + | + | + | ± | + | + | + |

| | K253A | Q254A | A255F | A256F | G257A | D258A | W259A | H260A |
|---|---|---|---|---|---|---|---|---|
| 18-0211B | + | + | + | + | + | + | ± | + |
| 33-0503E | + | + | + | + | + | + | − | + |
| 37-0511F | + | + | + | + | + | + | − | ± |
| 49-0703G | + | + | + | + | + | + | − | + |
| 50-0704C | + | + | + | + | + | + | − | + |
| 53-0707E | + | + | + | + | + | + | − | ± |
| 64-0807A | + | + | + | + | + | + | − | + |
| 65-0810G | ± | + | + | + | + | ± | − | + |
| 80-1104A | + | + | + | + | + | + | + | + |
| 83-1110B | + | + | + | + | + | + | − | + |
| 84-1111F | + | + | + | + | + | + | ± | + |
| 89-1207D | + | + | + | + | + | + | ± | + |
| 93-1310F | + | + | + | + | + | + | + | ± |
| 94-1311E | + | + | + | + | + | + | − | ± |
| 96-1403F | + | + | + | + | + | + | + | + |

It is found that the SPNS2 neutralizing antibody has an essential amino acid for binding to SPNS2 through the extracellular loop. The results suggest that the SPNS2 neutralizing antibody recognizes the steric structure of SPNS2. From a comprehensive viewpoint on the amino acid residue necessary for each SPNS2 neutralizing antibody, the extracellular loop 1 is a sequence including at least Leu (Leu at the 127-th site in SEQ ID NO: 1) at the first site from the N terminal in SEQ ID NO: 3 to Gly (Gly at the 139-th site in SEQ ID NO: 1) at the 13-th site; the extracellular loop 3 is a sequence including at least Gln (Gln at 190-th site in SEQ ID NO: 1) at the second site from the N-terminal in SEQ ID NO: 4 to Arg (Arg at the 200-th site in SEQ ID NO: 1) at the 12-nd site; and the extracellular loop 5 is a sequence including at least Val (Val at the 252-nd site in SEQ ID NO: 1) at the first site from the N terminal in SEQ ID NO: 5 to His (His at the 260-th site in SEQ ID NO: 1) at the 9-th site. The antibody inhibiting S1P transport of SPNS2 binds to the extracellular loop 1, extracellular loop 3, or extracellular loop 5 to inhibit structural modification necessary for S1P transport.

[Example 12] Evaluation of Effects of the Anti-SPNS2 Antibody on the S1P Transport Ability Through SPNS2 by S1P Bioassay In order to detect the inhibitory action of the anti-SPNS2 antibody to the S1P transport through SPNS2, a bioassay process was constructed using activation of the downstream signal of the SP receptor as an index.

The human or mouse SPNS2 and human SphK1gene double stable expression Flp-in 293 cells were used to produce S1P. The human S1PR3 stable expression CHO cells were used to detect S1P. In order to determine the SP transport ability of SPNS2, the culture supernatant of the SPNS2 and SphK1 double stable expression cell line was added to S1PR3 stable expression cell line, and an increase in intracellular concentration of Ca', which was a S1PR3 downstream signal, was determined with a $Ca^{2+}$ fluorescent detecting agent (FLIPR Calcium 6 Evaluation Kit) (Molecular Devices, R8191).

Figure 5:
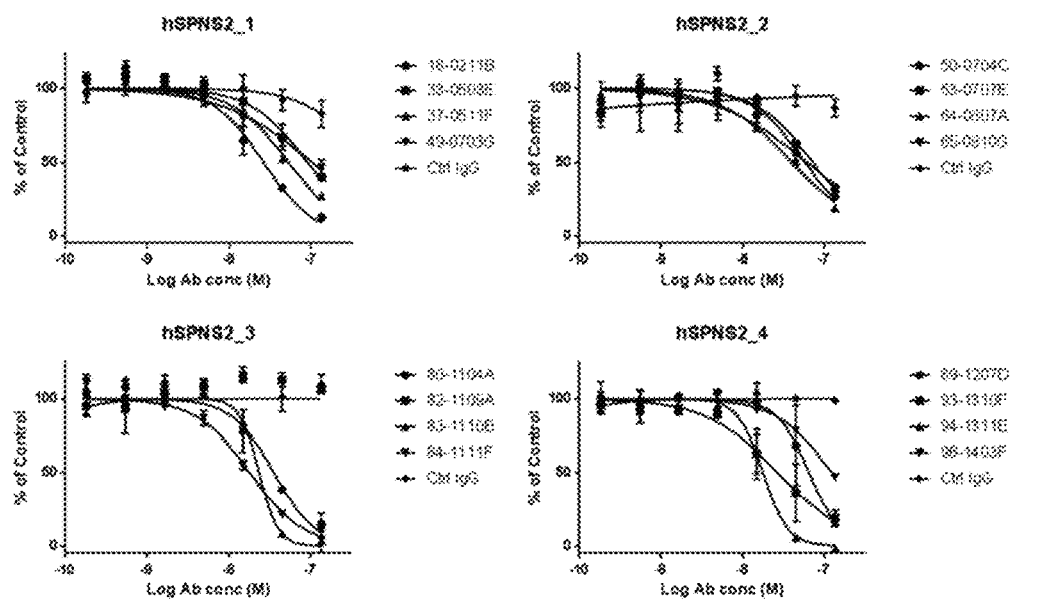
FIG. 5 is a graph showing FLIPR measurement results of the activities of SPNS2 neutralizing antibodies to inhibit S1P production by human SPNS2 expressing cells.
Figure 6:
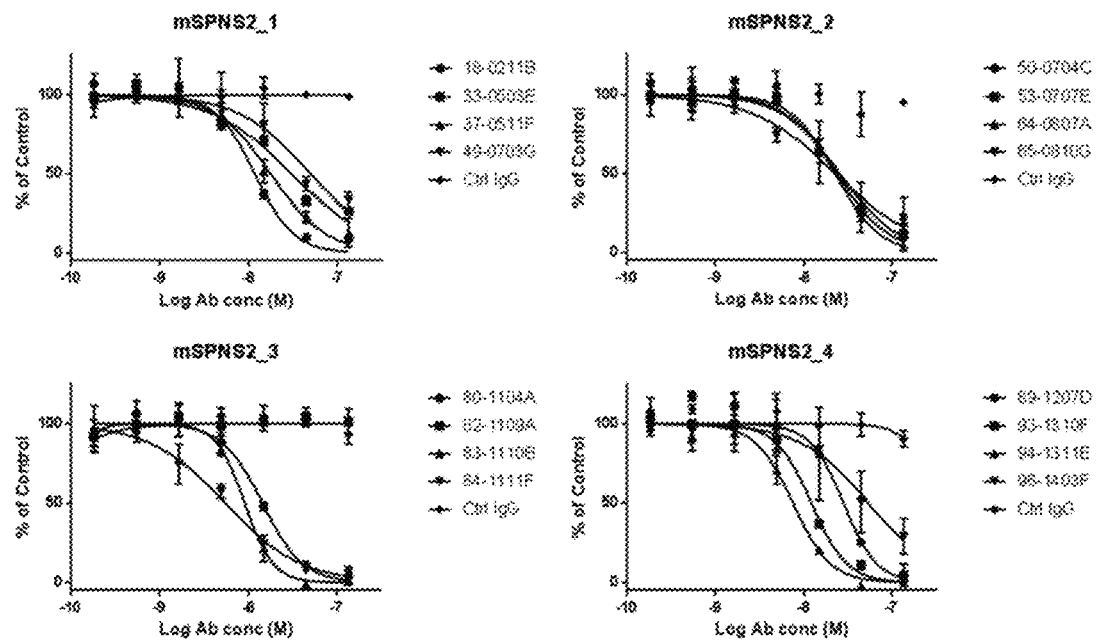
FIG. 6 is a graph showing FLIPR measurement results of the activities of SPNS2 neutralizing antibodies to inhibit S1Pproduction by mouse SPNS2 expressing cells.

The human or mouse SPNS2 and human SphK1 double stable expression cell lines were seeded onto a poly D lysine coat 96-well plate (Corning, 356461) in a density of 100 μL/well (5×104 cells/well), and a S1PR3 stable expression cell line was seeded onto a poly D lysine coat 96-well Black/Clear plate (Corning, 356640) in a density of 100 μL/well (2×10⁴ cells/well) in a F12 culture medium containing 2% serum and 0.8% BSA. These lines were cultivated overnight. The next day, the culture supernatant of the human or mouse SPNS2 and human SphK1 double stable expression cell line was removed. DMEM containing 1% BSA (200 μL) was added to a diluted solution (100 μL) of anti-SPNS2 antibody (20 μg/mL) to prepare seven-step diluted solutions by three fold serial dilution. Each antibody solution was added in a volume of 100 μL/well and reacted for 4 hours at 37° C., and then the supernatant was recovered. An increase in intracellular Ca' concentration in the S1PR3 stable expression cell line caused by addition of 100-fold diluted culture supernatant was monitored with a real-time fluorescent monitor FLIPR Tetra (Molecular Devices) in accordance with the manual attached to a FLIPR (trademark) $Ca^{2+}$ fluorescent detecting agent (FLIPR Calcium 6 Evaluation Kit) (Molecular Devices, R8191) to determine the S1Pcontent in the supernatant. The inhibitory activity of the anti-SPNS2 antibody was calculated from the activity (100%) of a group treated with only DMEM containing 1% BSA. FIG. 5 shows the inhibitory effect on the human SPNS2 and FIG. 6 shows the inhibitory effect on the mouse SPNS2. Table 9 shows the logarithmic value of the concentration indicating 50% inhibitory activity (pIC50) of each antibody.

Fifty antibody clones, 18-0211B, 33-0503E, 37-0511F, 49-0703G, 50-0704C, 53-0707E, 64-0807A, 65-0810G, 80-1104A, 83-1110B, 84-1111F, 89-1207D, 93-1310F, 94-1311E, and 96-1403F exhibited inhibitory activity to S1P transport ability through SPNS2. In contrast, 82-1109A exhibited no inhibitory activity.

TABLE 9

|  | Human SPNS2 pIC50 (M) | Mouse SPNS2 pIC50 (M) |
|---|---|---|
| 18-0211B | 7.6 | 7.9 |
| 33-0503E | 7.0 | 7.5 |
| 37-0511F | 7.3 | 7.8 |
| 49-0703G | 7.0 | 7.3 |
| 50-0704C | 7.2 | 7.6 |
| 53-0707E | 7.1 | 7.6 |
| 64-0807A | 7.4 | 7.6 |
| 65-0810G | 7.2 | 7.6 |
| 80-1104A | 7.5 | 7.8 |
| 83-1110B | 7.6 | 8.0 |
| 84-1111F | 7.7 | 8.3 |
| 89-1207D | 7.2 | 7.6 |
| 93-1310F | 7.6 | 7.9 |
| 94-1311E | 7.8 | 8.1 |
| 96-1403F | 6.9 | 7.3 |

[Example 13] Evaluation of Effects of Anti-SPNS2 Antibody on S1P Transport Ability Through SPNS2 by Mass Spectroscopic Analysis for Detection of S1P The S1P in living samples is usually determined by mass spectrometry.

The human or mouse SPNS2 and human SphK1 double stable expression cell line was seeded onto a poly D lysine coat 96-well plate (Corning, 356461) in a density of 100 µL/well ($5 \times 10^4$ cells/well), and was cultivated overnight. The next day, the supernatant of the human or mouse SPNS2 and human SphK1 double stable expression cell line was removed. DMEM containing 1% BSA (200 µL) was added to a diluted solution (100 µL) of anti-SPNS2 antibody (20 µg/mL) to prepare seven-step diluted solutions by three fold serial dilution. Each antibody solution was added in a volume of 100 µL/well and reacted for 4 hours at 37° C., and then the supernatant was recovered. Each recovered supernatant (50 µL) was diluted with methanol (150 µL) containing 100 nM internal standard (C17-S1P Avanti Polar Lipids, 860641P), the solution was thoroughly agitated with a vortex mixer, and then the protein was removed by centrifugation at 12000 rpm for 5 min. The resulting supernatant was subjected to mass spectrometry (Shimadzu LCMS-8030). S1P was detected with the parent ion at m/z: 380.15 and a fragment ion at m/z: 264.30, the internal standard C17-S1P was detected with the parent ion at m/z: 366.20 and a fragment ion at m/z: 250.25. The conditions of liquid chromatography are as follows: Solution A (0.1% formic acid), solution B (0.1% formic acid containing MeCN/MeOH 3:1), HPLC column (Shimadzu Luna C8 (2) 3.0 µm, 30 mm×4.60 mm, 00A-4248-E0), injection volume: 60 µL, temperature of the sample cooler: 10° C., temperature of the column oven: 40° C., and flow rate: 1 mL/min. As an eluent, 60% solution B was fed for 2 minutes 50 seconds, the concentration of the solution B was increased to 98% for 10 seconds, 98% solution B was fed for 1 minute 50 seconds, and 60% solution B was fed for 1 minute 10 seconds. The area of the target peak in each run was determined. The inhibitory activity of the anti-SPNS2 antibody was calculated from the activity (100%) of a group treated with only DMEM containing 1% BSA.

Figure 7:
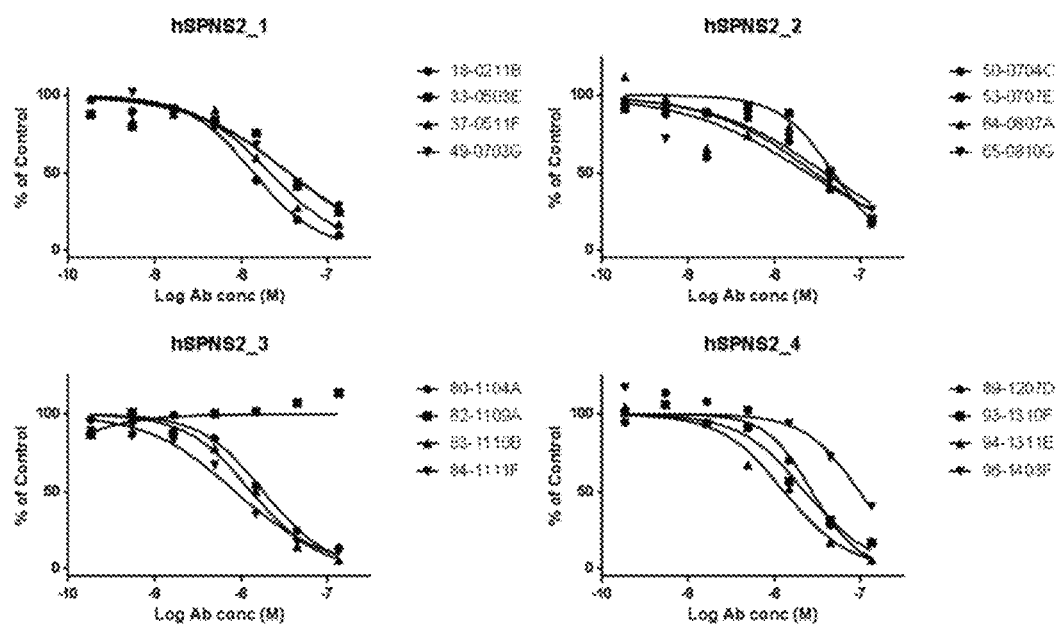
FIG. 7 is a graph showing LC-MS/MS measurement results of the activities of SPNS2 neutralizing antibodies to inhibit S1Pproduction by human SPNS2 expressing cells.
Figure 8:
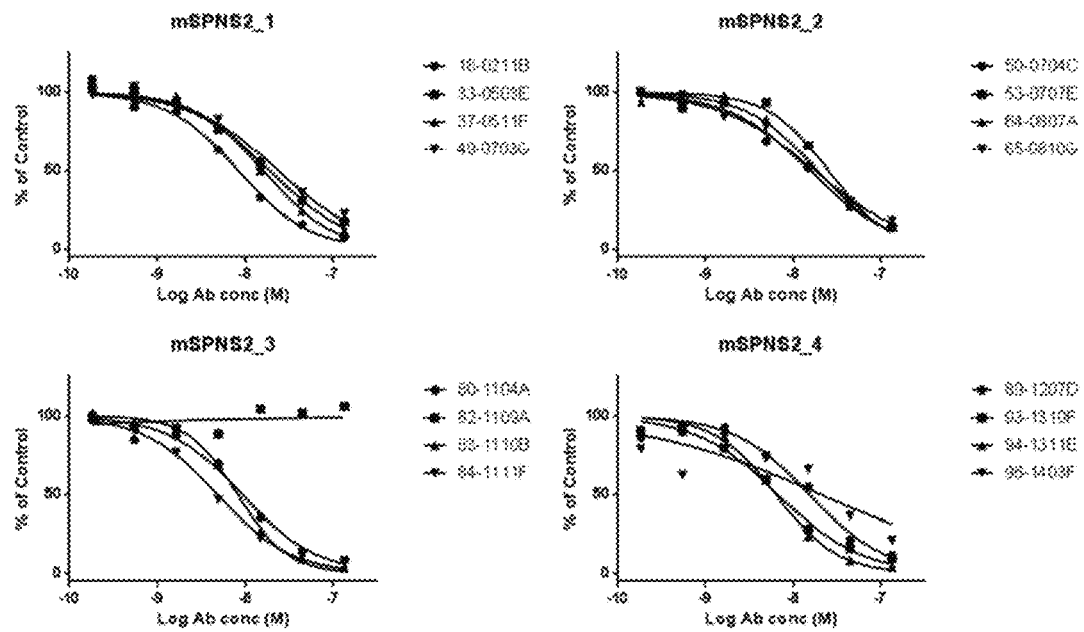
FIG. 8 is a graph showing LC-MS/MS measurement results of the activities of SPNS2 neutralizing antibodies to inhibit S1Pproduction by mouse SPNS2 expressing cells.

FIG. 7 shows the inhibitory effect on human SPNS2, and FIG. 8 shows the inhibitory effect on mouse SPNS2. Table 10 shows the logarithmic value of the concentration indicating 50% inhibitory activity (pIC50) of each antibody. Fifty antibody clones, 18-0211B, 33-0503E, 37-0511F, 49-0703G, 50-0704C, 53-0707E, 64-0807A, 65-0810G, 80-1104A, 83-1110B, 84-1111F, 89-1207D, 93-1310F, 94-1311E, and 96-1403F exhibited inhibitory activity to SP transport ability through SPNS2. In contrast, 82-1109A exhibited no inhibitory activity.

TABLE 10

|  | Human SPNS2 pIC50 (M) | Mouse SPNS2 pIC50 (M) |
|---|---|---|
| 18-0211B | 7.9 | 8.1 |
| 33-0503E | 7.4 | 7.7 |
| 37-0511F | 7.7 | 7.8 |
| 49-0703G | 7.4 | 7.6 |
| 50-0704C | 7.6 | 7.8 |
| 53-0707E | 7.3 | 7.6 |
| 64-0807A | 7.5 | 7.7 |
| 65-0810G | 7.4 | 7.8 |
| 80-1104A | 7.7 | 8.0 |
| 83-1110B | 7.9 | 8.1 |
| 84-1111F | 8.1 | 8.3 |
| 89-1207D | 7.6 | 7.8 |
| 93-1310F | 7.6 | 8.2 |
| 94-1311E | 7.9 | 8.2 |
| 96-1403F | 7.0 | 7.7 |

[Example 14] Homology Analysis Between SPNS2 Neutralizing Antibody Clones

In Examples 12 and 13, fifteen antibody clones, 18-0211B, 33-0503E, 37-0511F, 49-0703G, 50-0704C, 53-0707E, 64-0807A, 65-0810G, 80-1104A, 83-1110B, 84-1111F, 89-1207D, 93-1310F, 94-1311E and 96-1403F exhibit inhibitory activity (neutralization activity) to the SIP transport ability of SPNS2. The results suggest that these are SPNS2 neutralizing antibodies. To prove the suggestion, the fifteen clones were subjected to homology analysis on the heavy chain (H chain) variable region and light chain (L chain) variable region. The homology analysis of the amino acid sequence (correspondence with SEQ ID NO is listed in Table 5) in the heavy chain (H chain) variable region and light chain (L chain) variable region of each clone was carried out under the conditions of Matrix: EBLOSUM62, Gap open: 100, Gap extend: 0.5, End Gap Penalty: false, End Gap Open Penalty: 100 and End Gap Extension Penalty: 0.5 in accordance with the Needleman-Wunsch algorithm (Journal of Molecular Biology, 1970 Vol. 48 pp443-453). The phylogenetic tree analysis was carried out by the PRRN method (genome.jp/tools-bin/prrn). FIG. 9-1 shows the results of the homology analysis on the heavy chain variable region of each clone; and FIG. 9-2 shows the results of the homology analysis on the light chain variable region of each clone. In the upper half of each drawing, the % values indicate, from the top, identity (the rate of amino acids with complete identity-), homology or similarity (the rate of amino acids with identity or similarity), or gap (no amino acid residue is found at the corresponding sites)

between the corresponding amino acid sequences. In the lower half of each drawing, the fractional values indicate, from the top, the number of amino acid residues (numerator) counted in the identity, similarity, and gap to the full length (denominator) of the corresponding aligned amino acids.

The results of the homology analysis on the amino acid sequence in the heavy chain variable region demonstrate that 80% or more homology was found between eight antibody clones of 18-0211B, 33-0503E, 49-0703G, 50-0704C, 64-0807A, 65-0810G, 84-1111F, 89-1207D, between three clones of 80-1104A, 93-1310F, and 96-1403F, and four clones of 37-0511F, 53-0707E, 83-1110B and 94-1311E; in particular, 90% or more homology and 87% or more identity were found between four clones of 18-0211B, 49-0703G, 50-0704C, and 89-1207D, between two clones of 64-0807A and 84-1111F, between three clones of 80-1104A, 93-1310F, and 96-1403F, and between three clones of 37-0511F, 53-0707E, and 94-1311E. The results of the homology analysis on the amino acid sequence in the light chain variable region demonstrate that 80% or more homology was found between eight clones of 18-0211B, 33-0503E, 49-0703G, 50-0704C, 64-0807A, 65-0810G, 84-1111F, and 89-1207D, between three clones of 80-1104A, 93-1310F, and 96-1403F, and between four clones of 37-0511F, 53-0707E, 83-1110B, and 94-1311E; in particular, 95% or more homology and 90% or more identity were found between four clones of 18-0211B, 49-0703G, 50-0704C, and 89-1207D, between two clones of 64-0807A and 84-1111F, between three clones of 80-1104A, 93-1310F, and 96-1403F, and between three clones of 37-0511F, 53-0707E, and 94-1311E.

Figures 1, 10:
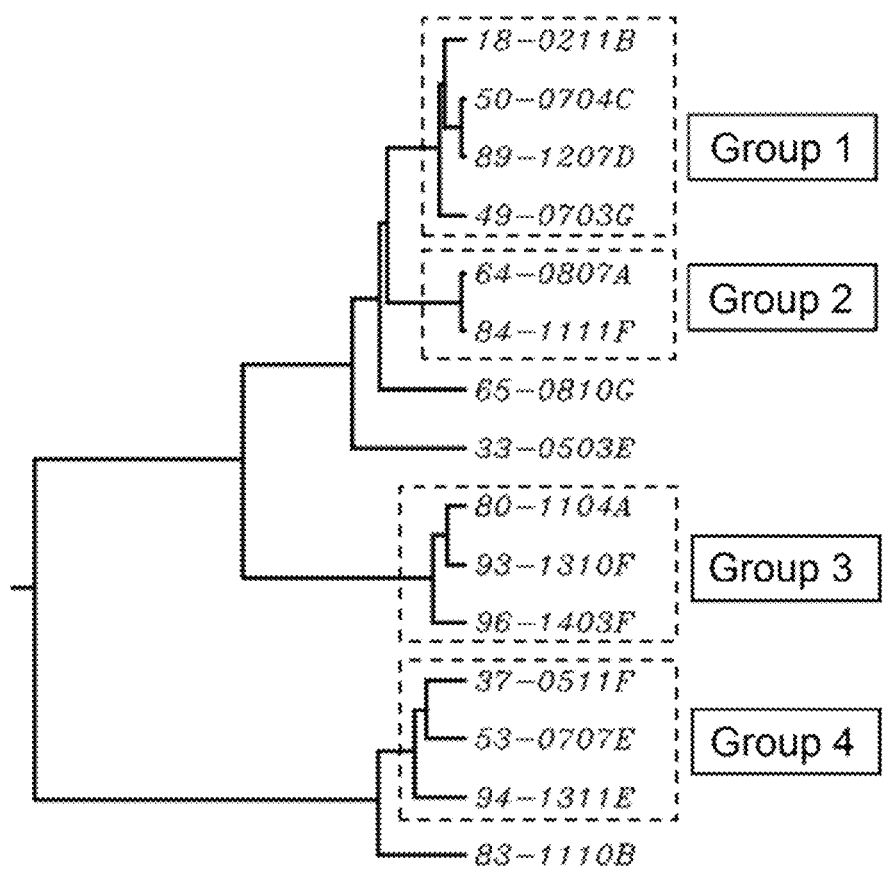
Figures 2, 10:
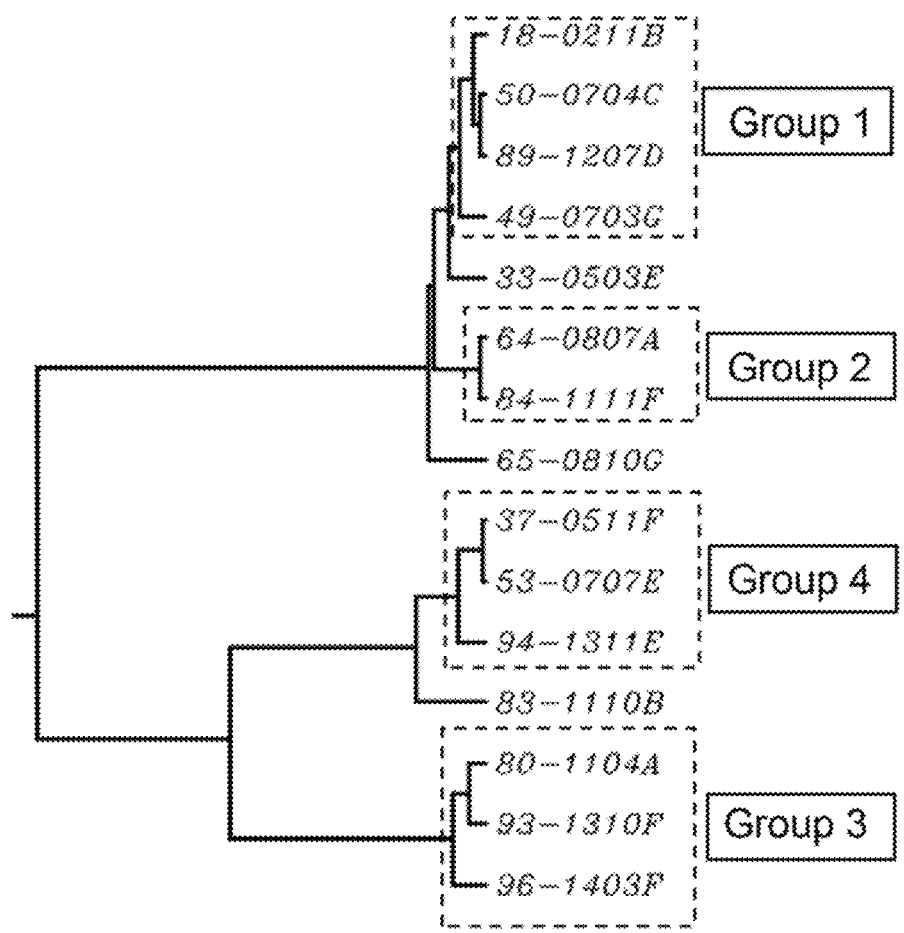

On the similarity of the heavy chain variable region and the light chain variable region, the results of the phylogenetic tree analysis shown in FIG. 10-1 (heavy chain variable region) and FIG. 10-2 (light chain variable region) also demonstrate that similar amino acid sequences of antibodies were found between four clones of 18-0211B, 49-0703G, 50-0704C, and 89-1207D, between two clones 64-0807A and 84-1111F, between three clones of 80-1104A, 93-1310F, and 96-1403F, and between three clones of 37-0511F, 53-0707E, and 94-1311E. Based on these results, the fifteen antibody clones are categorized into Group1 of four clones: 18-0211B, 49-0703G, 50-0704C, and 89-1207D, Group 2 of two clones: 64-0807A and 84-1111F, Group 3 of three clones: 80-1104A, 93-1310F, and 96-1403F, and Group 4 of three clones: 37-0511F, 53-0707E, and 94-1311E. Clones 33-0503E, 65-0810G, and 83-1110B are not categorized into any of Groups 1 to 4. FIGS. 11-1 to 11-5 show comparison between the amino acid sequence (one-character symbol) in the heavy chain variable region and the light chain variable region of antibodies belonging to each group and the contradistinction to the Kabat number (Kabat No.). The amino acid sequences in the heavy chain variable region and the light chain variable region corresponding to each clone are listed in a column, and the amino acid residues different between clones in the same group are hatched.

[Example 15] Evaluation of Decrease in Lymphocytes in Blood Affected by SPNS2 Neutralizing Antibody It has been known that SPNS2 knockout mice have reduced lymphocytes in the blood compared to native mice. A mouse IgG1 chimera antibody of clone 94-1311E was prepared, and the SPNS2 neutralizing antibody was administered to mice to confirm the in vivo drug efficacy of the neutralizing antibody.

The mouse IgG1 chimera antibody (heavy chain: SEQ ID NO: 345 and light chain: SEQ ID NO: 346) of the 94-1311E clone was prepared in a transient expression system using ExpiCHO cells. The variable regions of the heavy chain and light chain of the 94-1311E clone were incorporated into constant regions of the heavy chain and kappa light chain of mouse IgG1 of the expression vector (pcDNA 3.4 TOPO (trademark) vector) (A14697, Thermo Fisher) (heavy chain: SEQ ID NO: 347 and light chain: SEQ ID NO: 348). Each expression vector was introduced into the ExpiCHO cells and cultured for about two weeks in accordance with a Max titer protocol described in the manual attached to ExpiCHO cells. The antibody in the culture supernatant was purified with Ab-Capcher ExTra (trademark) (P-003, ProteNova) in accordance with an attached protocol.

The mouse IgG1 chimera antibody of the 94-1311E clone was subcutaneously administered to eight-week old C57BL/6J mouse (male) at a frequency of once every three days for 28 days. After 28 days from the administration, a blood sample was taken and the number of blood lymphocytes was determined with a flow cytometer (BD LSR Fortessa, Becton Dickinson).

Fluorescently labeled antibodies (10 μL) were each added to heparinaized blood (25 μL) to be reacted for 15 minutes at room temperature. Used fluorescently labeled antibodies were Alexa Fluor (trademark) 488 anti-mouse CD45 Antibody (103122, BioLegend), Brilliant Violet 421 (trademark) anti-mouse IgD Antibody (405725, BioLegend), Brilliant Violet 605 (trademark) anti-mouse CD19 Antibody (115540, BioLegend), PE anti-mouse CD8a Antibody (100708, BioLegend), PE/Cy7 anti-mouse CD23 Antibody (101614, BioLegend), Alexa Fluor (trademark) 700 anti-mouse CD4 Antibody (100430, BioLegend), and Brilliant Violet 785 (trademark) anti-mouse CD3 Antibody (100232, BioLegend) which were each dissolved in cell staining buffer (420201, BioLegend). FACS Lysing Solution (200 μL) (349202, Becton Dickinson) was added to each reaction solution, and was stirred for 20 minutes at room temperature in the dark. The reaction solution was filtered through a 40 μm multi-screen mesh plate (MANMN 4010, Merck). The filtrate was subjected to measurement with a flow cytometer (BD LSR Fortessa, Becton Dickinson) in according to the attached manual. The results measured with the flow cytometer were analyzed with an analytical software FlowJo (Becton Dickinson). Gated cell fractions were produced by FSC and SSC. The cell fraction was gated with Alexa Fluor (trademark) 488 and assigned to CD45 positive cells. The CD45 positive cells were gated with Brilliant Violet 605 (trademark) and Brilliant Violet 785 (trademark), and assigned to CD19 positive cells and CD3 positive cells, respectively. The CD19 positive cells were gated with Brilliant Violet 421 (trademark) and PE/Cy7 and assigned to IgD positive and CD23 positive cells (referred to as B cells). The CD3 positive cells were gated with Alexa Fluor (trademark) 700 and PE, and assigned to CD4 positive cell (referred to as CD4+ T cells) and CD8 positive cells (referred to as CD8+ T cells). Table 11 shows the rate of the number of lymphocytes to the number of CD45 positive cells.

TABLE 11

| Group | CD4+ T cell | CD8+ T cell |
| --- | --- | --- |
| Solvent administered group | 13.9 | 8.3 |
| Antibody administered group (low dose) | 6.9 | 5.2 |
| Antibody administered group (medium dose) | 6.1 | 5.3 |
| Antibody administered group (high dose) | 4.4 | 3.8 |

The SPNS2 neutralizing antibody significantly decreased CD4+ T cells and CD8+ T cells in blood compared to the solvent administered group. The results demonstrate that the SPNS2 neutralizing antibody has an in vivo lymphopenic effect.

The invention claimed is:

1. A Spinster homologue 2 (SPNS2) neutralizing antibody or antibody fragment, which specifically binds to extracellular loop 1 (SEQ ID NO:3), extracellular loop 3 (SEQ ID NO:4), or extracellular loop 5 (SEQ ID NO:5) of SPNS2 of a vertebrate and thereby exhibits an activity to inhibit its transport of sphingosine 1 phosphate (S1P).

2. The SPNS2 neutralizing antibody or antibody fragment according to claim 1, which exhibits at least one of the following features:
   (1) said antibody exhibits an EC50 value of $1\times10^{-7}$ M or less measured by cell-based ELISA using SPNS2 expressing cells; and
   (2) said antibody inhibits the transport of S1Pin SPNS2 expressing cells at an IC50 value of $1\times10^{-7}$ M or less.

3. The SPNS2 neutralizing antibody or antibody fragment according to claim 1, which binds to extracellular loop 1 (SEQ ID NO:3) or extracellular loop 5 (SEQ ID NO:5) of SPNS2 to thereby inhibit the transport of S1P.

4. The SPNS2 neutralizing antibody or antibody fragment according to claim 1, wherein the SPNS2 is human SPNS2, and wherein said SPNS2 neutralizing antibody or antibody fragment, optionally exhibits, when administered to a vertebrate, an activity to induce a decrease in the number of blood lymphocytes in the vertebrate.

5. The SPNS2 neutralizing antibody or antibody fragment according to claim 1, further comprising a framework sequence of an immunoglobulin, optionally wherein the framework sequence of an immunoglobulin is a framework sequence of a class of an immunoglobulin of a human or a non-human animal compising selected from the group consisting of a monkey, a mousey and a rat.

6. The SPNS2 neutralizing antibody or antibody fragment according to claim 1, further comprising, as a constant region, a constant region of a class of an immunoglobulin of a human or a non-human animal selected from the group consisting of a mouse, a rat, and a monkey.

7. The SPNS2 neutralizing antibody or antibody fragment, according to claim 1, which is a Fab, scFv, Diabody or bispecific antibody.

8. A pharmaceutical composition comprising the SPNS2 neutralizing antibody or antibody fragment, according to claim 1,
   and further comprising a pharmaceutically acceptable diluent and/or carrier and/or other additive and/or further comprising an additional active ingredient,
   wherein the additional active ingredient is selected from the group comprising azelastine, oxatomide, mequitazine, fexofenadine, epinastine, ebastin, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorcyclizine, cyproheptadine, mesalazine, interferon beta 1b, interferon beta 1a, fingolimod hydrochloride, natalizumab, glatiramer acetate, dimethyl fumarate, and apremilast, or wherein the active ingredient is selected from the group comprising corticosteroid, antiemetic, ondansetron hydrochloride, granisetron hydrochloride, metroclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesics, ibuprofen, naproxen, choline magnesium trisalicylate, oxycodone hydrochloride, anti-angiogenics, antithrombotics, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative drugs, farnesyl protein transferase inhibitor, $\alpha v\beta 3$ inhibitor, $\alpha v\beta 5$ inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

9. A method for the treatment, suppression, or prevention of cancer or autoimmune disease of a vertebrate, comprising administering, to a subject in need thereof, the pharmaceutical composition according to claim 8.

10. A nucleic acid molecule comprising a polynucleotide sequence encoding the SPNS2 neutralizing antibody or antibody fragment according to claim 1.

11. A cloning vector or expression vector comprising at least one nucleic acid molecule according to claim 10.

12. A recombinant cell prepared via introduction of the vector according to claim 11 into a host cell.

13. A process of producing an SPNS2 neutralizing antibody or antibody fragment, comprising: culturing a recombinant cell comprising a vector comprising a polynucleotide sequence encoding the SPNS2 neutralizing antibody or antibody fragment, according to claim 1; and purifying the resultant SPNS2 neutralizing antibody or antibody fragment.

14. A pharmaceutical composition comprising the nucleic acid molecule according to claim 10, and further comprising a pharmaceutically acceptable diluent and/or carrier and/or other additive and/or further comprising an additional active ingredient,
   wherein the additional active ingredient is selected from the group comprising azelastine, oxatomide, mequitazine, fexofenadine, epinastine, ebastin, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorcyclizine, cyproheptadine, mesalazine, interferon beta 1b, interferon beta 1a, fingolimod hydrochloride, natalizumab, glatiramer acetate, dimethyl fumarate, and apremilast, or wherein the active ingredient is selected from the group comprising corticosteroid, antiemetic, ondansetron hydrochloride, granisetron hydrochloride, metroclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesics, ibuprofen, naproxen, choline magnesium trisalicylate, oxycodone hydrochloride, anti-angiogenics, antithrombotics, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative drugs, farnesyl protein transferase inhibitor, $\alpha v\beta 3$ inhibitor, $\alpha v\beta 5$ inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

15. A pharmaceutical composition comprising the vector according to claim 11, and further comprising a pharmaceutically acceptable diluent and/or carrier and/or other additive and/or further comprising an additional active ingredient,
wherein the additional active ingredient is selected from the group comprising azelastine, oxatomide, mequitazine, fexofenadine, epinastine, ebastin, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorcyclizine, cyproheptadine, mesalazine, interferon beta 1b, interferon beta 1a, fingolimod hydrochloride, natalizumab, glatiramer acetate, dimethyl fumarate, and apremilast, or wherein the active ingredient is selected from the group comprising corticosteroid, antiemetic, ondansetron hydrochloride, granisetron hydrochloride, metroclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesics, ibuprofen, naproxen, choline magnesium trisalicylate, oxycodone hydrochloride, anti-angiogenics, antithrombotics, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative drugs, farnesyl protein transferase inhibitor, $\alpha v\beta 3$ inhibitor, $\alpha v\beta 5$ inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

16. A pharmaceutical composition comprising the recombinant cell according to claim 12, and further comprising a pharmaceutically acceptable diluent and/or carrier and/or other additive and/or further comprising an additional active ingredient,
wherein the additional active ingredient is selected from the group comprising azelastine, oxatomide, mequitazine, fexofenadine, epinastine, ebastin, cetirizine, levocetirizine, bepotastine, emedastine, olopatadine, loratadine, levocabastine, ozagrel, seratrodast, ramatroban, pranlukast, montelukast, zafirlukast, suplatast, diphenhydramine, dimenhydrinate, diphenylpyraline, clemastine, chlorpheniramine, triprolidine, promethazine, alimemazine, hydroxyzine, homochlorcyclizine, cyproheptadine, mesalazine, interferon beta 1b, interferon beta 1a, fingolimod hydrochloride, natalizumab, glatiramer acetate, dimethyl fumarate, and apremilast, or wherein the active ingredient is selected from the group comprising corticosteroid, antiemetic, ondansetron hydrochloride, granisetron hydrochloride, metroclopramide, domperidone, haloperidol, cyclizine, lorazepam, prochlorperazine, dexamethasone, levomepromazine, tropisetron, cancer vaccine, GM-CSF inhibitor, GM-CSF DNA vaccine, cell-based vaccine, dendritic cell vaccine, recombinant virus vaccine, heat shock protein (HSP) vaccine, homologous tumor vaccine, autologous tumor vaccine, analgesics, ibuprofen, naproxen, choline magnesium trisalicylate, oxycodone hydrochloride, anti-angiogenics, antithrombotics, anti-PD-1 antibody, nivolumab, pembrolizumab, anti-PD-L1 antibody, atezolizumab, anti-CTLA4 antibody, ipilimumab, anti-CD20 antibody, rituximab, anti-HER2 antibody, trastuzumab, anti-CCR4 antibody, mogamulizumab, anti-VEGF antibody, bevacizumab, anti-VEGF receptor antibody, soluble VEGF receptor fragment, anti-TWEAK antibody, anti-TWEAK receptor antibody, soluble TWEAK receptor fragment, AMG 706, AMG 386, antiproliferative drugs, farnesyl protein transferase inhibitor, $\alpha v\beta 3$ inhibitor, $\alpha v\beta 5$ inhibitor, p53 inhibitor, Kit receptor inhibitor, ret receptor inhibitor, PDGFR inhibitor, growth hormone secretion inhibitor, angiopoietin inhibitor, tumor-infiltrating macrophage inhibitor, c-fms inhibitor, anti-c-fms antibody, CSF-1 inhibitor, anti-CSF-1 antibody, soluble c-fms fragment, pegvisomant, gemcitabine, panitumumab, irinotecan, and SN-38.

17. Spinster homologue 2 (SPNS2) neutralizing antibody or antibody fragment, which specifically binds to SPNS2 of a vertebrate and thereby exhibits an activity to inhibit its transport of sphingosine 1 phosphate (S1P), comprising:
(1) as a CDR-H1 sequence, the amino acid sequence defined in SEQ ID NO:98 or an amino acid sequence derived from the amino acid sequence defined in SEQ ID NO:98 via substitution, deletion, or addition of one or two amino acid residues;

as a CDR-H2 sequence, the amino acid sequence defined in SEQ ID NO:108 or SEQ ID NO:111 or an amino acid sequence derived from the amino acid sequence defined in SEQ ID NO:108 or SEQ ID NO:111 via substitution, deletion, or addition of one or two amino acid residues;

as a CDR-H3 sequence, the amino acid sequence defined in SEQ ID NO:120 or SEQ ID NO:123 or an amino acid sequence derived from the amino acid sequence defined in SEQ ID NO:120 or SEQ ID NO:123 via substitution, deletion, or addition of one or two amino acid residues;

as a CDR-L1 sequence, the amino acid sequence defined in SEQ ID NO:129 or SEQ ID NO:132 or an amino acid sequence derived from the amino acid sequence defined in SEQ ID NO:129 or SEQ ID NO:132 via substitution, deletion, or addition of one or two amino acid residues;

as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and as a CDR-L3 sequence, the amino acid sequence as defined in any one of SEQ ID NO:149, SEQ ID NO:152 or SEQ ID NO:157 or an amino acid sequence derived from the amino acid sequence as defined in any one of SEQ ID NO:149, SEQ ID NO:152 or SEQ ID NO:157 via substitution, deletion, or addition of one or two amino acid residues;

(2) as a CDR-H1 sequence, the amino acid sequence defined in SEQ ID NO:101 or an amino acid sequence derived from the amino acid sequence defined in SEQ ID NO:101 via substitution, deletion, or addition of one or two amino acid residues;

as a CDR-H2 sequence, the amino acid sequence defined in SEQ ID NO:113 or an amino acid sequence derived from the amino acid sequence defined in SEQ ID NO:113 via substitution, deletion, or addition of one or two amino acid residues;

as a CDR-H3 sequence, the amino acid sequence defined in SEQ ID NO:124 or an amino acid sequence derived from the amino acid sequence defined in SEQ ID NO:124 via substitution, deletion, or addition of one or two amino acid residues;

as a CDR-L1 sequence, the amino acid sequence defined in SEQ ID NO:134 or an amino acid sequence derived from the amino acid sequence defined in SEQ ID NO:134 via substitution, deletion, or addition of one or two amino acid residues;

as a CDR-L2 sequence, the amino acid sequence defined in SEQ ID NO:142 or an amino acid sequence derived from the amino acid sequence defined in SEQ ID NO:142 via substitution, deletion, or addition of one or two amino acid residues; and as a CDR-L3 sequence, the amino acid sequence defined in SEQ ID NO:153 or an amino acid sequence derived from the amino acid sequence defined in SEQ ID NO:153 via substitution, deletion, or addition of one or two amino acid residues;

(3) as a CDR-H1 sequence, the amino acid sequence defined in SEQ ID NO:103 or SEQ ID NO:105 or an amino acid sequence derived from the amino acid sequence defined in SEQ ID NO:103 or SEQ ID NO:105 via substitution, deletion, or addition of one or two amino acid residues;

as a CDR-H2 sequence, the amino acid sequence defined in SEQ ID NO:115 or SEQ ID NO:118 or an amino acid sequence derived from the amino acid sequence defined in SEQ ID NO:115 or SEQ ID NO:118 via substitution, deletion, or addition of one or two amino acid residues;

as a CDR-H3 sequence, the amino acid sequence defined in SEQ ID NO:126 or SEQ ID NO:127 or an amino acid sequence derived from the amino acid sequence defined in SEQ ID NO:126 or SEQ ID NO:127 via substitution, deletion, or addition of one or two amino acid residues;

as a CDR-L1 sequence, the amino acid sequence defined in SEQ ID NO:136 or an amino acid sequence derived from the amino acid sequence defined in SEQ ID NO:136 via substitution, deletion, or addition of one or two amino acid residues;

as a CDR-L2 sequence, the amino acid sequence as defined in any one of SEQ ID NO:144, SEQ ID NO:146 or SEQ ID NO:147 or an amino acid sequence derived from the amino acid sequence as defined in any one of SEQ ID NO:144, SEQ ID NO:146 or SEQ ID NO:147 via substitution, deletion, or addition of one or two amino acid residues; and as a CDR-L3 sequence, the amino acid sequence defined in SEQ ID NO:155 or SEQ ID NO:158 or an amino acid sequence derived from the amino acid sequence defined in SEQ ID NO:155 or SEQ ID NO:158 via substitution, deletion, or addition of one or two amino acid residues;

(4) as a CDR-H1 sequence, the amino acid sequence defined in SEQ ID NO:100 or SEQ ID NO:106 or an amino acid sequence derived from the amino acid sequence defined in SEQ ID NO:100 or SEQ ID NO:106 via substitution, deletion, or addition of one or two amino acid residues;

as a CDR-H2 sequence, the amino acid sequence as defined in any one of SEQ ID NO:110, SEQ ID NO:112 or SEQ ID NO:117 or an amino acid sequence derived from the amino acid sequence as defined in any one of SEQ ID NO:110, SEQ ID NO:112 or SEQ ID NO:117 via substitution, deletion, or addition of one or two amino acid residues;

as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues;

as a CDR-L1 sequence, the amino acid sequence as defined in any one of SEQ ID NO:131, SEQ ID NO:133 or SEQ ID NO:138 or an amino acid sequence derived from the amino acid sequence as defined in any one of SEQ ID NO:131, SEQ ID NO:133 or SEQ ID NO:138 via substitution, deletion, or addition of one or two amino acid residues;

as a CDR-L2 sequence, the amino acid sequence defined in SEQ ID NO:141 or an amino acid sequence derived from the amino acid sequence defined in SEQ ID NO:141 via substitution, deletion, or addition of one or two amino acid residues; and as a CDR-L3 sequence, the amino acid sequence defined in SEQ ID NO:151 or an amino acid sequence derived from the amino acid sequence defined in SEQ ID NO:151 via substitution, deletion, or addition of one or two amino acid residues;

(5) as a CDR-H1 sequence, the amino acid sequence defined in SEQ ID NO:99 or an amino acid sequence derived from the amino acid sequence defined in SEQ ID NO:99 via substitution, deletion, or addition of one or two amino acid residues;
   as a CDR-H2 sequence, the amino acid sequence defined in SEQ ID NO:109 or an amino acid sequence derived from the amino acid sequence defined in SEQ ID NO:109 via substitution, deletion, or addition of one or two amino acid residues;
   as a CDR-H3 sequence, the amino acid sequence defined in SEQ ID NO:121 or an amino acid sequence derived from the amino acid sequence defined in SEQ ID NO:121 via substitution, deletion, or addition of one or two amino acid residues;
   as a CDR-L1 sequence, the amino acid sequence defined in SEQ ID NO:130 or an amino acid sequence derived from the amino acid sequence defined in SEQ ID NO:130 via substitution, deletion, or addition of one or two amino acid residues;
   as a CDR-L2 sequence, the amino acid sequence defined in SEQ ID NO:140 or an amino acid sequence derived from the amino acid sequence defined in SEQ ID NO:140 via substitution, deletion, or addition of one or two amino acid residues; and
   as a CDR-L3 sequence, the amino acid sequence defined in SEQ ID NO:150 or an amino acid sequence derived from the amino acid sequence defined in SEQ ID NO:150 via substitution, deletion, or addition of one or two amino acid residues;
(6) as a CDR-H1 sequence, the amino acid sequence defined in SEQ ID NO:102 or an amino acid sequence derived from the amino acid sequence defined in SEQ ID NO:102 via substitution, deletion, or addition of one or two amino acid residues;
   as a CDR-H2 sequence, the amino acid sequence defined in SEQ ID NO:114 or an amino acid sequence derived from the amino acid sequence defined in SEQ ID NO:114 via substitution, deletion, or addition of one or two amino acid residues;
   as a CDR-H3 sequence, the amino acid sequence defined in SEQ ID NO:125 or an amino acid sequence derived from the amino acid sequence defined in SEQ ID NO:125 via substitution, deletion, or addition of one or two amino acid residues;
   as a CDR-L1 sequence, the amino acid sequence defined in SEQ ID NO:135 or an amino acid sequence derived from the amino acid sequence defined in SEQ ID NO:135 via substitution, deletion, or addition of one or two amino acid residues;
   as a CDR-L2 sequence, the amino acid sequence defined in SEQ ID NO:143 or an amino acid sequence derived from the amino acid sequence defined in SEQ ID NO:143 via substitution, deletion, or addition of one or two amino acid residues; and
   as a CDR-L3 sequence, the amino acid sequence defined in SEQ ID NO:154 or an amino acid sequence derived from the amino acid sequence defined in SEQ ID NO:154 via substitution, deletion, or addition of one or two amino acid residues; or
(7) as a CDR-H1 sequence, the amino acid sequence defined in SEQ ID NO:104 or an amino acid sequence derived from the amino acid sequence defined in SEQ ID NO:104 via substitution, deletion, or addition of one or two amino acid residues;
   as a CDR-H2 sequence, the amino acid sequence defined in SEQ ID NO:116 or an amino acid sequence derived from the amino acid sequence defined in SEQ ID NO:116 via substitution, deletion, or addition of one or two amino acid residues;
   as a CDR-H3 sequence, the amino acid sequence defined in SEQ ID NO:122 or an amino acid sequence derived from the amino acid sequence defined in SEQ ID NO:122 via substitution, deletion, or addition of one or two amino acid residues;
   as a CDR-L1 sequence, the amino acid sequence defined in SEQ ID NO:137 or an amino acid sequence derived from the amino acid sequence defined in SEQ ID NO:137 via substitution, deletion, or addition of one or two amino acid residues;
   as a CDR-L2 sequence, the amino acid sequence defined in SEQ ID NO:145 or an amino acid sequence derived from the amino acid sequence defined in SEQ ID NO:145 via substitution, deletion, or addition of one or two amino acid residues; and
   as a CDR-L3 sequence, the amino acid sequence defined in SEQ ID NO:156 or an amino acid sequence derived from the amino acid sequence defined in SEQ ID NO:156 via substitution, deletion, or addition of one or two amino acid residues; or
(8) as a CDR-H1 sequence, an amino acid sequence having a homology of 80% or more to SEQ ID NO:98;
   as a CDR-H2 sequence, an amino acid sequence having a homology of 88% or more to SEQ ID NO:108 or SEQ ID NO:111;
   as a CDR-H3 sequence, an amino acid sequence having a homology of 83% or more to SEQ ID NO:120 or SEQ ID NO:123;
   as a CDR-L1 sequence, an amino acid sequence having a homology of 84% or more to SEQ ID NO:129 or SEQ ID NO:132;
   as a CDR-L2 sequence, an amino acid sequence having a homology of 85% or more to SEQ ID NO:140; and
   as a CDR-L3 sequence, an amino acid sequence having a homology of 88% or more to any one of SEQ ID NO:149, SEQ ID NO:152 or SEQ ID NO:157;
(9) as a CDR-H1 sequence, an amino acid sequence having a homology of 80% or more to SEQ ID NO:101;
   as a CDR-H2 sequence, an amino acid sequence having a homology of 88% or more to SEQ ID NO:113;
   as a CDR-H3 sequence, an amino acid sequence having a homology of 88% or more to SEQ ID NO:124;
   as a CDR-L1 sequence, an amino acid sequence having a homology of 84% or more to SEQ ID NO:134;
   as a CDR-L2 sequence, an amino acid sequence having a homology of 85% or more to SEQ ID NO:142; and
   as a CDR-L3 sequence, an amino acid sequence having a homology of 88% or more to SEQ ID NO:153;
(10) as a CDR-H1 sequence, an amino acid sequence having a homology of 80% or more to SEQ ID NO:103 or SEQ ID NO:105;
   as a CDR-H2 sequence, an amino acid sequence having a homology of 89% or more to SEQ ID NO:115 or SEQ ID NO:118;
   as a CDR-H3 sequence, an amino acid sequence having a homology of 85% or more to SEQ ID NO:126 or SEQ ID NO:127;
   as a CDR-L1 sequence, an amino acid sequence having a homology of 81% or more to SEQ ID NO:136;
   as a CDR-L2 sequence, an amino acid sequence having a homology of 85% or more to any one of SEQ ID NO:144, SEQ ID NO:146 or SEQ ID NO:147; and as a CDR-L3 sequence, an amino acid sequence having a homology of 88% or more to SEQ ID NO:155 or SEQ ID NO:158;

(11) as a CDR-H1 sequence, an amino acid sequence having a homology of 80% or more to SEQ ID NO:100 or SEQ ID NO:106;
as a CDR-H2 sequence, an amino acid sequence having a homology of 88% or more to any one of SEQ ID NO:110, SEQ ID NO:112 or SEQ ID NO:117;
as a CDR-H3 sequence, an amino acid sequence having a homology of 83% or more to SEQ ID NO:122;
as a CDR-L1 sequence, an amino acid sequence having a homology of 81% or more to any one of SEQ ID NO:131, SEQ ID NO:133 or SEQ ID NO:138;
as a CDR-L2 sequence, an amino acid sequence having a homology of 85% or more to SEQ ID NO:141; and
as a CDR-L3 sequence, an amino acid sequence having a homology of 88% or more to SEQ ID NO:151;

(12) as a CDR-H1 sequence, an amino acid sequence having a homology of 80% or more to SEQ ID NO:99;
as a CDR-H2 sequence, an amino acid sequence having a homology of 88% or more to SEQ ID NO:109;
as a CDR-H3 sequence, an amino acid sequence having a homology of 80% or more to SEQ ID NO:121;
as a CDR-L1 sequence, an amino acid sequence having a homology of 84% or more to SEQ ID NO:130;
as a CDR-L2 sequence, an amino acid sequence having a homology of 85% or more to SEQ ID NO:140; and
as a CDR-L3 sequence, an amino acid sequence having a homology of 88% or more to SEQ ID NO:150;

(13) as a CDR-H1 sequence, an amino acid sequence having a homology of 80% or more to SEQ ID NO:102;
as a CDR-H2 sequence, an amino acid sequence having a homology of 88% or more to SEQ ID NO:114;
as a CDR-H3 sequence, an amino acid sequence having a homology of 83% or more to SEQ ID NO:125;
as a CDR-L1 sequence, an amino acid sequence having a homology of 84% or more to SEQ ID NO:135;
as a CDR-L2 sequence, an amino acid sequence having a homology of 85% or more to SEQ ID NO:143; and
as a CDR-L3 sequence, an amino acid sequence having a homology of 88% or more to SEQ ID NO:154; or

(14) as a CDR-H1 sequence, an amino acid sequence having a homology of 80% or more to SEQ ID NO:104;
as a CDR-H2 sequence, an amino acid sequence having a homology of 88% or more to SEQ ID NO:116;
as a CDR-H3 sequence, an amino acid sequence having a homology of 83% or more to SEQ ID NO:122;
as a CDR-L1 sequence, an amino acid sequence having a homology of 81% or more to SEQ ID NO:137;
as a CDR-L2 sequence, an amino acid sequence having a homology of 85% or more to SEQ ID NO:145; and
as a CDR-L3 sequence, an amino acid sequence having a homology of 88% or more to SEQ ID NO:156; or

(15) as a CDR-H1 sequence, the amino acid sequence defined in SEQ ID NO:98;
as a CDR-H2 sequence, the amino acid sequence defined in SEQ ID NO:108 or the amino acid sequence derived from SEQ ID NO:108 via substitution of the 1st amino acid residue Thr with Ser;
as a CDR-H3 sequence, the amino acid sequence defined in SEQ ID NO:123 or an amino acid sequence derived from SEQ ID NO:123 via substitution of the 4th amino acid residue Ser with Thr;
as a CDR-L1 sequence, the amino acid sequence defined in SEQ ID NO:129 or an amino acid sequence derived from SEQ ID NO:129 via substitution of the 1st amino acid residue Thr with Lys and/or substitution of the 4th amino acid residue Ile with Thr;
as a CDR-L2 sequence, the amino acid sequence defined in SEQ ID NO:140; and
as a CDR-L3 sequence, the amino acid sequence defined in SEQ ID NO:149 or an amino acid sequence derived from SEQ ID NO:149 via substitution of the 5th amino acid residue Ser with Asn and/or substitution of the 7th amino acid residue Ile with Met;

(16) as a CDR-H1 sequence, the amino acid sequence defined in SEQ ID NO:101;
as a CDR-H2 sequence, the amino acid sequence defined in SEQ ID NO:113;
as a CDR-H3 sequence, the amino acid sequence defined in SEQ ID NO:124;
as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;

(17) as a CDR-H1 sequence, the amino acid sequence defined in SEQ ID NO:105 or an amino acid sequence derived from SEQ ID NO:105 via substitution of the 1st amino acid residue Asp with Glu;
as a CDR-H2 sequence, the amino acid sequence defined in SEQ ID NO:115 or an amino acid sequence derived from SEQ ID NO:115 via substitution of the 9th amino acid residue Tyr with Ser and/or substitution of the 17th amino acid residue Val with Ile;
as a CDR-H3 sequence, the amino acid sequence defined in SEQ ID NO:126 or an amino acid sequence derived from SEQ ID NO:126 via substitution of the 9th amino acid residue Ser with Gly;
as a CDR-L1 sequence, the amino acid sequence defined in SEQ ID NO:136;
as a CDR-L2 sequence, the amino acid sequence defined in SEQ ID NO:146 or an amino acid sequence derived from SEQ ID NO:146 via substitution of the 6th amino acid residue Ile with Met and/or substitution of the 7th amino acid residue Ser with Ala; and
as a CDR-L3 sequence, the amino acid sequence defined in SEQ ID NO:158 or an amino acid sequence derived from SEQ ID NO:158 via substitution of the 3rd amino acid residue Thr with Ser and/or substitution of the 5th amino acid residue Ser with Asn;

(18) as a CDR-H1 sequence, the amino acid sequence defined in SEQ ID NO:100 or an amino acid sequence derived from SEQ ID NO:100 via substitution of the 1st amino acid residue Arg with Ala;
as a CDR-H2 sequence, the amino acid sequence defined in SEQ ID NO:110 or an amino acid sequence derived from SEQ ID NO:110 via substitution of the 8th amino acid residue Thr with Ser and/or substitution of the 17th amino acid residue Asn with Lys;
as a CDR-H3 sequence, the amino acid sequence defined in SEQ ID NO:122;
as a CDR-L1 sequence, the amino acid sequence defined in SEQ ID NO:133 or an amino acid sequence derived from SEQ ID NO:133 via one or more selected from substitution of the 2nd amino acid residue Ala with Pro, substitution of the 5th amino acid residue Asn with Ser, and substitution of the 8th amino acid Ser with Asn;
as a CDR-L2 sequence, the amino acid sequence defined in SEQ ID NO:141; and
as a CDR-L3 sequence, the amino acid sequence defined in SEQ ID NO:151;

(19) as a CDR-H1 sequence, the amino acid sequence defined in SEQ ID NO:99;
as a CDR-H2 sequence, the amino acid sequence defined in SEQ ID NO:109;
as a CDR-H3 sequence, the amino acid sequence defined in SEQ ID NO:121;
as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;

(20) as a CDR-H1 sequence, the amino acid sequence defined in SEQ ID NO:102;
as a CDR-H2 sequence, the amino acid sequence defined in SEQ ID NO:114;
as a CDR-H3 sequence, the amino acid sequence defined in SEQ ID NO:125;
as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154; or

(21) as a CDR-H1 sequence, the amino acid sequence defined in SEQ ID NO:104;
as a CDR-H2 sequence, the amino acid sequence defined in SEQ ID NO:116;
as a CDR-H3 sequence, the amino acid sequence defined in SEQ ID NO:122;
as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156; or

(22) as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:120;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;

(23) as a CDR-H1 sequence, the amino acid sequence defined in SEQ ID NO:99;
as a CDR-H2 sequence, the amino acid sequence defined in SEQ ID NO:109;
as a CDR-H3 sequence, the amino acid sequence defined in SEQ ID NO:121;
as a CDR-L1 sequence, the amino acid sequence defined in SEQ ID NO:130;
as a CDR-L2 sequence, the amino acid sequence defined in SEQ ID NO:140; and
as a CDR-L3 sequence, the amino acid sequence defined in SEQ ID NO:150;

(24) as a CDR-H1 sequence, the amino acid sequence defined in SEQ ID NO:100;
as a CDR-H2 sequence, the amino acid sequence defined in SEQ ID NO:110;
as a CDR-H3 sequence, the amino acid sequence defined in SEQ ID NO:122;
as a CDR-L1 sequence, the amino acid sequence defined in SEQ ID NO:131;
as a CDR-L2 sequence, the amino acid sequence defined in SEQ ID NO:141; and
as a CDR-L3 sequence, the amino acid sequence defined in SEQ ID NO:151;

(25) as a CDR-H1 sequence, the amino acid sequence defined in SEQ ID NO:98;
as a CDR-H2 sequence, the amino acid sequence defined in SEQ ID NO:111;
as a CDR-H3 sequence, the amino acid sequence defined in SEQ ID NO:123;
as a CDR-L1 sequence, the amino acid sequence defined in SEQ ID NO:132;
as a CDR-L2 sequence, the amino acid sequence defined in SEQ ID NO:140; and
as a CDR-L3 sequence, the amino acid sequence defined in SEQ ID NO:152;

(26) as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:123;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:149;

(27) as a CDR-H1 sequence, the amino acid sequence defined in SEQ ID NO:100;
as a CDR-H2 sequence, the amino acid sequence defined in SEQ ID NO:112;
as a CDR-H3 sequence, the amino acid sequence defined in SEQ ID NO:122;
as a CDR-L1 sequence, the amino acid sequence defined in SEQ ID NO:133;
as a CDR-L2 sequence, the amino acid sequence defined in SEQ ID NO:141; and
as a CDR-L3 sequence, the amino acid sequence defined in SEQ ID NO:151;

(28) as a CDR-H1 sequence, the amino acid sequence defined in SEQ ID NO:101;
as a CDR-H2 sequence, the amino acid sequence defined in SEQ ID NO:113;
as a CDR-H3 sequence, the amino acid sequence defined in SEQ ID NO:124;
as a CDR-L1 sequence, the amino acid sequence defined in SEQ ID NO:134;
as a CDR-L2 sequence, the amino acid sequence defined in SEQ ID NO:142; and
as a CDR-L3 sequence, the amino acid sequence defined in SEQ ID NO:153;

(29) as a CDR-H1 sequence, the amino acid sequence defined in SEQ ID NO:102;
as a CDR-H2 sequence, the amino acid sequence defined in SEQ ID NO:114;
as a CDR-H3 sequence, the amino acid sequence defined in SEQ ID NO:125;

as a CDR-L1 sequence, the amino acid sequence defined in SEQ ID NO:135;
as a CDR-L2 sequence, the amino acid sequence defined in SEQ ID NO:143; and
as a CDR-L3 sequence, the amino acid sequence defined in SEQ ID NO:154;

(30) as a CDR-H1 sequence, the amino acid sequence defined in SEQ ID NO:103;
as a CDR-H2 sequence, the amino acid sequence defined in SEQ ID NO:115;
as a CDR-H3 sequence, the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:144; and
as a CDR-L3 sequence, the amino acid sequence defined in SEQ ID NO:155;

(31) as a CDR-H1 sequence, the amino acid sequence defined in SEQ ID NO:104;
as a CDR-H2 sequence, the amino acid sequence defined in SEQ ID NO:116;
as a CDR-H3 sequence, the amino acid sequence defined in SEQ ID NO:122;
as a CDR-L1 sequence, the amino acid sequence defined in SEQ ID NO:137;
as a CDR-L2 sequence, the amino acid sequence defined in SEQ ID NO:145; and
as a CDR-L3 sequence, the amino acid sequence defined in SEQ ID NO:156;

(32) as a CDR-H1 sequence, the amino acid sequence defined in SEQ ID NO:98;
as a CDR-H2 sequence, the amino acid sequence defined in SEQ ID NO:108;
as a CDR-H3 sequence, the amino acid sequence defined in SEQ ID NO:123;
as a CDR-L1 sequence, the amino acid sequence defined in SEQ ID NO:129;
as a CDR-L2 sequence, the amino acid sequence defined in SEQ ID NO:140; and
as a CDR-L3 sequence, the amino acid sequence defined in SEQ ID NO:157;

(33) as a CDR-H1 sequence, the amino acid sequence defined in SEQ ID NO:105;
as a CDR-H2 sequence, the amino acid sequence defined in SEQ ID NO:115;
as a CDR-H3 sequence, the amino acid sequence defined in SEQ ID NO:126;
as a CDR-L1 sequence, the amino acid sequence defined in SEQ ID NO:136;
as a CDR-L2 sequence, the amino acid sequence defined in SEQ ID NO:146; and
as a CDR-L3 sequence, the amino acid sequence defined in SEQ ID NO:158;

(34) as a CDR-H1 sequence, the amino acid sequence defined in SEQ ID NO:106;
as a CDR-H2 sequence, the amino acid sequence defined in SEQ ID NO:117;
as a CDR-H3 sequence, the amino acid sequence defined in SEQ ID NO:122;
as a CDR-L1 sequence, the amino acid sequence defined in SEQ ID NO:138;
as a CDR-L2 sequence, the amino acid sequence defined in SEQ ID NO:141; and
as a CDR-L3 sequence, the amino acid sequence defined in SEQ ID NO:151; or

(35) as a CDR-H1 sequence, the amino acid sequence defined in SEQ ID NO:105;
as a CDR-H2 sequence, the amino acid sequence defined in SEQ ID NO:118;
as a CDR-H3 sequence, the amino acid sequence defined in SEQ ID NO:127;
as a CDR-L1 sequence, the amino acid sequence defined in SEQ ID NO:136;
as a CDR-L2 sequence, the amino acid sequence defined in SEQ ID NO:147; and
as a CDR-L3 sequence, the amino acid sequence defined in SEQ ID NO:158.

* * * * *